US008318931B2

(12) United States Patent
Kokubo et al.

(10) Patent No.: US 8,318,931 B2
(45) Date of Patent: Nov. 27, 2012

(54) CHEMOKINE RECEPTOR ANTAGONISTS AND USE THEREOF

(75) Inventors: Masaya Kokubo, Mishima-gun (JP); Motoyuki Tanaka, Mishima-gun (JP); Hiroshi Ochiai, Mishima-gun (JP); Yoshikazu Takaoka, Mishima-gun (JP); Shiro Shibayama, Tsukuba (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 950 days.

(21) Appl. No.: 12/091,403

(22) PCT Filed: Oct. 27, 2006

(86) PCT No.: PCT/JP2006/321569

§ 371 (c)(1),
(2), (4) Date: Apr. 24, 2008

(87) PCT Pub. No.: WO2007/049771

PCT Pub. Date: May 3, 2007

(65) Prior Publication Data

US 2009/0118279 A1 May 7, 2009

(30) Foreign Application Priority Data

Oct. 28, 2005 (JP) ................................ 2005-313796

(51) Int. Cl.
*A61P 35/00* (2006.01)
*C07D 471/10* (2006.01)

(52) U.S. Cl. ......................................... 544/127; 546/16

(58) Field of Classification Search ........................ None
See application file for complete search history.

(56) References Cited

FOREIGN PATENT DOCUMENTS

| | | | |
|---|---|---|---|
| EP | 1550657 | A1 | 7/2005 |
| JP | 2002-503210 | A | 1/2002 |
| JP | 2003-512349 | A | 4/2003 |
| WO | 97/44329 | A1 | 11/1997 |
| WO | 01/28987 | A1 | 4/2001 |
| WO | 2004/018425 | A1 | 3/2004 |
| WO | 2004/041279 | A1 | 5/2004 |
| WO | 2005/085209 | A | 9/2005 |
| WO | 2006/022454 | A1 | 3/2006 |

OTHER PUBLICATIONS

Rautio et al., Prodrugs: Design and Clinical Applications, 7 Nat. Rev. Drug Dis., 255-70 (2008).*
Vippagunta et al., Crystalline solids, 48 Adv. Drug Delivery Rev. 3-26 (2001).*
Skerlj et al., Synthesis and SAR of Novel CXCR4 Antagonists that are Potent Inhibitors of T Tropic (XR) HIV-1 Replication, 21 Bioorg. & Med. Chem. Letts. 262-266 (2011).*
European Patent Office, Search Report issued on Oct. 7, 2011 in the corresponding European Patent Application No. 06822530.9.
Extended European Search Report issued on Sep. 17, 2010 in counterpart European Application No. 06822530.9.
Japanese Patent Office, communication dated Jun. 15, 2012, issued in a counterpart Japanese Application No. 2007-542710.
Japanese Patent Office, Notification of Reasons for Refusal issued on Sep. 3, 2012 in a counterpart Japanese Application No. 2007-542710.

* cited by examiner

*Primary Examiner* — Janet Andres
*Assistant Examiner* — Timothy R Rozof
(74) *Attorney, Agent, or Firm* — Sughrue Mion, PLLC

(57) ABSTRACT

The present invention relates to a compound represented by formula (I):

(I)

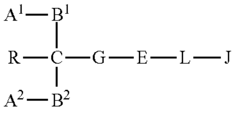

wherein all symbols are as defined here, a salt thereof, a solvate thereof, or a prodrug thereof.
The compound of the present invention has an antagonistic activity against CXCR4 and is therefore useful as a preventive and/or therapeutic agent for CXCR4-mediated diseases, for example, inflammatory and immune diseases (for example, rheumatoid arthritis, arthritis, retinopathy, pulmonary fibrosis, rejection of transplanted organ, etc.), allergic diseases, infections (for example, human immunodeficiency virus infection, acquired immunodeficiency syndrome, etc.), psychoneurotic diseases, cerebral diseases, cardiovascular disease, metabolic diseases, and cancerous diseases (for example, cancer, cancer metastasis, etc.), or an agent for regeneration therapy.

15 Claims, No Drawings

CHEMOKINE RECEPTOR ANTAGONISTS AND USE THEREOF

TECHNICAL FIELD

The present invention relates to compounds having a basic group which is useful as medicaments, and use thereof.

More specifically, the present invention relates to (1) compounds represented by formula (I):

(I)

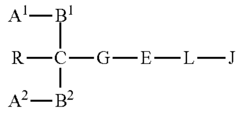

wherein all symbols are as defined hereinafter, and salts thereof, N-oxides thereof or solvates thereof or prodrugs thereof, (2) use thereof, and (3) a method for producing the same.

BACKGROUND ART

Chemokine is known as a basic protein which has chemotaxis and an activating effect on endogenous leucocytes and also has strong heparin-binding abilities. It is now considered that chemokine is associated with not only control of infiltration of specific leucocytes upon inflammatory and immune responses, but also development, homing of lymphocytes under physiological conditions and migration of hemocyte precursor cells and somatic cells.

Differentiation, proliferation and cell death of blood cells are controlled by various cytokines. Inflammation occurs at a local region in a living body. Differentiation and maturation of lymphocytes, and the like are carried out at a specific site. More particularly, required various cells migrate and accumulate in the specific site and a sequence of inflammatory and immune responses arise. Thus, as well as differentiation, proliferation and death of cells, cell migration is also an essential phenomenon to an immune system.

In the living body, migration of blood cells start with shifting hemopoiesis that started at AGM (Aorta Gonad Mesonephros) region via fetal liver to permanent hematopoiesis at bone marrow in a development course. Moreover, precursors of T cells and thymus dendritic cells migrate from fetal liver into bone marrow and then into the thymus gland. They differentiate under thymus environment. The T cells are subjected to clonal selection migrates into secondary lymphoid tissues, where they contribute to immune responses in periphery. Skin Langerhans cells that caught antigen, thereby undergone activation and differentiation migrate to T cell region in a topical lymph node, where they activate naive T cells therein as dendritic cells. The memory T cells again perform its homing into the lymph node via lymphatic and blood vessels. In addition, B cells, T cells in intestinal epithelia, γδT cells, NKT cells, and dendritic cells migrate from bone marrow not via thymus, differentiate and contribute to immune responses.

Chemokine is very involved in these various cell migrations. For example, SDF-1 (Stromal cell derived factor-1) and its receptor, CXCR4 also act on various immune- and inflammatory reactions. For example, they have been reported to be associated with accumulation and activation of CD4+T cells in a synovial membrane from a human patient suffering from rheumatoid arthritis (J. Immunol., 165, 6590-6598 (2000)). In addition, in a CIA model mouse, CXCR4 inhibitor inhibited accumulation of leucocytes in a joint and dramatically reduced arthritis score (J. Immunol., 167, 4648-4692 (2001)). In a mouse OVA-induced airway hypersensitive model, an anti-CXCR4 antibody reduced the number of eosinophiles accumulating in pulmonary interstitial tissues and prevented airway hypersensitivity (J. Immunol., 165, 499-508 (2000)).

There has been reported that SDF-1 and its receptor, CXCR4 play an important role in maintaining hemopoietic stem cells in bone marrow J. Exp. Med., 185, 111-120 (1997), Blood, 97, 3354-3360 (2001)). Accordingly, control of SDF-1 and CXCR4 is expected to modulate recruitment of hemopoietic stem cells to peripheral blood and is useful for peripheral blood stem cell transplantation and reproduction transplantation treatment.

SDF-1 and CXCR4 are associated with infiltration of various cancer cells such as breast cancer, prostate cancer, and ovarian cancer (Nature, 410, 50-56 (2001), Cancer Res., 62, 1832-1837 (2002), Cancer Res., 62, 5930-5938 (2002)). In a model of a SCID mouse which is transferred a human breast cancer cell strain into, an anti-CXCR4 antibody prevented metastasis of breast cancer cells to lung (Nature, 410, 50-56 (2001)). In human ovarian epithelial tumor, highly expression of SDF-1 promotes accumulation of plasmacytoid dendritic cells and inhibits the act of bone marrow dendritic cells associated with tumor immune and suppresses tumor immune (Nat. Med., 12, 1339 (2001)). Moreover, SDF-1 is associated with proliferation and migration of non-Hodgkin's lymphoma cells, and in a model of a NOD/SCID mouse which is transferred a human non-Hodgkin's lymphoma cells into, an anti-CXCR4 antibody inhibited proliferation of the tumor cells and improved mouse mortality (Cancer Res., 62, 3106-3112 (2002)).

SDF-1 and CXCR4 play an important role for formation of hippocampus dentate gyrus granulocyte, that is essential for memory and learning and are associated with development of a disease associated with adult plasticity and pathology of hippocampus, for example Alzheimer's disease, stroke and epilepsy (Development, 129, 4249-4260 (2002), Trends in Neuroscience, 25, 548-549 (2002)).

SDF-1 and CXCR4 are essential for a function of self-reactive B cells associated with development of diabetes. In NOD mouse, an anti-SDF-1 antibody reduced blood glucose level and the number of mature IgM+B cells in a periphery tissue (Immunology, 107, 222-232 (2002)). In a human arteriosclerotic plaque, SDF-1 was highly expressed and activated blood platelets (Circ. Res., 86, 131-138 (2000)).

SDF-1 and CXCR4 are involved in residence of hemopoietic stem cells and hemopoietic precursor cells in bone marrow. CXCR4 antagonist, AMD 3100 in combination with G-CSF increased the numbers of hemopoietic stem cells and hemopoietic precursor cells in periphery blood (Journal Experimental Medicine, 2001, 1307-1318 (2005)).

In addition, the results of SDF-1/CXCR4 knock-out mice showed that SDF-1 is essential for functions of central nervous system, heart and vessels of gastrointestinal tract in addition to lymphocytes (Nature, 382, 635-639 (1996), Nature, 393, 591-594 (1998), Nature, 393, 595-599 (1998)). Accordingly, it may be associated with a disease of these tissues.

Thus, chemokine receptors are expressed at various specific cells and at a specific time. They are largely associated with the control of inflammatory- and immune-responses through a mechanism by which their effector cells accumulate in a site where chemokine is produced.

Acquired immunodeficiency syndrome (also called AIDS) that caused by infection of human immunodeficiency virus (hereinafter abbreviated to HIV) is one of diseases for which therapies are the most eagerly desired lately. Once HIV infection has been established in a main target cell, CD4+ cell, HIV repetitively proliferates in a patient's body and in the event deathly destroys T cells responsible for immunological functions by necrosis. In this process, immunological functions are gradually deteriorated, various immunocompromised states become to develop such as fever, diarrhea and swelling of a lymph node, and various opportunistic infections such as carinii pneumonia are easily complicated. It is well known that such a state is the onset of AIDS and induces malignant tumors such as Kaposi's sarcoma and becomes severe.

Currently, various preventive and therapeutic treatments for AIDS are tried as follows: for example, (1) inhibition of HIV proliferation by administration of reverse transcriptase inhibitors and protease inhibitors, and (2) prevention or alleviation of opportunistic infections by administration of an immunostimulant, etc.

HIV mainly infects helper T cells which play a key role in the immune system. Since 1985, it has been known that in this process HIV utilizes a membrane protein CD4 that is expressed on the membrane of T cells (Cell, 52, 631 (1985)). CD4 molecule consists of 433 amino acid residues and is expressed in macrophages, some B cells, vascular endothelial cells, Langerhans cells in skin tissues, dendritic cells located in lymphatic tissues, glia cells of central nervous system and the like in addition to mature helper T cells. However, as it becomes obvious that HIV infection cannot be established with only CD4 molecule, the possible presence of some factor that is responsible for infection of cell with HIV, other than CD4 molecule, has been suggested.

In 1996, a cell membrane protein called Fusin has been identified as a factor responsible for HIV infection other than a CD4 molecule (Science, 272, 872 (1996)). This Fusin molecule has been demonstrated to be a receptor for SDF-1, namely, CXCR4. In addition, it has been shown that SDF-1 specifically inhibits infection of T cell-directed (X4) HIV in vitro (Nature, 382, 829 (1996), Nature, 382, 833 (1996)). This may be considered that SDF-1 binds to CXCR4 prior to HIV, thereby taking away a scaffold for infecting a cell from HIV resulting in inhibition of HIV infection.

Also, at the same period, there has been found that another chemokine receptor CCR5, that is a receptor for RANTES, MIP-1α, and MIP-1β, is utilized at infection of macrophage-directed (R5) HIV (Science, 272, 1955 (1996)).

Accordingly, those which can compete with HIV for CXCR4 and CCR5 or those which bind to a HIV virus and prevent for said virus from binding to CXCR4 and CCR5 may be a HIV infection inhibitor. In addition, there is a case where a low molecular weight compound discovered as a HIV infection inhibitor was showed to be indeed an antagonist of CXCR4 (Nature Medicine, 4, 72 (1998)).

As described above, compounds having an antagonistic activity against CXCR4 is effective, such as, for prevention and/or treatment of inflammatory and immune diseases, allergic diseases, infections (particularly HIV infection), and diseases associated with the infection, psychoneurotic diseases, cerebral diseases, cardiovascular diseases, metabolic diseases, cancerous diseases and the like. Also, the compounds are useful for cell medical treatment and regeneration therapy.

Heretofore, some compounds having an antagonistic activity against CXCR4 have been reported. For example, it is disclosed that a compound represented by formula (X):

(X)

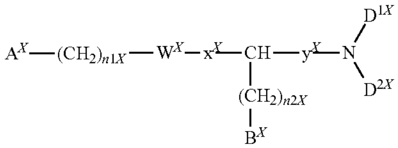

wherein $A^X$ represents

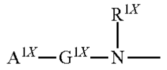

or

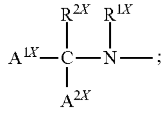

$A^{1X}$ and $A^{2X}$ each independently represents a hydrogen atom, an optionally substituted monocyclic or polycyclic heteroaromatic ring, or an optionally substituted monocyclic or polycyclic aromatic ring; $G^{1X}$ represents a single bond or —$CR^{2X}R^{3X}$—; $R^{1X}$, $R^{2X}$ and $R^{3X}$ represent an optionally substituted alkyl group having 1 to 6 carbon atom(s); $W^X$ represents an optionally substituted alkylene group having 1 to 7 carbon atom(s), an optionally substituted monocyclic or polycyclic heteroaromatic ring, or an optionally substituted monocyclic or polycyclic aromatic ring; $x^X$ represents -$z^{1X}$-CO-$z^{2X}$-; $z^{1X}$ and $z^{2X}$ each independently represents a single bond or $NR^{13X}$; $y^X$ represents —CO—; $D^{1X}$ and $D^{2X}$ each independently represents a hydrogen atom or -$G^{2X}$-$R^{4X}$; $G^{2X}$ represents an optionally substituted alkylene group having 1 to 15 carbon atom(s); $R^{4X}$ represents a hydrogen atom, an optionally substituted monocyclic or polycyclic heteroaromatic ring, or an optionally substituted monocyclic or polycyclic aromatic ring; n2X represents 0 to 4; n1X represents 0 to 3; and $B^X$ represents —$NR^{6X}R^{7X}$, and only required portions were extracted with respect to definition of each group), or a pharmaceutically acceptable salt has an antagonistic activity against CXCR4 (see WO2003/029218 pamphlet).

Also, it is disclosed that a compound represented by formula (Y):

(Y)

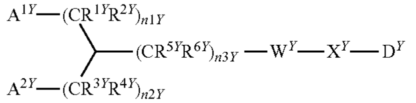

wherein n1Y, n2Y and n3Y represent 0 to 3; $R^{1Y}$, $R^{2Y}$, $R^{3Y}$, $R^{4Y}$, $R^{5Y}$ and $R^{6Y}$ each independently represents a hydrogen atom, or an optionally substituted alkyl group having 1 to 15 carbon atom(s); $A^{1Y}$ and $A^{2Y}$ each independently represents an optionally substituted monocyclic or polycyclic heteroaromatic ring; $W^Y$ represents an optionally substituted alkylene group having 1 to 15 carbon atom(s); $X^Y$ represents O, $CH_2$, or $NR^{11Y}$; $D^Y$ represents -$Q^Y$-$Y^Y$—$B^Y$; $Q^Y$ represents a single bond or —CO— when $X^Y$ is $NR^{11Y}$; $Y^Y$ represents —$(CR^{18Y}R^{19Y})_{m3Y}$—; $R^{18Y}$ and $R^{19Y}$ each independently represents a hydrogen atom, or an optionally substituted alkyl group having 1 to 15 carbon atom(s); m3Y represents 0 to 6; $B^Y$ represents —$NR^{25Y}R^{26Y}$; and $R^{25Y}$ and $R^{26Y}$ represent a hydrogen atom or an optionally substituted alkyl group having 1 to 15 carbon atom(s) when $X^Y$ is not $CH_2$, and only required portions were extracted with respect to definition of each group), or a pharmaceutically acceptable salt or a prodrug thereof has an antagonistic activity against CXCR4 (see WO2004/024697 pamphlet).

Furthermore, it is disclosed that a compound represented by formula (Z):

(Z)

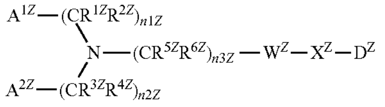

wherein n1Z, n2Z and n3Z represent 0 to 3; $R^{1Z}$, $R^{2Z}$, $R^{3Z}$, $R^{4Z}$, $R^{5Z}$ and $R^{6Z}$ each independently represents a hydrogen atom, or an optionally substituted alkyl group having 1 to 15 carbon atom(s), and $R^{5Z}$ and $R^{6Z}$ may form a carbonyl group together with a carbon atom; $A^{1Z}$ and $A^{2Z}$ each independently represents an optionally substituted monocyclic or polycyclic heteroaromatic ring; $W^Z$ represents an optionally substituted benzene ring; $X^Z$ represents O, $CH_2$, or $NR^{11Z}$; $D^Z$ represents $-Q^Z-Y^Z—B^Z$; $Q^Z$ represents a single bond, —CO—, —CONH—, or $NR^{12Z}$ when $X^Z$ is $CH_2$; $Y^Z$ represents $—(CR^{18Z}R^{19Z})_{m3z}—$; $R^{18z}$ and $R^{19z}$ each independently represents a hydrogen atom, or an optionally substituted alkyl group having 1 to 15 carbon atom(s); m3Z represents 0 to 6; $B^Z$ represents $—NR^{25Z}R^{26Z}$; and $R^{25Z}$ and $R^{26Z}$ represent a hydrogen atom, or an optionally substituted alkyl group having 1 to 15 carbon atom(s) when $X^Z$ is not $CH_2$, and only required portions were extracted with respect to definition of each group), or a pharmaceutically acceptable salt or a prodrug thereof has an antagonistic activity against CXCR4 (se WO2005/085209 pamphlet).

| | |
|---|---|
| Patent Literature 1 | WO2003/029218 pamphlet |
| Patent Literature 2 | WO2004/024697 pamphlet |
| Patent Literature 3 | WO2005/085209 pamphlet |

DISCLOSURE OF THE INVENTION

It is earnestly desired to develop a CXCR4 antagonist which is useful as a preventive and/or therapeutic agent for inflammatory and immune diseases (for example, rheumatoid arthritis, arthritis, retinopathy, pulmonary fibrosis, rejection of transplanted organ, etc.), allergic diseases, infections (for example, human immunodeficiency virus infection, acquired immunodeficiency syndrome, etc.), and cancerous diseases (for example, cancer, cancer metastasis, etc.), or an agent for regeneration therapy, and also causes less side effect and is safe.

The present inventors have intensively studied and found that a compound represented by formula (I) described hereinafter surprisingly has a strong antagonistic activity against CXCR4, and thus the present invention has been completed.

The present invention relates to

[1] A compound represented by formula (I):

(I)

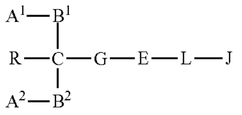

wherein $A^1$ and $A^2$ each independently represents a group having a basic group;

$B^1$ and $B^2$ each independently represents a bond, or a spacer having a main chain of 1 to 4 atom(s);

E represents a spacer having a main chain of 1 to 10 atom(s);

L represents a bond, or a spacer having a main chain of 1 to 4 atom(s);

J represents (1) an aliphatic hydrocarbon group which is substituted with a group having a basic group, and also may have a substituent(s), (2) a monocyclic or condensed cyclic group which is substituted with a group having a basic group, and also may have a substituent(s), (3) a spiro-bound cyclic group which may be substituted with a group having a basic group, and also may have a substituent(s), or (4) a bridged cyclic group which may be substituted with a group having a basic group, and also may have a substituent(s);

G represents $G^A$ or $G^{1A}$-$G^{2A}$-$G^{3A}$;

$G^A$ represents a bond, a carbon atom which may have a substituent(s), or a nitrogen atom which may have a substituent;

$G^{1A}$ represents a carbon atom which may have a substituent(s);

$G^{2A}$ represents a carbon atom which may have a substituent(s), a nitrogen atom which may have a substituent, an optionally oxidized sulfur atom or an oxygen atom;

$G^{3A}$ represents a bond, or a carbon atom which may have a substituent(s); and R represents a hydrogen atom, or a substituent), a salt thereof, a solvate thereof, or a prodrug thereof;

[2] The compound according to the above-described [1], wherein R is a hydrogen atom, a salt thereof, a solvate thereof, or a prodrug thereof;

[3] The compound according to the above-described [1], wherein $A^1$ and $A^2$ each independently represents a nitrogen-containing heterocyclic ring which may have a substituent(s), a salt thereof, a solvate thereof, or a prodrug thereof;

[4] The compound according to the above-described [3], wherein the nitrogen-containing heterocyclic ring is an imidazole ring, a benzoimidazole ring, or a pyridine ring, a salt thereof, a solvate thereof, or a prodrug thereof;

[5] The compound according to the above-described [1], wherein the spacer having a main chain of 1 to 4 atom(s) represented by $B^1$ and $B^2$ is $—CH_2—$, a salt thereof, a solvate thereof, or a prodrug thereof;

[6] The compound according to the above-described [1], wherein G is —CO—, $—CH_2—$, —CH(OH)—, or —NH—, a salt thereof, a solvate thereof, or a prodrug thereof;

[7] The compound according to the above-described [1], wherein E is a benzene ring or a cyclohexane ring, a salt thereof, a solvate thereof, or a prodrug thereof;

[8] The compound according to the above-described [1], wherein L is $—CH_2—$ or $—CH_2—NH—$ (provided that a nitrogen atom is bonded to J), a salt thereof, a solvate thereof, or a prodrug thereof;

[9] The compound according to the above-described [1], wherein J is (3) a spiro-bound cyclic group which may be substituted with a group having a basic group, and also may have a substituent(s), or (4) a bridged cyclic group which may be substituted with a group having a basic group, and also may have a substituent(s), a salt thereof, a solvate thereof, or a prodrug thereof;

[10] The compound according to the above-described [9], wherein J is a spiro-bound polycyclic heterocyclic ring or bridged polycyclic heterocyclic ring, which has at least one nitrogen atom, and also may have an oxygen atom(s) and/or an optionally oxidized sulfur atom(s) and which may be substituted with a group having a basic group, and also may have a substituent(s), a salt thereof, a solvate thereof, or a prodrug thereof;

[11] The compound according to the above-described [9], wherein the spiro-bound polycyclic heterocyclic ring or bridged polycyclic heterocyclic ring which has at least one nitrogen atom, and also may have an oxygen atom and/or an optionally oxidized sulfur atom is:

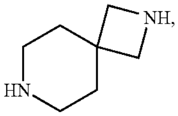, 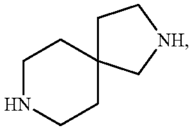,
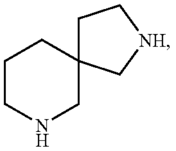, 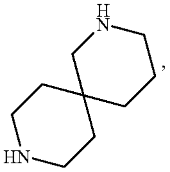,
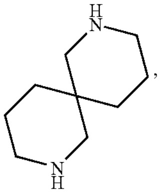, 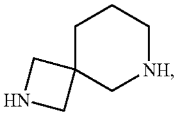,
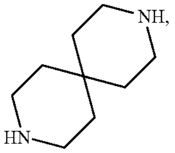, 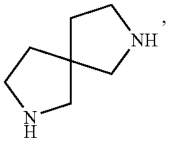,
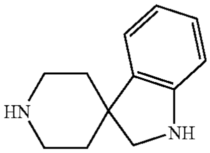, 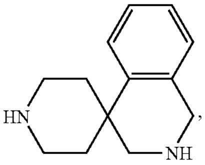,
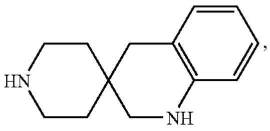, 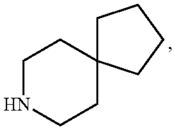,
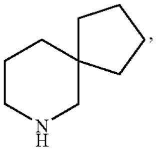, 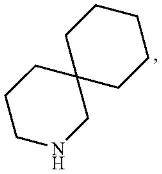, 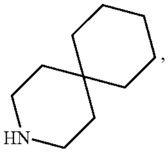,
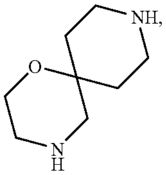, 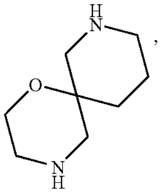, 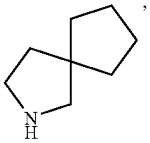,
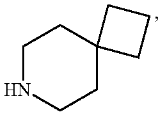, 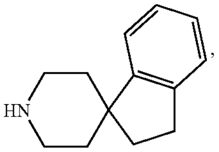, -continued

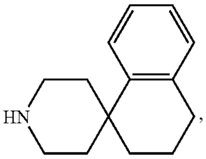, 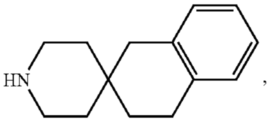,
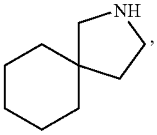, 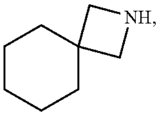,
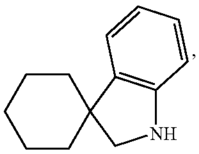, 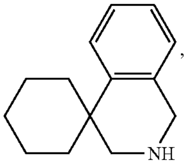,
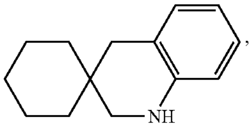, 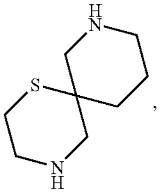,
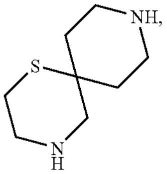, 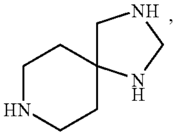,
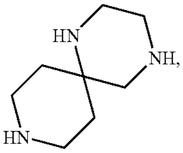, 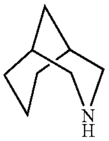, 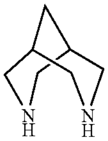 or
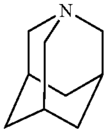

wherein the nitrogen atom of —NH— may have a substituent(s), a salt thereof, a solvate thereof, or a prodrug thereof;

[12] The compound according to the above-described [10], wherein the spiro-bound polycyclic heterocyclic ring is a 7- to 15-membered spiro-bound bicyclic heterocyclic ring which consists of (i) a monocyclic ring composed of at least one nitrogen atom and carbon atoms and/or (ii) a monocyclic ring composed of at least one nitrogen atom, one oxygen atom and carbon atoms, a salt thereof, a solvate thereof, or a prodrug thereof;

[13] The compound according to the above-described [12], wherein the 7- to 15-membered spiro-bound bicyclic heterocyclic ring is:

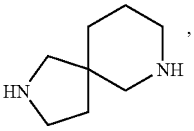, 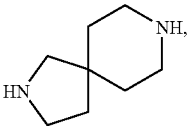,

-continued

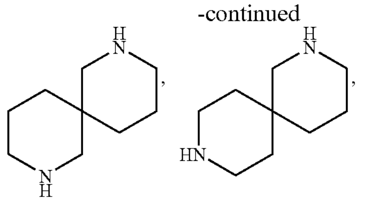

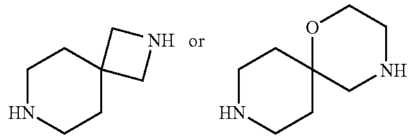

wherein the nitrogen atom of —NH— may have a substituent(s), a salt thereof, a solvate thereof, or a prodrug thereof;

[14] The compound according to the above-described [1], wherein formula (I) is formula (I-1):

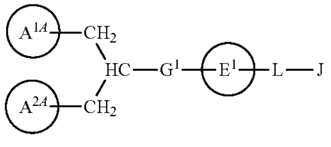

(I-1)

wherein ring $A^{1A}$ and ring $A^{2A}$ each independently represents an imidazole ring which may have a substituent(s), a benzoimidazole ring which may have a substituent(s), or a pyridine ring which may have a substituent(s), $G^1$ represents —CO—, —$CH_2$—, —CH(OH)—, or —NH—, and ring $E^1$ represents a 3- to 8-membered monocyclic group which may have a substituent(s), and other symbols are as defined in the above-described [1], a salt thereof, a solvate thereof, or a prodrug thereof;

[15] The compound according to the above-described [14], wherein

—L—J is 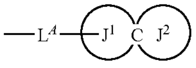

wherein $L^A$ represents (a)-(an aliphatic hydrocarbon having 1 to 3 carbon atoms(s) which may have a substituent(s))-(a nitrogen atom which may have a substituent)-, or (b) a divalent aliphatic hydrocarbon having 1 to 4 carbon atoms(s) which may have a substituent(s), (a) when $L^A$ is -(an aliphatic hydrocarbon having 1 to 3 carbon atoms(s) which may have a substituent(s))-(a nitrogen atom which may have a substituent)-, ring $J^1$ represents a 3- to 10-membered monocyclic or bicyclic heterocyclic ring composed of (i) a C3-10 monocyclic or bicyclic carbocyclic ring, or (ii) a 3- to 10-membered monocyclic or bicyclic heterocyclic ring composed of a carbon atom(s), an oxygen atom(s) and/or an optionally oxidized sulfur atom(s), (b) when $L_A$ is a divalent aliphatic hydrocarbon having 1 to 4 carbon atoms(s) which may have a substituent(s), ring $J^1$ represents a 3- to 10-membered monocyclic or bicyclic heterocyclic ring which has at least one nitrogen atom, and also may have an oxygen atom and/or an optionally oxidized sulfur atom, ring $J^2$ represents (i) a C3-10 monocyclic or bicyclic carbocyclic ring substituted with a group having a basic group, (ii) a 3- to 10-membered monocyclic or bicyclic heterocyclic ring composed of a carbon atom(s), an oxygen atom(s) and/or an optionally oxidized sulfur atom(s), which is substituted with a group having a basic group, or (iii) a 3- to 10-membered monocyclic or bicyclic heterocyclic ring which has at least one nitrogen atom and also may have an oxygen atom or an optionally oxidized sulfur atom, and also may be substituted with a group having a basic group, ring $J^1$ and ring $J^2$ may have 1 to 8 substituent(s) on the substitutable position and, when two or more substituents are present, plural substituents may be the same or different, wherein a nitrogen atom which may have a substituent in $L_A$ is bonded to ring $J^1$, a salt thereof, a solvate thereof, or a prodrug thereof;

[16] The compound according to the above-described [15], wherein

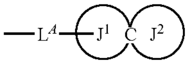 is

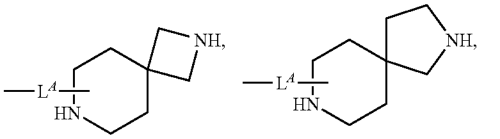

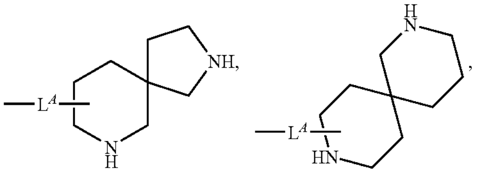

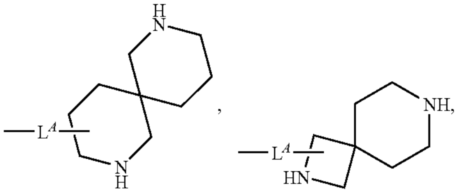

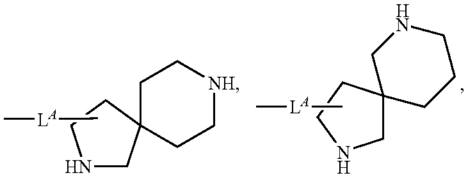

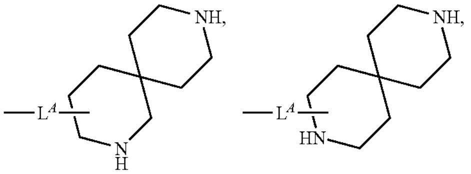

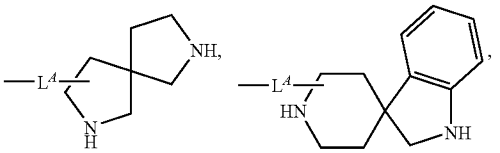

-continued
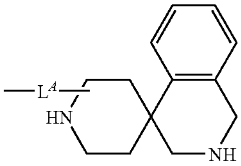,
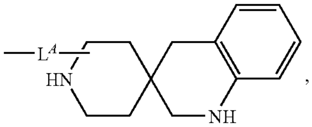,
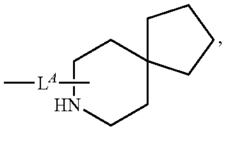, 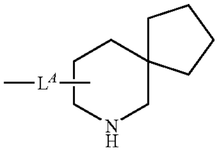,
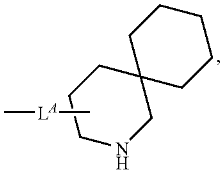, 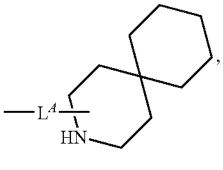,
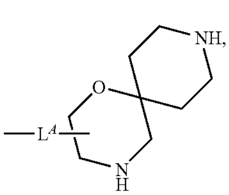, 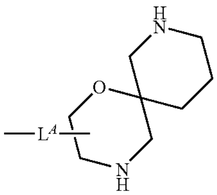,
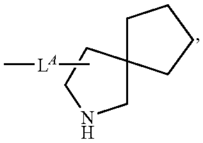, 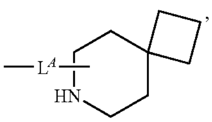,
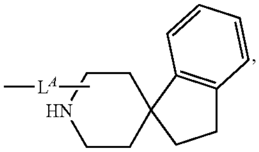, 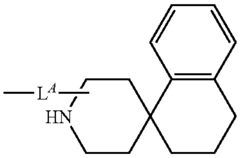,
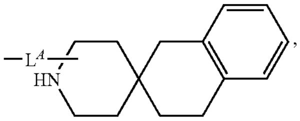, 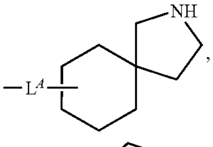,
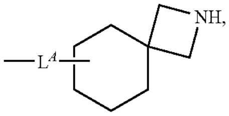, 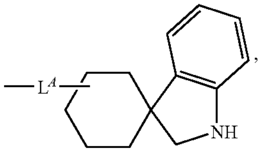,
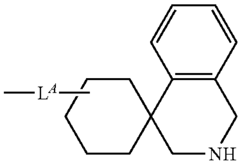,
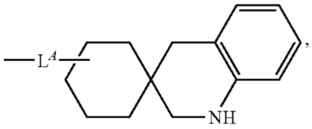,
-continued
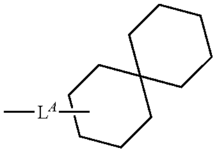, 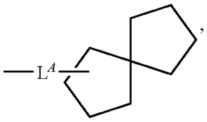,
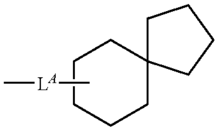, 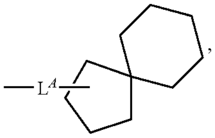,
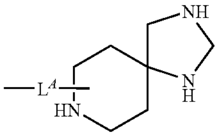, 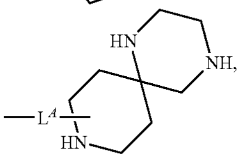,
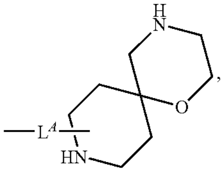, 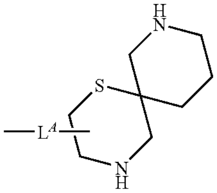 or
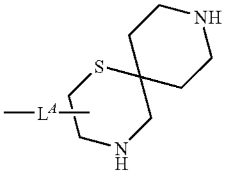
wherein $L_A$ is as defined in the above-described [15], wherein $L_A$ may be bonded to the nitrogen atom of —NH— and the nitrogen atom of —NH— may have a substituent(s), a salt thereof, a solvate thereof, or a prodrug thereof;
[17] The compound according to the above-described [1], wherein
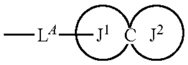 is
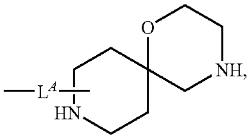 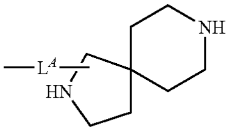,
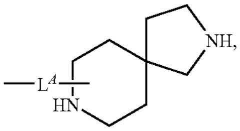 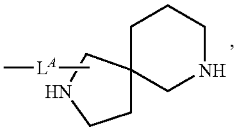,
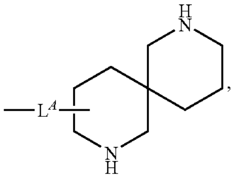, 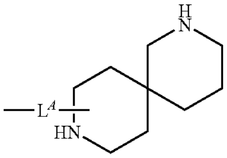 or
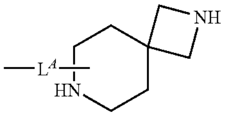

wherein $L_A$ is as defined in the above-described [15], wherein $L_A$ may be bonded to the nitrogen atom of —NH— and the nitrogen atom of —NH— may have a substituent(s), a salt thereof, a solvate thereof, or a prodrug thereof;

[18] The compound according to the above-described [1], wherein formula (I) is formula (I-4):

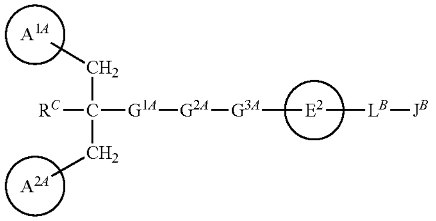

(I-4)

wherein ring $E^2$ represents a benzene ring which may have a substituent(s), a cyclohexane ring which may have a substituent(s), a cyclopentane ring which may have a substituent(s), a pyrrolidine ring which may have a substituent(s), or a piperidine ring which may have a substituent(s);

$R^C$ represents (1) a hydrogen atom, (2) cyano group, (3) a carboxyl group which may be protected with a protective group, (4) a hydroxyl group which may be protected with a protective group, (5) a C1-4 alkyl group which may be substituted with a hydroxyl group which may be protected with a protective group, or (6) an amino group which may be protected with a protective group; and $-L^B-J^B$ represents (a) $-L^{1B}-J^{1B}$ wherein $L^{1B}$ represents $—CH_2—NH—$ or —CO—NH— (provided that the nitrogen atom is bonded to $J^{1B}$, and $J^{1B}$ represents a C4-7 monocyclic carbocyclic ring substituted with a mono- or di-substituted amino group), or (b)

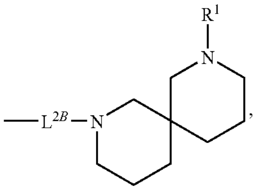

,

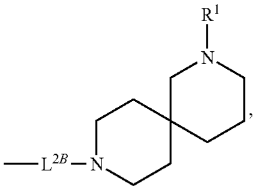

,

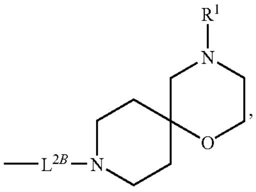

,

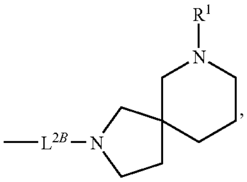

,

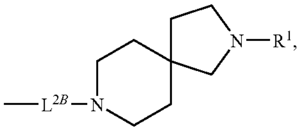

,

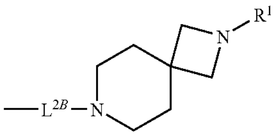

or

-continued

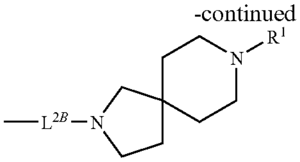

wherein $L^{2B}$ represents a carbon atom which may have a substituent(s) and $R^1$ represents a hydrogen atom or a substituent), and other symbols are as defined in the above-described [1] and [14], a salt thereof, a solvate thereof, or a prodrug thereof;

[19] The compound according to the above-described [18], wherein the protective group is a C1-4 alkyl group which may be substituted with an oxo group, a salt thereof, a solvate thereof, or a prodrug thereof;

[20] The compound according to the above-described [18], wherein the substituent of the carbon atom which may have a substituent(s) represented by $G^{1A}$ is absent, a hydroxyl group, an oxo group, or a C1-4 alkyl group, a salt thereof, a solvate thereof, or a prodrug thereof;

[21] The compound according to the above-described [18], wherein $G^{2A}$ is a nitrogen atom which may have a substituent and $G^{3A}$ is a carbon atom which may have a substituent(s), a salt thereof, a solvate thereof, or a prodrug thereof;

[22] The compound according to the above-described [21], wherein the substituent of the carbon atom which may have a substituent(s) represented by $G^{2A}$ is (1) absent, (2) a C1-4 alkyl group, (3) a C1-4 alkyl group substituted with a hydroxyl group which may be protected with a protective group, (4) a C1-4 alkyl group substituted with an amino group which may be protected with a protective group, (5) a C1-4 alkyl group substituted with a carboxyl group which may be protected with a protective group, or (6) a C1-4 alkyl group substituted with a pyrrolidine ring, a piperidine ring or a morpholine ring, a salt thereof, a solvate thereof, or a prodrug thereof;

[23] The compound according to the above-described [22], wherein the protective group is a C1-4 alkyl group which may be substituted with an oxo group, a salt thereof, a solvate thereof, or a prodrug thereof;

[24] The compound according to the above-described [21], wherein the substituent of the carbon atom which may have a substituent(s) represented by $G^{3A}$ is absent, a C1-4 alkyl group, a hydroxyl group or an oxo group, a salt thereof, a solvate thereof, or a prodrug thereof;

[25] The compound according to the above-described [18], wherein $-L^B-J^B$ is (a) $-L^{1B}-J^{1B}$ (symbols in the group are as defined in the above-described [18]), a salt thereof, a solvate thereof, or a prodrug thereof;

[26] The compound according to the above-described [18], wherein $-L^B-J^B$ is (b)

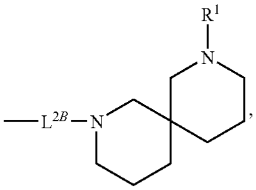

,

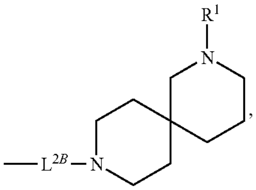

,

-continued

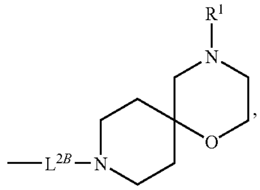,

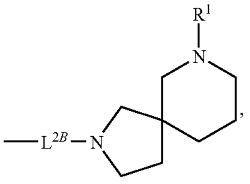,

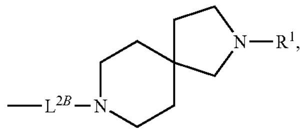

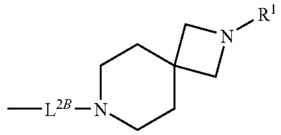

or

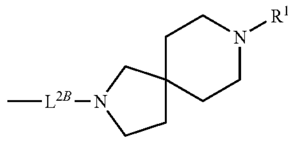

wherein symbols are as defined in the above-described [18], a salt thereof, a solvate thereof, or a prodrug thereof;

[27] The compound according to the above-described [18], wherein formula (I) is formula (I-4-a):

(I-4-a)

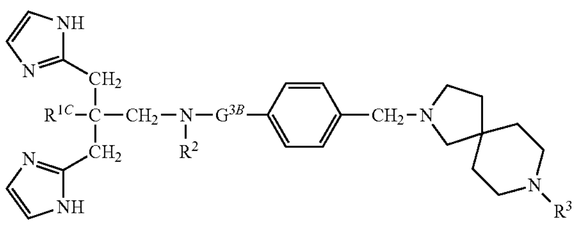

wherein $G^{3B}$ represents —$CH_2$— or —CO—, $R^{1C}$ represents a hydrogen atom, a cyano group, a C1-4 alkyl group substituted with a hydroxyl group, or a C1-4 alkyl group substituted with an acetyloxy group, $R^2$ represents a hydrogen atom, or a hydroxyethyl, acetyl, methoxyethyl, pyrrolidinylethyl, morpholinylethyl, hydroxymethylcarbonyl, dimethylaminoethyl or acetylaminoethyl group, and $R^3$ represents a C1-4 alkyl group, a C5-7 saturated monocyclic carbocyclic ring or a (3-methyl-2-thienyl)methyl group), a salt thereof, a solvate thereof, or a prodrug thereof;

[28] The compound according to the above-described [1], wherein formula (I) is formula (I-5):

(I-5)

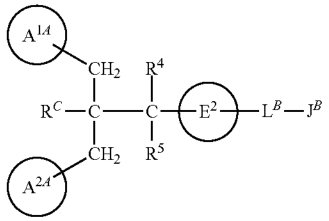

wherein $R^4$ and $R^5$ represent a hydrogen atom or a substituent and other symbols are as defined in the above-described [14] and [18], a salt thereof, a solvate thereof, or a prodrug thereof;

[29] The compound according to the above-described [1], wherein formula (I) is formula (I-6):

(I-6)

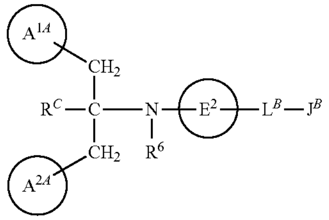

wherein $R^6$ represents a hydrogen atom or a substituent and other symbols are as defined in the above-described [14] and [18], a salt thereof, a solvate thereof, or a prodrug thereof;

[30] The compound according to the above-described [1], which is

2-{4-[3-(1H-imidazol-2-yl)-2-(1H-imidazol-2-ylmethyl)propoxy]benzyl}-8-[(3-methyl-2-thienyl)methyl]-2,8-diazaspiro[4.5]decane, N-[3-(1H-imidazol-2-yl)-2-(1H-imidazol-2-ylmethyl)propyl]-N-[4-({8-[(3-methyl-2-thienyl)methyl]-2,8-diazaspiro[4.5]dec-2-yl}methyl)benzyl]acetoamide, 8-cyclohexyl-2-{4-[3-(1H-imidazol-2-yl)-2-(1H-imidazol-2-ylmethyl)propyl]benzyl}-2,8-diazaspiro[4.5]decane, 3-({4-[(8-cyclohexyl-2,8-diazaspiro[4.5]dec-2-yl)methyl]benzyl}amino)-2,2-bis(1H-imidazol-2-ylmethyl)-1-propanol, 2-{{4-[(8-cyclohexyl-2,8-diazaspiro[4.5]dec-2-yl)methyl]benzyl}[3-(1H-imidazol-2-yl)-2-(1H-imidazol-2-ylmethyl)propyl]amino}ethanol, N-[2-cyano-3-(1H-imidazol-2-yl)-2-(1H-imidazol-2-ylmethyl)propyl]-N-{4-[(8-cyclohexyl-2,8-diazaspiro[4.5]dec-2-yl)methyl]benzyl}acetoamide, N-[3-(1H-imidazol-2-yl)-2-(1H-imidazol-2-ylmethyl)propyl]-4-[(8-isobutyl-2,8-diazaspiro[4.5]dec-2-yl)methyl]benzamide, N-[3-(1H-imidazol-2-yl)-2-(1H-imidazol-2-ylmethyl)propyl]-4-[(8-isobutyl-2,8-diazaspiro[4.5]dec-2-yl)methyl]-N-(2-methoxyethyl)benzamide, N-[3-(1H-imidazol-2-yl)-2-(1H-imidazol-2-ylmethyl)propyl]-4-[(8-isobutyl-2,8-diazaspiro[4.5]dec-2-yl)methyl]-N-[2-(1-pyrrolidinyl)ethyl]benzamide, 2-hydroxy-N-[3-(1H-imidazol-2-yl)-2-(1H-imidazol-2-ylmethyl)propyl]-N-{4-[(8-isobutyl-2,8-diazaspiro[4.5]dec-2-yl)methyl]benzyl}acetoamide, N-[3-hydroxy-2,2-bis(1H-imidazol-2-ylmethyl)propyl]-N-{4-[(8-isobutyl-2,8-diazaspiro[4.5]dec-2-yl)methyl]benzyl}acetoamide, N-[2-(dimethylamino)ethyl]-N-[3-(1H-imidazol-2-yl)-2-(1H-imidazol-2-ylmethyl)propyl]-4-[(8-isobutyl-2,8-diazaspiro[4.5]dec-2-yl)methyl]benzamide, N-(2-acetoamideethyl)-N-[3-(1H-imidazol-2-yl)-2-(1H-imidazol-2-ylmethyl)propyl]-4-[(8-isobutyl-2,8-diazaspiro[4.5]dec-2-yl)methyl]benzamide, N-[3-(1H-imidazol-2-yl)-2-(1H-imidazol-2-ylmethyl)propyl]-4-[(8-isobutyl-2,8-diazaspiro[4.5]dec-2-yl)methyl]-N-[2-(4-morpholinyl)ethyl]benzamide, or 3-({4-[(8-cyclohexyl-2,8-diazaspiro[4.5]dec-2-yl)methyl]benzoyl}amino)-2,2-bis(1H-imidazol-2-ylmethyl)propyl acetate, a salt thereof, a solvate thereof, or a prodrug thereof;

[31] A pharmaceutical composition comprising a compound represented by formula (I) according to the above-described [1], a salt thereof, a solvate thereof, or a prodrug thereof;

[32] The pharmaceutical composition according to the above-described [31], which is a CXCR4 antagonist;

[33] The pharmaceutical composition according to the above-described [31], which is preventive and/or therapeutic agent for CXCR4-mediated diseases, or an agent for regeneration therapy;

[34] The pharmaceutical composition according to the above-described [33], wherein the CXCR4-mediated disease is human immunodeficiency virus infection, acquired immunodeficiency syndrome, cancer, cancer metastasis, rheumatoid arthritis, arthritis, retinopathy, pulmonary fibrosis or rejection of transplanted organ, or the agent for regeneration therapy is an agent for transplantation medical treatment;

[35] The pharmaceutical composition according to the above-described [33], wherein the CXCR4-mediated disease is human immunodeficiency virus infection;

[36] A medicament comprising a compound represented by formula (I) according to the above-described [1], a salt thereof, a solvate thereof, or a prodrug thereof, and one or more kinds selected from reverse transcriptase inhibitor, protease inhibitor, CCR2 antagonist, CCR3 antagonist, CCR4 antagonist, CCR5 antagonist, CXCR4 antagonist, HIV integrase inhibitor, fusion inhibitor, CD4 antagonist, antibody against surface antigen of HIV, Short Interfering RNA targeting a HIV-related factor, and vaccine of HIV;

[37] A method for antagonizing CXCR4 in a mammal, comprising administering an effective dosage of a compound represented by formula (I) according to the above-described [1], a salt thereof, a solvate thereof, or a prodrug thereof to the mammal;

[38] A method of prevention and/or treatment for CXCR4-mediated diseases in a mammal, comprising administering an effective dosage of a compound represented by formula (I) according to the above-described [1], a salt thereof, a solvate thereof, or a prodrug thereof to the mammal;

[39] Use of a compound represented by formula (I) according to the above-described [1], a salt thereof, a solvate thereof or a prodrug thereof for production of a CXCR4 antagonist;

[40] Use of a compound represented by formula (I) according to the above-described [1], a salt thereof, a solvate thereof or a prodrug thereof for production of a preventive and/or therapeutic agent for CXCR4-mediated diseases;

[41] The compound according to [14], wherein -L-J is

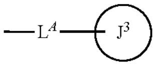

wherein ring $J^3$ represents (i) a bridged polycyclic carbocyclic ring substituted with a group having a basic group, (ii) a bridged polycyclic heterocyclic ring composed of a carbon atom(s), an oxygen atom(s) and/or an optionally oxidized sulfur atom(s), which is substituted with a group having a basic group, or (iii) a bridged polycyclic heterocyclic ring which has at least one nitrogen atom and also may have an oxygen atom(s) and/or an optionally oxidized sulfur atom(s), and which may be substituted with a group having a basic group, ring $J^3$ may have 1 to 8 substituent(s) on the substitutable position and, when two or more substituents are present, plural substituents may be the same or different, and $L^A$ is as defined in [15];

[42] The compound according to [14], wherein -L-J is

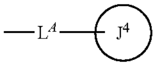

wherein ring $J^4$ represents (i) a C3-15 monocyclic or condensed carbocyclic ring substituted with a group having a basic group, (ii) a 3- to 15-membered monocyclic or condensed heterocyclic ring composed of a carbon atom, an oxygen atom and/or an optionally oxidized sulfur atom, which is substituted with a group having a basic group, or (iii) a 3- to 15-membered monocyclic or condensed heterocyclic ring which has at least one nitrogen atom and also may have an oxygen atom and/or an optionally oxidized sulfur atom, and which may be substituted with a group having a basic group, ring $J^4$ may have 1 to 8 substituent(s) on the substitutable position and, when two or more substituents are present, plural substituents may be the same or different, and $L_A$ is as defined in [15]; and

[43] A method for producing a compound represented by formula (I), a salt thereof, an N-oxide thereof or a solvate thereof, or a prodrug thereof.

EFFECT OF THE INVENTION

The compound of the present invention has an antagonistic activity against CXCR4 and is therefore useful as a preventive and/or therapeutic agent for diseases associated with CXCR4, namely, CXCR4-mediated diseases.

BEST MODE FOR CARRYING OUT THE INVENTION

In the present specification, "bond" means to directly bind without mediating the other atom therebetween.

In the present specification, "cyclic group" includes, for example, a monocyclic or condensed ring, a bridged ring, a spiro-bound ring and the like. This "monocyclic or condensed ring" includes, for example, a C3-15 monocyclic or condensed carbocyclic ring, a 3- to 15-membered monocyclic or condensed heterocyclic ring having, as a heteroatom, 1 to 4 nitrogen atom(s), 1 to 2 oxygen atom(s) and/or 1 to 2 sulfur atom(s) and the like. The "C3-15 monocyclic or condensed carbocyclic ring" includes a C3-15 monocyclic or condensed unsaturated carbocyclic ring, or partially or completely saturated one thereof. Examples of the "C3-15 monocyclic or condensed unsaturated carbocyclic ring, or partially or completely saturated one thereof" include, for example, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, heptalene, perhydroheptalene, biphenylene, as-indacene, s-indacene, acenaphthylene, acenaphthene, fluorene, phenalene, phenanthrene, anthracene, and 1,2,3,5,6,7-hexahydro-s-indacene rings. Among these, examples of the "C3-15 monocyclic or condensed aromatic carbocyclic ring" include benzene, azulene, naphthalene, phenanthrene, anthracene rings and the like.

Examples of the "3- to 15-membered monocyclic or condensed heterocyclic ring having, as a heteroatom, 1 to 4 nitrogen atom(s), 1 to 2 oxygen atom(s) and/or 1 to 2 sulfur atom(s)" include a 3- to 15-membered monocyclic or condensed unsaturated heterocyclic ring having, as a heteroatom, 1 to 4 nitrogen atom(s), 1 to 2 oxygen atom(s) and/or 1 to 2 sulfur atom(s), or partially or completely saturated one thereof. Examples of the "3- to 15-membered monocyclic or condensed unsaturated heterocyclic ring having, as a heteroatom, 1 to 4 nitrogen atom(s), 1 to 2 oxygen atom(s) and/or 1 to 2 sulfur atom(s), or partially or completely saturated one thereof" include, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzoazepine, benzodiazepine, benzofurazan, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydro benzoazepin, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindane, benzodioxane, chroman, benzodithiolane, benzodithiane, 6,7-dihydro-5H-cyclopenta[b]pyrazine, 5H-cyclopenta[b]pyrazine, imidazo[2,1-b][1,3]thiazole, pyrido[2,3-b]pyrazine, pyrido[3,4-b]pyrazine, [1,3]thiazolo[4,5-b]pyrazine, thieno[2,3-b]pyrazine, 3,4-dihydro-2H-pyrazino[2,3-b][1,4]oxazine, 6,7-dihydro-5H-cyclopenta[b]pyrazine, imidazo[1,2-a]pyrazine, 6,7-dihydro-5H-cyclopenta[b]pyridine, furo[3,2-b]pyridine, pyrido[2,3-d]pyrimidine, 2,3-dihydro-1H-pyrrolo[2,3-b]pyridine, 5,6,7,8-tetrahydro-1,6-naphthylidine, 6,7,8,9-tetrahydro-5H-pyrido[2,3-d]azepine, 3,4-dihydro-2H-pyrano[3,2-c]pyridine, 2,3-dihydrofuro[3,2-c]pyridine, hexahydro-1H-pyrrolidine, octahydrocyclopenta[c]pyrrole, octahydrocyclopenta[b]pyrrole, octahydropyrrolo[3,2-b]pyrrole, octahydropyrrolo[3,4-c]pyrrole, hexahydro-2H-furo[3,2-b]pyrrole, hexahydro-2H-thieno[3,2-b]pyrrole, decahydroquinoline, decahydro-2,6-naphthylidine, octahydro-2H-quinolidine, octahydro-1H-pyrido[1,2-c]pyrimidine, octahydro-2H-1,4-benzooxazine, decahydro-1,5-naphthylidine, octahydro-1H-pyrrolo[3,4-b]pyridine, octahydro-1H-pyrrolo[3,4-c]pyridine rings and the like. Among these, examples of the "3- to 15-membered monocyclic or condensed heterocyclic ring having, as a heteroatom, 1 to 4 nitrogen atom(s), 1 to 2 oxygen atom(s) and/or 1 to 2 sulfur atom(s)" include pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthylidine, quinoxaline, quinazoline, cinnoline, benzoxazole, benzothiazole, benzimidazole, benzofurazan, benzothiadiazole, benzotriazole, carbazole, β-carboline, acridine, phenazine, dibenzofuran, dibenzothiophene, phenanthridine, phenanthroline, perimidine rings and the like.

The "bridged ring" includes a bridged polycyclic carbocyclic ring and a bridged polycyclic heterocyclic ring. The "bridged polycyclic carbocyclic ring" includes, for example, a C4-15 bridged polycyclic carbocyclic ring. Examples of the "C4-15 bridged polycyclic carbocyclic ring" include bicyclo[2.2.1]heptane, bicyclo[2.2.1]hept-2-ene, bicyclo[3.1.1]heptane, bicyclo[3.1.1]hept-2-ene, bicyclo[3.2.1]octane, bicyclo[2.2.2]octane, bicyclo[2.2.2]oct-2-ene, adamantane, noradamantane, bicyclo[2.1.1]hexane, bicyclo[3.3.1]nonane, bicyclo[3.2.1]octane, bicyclo[3.3.2]decane ring and the like.

Examples of the "bridged polycyclic heterocyclic ring" include, for example, a polycyclic heterocyclic bridged ring having, as a heteroatom, 1 to 4 nitrogen atom(s), 1 to 2 oxygen atom(s) and/or 1 to 2 sulfur atom(s). Examples of the "polycyclic heterocyclic bridged ring having, as a heteroatom, 1 to 4 nitrogen atom(s), 1 to 2 oxygen atom(s) and/or 1 to 2 sulfur atom(s)" include, for example, a "4- to 15-membered polycyclic heterocyclic bridged ring having, as a heteroatom, 1 to 4 nitrogen atom(s), 1 to 2 oxygen atom(s) and/or 1 to 2 sulfur atom(s)". Examples of the "4- to 15-membered polycyclic heterocyclic bridged ring having, as a heteroatom, 1 to 4 nitrogen atom(s), 1 to 2 oxygen atom(s) and/or 1 to 2 sulfur atom(s)" include azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, 1-azatricyclo[3.3.1.1$^{3,7}$]decane, 3-azabicyclo[3.3.1]nonane, 3,7-diazabicyclo[3.3.1]nonane rings and the like.

The "spiro-bound ring" includes a spiro-bound polycyclic carbocyclic ring and a spiro-bound polycyclic heterocyclic ring. Examples of the "spiro-bound polycyclic carbocyclic ring" include spiro[4.4]nonane, spiro[4.5]decane, spiro[5.5]undecane, spiro[3.4]octane, spiro[3.5]nonane rings and the like.

The "spiro-bound polycyclic heterocyclic ring" includes a spiro-bound polycyclic heterocyclic ring having, as a heteroatom, 1 to 4 nitrogen atom(s), 1 to 2 oxygen atom(s) and/or 1 to 2 sulfur atom(s). The "spiro-bound polycyclic heterocyclic ring having, as a heteroatom, 1 to 4 nitrogen atom(s), 1 to 2 oxygen atom(s) and/or 1 to 2 sulfur atom(s)" include a 7- to 15-membered spiro-bound polycyclic heterocyclic ring having, as a heteroatom, 1 to 4 nitrogen atom(s), 1 to 2 oxygen atom(s) and/or 1 to 2 sulfur atom(s). Examples of the "7- to 15-membered spiro-bound polycyclic heterocyclic ring having, as a heteroatom, 1 to 4 nitrogen atom(s), 1 to 2 oxygen atom(s) and/or 1 to 2 sulfur atom(s)" herein include azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro[5.5]undecane, dioxaspiro[5.5]undecane, 2,7-diazaspiro[3.5]nonane, 2,8-diazaspiro[4.5]decane, 2,7-diazaspiro[4.5]decane, 2,9-diazaspiro[5.5]undecane, 2,8-diazaspiro[5.5]undecane, 3,9-diazaspiro[5.5]undecane, 2,7-diazaspiro[4.4]nonane, 1,2-dihydrospiro[indole-3,4'-piperidine], 2,3-dihydro-1H-spiro[isoquinoline-4,4'-piperidine], 1',4'-dihydro-2'H-spiro[piperidine-4,3'-quinoline], 2',3'-dihydro-1'H-spiro[piperidine-4,4'-quinoline], 8-azaspiro[4.5]decane, 7-azaspiro[4.5]decane, 3-azaspiro[5.5]undecane, 2-azaspiro[5.5]undecane, 1-oxa-4,8-diazaspiro[5.5]undecane, 1-oxa-4,9-diazaspiro[5.5]undecane, 3,4-dihydrospiro[chromene-2,4'-piperidine], 2-azaspiro[4.4]nonane, 7-azaspiro[3.5]nonane, 2,3-dihydrospiro[indene-1,4'-piperidine], 3,4-dihydro-2H-spiro[naphthalene-1,4'-piperidine], 3,4-dihydro-1H-spiro[naphthalene-2,4'-piperidine], 2-azaspiro[4.5]decane, 2-azaspiro[3.5]nonane, 1',2'-dihydrospiro[cyclohexane-1,3'-indole], 2',3'-dihydro-1'H-spiro[cyclohexane-1,4'-isoquinoline], 1',4'-dihydro-2'H-spiro[cyclohexane-1,3'-quinoline], 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, 1-thia-4,8-diazaspiro[5.5]undecane rings and the like.

In the present specification, "aliphatic hydrocarbon group" includes, for example, "linear or branched aliphatic hydrocarbon group". Examples of the "linear or branched aliphatic hydrocarbon group" include "aliphatic hydrocarbon group having 1 to 8 carbon atom(s)", and examples of "aliphatic hydrocarbon group having 1 to 8 carbon atom(s)" include C1-8 alkyl group, C2-8 alkenyl group, and C2-8 alkynyl group.

Examples of the C1-8 alkyl group include methyl, ethyl, propyl, butyl, pentyl, hexyl, heptyl, and octyl groups, and isomer groups thereof. The isomer groups of propyl include, for example, isopropyl and the isomer groups of butyl include, for example, sec-butyl, tert-butyl.

Examples of the C2-8 alkenyl group include vinyl, propenyl, butenyl, pentenyl, hexenyl, heptenyl, octenyl, butadienyl, pentadienyl, hexadienyl, heptadienyl, octadienyl, hexatrienyl, heptatrienyl, and octatrienyl groups, and isomer groups thereof.

Examples of the C2-8 alkynyl group include ethynyl, propynyl, butynyl, pentynyl, hexynyl, heptynyl, octynyl, butadiynyl, pentadiynyl, hexadiynyl, heptadiynyl, octadiynyl, hexatriynyl, heptatriynyl, and octatriynyl groups, and isomer groups thereof.

Examples of the C1-4 alkyl group include methyl, ethyl, propyl, isopropyl, butyl, sec-butyl, and tert-butyl group.

In the present specification, "group having a basic group" represented by $A^1$ and $A^2$ is not specifically limited as long as it has a basic group. Examples thereof include (1) basic group, (2) aliphatic hydrocarbon group which is substituted with a basic group, and also may have a substituent(s), and (3) cyclic group which is substituted with a basic group, and also may have a substituent(s).

The "aliphatic hydrocarbon group" in the "aliphatic hydrocarbon group which is substituted with a basic group, and also may have a substituent(s)" has the same meaning as in the aliphatic hydrocarbon group.

The "cyclic group" in the "cyclic group which is substituted with a basic group, and also may have a substituent(s)" has the same meaning as in the cyclic group.

The "substituent" in the "aliphatic hydrocarbon group which is substituted with a basic group, and also may have a substituent(s)" or the "cyclic group which is substituted with a basic group, and also may have a substituent(s)" is not specifically limited as long as it is a substituent. Examples thereof include the following substituents defined as T.

Examples of T include:

(1) aliphatic hydrocarbon group, (2) C1-8 alkylidene group (for example, methylidene, ethylidene, propylidene, butylidene, pentylidene, hexylidene, heptylidene, or octylidene group, and isomer thereof, etc.), (3) cyclic group,
(4) aliphatic hydrocarbon group substituted with a cyclic group (for example, cyclopropylmethyl, cyclopentylmethyl, cyclohexylmethyl, phenylmethyl, naphthyl methyl, pyridinyl methyl, cyclopropyl ethyl, cyclopentylethyl, cyclohexylethyl, phenylethyl, naphthylethyl, pyridinylethyl, cyclopropylpropyl, cyclopentylpropyl, cyclohexylpropyl, phenylmethyl, phenylpropyl, naphthylpropyl, pyridinylpropyl, etc.),
(5) hydroxyl group,
(6) —O-aliphatic hydrocarbon group (for example, methoxy, ethoxy, propoxy, isopropoxy, butoxy, isobutoxy, tert-butoxy, pentoxy, hexyloxy, heptyloxy, octyloxy, propenyloxy, butenyloxy, pentenyloxy, hexenyloxy, propynyloxy, butynyloxy, pentynyloxy, hexynyloxy, etc.),
(7) —O-cyclic group (for example, cyclopropyloxy, cyclopentyloxy, cyclohexyloxy, phenoxy, naphthyloxy, pyridinyloxy, etc.),
(8) —O-aliphatic hydrocarbon-cyclic group (for example, cyclopentylmethoxy, cyclohexylmethoxy, phenylmethoxy, etc.),
(9) mercapto group,
(10) —S-aliphatic hydrocarbon group (for example, methylthio, ethylthio, propylthio, isopropylthio, butylthio, isobutylthio, tert-butylthio, pentylthio, hexylthio, heptylthio, octylthio, propenylthio, butenylthio, pentenylthio, hexenylthio, propynylthio, butynylthio, pentynylthio, hexynylthio, etc.),
(11) —S-cyclic group (for example, cyclopropylthio, cyclopentylthio, cyclohexylthio, phenylthio, naphthylthio, pyridinylthio, etc.),
(12) —S-aliphatic hydrocarbon-cyclic group (for example, cyclopentylmethylthio, cyclohexylmethylthio, phenylmethylthio, etc.),
(13) —S(O)-aliphatic hydrocarbon group (for example, methylsulfinyl, ethylsulfinyl, propylsulfinyl, isopropylsulfinyl, butylsulfinyl, isobutylsulfinyl, tert-butylsulfinyl, pentylsulfinyl, hexylsulfinyl, heptylsulfinyl, octylsulfinyl, propenylsulfinyl, butenylsulfinyl, pentenylsulfinyl, hexenylsulfinyl, propynylsulfinyl, butynylsulfinyl, pentynylsulfinyl, hexynylsulfinyl, etc.),
(14) —S(O)-cyclic group (for example, cyclopropylsulfinyl, cyclopentylsulfinyl, cyclohexylsulfinyl, phenylsulfinyl, naphthylsulfinyl, pyridinylsulfinyl, etc.),
(15) —S(O)-aliphatic hydrocarbon-cyclic group (for example, cyclopentylmethylsulfinyl, cyclohexylmethylsulfinyl, phenylmethylsulfinyl, etc.),
(16) —$SO_2$-aliphatic hydrocarbon group (for example, methylsulfonyl, ethylsulfonyl, propylsulfonyl, isopropylsulfonyl, butylsulfonyl, isobutylsulfonyl, tert-butylsulfonyl, pentylsulfonyl, hexylsulfonyl, heptylsulfonyl, octylsulfonyl, propenylsulfonyl, butenylsulfonyl, pentenylsulfonyl, hexenylsulfonyl, propynylsulfonyl, butynylsulfonyl, pentynylsulfonyl, hexynylsulfonyl, etc.),
(17) —$SO_2$-cyclic group (for example, cyclopropylsulfonyl, cyclopentylsulfonyl, cyclohexylsulfonyl, phenylsulfonyl, naphthylsulfonyl, pyridinylsulfonyl, etc.),
(18) —$SO_2$-aliphatic hydrocarbon-cyclic group (for example, cyclopentylmethylsulfonyl, cyclohexylmethylsulfonyl, phenylmethylsulfonyl, etc.),
(19) —O—CO-aliphatic hydrocarbon group (for example, methanoyloxy, ethanoyloxy, propanoyloxy, isopropanoyloxy, butanoyloxy, isobutanoyloxy, tert-butanoyloxy, pentanoyloxy, hexanoyloxy, heptanoyloxy, octanoyloxy, propenoyloxy, butenoyloxy, pentenoyloxy, hexenoyloxy, propynoyloxy, butynoyloxy, pentynoyloxy, hexynoyloxy, etc.),
(20) —O—CO-cyclic group (for example, cyclopropylcarbonyloxy, cyclopentylcarbonyloxy, cyclohexylcarbonyloxy, phenylcarbonyloxy, naphthylcarbonyloxy, pyridinylcarbonyloxy, etc.),
(21) —O—CO-aliphatic hydrocarbon-cyclic group (for example, cyclopentylmethanoyloxy, cyclohexylmethanoyloxy, phenylmethanoyloxy, etc.),
(22) —CO-aliphatic hydrocarbon group (for example, methanoyl, ethanoyl, propanoyl, isopropanoyl, butanoyl, isobutanoyl, tert-butanoyl, pentanoyl, hexanoyl, heptanoyl, octanoyl, propenoyl, butenoyl, pentenoyl, hexenoyl, propynoyl, butynoyl, pentynoyl, hexynoyl, etc.),
(23) —CO-cyclic group (for example, cyclopropylcarbonyl, cyclopentylcarbonyl, cyclohexylcarbonyl, phenylcarbonyl, naphthylcarbonyl, pyridinylcarbonyl, etc.),
(24) —CO-aliphatic hydrocarbon-cyclic group (for example, cyclopentylmethanoyl, cyclohexylmethanoyl, phenylmethanoyl, etc.),
(25) oxo group,
(26) thioxo group,
(27) sulfino group,
(28) sulfo group,
(29) amino group,
(30) mono- or di-substituted amino group ("substituent" in "mono- or di-substituted amino group" herein includes, for example, (1) aliphatic hydrocarbon group, (2) cyclic group, and (3) aliphatic hydrocarbon group substituted with a cyclic group, and examples thereof include methylamino, ethylamino, propylamino, isopropylamino, butylamino, isobutylamino, tert-butylamino, pentylamino, hexylamino, heptylamino, octylamino, dimethylamino, diethylamino, dipropylamino, dibutylamino, dipentylamino, dihexylamino, diheptylamino, dioctylamino, N-methyl-N-ethylamino, cyclopropylamino, cyclopentylamino, cyclohexylamino, phenylamino, diphenylamino, dibenzylamino, N-phenyl-N-methylamino, N-phenyl-N-ethylamino, N-benzyl-N-methylamino, N-benzyl-N-ethylamino, N-cyclohexyl-N-propylamino, etc.),
(31) sulfamoyl group,
(32) mono- or di-substituted sulfamoyl group ("substituent" in "mono- or di-substituted sulfamoyl group" include, for example, (1) aliphatic hydrocarbon group, (2) cyclic group, and (3) aliphatic hydrocarbon group substituted with a cyclic group, and examples thereof include N-methylsulfamoyl, N-ethylsulfamoyl, N-propylsulfamoyl, N-isopropylsulfamoyl, N-butylsulfamoyl, N-isobutylsulfamoyl, N-(tert-butyl)sulfamoyl, N-pentylsulfamoyl, N-hexylsulfamoyl, N-heptylsulfamoyl, N-octylsulfamoyl, N,N-dimethylsulfamoyl, N,N-diethylsulfamoyl, N,N-dipropylsulfamoyl, N,N-dibutylsulfamoyl, N,N-dipentylsulfamoyl, N,N-dihexylsulfamoyl, N-methyl-N-ethylsulfamoyl, N-cyclopropylsulfamoyl, N-cyclopentylsulfamoyl, N-cyclohexylsulfamoyl, N-phenylsulfamoyl, N,N-diphenylsulfamoyl, N,N-dibenzylsulfamoyl, N-phenyl-N-methylsulfamoyl, N-phenyl-N-ethylsulfamoyl, N-benzyl-N-methylsulfamoyl, N-benzyl-N-ethylsulfamoyl, N-cyclohexyl-N-propylamino, etc.),
(33) carboxy group,
(34) —COO-aliphatic hydrocarbon group (for example, methoxycarbonyl, ethoxycarbonyl, propoxycarbonyl, isopropoxycarbonyl, butoxycarbonyl, isobutoxycarbonyl, tert-butoxycarbonyl, pentoxycarbonyl, hexyloxycarbonyl, heptyloxycarbonyl, octyloxycarbonyl, propenyloxycarbonyl, butenyloxycarbonyl, pentenyloxycarbonyl, hexenyloxycarbonyl, propynyloxycarbonyl, butynyloxycarbonyl, pentynyloxycarbonyl, hexynyloxycarbonyl, etc.),

(35) —COO-cyclic group (for example, cyclopropyloxycarbonyl, cyclopentyloxycarbonyl, cyclohexyloxycarbonyl, phenoxycarbonyl, naphthyloxycarbonyl, pyridinyloxycarbonyl, etc.),

(36) —COO-aliphatic hydrocarbon-cyclic group (for example, cyclopentylmethoxycarbonyl, cyclohexylmethoxycarbonyl, phenylmethoxycarbonyl, etc.),

(37) carbamoyl group,

(38) mono- or di-substituted carbamoyl group ("substituent" in "mono- or di-substituted carbamoyl group" herein includes, for example, (1) aliphatic hydrocarbon group, (2) cyclic group, and (3) aliphatic hydrocarbon group substituted with a cyclic group, and examples thereof include N-methylcarbamoyl, N-ethylcarbamoyl, N-propylcarbamoyl, N-isopropylcarbamoyl, N-butylcarbamoyl, N-isobutylcarbamoyl, N-(tert-butyl)carbamoyl, N-pentylcarbamoyl, N-hexylcarbamoyl, N-heptylcarbamoyl, N-octylcarbamoyl, N-cyclopropylcarbamoyl, N-cyclopentylcarbamoyl, N-cyclohexylcarbamoyl, N-phenylcarbamoyl, N,N-dimethylcarbamoyl, N,N-diethylcarbamoyl, N,N-dipropylcarbamoyl, N,N-dibutylcarbamoyl, N,N-dipentylcarbamoyl, N,N-dihexylcarbamoyl, N-methyl-N-ethylcarbamoyl, N,N-diphenylcarbamoyl, N,N-dibenzylcarbamoyl, N-phenyl-N-methylcarbamoyl, N-phenyl-N-ethylcarbamoyl, N-benzyl-N-methylcarbamoyl, N-benzyl-N-ethylcarbamoyl, etc.),

(39) —NH—CO-aliphatic hydrocarbon group (for example, methanoylamino, ethanoylamino, propanoylamino, isopropanoylamino, butanoylamino, isobutanoylamino, tert-butanoylamino, pentanoylamino, hexanoylamino, heptanoylamino, octanoylamino, propenoylamino, butenoylamino, pentenoylamino, hexenoylamino, propynoylamino, butynoylamino, pentynoylamino, hexynoylamino, etc.),

(40) —NH—CO-cyclic group (for example, cyclopropylcarbonylamino, cyclopentylcarbonylamino, cyclohexylcarbonylamino, phenylcarbonylamino, naphthylcarbonylamino, pyridinylcarbonylamino, etc.),

(41) —NH—CO-aliphatic hydrocarbon-cyclic group (for example, cyclopentylmethanoylamino, cyclohexylmethanoylamino, phenylmethanoylamino, etc.),

(42) —NH—$SO_2$-aliphatic hydrocarbon group (for example, methylsulfonylamino, ethylsulfonylamino, propylsulfonylamino, isopropylsulfonylamino, butylsulfonylamino, isobutylsulfonylamino, tert-butylsulfonylamino, pentylsulfonylamino, hexylsulfonylamino, heptylsulfonylamino, octylsulfonylamino, propenylsulfonylamino, butenylsulfonylamino, pentenylsulfonylamino, hexenylsulfonylamino, propynylsulfonylamino, butynylsulfonylamino, pentynylsulfonylamino, hexynylsulfonyl, etc.),

(43) —NH—$SO_2$-cyclic group (for example, cyclopropylsulfonylamino, cyclopentylsulfonylamino, cyclohexylsulfonylamino, phenylsulfonylamino, naphthylsulfonylamino, pyridinylsulfonyl, etc.),

(44) —NH—$SO_2$-aliphatic hydrocarbon-cyclic group (for example, cyclopentylmethylsulfonylamino, cyclohexylmethylsulfonylamino, phenylmethylsulfonyl, etc.),

(45) cyano group,

(46) hydrazino group,

(47) nitro group,

(48) nitroso group,

(49) imino group,

(50) mono-substituted imino group ("substituent" in the mono-substituted imino group includes, for example, (1) aliphatic hydrocarbon group, (2) cyclic group, (3) aliphatic hydrocarbon group substituted with a cyclic group, (4) hydroxyl group, (5) —O-aliphatic hydrocarbon group, (6) —O-cyclic group, and (7) —O-aliphatic hydrocarbon-cyclic group, and examples thereof include methylimino, ethylimino, propylimino, isopropylimino, butylimino, isobutylimino, (tert-butyl)imino, pentylimino, hexylimino, heptylimino, octylimino, cyclopropylimino, cyclopentylimino, cyclohexylimino, phenylimino, benzylimino, hydroxyimino, ethoxyimino, propoxyimino, isopropoxyimino, butoxyimino, cyclopentoxyimino, cyclohexyloxyimino, phenoxyimino, benzyloxyimino, etc.),

(51) halogen atom (for example, fluorine atom, chlorine atom, bromine atom, iodine atom, etc.),

(52) methyl group substituted with 1 to 3 halogen atom(s) (for example, fluoromethyl, difluoromethyl, trifluoromethyl, trichloromethyl, etc.), and

(53) methoxy group substituted with 1 to 3 halogen atom(s) (for example, fluoromethoxy, difluoromethoxy, trifluoromethoxy, trichloromethoxy, etc.). These optional substituents may be substituted on the optional substitutable position in optional substitutable number. The number of substituents is preferably from 1 to 8, and more preferably from 1 to 5. The "aliphatic hydrocarbon group" and the "cyclic group" in T are as defined above. Also, "-aliphatic hydrocarbon-" means a divalent aliphatic hydrocarbon group and includes, for example, a divalent group in which one optional hydrogen atom is further removed from the "aliphatic hydrocarbon group".

The "basic group" in the "group having a basic group" is not specifically limited as long as it has a basic nitrogen atom. Examples thereof include (a) amino group, (b) amidino group, (c) guanidino group, (d) hydrazino group, (e) mono- or di-substituted amino group, (f) mono-, di- or tri-substituted amidino group, (g) mono-, di-, tri- or tetra-substituted guanidino group, (h) mono-, di- or tri-substituted hydrazino group, and (i) nitrogen-containing heterocyclic ring which may have a substituent(s). Examples of the "substituent" in the "mono- or di-substituted amino group" herein include (1) cyclic group substituted with a substituent(s) (substituent includes those exemplified as for the above-described T and cyclic group is as defined above), (2) aliphatic hydrocarbon group substituted with a substituent(s) (substituent includes those exemplified as for the above-described T and aliphatic hydrocarbon is as defined above), (3) aliphatic hydrocarbon group substituted with a cyclic group substituted with a substituent(s) (substituent includes those exemplified as for the above-described T and aliphatic hydrocarbon and cyclic groups are as defined above), and (4) substituents exemplified as for the above-described T. These optional substituents may be substituted on the optional substitutable position in optional substitutable number. The number of substituents is preferably from 1 to 8, and more preferably from 1 to 5. Examples thereof include methylamino, ethylamino, propylamino, isopropylamino, butylamino, isobutylamino, tert-butylamino, pentylamino, hexylamino, heptylamino, octylamino, dimethylamino, diethylamino, dipropylamino, dibutylamino, dipentylamino, dihexylamino, diheptylamino, dioctylamino, N-methyl-N-ethylamino, cyclopropylamino, cyclopentylamino, cyclohexylamino, phenylamino, diphenylamino, dibenzylamino, N-phenyl-N-methylamino, N-phenyl-N-ethylamino, N-benzyl-N-methylamino, N-benzyl-N-ethylamino, N-benzyl-N-cyclohexylamino, N-cyclohexyl-N-propylamino, N-cyclohexyl-N-(3-hydroxypropyl)amino, N-(4-hydroxycyclohexyl)-N-propylamino, N-(4-hydroxycyclohexyl)-N-(3-hydroxypropyl)amino, N-(4-hydroxycyclohexyl)methyl-N-propylamino, N-cyclohexyl-N-acetylamino, N-(3-methoxypropyl)-N-propylamino, N-(2-carboxyethyl)-N-propylamino, N-(2-ethylpropyl)-N- propylamino, N-cyclohexyl-N-(methylsulfonyl)amino, N-(tetrahydropyran-4-yl)-N-propylamino, and N-(indan-2-yl)-N-propylamino.

Examples of the "substituent" in the "mono-, di- or tri-substituted amidino group" include (1) aliphatic hydrocarbon group (which is as defined above), (2) cyclic group (which is as defined above), (3) aliphatic hydrocarbon group substituted with a cyclic group (aliphatic hydrocarbon and cyclic groups are as defined above). Examples of the "mono-, di- or tri-substituted amidino group" include methylamidino, ethylamidino, propylamidino, isopropylamidino, butylamidino, isobutylamidino, tert-butylamidino, pentylamidino, hexylamidino, heptylamidino, octylamidino, N,N-dimethylamidino, N,N'-dimethylamidino, N,N,N'-trimethylamidino, N,N-diethylamidino, N,N'-diethylamidino, N,N,N'-triethylamidino, N,N-dipropylamidino, N,N'-dipropylamidino, N,N,N'-tripropylamidino, N,N-dibutylamidino, N,N'-dibutylamidino, N,N,N'-tributylamidino, N,N-dipentylamidino, N,N'-dipentylamidino, N,N,N'-tripentylamidino, N,N-dihexylamidino, N,N'-dihexylamidino, N,N,N'-trihexylamidino, N,N-diheptylamidino, N,N'-diheptylamidino, N,N,N'-triheptylamidino, N,N-dioctylamidino, N,N'-dioctylamidino, N,N,N'-trioctylamidino, N-methyl-N-ethylamidino, N-methyl-N'-ethylamidino, cyclopropylamidino, cyclopentylamidino, cyclohexylamidino, phenylamidino, N,N-diphenylamidino, N,N'-diphenylamidino, N,N,N'-triphenylamidino, N,N-dibenzylamidino, N,N'-dibenzylamidino, N,N,N'-tribenzylamidino, N-phenyl-N'-methylamidino, N-phenyl-N'-ethylamidino, N-benzyl-N-methylamidino, and N-benzyl-N-ethylamidino.

Examples of the "substituent" in the "mono-, di-, tri- or tetra-substituted guanidino group" include (1) aliphatic hydrocarbon group (which is as defined above), (2) cyclic group (which is as defined above), and (3) aliphatic hydrocarbon group substituted with a cyclic group (aliphatic hydrocarbon and cyclic groups are as defined above). Examples of the "mono-, di-, tri- or tetra-substituted guanidino group" include, for example, methylguanidino, ethylguanidino, propylguanidino, isopropylguanidino, butylguanidino, isobutylguanidino, tert-butylguanidino, pentylguanidino, hexylguanidino, heptylguanidino, octylguanidino, N,N-dimethylguanidino, N,N'-dimethylguanidino, N,N,N'-trimethylguanidino, N,N,N',N"-tetramethylguanidino, N,N-diethylguanidino, N,N'-diethylguanidino, N,N,N'-triethylguanidino, N,N,N',N"-tetraethylguanidino, N,N-dipropylguanidino, N,N'-dipropylguanidino, N,N,N'-tripropylguanidino, N,N,N',N"-tetrapropylguanidino, N,N-dibutylguanidino, N,N'-dibutylguanidino, N,N,N'-tributylguanidino, N,N,N',N"-tetrabutylguanidino, N,N-dipentylguanidino, N,N'-dipentylguanidino, N,N,N'-tripentylguanidino, N,N,N',N"-tetrapentylguanidino, N,N-dihexylguanidino, N,N'-dihexylguanidino, N,N,N'-trihexylguanidino, N,N,N',N"-tetrahexylguanidino, N,N-diheptylguanidino, N,N'-diheptylguanidino, N,N,N'-triheptylguanidino, N,N,N',N"-tetraheptylguanidino, N,N-dioctylguanidino, N,N'-dioctylguanidino, N,N,N'-trioctylguanidino, N,N,N',N"-tetraoctylguanidino, N-methyl-N-ethylguanidino, N-methyl-N'-ethylguanidino, cyclopropylguanidino, cyclopentylguanidino, cyclohexylguanidino, phenylguanidino, N,N-diphenylguanidino, N,N'-diphenylguanidino, N,N,N'-triphenylguanidino, N,N,N',N"-tetraphenylguanidino, N,N-dibenzylguanidino, N,N'-dibenzylguanidino, N,N,N'-tribenzylguanidino, N,N,N',N"-tetrabenzylguanidino, N-phenyl-N'-methylguanidino, N-phenyl-N'-ethylguanidino, N-benzyl-N-methylguanidino, and N-benzyl-N-ethylguanidino.

Examples of the "substituent" in the "mono-, di- or tri-substituted hydrazino group" include (1) aliphatic hydrocarbon group (which is as defined above), (2) cyclic group (which is as defined above), and (3) aliphatic hydrocarbon group substituted with a cyclic group (aliphatic hydrocarbon and cyclic groups are as defined above). Examples of the "mono-, di- or tri-substituted hydrazino group" include, for example, methylhydrazino, ethylhydrazino, propylhydrazino, isopropylhydrazino, butylhydrazino, isobutylhydrazino, tert-butylhydrazino, pentylhydrazino, hexylhydrazino, heptylhydrazino, octylhydrazino, N,N-dimethylhydrazino, N,N'-dimethylhydrazino, N,N,N'-trimethylhydrazino, N,N-diethylhydrazino, N,N'-diethylhydrazino, N,N,N'-triethylhydrazino, N,N-dipropylhydrazino, N,N'-dipropylhydrazino, N,N,N'-tripropylhydrazino, N,N-dibutylhydrazino, N,N'-dibutylhydrazino, N,N,N'-tributylhydrazino, N,N-dipentylhydrazino, N,N'-dipentylhydrazino, N,N,N'-tripentylhydrazino, N,N-dihexylhydrazino, N,N'-dihexylhydrazino, N,N,N'-trihexylhydrazino, N,N-diheptylhydrazino, N,N'-diheptylhydrazino, N,N,N'-triheptylhydrazino, N,N-dioctylhydrazino, N,N'-dioctylhydrazino, N,N,N'-trioctylhydrazino, N-methyl-N-ethylhydrazino, N-methyl-N'-ethylhydrazino, cyclopropylhydrazino, cyclopentylhydrazino, cyclohexylhydrazino, phenylhydrazino, N,N-diphenylhydrazino, N,N'-diphenylhydrazino, N,N,N'-triphenylhydrazino, N,N-dibenzylhydrazino, N,N'-dibenzylhydrazino, N,N,N'-tribenzylhydrazino, N-phenyl-N'-methylhydrazino, N-phenyl-N'-ethylhydrazino, N-benzyl-N-methylhydrazino, and N-benzyl-N-ethylhydrazino.

The "nitrogen-containing heterocyclic ring" in the "nitrogen-containing heterocyclic ring which may have a substituent(s)" include, for example, a heterocyclic ring which is a 3- to 11-membered monocyclic or bicyclic heterocyclic ring having, as a heteroatom, at least one nitrogen atom, and also may have an oxygen atom(s) and/or an optionally oxidized sulfur atom(s) and has basicity and the like. Example of the "heterocyclic ring which is a 3- to 11-membered monocyclic or bicyclic heterocyclic ring having, as a heteroatom, at least one nitrogen atom, and also may have an oxygen atom(s) and/or an optionally oxidized sulfur atom(s) and has basicity" herein, include pyrrole, imidazole, triazole, pyrazole, pyridine, pyrazine, pyrimidine, pyridazine, azepine, diazepine, oxazole, thiazole, isoxazole, isothiazole, indole, isoindole, quinoline, isoquinoline, benzoxazole, benzothiazole, benzimidazole, aziridine, azetidine, pyrrolidine, piperidine, piperazine, morpholine, thiomorpholine, perhydroazepine, perhydrodiazepine, indoline, isoindoline, quinazoline, tetrahydroquinoline, perhydroquinoline, tetrahydroisoquinoline, perhydroisoquinoline, tetrahydronaphthyridine, quinoxaline, tetrahydroquinoxaline, dihydrobenzimidazole, perhydrobenzimidazole, carbazole, tetrahydrocarbazole, azabicyclo[3.2.1]octane, quinuclidine, 2,8-diazaspiro[4.5]decane, 1,4,9-triazaspiro[5.5]undecane, 3,9-diazaspiro[5.5]undecane, 2,9-diazaspiro[5.5]undecane, 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, and 1-thia-4,8-diazaspiro[5.5]undecane ring.

The "substituent" in the "nitrogen-containing heterocyclic ring which may have a substituent(s)" includes those exemplified as for the above-described T. These optional substituents may be substituted on the optional substitutable position in optional substitutable number. The number of substituents is preferably from 1 to 8, and more preferably from 1 to 5.

In the present specification, examples of the "substituent" of the "an imidazole ring which may have a substituent(s), a benzoimidazole ring which may have a substituent(s), or a pyridine ring which may have a substituent(s)" represented by ring $A^{1A}$ and ring $A^{2A}$ include those exemplified as for the above-described T and these optional substituents may be substituted on the substitutable position and the number of substituents is from 1 to 5, and preferably from 1 to 2.

In the present specification, "spacer having a main chain of 1 to 4 atom(s)" represented by $B^1$ and $B^2$, and "spacer having a main chain of 1 to 4 atom(s)" represented by L mean the space wherein 1 to 4 atom(s) of the main chain are arranged in a line. The "number of atoms of main chain" is counted so that the number of atoms of the main chain is minimized. For example, it is counted that the number of atoms of 1,2-cyclopentylene is 2 and the number of atoms of 1,3-cyclopentylene is 3. Examples of the "spacer having a main chain of 1 to 4 atom(s)" include divalent group composed of 1 to 4 groups selected optionally from —O—, —S—, —CO—, —SO—, —SO2—, divalent nitrogen atom which may have a substituent, divalent aliphatic hydrocarbon group having 1 to 4 carbon atom(s) which may have a substituent(s), and divalent 3- to 8-membered monocyclic cyclic group which may have a substituent(s), wherein 1 to 4 atom(s) of the main chain are arranged in a line.

The "divalent nitrogen atom which may have a substituent" represents, in addition to —NH—, those wherein hydrogen atom in the "—NH-" group are optionally substituted with (1) aliphatic hydrocarbon group, (2) cyclic group, (3) aliphatic hydrocarbon group substituted with a cyclic group, (4) hydroxyl group, (5) —O-aliphatic hydrocarbon group, (6) —O-cyclic group, (7) —O-aliphatic hydrocarbon-cyclic group, (8) —$SO_2$-aliphatic hydrocarbon group, (9) —$SO_2$-cyclic group, (10) —$SO_2$-aliphatic hydrocarbon-cyclic group, (11) —CO-aliphatic hydrocarbon, (12) —CO-cyclic group, (13) —CO-aliphatic hydrocarbon-cyclic group, (14) carboxy group, (15) —COO-aliphatic hydrocarbon, (16) —COO-cyclic group, or (17) —COO-aliphatic hydrocarbon-cyclic group, among the substituents exemplified as for the above-described T.

Examples of the "divalent aliphatic hydrocarbon group having 1 to 4 carbon atom(s)" in the "divalent aliphatic hydrocarbon group having 1 to 4 carbon atom(s) which may have a substituent(s)" include C1-4 alkylene group (for example, $—CH_2—$, $—(CH_2)_2—$, $—(CH_2)_3—$, $—(CH_2)_4—$, etc.), C2-4 alkenylene group (for example, —CH═CH—, $—CH_2—CH═CH—$, $—CH═CH—CH_2—$, $—(CH_2)_2—CH═CH—$, $—CH═CH—(CH_2)_2—$, $—CH_2—CH═CH—CH_2—$, etc.), and C2-4 alkynylene group (for example, —C≡C—, $—CH_2—C≡C—$, $—C≡C—CH_2—$, $—(CH_2)_2—C≡C—$, $—C≡C—(CH_2)_2—$, $—CH_2—C≡C—CH_2—$, etc.). Examples of the "substituent" in the "divalent aliphatic hydrocarbon group having 1 to 4 carbon atom(s) which may have a substituent(s)" include those exemplified as for the above-described T, and these optional substituents may be substituted on the substitutable position and the number of substituents is from 1 to 5, and preferably from 1 to 2.

Examples of the "divalent 3- to 8-membered monocyclic cyclic group" in the "divalent 3- to 8-membered monocyclic cyclic group which may have a substituent(s)" include divalent group which can be obtained by eliminating optional two hydrogen atoms from the "C3-8 monocyclic cyclic group". Examples of the "C3-8 monocyclic cyclic group" herein include "C3-8 monocyclic carbocyclic ring" and "3- to 8-membered monocyclic heterocyclic ring". The "C3-8 monocyclic carbocyclic ring" includes C3-8 monocyclic unsaturated carbocyclic ring, and partially or completely saturated one thereof. Examples of the "C3-8 monocyclic unsaturated carbocyclic ring, and partially or completely saturated one thereof" include cyclopropane, cyclobutane, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene, and benzene rings. Among these, the "C3-8 monocyclic aromatic carbocyclic ring" includes, for example, benzene ring.

Examples of the "3- to 8-membered monocyclic heterocyclic ring" include "3- to 8-membered monocyclic heterocyclic ring having, as a heteroatom, 1 to 4 nitrogen atom(s), 1 to 2 oxygen atom(s) and/or 1 to 2 sulfur atom(s)". The "3- to 8-membered monocyclic heterocyclic ring having, as a heteroatom, 1 to 4 nitrogen atom(s), 1 to 2 oxygen atom(s) and/or 1 to 2 sulfur atom(s)" herein includes 3- to 8-membered monocyclic unsaturated heterocyclic ring having, as a heteroatom, 1 to 4 nitrogen atom(s), 1 to 2 oxygen atom(s) and/or 1 to 2 sulfur atom(s), and partially or completely saturated one thereof. Examples of the "3- to 8-membered monocyclic unsaturated heterocyclic ring having, as a heteroatom, 1 to 4 nitrogen atom(s), 1 to 2 oxygen atom(s) and/or 1 to 2 sulfur atom(s), and partially or completely saturated one thereof" include pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, aziridine, azetidine, pyrroline, pyrrolidine, imidazoline, imidazolidine, triazoline, triazolysine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane rings and the like. Among these, examples of the "3- to 8-membered monocyclic aromatic heterocyclic ring having, as a heteroatom, 1 to 4 nitrogen atom(s), 1 to 2 oxygen atom(s)

and/or 1 to 2 sulfur atom(s)" include pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole rings and the like. Examples of the "substituent" in the "divalent 3- to 8-membered monocyclic cyclic group which may have a substituent(s)" include (1) aliphatic hydrocarbon group substituted with a substituent(s) (a substituent herein includes those exemplified as for T), (2) cyclic group substituted with a substituent(s) (a substituent herein includes those exemplified as for T), and (3) substituents exemplified as for T, and the like, and these optional substituents may be substituted on the substitutable position and the number of substituents is from 1 to 8, and preferably from 1 to 5.

In the present specification, the "spacer having a main chain of 1 to 10 atom(s)" represented by E means the space wherein 1 to 10 atom(s) of the main chain are arranged in a line. The "number of atoms of main chain" is counted so that the number of atoms of the main chain is minimized. For example, it is counted that the number of atoms of

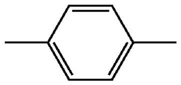

is 4, the number of atoms of

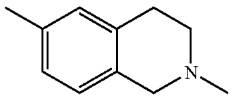

is 6 and the number of atoms of

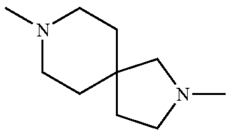

is 6. Examples of the "spacer having a main chain of 1 to 10 atom(s)" include divalent group composed of 1 to 10 groups selected optionally from —O—, —S—, —CO—, —SO—, —$SO_2$—, divalent nitrogen atom which may have a substituent, divalent aliphatic hydrocarbon group having 1 to 10 carbon atom(s) which may have a substituent(s), and divalent 3- to 15-membered monocyclic cyclic group which may have a substituent(s), wherein 1 to 10 atom(s) of the main chain are arranged in a line. The "divalent nitrogen atom which may have a substituent" is as defined above. Examples of the "divalent aliphatic hydrocarbon group having 1 to 10 carbon atom(s)" in the "divalent aliphatic hydrocarbon group having 1 to 10 carbon atom(s) which may have a substituent(s)" include C1-10 alkylene group (methylene, ethylene, trimethylene, tetramethylene, pentamethylene, hexamethylene, heptamethylene, octamethylene, nonamethylene, decamethylene group, and isomers thereof), C2-10 alkenylene group (ethenylene, propenylene, butenylene, pentenylene, hexenylene, heptenylene, octenylene, nonenylene, decenylene group, and isomers thereof), and C2-10 alkynylene group (ethynylene, propynylene, butynylene, pentynylene, hexynylene, heptynylene, octynylene, nonynylene, decynylene group, and isomers thereof). Also, examples of the "substituent" in the "optionally substituted divalent aliphatic hydrocarbon group having 1 to 10 carbon atom(s)" include (1) an aliphatic hydrocarbon group which is substituted with a substituent (wherein a substituent includes those exemplified as for T), (2) cyclic group substituted with a substituent(s) (wherein a substituent includes those exemplified as for T), and (3) substituents exemplified as for T, and these optional substituents may be substituted on the substitutable position and the number of substituents is from 1 to 5, and preferably from 1 to 2. The "divalent 3- to 15-membered cyclic group" in the "divalent 3- to 15-membered cyclic group which may have a substituent(s)" includes, for example, a divalent group which can be obtained by removing two optional hydrogen atoms from the "3- to 15-membered cyclic group". Examples of the "3- to 15-membered cyclic group" here include the C3-15 monocyclic or condensed carbocyclic ring defined above, a C4-15 bridged polycyclic carbocyclic ring, or a C7-15 spiro-bound polycyclic carbocyclic ring, or a 3- to 15-membered monocyclic or condensed heterocyclic ring having, as a heteroatom, 1 to 4 nitrogen atom(s), 1 to 2 oxygen atom(s) and/or 1 to 2 sulfur atom(s), 4- to 15-membered bridged polycyclic heterocyclic ring having, as a heteroatom, 1 to 4 nitrogen atom(s), 1 to 2 oxygen atom(s) and/or 1 to 2 sulfur atom(s), and a 7- to 15-membered spiro-bound polycyclic heterocyclic ring having, as a heteroatom, 1 to 4 nitrogen atom(s), 1 to 2 oxygen atom(s) and/or 1 to 2 sulfur atom(s). The "substituent" in the "divalent 3- to 15-membered cyclic group which may have a substituent(s)" includes, for example, substituents exemplified as for T, and these optional substituents may be substituted on the substitutable position and the number of substituents is from 1 to 5, and preferably from 1 to 2.

In the present specification, the "3- to 8-membered monocyclic group which may have a substituent(s)" represented by the ring $E^1$ has the same meaning as defined in $B^1$.

In the present specification, examples of the "substituent" in the "benzene ring which may have a substituent(s), cyclohexane ring which may have a substituent(s), cyclopentane ring which may have a substituent(s), pyrrolidine ring which may have a substituent(s), or piperidine ring which may have a substituent(s)" represented by the ring $E^2$ include an aliphatic hydrocarbon group which may have a substituent(s), a —CO-aliphatic hydrocarbon group, carboxyl group, and a —COO-aliphatic hydrocarbon group. Examples of the "substituent" in the "aliphatic hydrocarbon group which may have a substituent(s)" here include a —CO-aliphatic hydrocarbon group, a carboxyl group, and a —COO-aliphatic hydrocarbon group.

In the present specification, "-(nitrogen atom which may have a substituent)-" in "-(aliphatic hydrocarbon having 1 to 3 carbon atom(s) which may have a substituent(s))-(nitrogen atom which may have a substituent)-" represented by $L^A$ has the same meaning as in the "divalent nitrogen atom which may have a substituent". Examples of the "aliphatic hydrocarbon having 1 to 3 carbon atom(s)" in the "aliphatic hydrocarbon having 1 to 3 carbon atom(s) which may have a substituent(s)" include C1 to 3 alkylene group (for example, methylene, ethylene, trimethylene, etc.), C2-3 alkenylene group (for example, ethenylene, propenylene, etc.), and C2-3 alkynylene group (for example, ethynylene, propynylene, etc.). Examples of the "substituent" in the "aliphatic hydrocarbon having 1 to 3 carbon atom(s) which may have a substituent(s)" include those exemplified as for T, and these optional substituents may be substituted on the substitutable position and the number of substituents is from 1 to 3.

In the present specification, the "divalent aliphatic hydrocarbon group having 1 to 4 carbon atom(s) which may have a substituent(s)" represented by $L_A$ is as defined above.

In the present specification, examples of "aliphatic hydrocarbon group which is substituted with a group having a basic group, and also may have a substituent(s)" represented by J include (1) an aliphatic hydrocarbon group which is substituted with a basic group, and also may have a substituent(s), (2) an aliphatic hydrocarbon group which is substituted with a cyclic group substituted with a basic group, and also may have a substituent(s), and (3) an aliphatic hydrocarbon group which is substituted with an aliphatic hydrocarbon group substituted with a basic group, and also may have a substituent(s). Also, examples of "monocyclic or condensed cyclic group which is substituted with a group having a basic group, and also may have a substituent(s)" represented by J include (1) a monocyclic or condensed cyclic group which is substituted with a basic group, and also may have a substituent(s), (2) a monocyclic or condensed cyclic group which is substituted with a cyclic group substituted with a basic group, and also may have a substituent(s), and (3) a monocyclic or condensed cyclic group which is substituted with an aliphatic hydrocarbon group substituted with a basic group, and also may have a substituent(s). Examples of "spiro-bound cyclic group which may be substituted with a group having a basic group, and also may have a substituent(s)" represented by J include (1) a spiro-bound cyclic group which may be substituted with a basic group, and also may have a substituent(s), (2) a spiro-bound cyclic group which may be substituted with a cyclic group substituted with a basic group, and also may have a substituent(s), and (3) a spiro-bound cyclic group which may be substituted with an aliphatic hydrocarbon group substituted with a basic group, and also may have a substituent(s). Also, examples of "bridged cyclic group which may be substituted with a group having a basic group, and also may have a substituent(s)" represented by J include (1) a bridged cyclic group which may be substituted with a basic group, and also may have a substituent(s), (2) a bridged cyclic group which may be substituted with a cyclic group substituted with a basic group, and also may have a substituent(s), and (3) a bridged cyclic group which may be substituted with an aliphatic hydrocarbon group substituted with a basic group, and also may have a substituent(s). Herein, the "monocyclic or condensed cyclic group" in the "monocyclic or condensed cyclic group which is substituted with a group having a basic group, and also may have a substituent(s)" has the same meaning as in the "monocyclic or condensed cyclic group in the "cyclic group". The "spiro-bound cyclic group" in the "spiro-bound cyclic group which may be substituted with a group having a basic group, and also may have a substituent(s)" has the same meaning as in the "spiro-bound polycyclic cyclic group" in the "cyclic group". The "bridged cyclic group" of the "bridged cyclic group which may be substituted with a group having a basic group, and also may have a substituent(s)" has the same meaning as in the "bridged polycyclic cyclic group" in the "cyclic group".

In the present specification, the "spiro-bound polycyclic heterocyclic ring or bridged polycyclic heterocyclic ring which has at least one nitrogen atom, and also may have an oxygen atom(s) and/or an optionally oxidized sulfur atom(s)" in the "spiro-bound polycyclic heterocyclic ring or bridged polycyclic heterocyclic ring which has at least one nitrogen atom and also may have an oxygen atom(s) and/or an optionally oxidized sulfur atom(s), and which may be substituted with a group having a basic group and also may have a substituent(s)" represented by J includes spiro-bound polycyclic heterocyclic ring which has at least one nitrogen atom, and also may have an oxygen atom(s) and/or an optionally oxidized sulfur atom(s), and bridged polycyclic heterocyclic ring which has at least one nitrogen atom, and also may have an oxygen atom(s) and/or an optionally oxidized sulfur atom(s). Examples of the "spiro-bound polycyclic heterocyclic ring which has at least one nitrogen atom, and also may have an oxygen atom(s) and/or an optionally oxidized sulfur atom(s)" include, for example, azaspiro[4.4]nonane, oxazaspiro[4.4]nonane, azaspiro[4.5]decane, oxazaspiro[4.5]decane, azaspiro[5.5]undecane, 2,7-diazaspiro[3.5]nonane, 2,8-diazaspiro[4.5]decane, 2,7-diazaspiro[4.5]decane-2,9-diazaspiro[5.5]undecane, 2,8-diazaspiro[5.5]undecane, 3,9-diazaspiro[5.5]undecane, 2,7-diazaspiro[4.4]nonane, 1,2-dihydrospiro[indole-3,4'-piperidine], 2,3-dihydro-1H-spiro[isoquinoline-4,4'-piperidine], 1',4'-dihydro-2'H-spiro[piperidine-4,3'-quinoline], 2',3'-dihydro-1'H-spiro[piperidine-4,4'-quinoline], 8-azaspiro[4.5]decane, 8-azaspiro[4.5]decane, 7-azaspiro[4.5]decane, 3-azaspiro[5.5]undecane, 2-azaspiro[5.5]undecane, 1-oxa-4,8-diazaspiro[5.5]undecane, 1-oxa-4,9-diazaspiro[5.5]undecane, 3,4-dihydrospiro[chromene-2,4'-piperidine], 2-azaspiro[4.4]nonane, 7-azaspiro[3.5]nonane, 2,3-dihydrospiro[indene-1,4'-piperidine], 3,4-dihydro-2H-spiro[naphthalene-1,4'-piperidine], 3,4-dihydro-1H-spiro[naphthalene-2,4'-piperidine], 2-azaspiro[4.5]decane, 2-azaspiro[3.5]nonane, 1',2'-dihydrospiro[cyclohexane-1,3'-indole], 2',3'-dihydro-1'H-spiro[cyclohexane-1,4'-isoquinoline], 1',4'-dihydro-2'H-spiro[cyclohexane-1,3'-quinoline], 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, 1-thia-4,8-diazaspiro[5.5]undecane and the like. Examples of the "bridged polycyclic heterocyclic ring which has at least one nitrogen atom, and also may have an oxygen atom(s) and/or an optionally oxidized sulfur atom(s)" include, for example, azabicyclo[2.2.1]heptane, azabicyclo[3.1.1]heptane, azabicyclo[3.2.1]octane, azabicyclo[2.2.2]octane, diazabicyclo[2.2.2]octane, 1-azatricyclo[3.3.1.1$^{3,7}$]decane, 3-azabicyclo[3.3.1]nonane, 3,7-diazabicyclo[3.3.1]nonane and the like.

In the present specification, the "7- to 15-membered bicyclic spiro-bound heterocyclic ring wherein a ring comprising the spiro-bound heterocyclic ring is a monocyclic ring composed of at least one nitrogen atom and carbon atoms, and/or a monocyclic ring composed of at least one nitrogen atom, one oxygen atom and carbon atoms" represented by J includes (1) 7- to 15-membered bicyclic spiro-bound heterocyclic ring which consists of two spiro-bound (a) 4- to 8-membered monocyclic rings composed of at least one nitrogen atom and carbon atoms, (2) 7- to 15-membered bicyclic spiro-bound heterocyclic ring which consists of spiro-bound (a) 4- to 8-membered monocyclic ring composed of at least one nitrogen atom and carbon atoms, and (b) 4- to 8-membered monocyclic ring composed of at least one nitrogen atom, one oxygen atom and carbon atoms, and (3) 7- to 15-membered bicyclic spiro-bound heterocyclic ring which consists of two spiro-bound (b) monocyclic rings composed of at least one nitrogen atom, one oxygen atom and carbon atoms "(1) 7- to 15-membered bicyclic spiro-bound heterocyclic ring which consists of two spiro-bound (a) 4- to 8-membered monocyclic rings composed of at least one nitrogen atom and carbon atoms" means that two rings selected optionally from "(a) 4- to 8-membered monocyclic ring composed of at least one nitrogen atom and carbon atoms" share one carbon atom. The shared carbon atom may be any carbon atom as long as it is a carbon atom constituting the monocyclic ring.

"(2) 7- to 15-membered bicyclic spiro-bound heterocyclic ring which consists of spiro-bound (a) 4- to 8-membered monocyclic ring composed of at least one nitrogen atom and carbon atoms, and (b) 4- to 8-membered monocyclic ring composed of at least one nitrogen atom, one oxygen atom and carbon atoms" means that one ring selected optionally from "(a) 4- to 8-membered monocyclic ring composed of at least one nitrogen atom and carbon atoms" and one ring selected optionally from "(b) 4- to 8-membered monocyclic ring composed of at least one nitrogen atom, one oxygen atom and carbon atoms" share one carbon atom. The shared carbon atom may be any carbon atom as long as it is a carbon atom constituting the monocyclic ring.

"(3) 7- to 15-membered bicyclic spiro-bound heterocyclic ring which consists of two spiro-bound (b) monocyclic rings composed of at least one nitrogen atom, one oxygen atom and carbon atoms" means that two rings selected optionally from "(b) monocyclic ring composed of at least one nitrogen atom, one oxygen atom and carbon atoms" shares one carbon atom. The shared carbon atom may be any carbon atom as long as it is a carbon atom constituting the monocyclic ring.

In addition, examples of the "4- to 8-membered monocyclic ring composed of at least one nitrogen atom and carbon atoms" include, for example, azetidine, pyrrolidine, piperidine, piperazine, azepane, 1,4-diazepane, azocane, 1,4-diazocane, 1,5-diazocane, and the like.

Examples of the "4- to 8-membered monocyclic ring composed of at least one nitrogen atom, one oxygen atom and carbon atoms" include, for example, 1,4-oxazepane, 1,4-oxazocane, 1,5-oxazocane and the like.

Examples of the "(1) 7- to 15-membered bicyclic spiro-bound heterocyclic ring which consists of two spiro-bound (a) 4- to 8-membered monocyclic rings composed of at least one nitrogen atom and carbon atoms", include, for example, 2,7-diazaspiro[3.5]nonane, 2,8-diazaspiro[4.5]decane, 2,7-diazaspiro[4.5]decane, 2,9-diazaspiro[5.5]undecane, 2,8-diazaspiro[5.5]undecane, 2,6-diazaspiro[3.5]nonane, 3,9-diazaspiro[5.5]undecane, 2,7-diazaspiro[4.4]nonane, 1,3,8-triazaspiro[4.5]decane, 1,4,9-triazaspiro[5.5]undecane and the like.

Examples of "(2) 7- to 15-membered bicyclic spiro-bound heterocyclic ring which consists of spiro-bound (a) 4- to 8-membered monocyclic ring composed of at least one nitrogen atom and carbon atoms, and (b) 4- to 8-membered monocyclic ring composed of at least one nitrogen atom, one oxygen atom and carbon atoms" include 1-oxa-4,9-diazaspiro[5.5]undecane, 1-oxa-4,8-diazaspiro[5.5]undecane and the like.

Examples of "(3) 7- to 15-membered bicyclic spiro-bound heterocyclic ring which consists of two spiro-bound (b) monocyclic rings composed of at least one nitrogen atom, one oxygen atom and carbon atoms" include 2,9-dioxa-5,12-diazaspiro[6.6]tridecane and the like.

Also, the "substituent" in the group J is not specifically limited. The substituent includes, for example, substituents exemplified as for T, and these optional substituents may be substituted on the substitutable position and the number of substituents is from 1 to 5. When J is substituted with a group having a basic group, optional substituents may be substituted on the substitutable position and the number of substituents is from 1 to 5. Furthermore, the "aliphatic hydrocarbon group", the "cyclic group" and the "group having a basic group" in J have the same meanings as in the "aliphatic hydrocarbon group", the "cyclic group" and the "group having a basic group" in $A^1$ and $A^2$, respectively.

In the present specification, the "C3-10 monocyclic or bicyclic carbocyclic ring" represented by ring $J^1$ includes a C3-10 monocyclic or bicyclic unsaturated carbocyclic ring, and partially or completely saturated one thereof. Examples thereof include, for example, benzene, azulene, naphthalene, cyclopropane, cyclobutane, cyclopentane, cyclohexane, cycloheptane, cyclooctane, cyclononane, cyclodecane, cyclohexene, cycloheptene, cyclooctene, cyclopentadiene, cyclohexadiene, cycloheptadiene, cyclooctadiene, pentalene, perhydropentalene, perhydroazulene, indene, perhydroindene, indane, dihydronaphthalene, tetrahydronaphthalene, perhydronaphthalene, heptalene, perhydroheptalene and the like.

In the present specification, the "3- to 10-membered monocyclic or bicyclic heterocyclic ring composed of a carbon atom(s), an oxygen atom(s) and/or an optionally oxidized sulfur atom(s)" represented by ring $J^1$ includes a 3- to 10-membered monocyclic or bicyclic unsaturated heterocyclic ring composed of a carbon atom(s), an oxygen atom(s) and/or an optionally oxidized sulfur atom(s), and partially or completely saturated one thereof. Examples thereof include, for example, furan, pyran, oxepine, thiophene, thiopyran, thiepine, benzofuran, isobenzofuran, benzothiophene, isobenzothiophene, dithianaphthalene, chromene, benzoxepine, benzothiepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, oxathiane, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, benzoxathiane, benzodioxepane, dioxolane, dioxane, dithiolane, dithiane, dioxaindane, benzodioxane, chroman, benzodithiolane, benzodithiane and the like.

In the present specification, the "3- to 10-membered monocyclic or bicyclic heterocyclic ring which has at least one nitrogen atom, and also may have an oxygen atom or an optionally oxidized sulfur atom" represented by ring $J^1$ includes a 3- to 10-membered monocyclic or bicyclic unsaturated heterocyclic ring which has at least one nitrogen atom, and also may have an oxygen atom(s) and/or an optionally oxidized sulfur atom(s), and partially or completely saturated one thereof. Examples thereof include, for example, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazol idine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, pyrrole, imidazole, triazole, tetrazole, pyrazole, pyridine, pyrazine, pyrimidine, pyridazine, azepine, diazepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, indazole, quinoline, isoquinoline, quinolizine, purine, phthalazine, pteridine, naphthyridine, quinoxaline, quinazoline, cinnoline, benzoxazole, benzothiazole, benzimidazole, benzoxazepine, benzoxadiazepine, benzothiepine, benzothiazepine, benzothiadiazepine, benzoazepine, benzodiazepine, benzofurazan, benzothiadiazole, benzotriazole and the like.

The "C3-10 monocyclic or bicyclic carbocyclic ring", "3- to 10-membered monocyclic or bicyclic heterocyclic ring composed of a carbon atom(s), an oxygen atom(s) and/or an optionally oxidized sulfur atom(s)", or "3- to 10-membered monocyclic or bicyclic heterocyclic ring which has at least one nitrogen atom and also may have an oxygen atom(s) or an optionally oxidized sulfur atom(s)" in the "C3-10 monocyclic or bicyclic carbocyclic ring substituted with a group having a basic group", "3- to 10-membered monocyclic or bicyclic heterocyclic ring composed of a carbon atom(s), an oxygen atom(s) and/or an optionally oxidized sulfur atom(s), which is substituted with a group having a basic group", or "3- to 10-membered monocyclic or bicyclic heterocyclic ring which has at least one nitrogen atom and also may have an oxygen atom(s) or an optionally oxidized sulfur atom(s), and also may be substituted with a group" represented by ring $J^2$ is as defined above. The "group having a basic group" here has the same meaning as the "group having a basic group" in the above described $A^1$ and $A^2$.

In the present specification, the "bridged polycyclic carbocyclic ring" in the "bridged polycyclic carbocyclic ring substituted with a group having a basic group" represented by ring $J^3$ has the same meaning as in the above-described "bridged polycyclic carbocyclic ring" in the "cyclic group".

In the present specification, examples of the "bridged polycyclic heterocyclic ring composed of a carbon atom(s), an oxygen atom(s) and/or an optionally oxidized sulfur atom(s)" of the "bridged polycyclic heterocyclic ring composed of a carbon atom(s), an oxygen atom(s) and/or an optionally oxidized sulfur atom(s), which is substituted with a group having a basic group" represented by ring $J^3$ include, for example, oxabicyclo[2.2.1]heptane oxabicyclo[3.2.1]octane and the like.

In the present specification, examples of the "bridged polycyclic heterocyclic ring which has at least one nitrogen atom, and also may have an oxygen atom(s) or an optionally oxidized sulfur atom(s)" of the "bridged polycyclic heterocyclic ring which may have at least one nitrogen atom, and also may have an oxygen atom(s) and/or an optionally oxidized sulfur atom(s), which may be substituted with a group having a basic group" represented by ring $J^3$ include, for example, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, 1-azatricyclo[3.3.1.$1^{3,7}$]decane, 3-azabicyclo[3.3.1]nonane, 3,7-diazabicyclo[3.3.1]nonane and the like.

The "group having a basic group" in ring $J^3$ has the same meaning as in the "group having a basic group" in the above-described $A^1$ and $A^2$.

In the present specification, the "C3-15 monocyclic or condensed carbocyclic ring" in the "C3-15 monocyclic or condensed carbocyclic ring substituted with a group having a basic group" represented by ring $J^4$ has the same meaning as in the "C3-15 monocyclic or condensed unsaturated carbocyclic ring, and partially or completely saturated one thereof" in the "cyclic group".

In the present specification, the "3- to 15-membered monocyclic or condensed heterocyclic ring" of the "3- to 15-membered monocyclic or condensed heterocyclic ring composed of a carbon atom(s), an oxygen atom(s) and/or an optionally oxidized sulfur atom(s), which is substituted with a group having a basic group" represented by ring $J^4$ includes a 3- to 15-membered monocyclic or condensed unsaturated heterocyclic ring composed of a carbon atom(s), an oxygen atom(s) and/or an optionally oxidized sulfur atom(s), and partially or completely saturated one thereof. Examples thereof include, for example, furan, pyran, oxepine, thiophene, thiopyran, thiepine, benzofuran, isobenzofuran, benzothiophene, isobenzothiophene, dithianaphthalene, chromene, benzoxepine, benzothiepine, dibenzofuran, xanthene, dibenzothiophene, phenoxathiin, thianthrene, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, oxathiane, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, benzoxathiane, benzodioxepane, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindane, benzodioxane, chroman, benzodithiolane, benzodithiane and the like.

In the present specification, the "3- to 15-membered monocyclic or condensed heterocyclic ring which has at least one nitrogen atom and also may have an oxygen atom(s) and/or an optionally oxidized sulfur atom(s)" of the "3- to 15-membered monocyclic or condensed heterocyclic ring which has at least one nitrogen atom and also may have an oxygen atom(s) and/or an optionally oxidized sulfur atom(s), which may be substituted with a group having a basic group" represented by ring $J^4$ includes a monocyclic or condensed 3- to 15-membered unsaturated heterocyclic ring which has at least one nitrogen atom and also may have an oxygen atom(s) and/or an optionally oxidized sulfur atom(s), and partially or completely saturated one thereof. Examples thereof include, for example, pyrrole, imidazole, triazole, tetrazole, pyrazole, pyridine, pyrazine, pyrimidine, pyridazine, azepin, diazepin, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepin, indole, isoindole, indolizine, indazole, quinoline, isoquinoline, quinolizine, purine, phthalazine, pteridine, naphthyridine, quinoxaline, quinazoline, cinnoline, benzoxazole, benzothiazole, benzimidazole, benzoxazepine, benzoxadiazepine, benzothiazepin, benzothiadiazepine, benzoxazepine, benzodiazepine, benzofurazan, benzothiadiazole, benzotriazole, carbazole, β-carboline, acridine, phenazine, phenothiazine, phenoxazine, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, dihydrobenzoxazepine, tetrahydrobenzoxazepine, dihydrocarbazole, tetrahydrocarbazole, perhydrocarbazole, dihydroacridine, tetrahydroacridine, perhydroacridine, hexahydro-1H-pyrrolidine, octahydrocyclopenta[c]pyrrole, octahydrocyclopenta[b]pyrrole, octahydropyrrolo[3,2-b]pyrrole, octahydropyrrolo[3,4-c]pyrrole, hexahydro-2H-furo[3,2-b]pyrrole, hexahydro-2H-thieno[3,2-b]pyrrole, decahydroquinoline, decahydro-2,6-naphthylidine, octahydro-2H-quinolidine, octahydro-1H-pyrido[1,2-c]pyrimidine, octahydro-2H-1,4-benzooxazine, decahydro-1,5-naphthylidine, octahydro-1H-pyrrolo[3,4-b]pyridine, octahydro-1H-pyrrolo[3,4-c]pyridine and the like.

The "group having a basic group" in ring $J^4$ has the same meaning as the "group having a basic group" in the above-described $A^1$ and $A^2$.

In the specification,

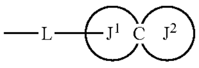 is 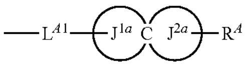

wherein $L^{A1}$ represents -(aliphatic hydrocarbon having 1 to 3 carbon atom(s) which may have a substituent(s))-(nitrogen atom which may have a substituent(s))-; ring $J^{1a}$ and ring $J^{2a}$ each independently represents (i) a C3-10 monocyclic or bicyclic carbocyclic ring, or (ii) a 3- to 10-membered monocyclic or bicyclic heterocyclic ring composed of a carbon atom(s), an oxygen atom(s) and/or an optionally oxidized sulfur atom(s); $R^A$ represents a group having a basic group; ring $J^{1a}$ and ring $J^{2a}$ may have a substituent(s) in substitutable number on the substitutable position and, when two or more substituents are present, plural substituents may be the same or different, provided that (a nitrogen atom which may have a substituent) in $L^A$ is bonded to ring $J^1$,

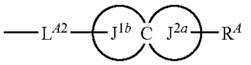

wherein $L^{A2}$ represents a divalent aliphatic hydrocarbon group having 1 to 4 carbon atom(s) which may have a substituent(s); ring $J^{1b}$ represents a 3- to 10-membered monocyclic or bicyclic heterocyclic ring which has at least one nitrogen atom and may also have an oxygen atom(s) and/or an optionally oxidized sulfur atom(s); ring $J^{1b}$ may have a substituent(s) in substitutable number on the substitutable position and, when two or more substituents are present, plural substituents may be the same or different; other symbols are as defined above,

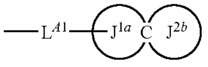

wherein ring $J^{2b}$ represents a 3- to 10-membered monocyclic or bicyclic heterocyclic ring which has at least one nitrogen atom and also may have an oxygen atom(s) or an optionally oxidized sulfur atom(s), which may be substituted with a group having a basic group; ring $J^{2b}$ may have a substituent(s) in substitutable number on the substitutable position and, when two or more substituents are present, plural substituents may be the same or different; other symbols are as defined above; or

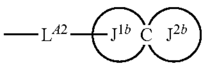

wherein all symbols are as defined above.

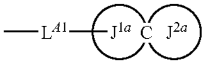

includes, for example,
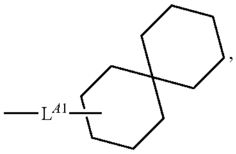
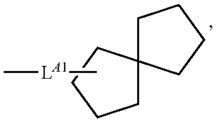
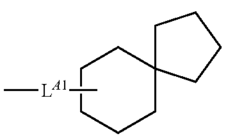
or
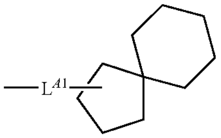
wherein all symbols are as defined above,
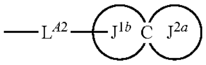
includes, for example,
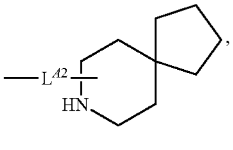
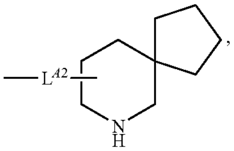
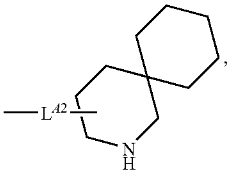
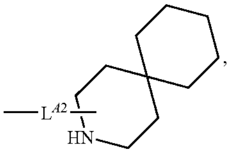
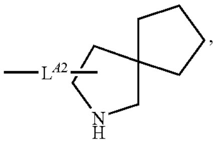
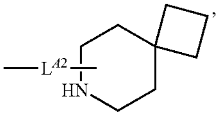
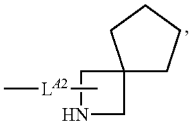
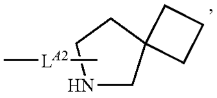
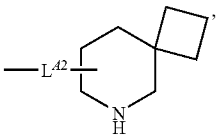
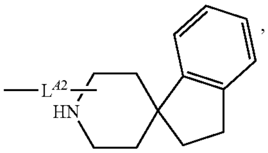
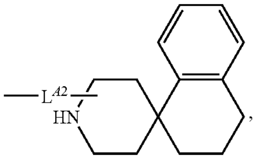
, or
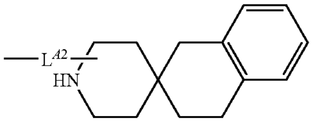
wherein all symbols are as defined above, with the proviso that $L^{A2}$ may be a substituent of a nitrogen atom of —NH—,
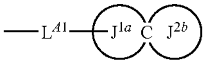
includes, for example,
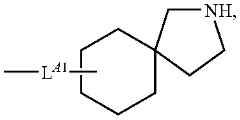
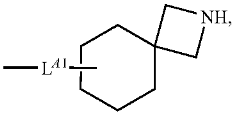
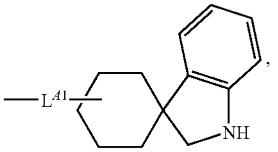
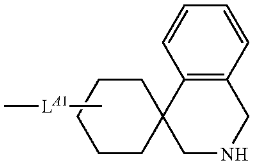
, or
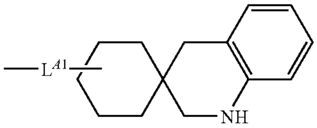
wherein all symbols are as defined above, with the proviso that a nitrogen atom of —NH— may have a substituent, and
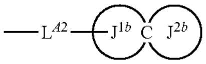
includes, for example,
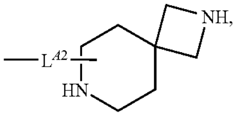
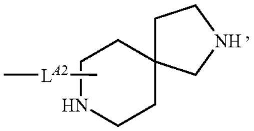
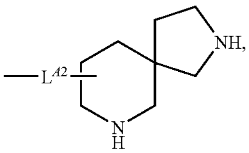
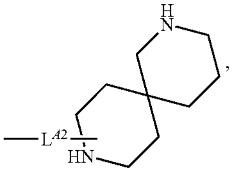
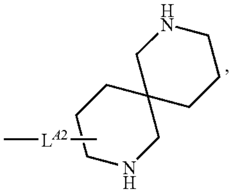
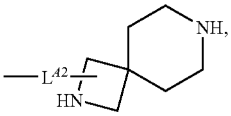

-continued

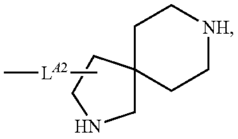
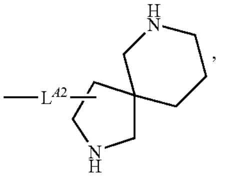
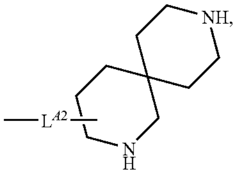
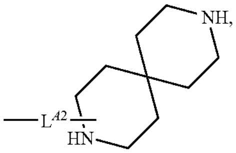
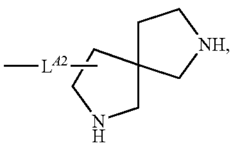
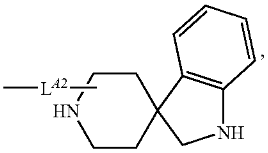
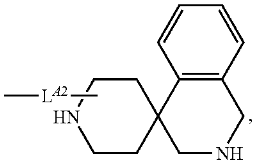
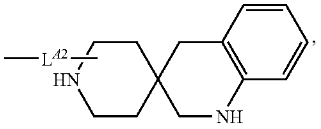
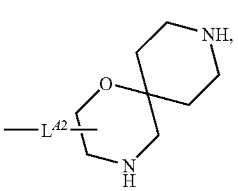
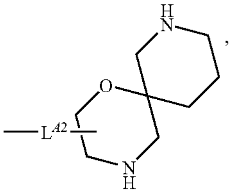
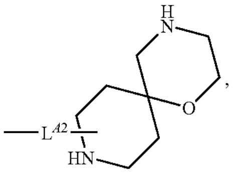
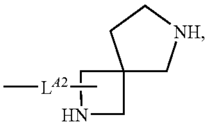
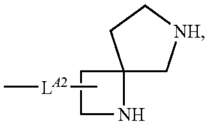
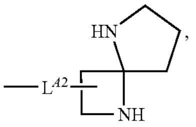
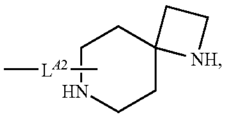
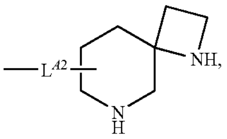
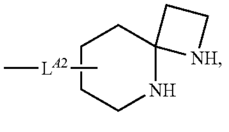
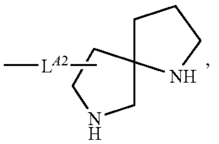
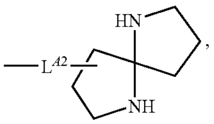
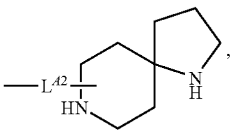

-continued

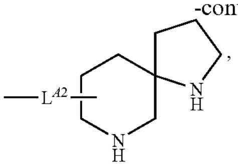
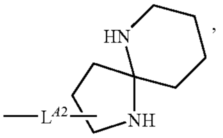
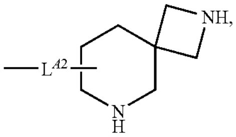
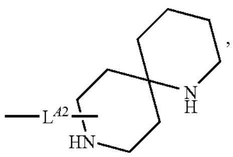
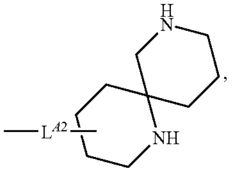
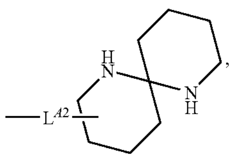
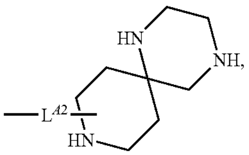
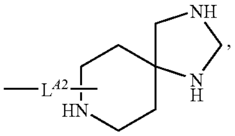
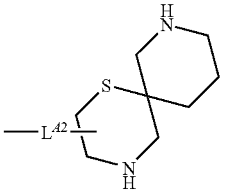
or
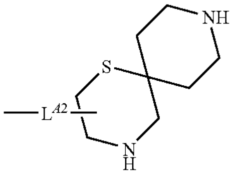

wherein all symbols are as defined above, with the proviso that $L^{A2}$ may be a substituent of a nitrogen atom of —NH— and a nitrogen atom of —NH— may have a substituent.

In the present specification, $L^{A1}$ has the same meaning as in the "-(aliphatic hydrocarbon having 1 to 3 carbon atoms(s) which may have a substituent(s))-(nitrogen atom which may have a substituent(s))-" in the above described $L^{A}$, and $L^{A2}$ has the same meaning as in the "-(aliphatic hydrocarbon having 1 to 3 carbon atoms(s) which may have a substituent(s))-(a nitrogen atom which may have a substituent)-" in the above described $L^{A}$.

In the present specification, the "(i) C3-10 monocyclic or bicyclic carbocyclic ring or (ii) 3- to 10-membered monocyclic or bicyclic heterocyclic ring composed of a carbon atom(s), an oxygen atom(s) and/or an optionally oxidized sulfur atom(s)" represented by ring $J^{1a}$ and ring $J^{2a}$ has the same meaning as in the "(i) C3-10 monocyclic or bicyclic carbocyclic ring or (ii) 3- to 10-membered monocyclic or bicyclic heterocyclic ring composed of a carbon atom(s), an oxygen atom(s) and/or an optionally oxidized sulfur atom(s)" in ring $J^{1}$.

In the present specification, the "3- to 10-membered monocyclic or bicyclic heterocyclic ring which has at least one nitrogen atom and also may have an oxygen atom(s) or an optionally oxidized sulfur atom(s)" represented by ring $J^{1b}$ has the same meaning as in the "3- to 10-membered monocyclic or bicyclic heterocyclic ring which has at least one nitrogen atom, and also may have an oxygen atom(s) and/or an optionally oxidized sulfur atom(s)" in ring $J^{1}$ In the present specification, "3- to 10-membered monocyclic or bicyclic heterocyclic ring which has at least one nitrogen atom and also may have an oxygen atom(s) or an optionally oxidized sulfur atom(s), and which may be substituted with a group having a basic group" represented by ring $J^{2b}$ has the same meaning as in the "3- to 10-membered monocyclic or bicyclic heterocyclic ring which has at least one nitrogen atom and also may have an oxygen atom(s) or an optionally oxidized sulfur atom(s), and which may be substituted with a group having a basic group" in ring $J^2$.

In the present specification, the "mono- or di-substituted amino group" in the "C4-7 monocyclic carbocyclic ring substituted with a mono- or di-substituted amino group" represented by $J^{1B}$ has the same meaning as in the "a mono- or di-substituted amino group" exemplified as for the "basic group". Also, examples of the "C4-7 monocyclic carbocyclic ring" include cyclobutane, cyclopentane, cyclohexane, cycloheptane, cyclopentene, cyclohexene, cycloheptene, cyclopentadiene, cyclohexadiene, cycloheptadiene, benzene ring and the like.

In the present specification, the "group having a basic group" of $R^A$ has the same meaning as in the "group having a basic group" in $A^1$ and $A^2$.

In the present specification, the "substituent" of the "may have a substituent(s) in substitutable number on the substitutable position" of ring $J^1$, ring $J^2$, ring $J^3$, ring $J^4$, ring $J^{1a}$, ring $J^{1b}$, ring $J^{2a}$ and ring $J^{2b}$ is not specifically limited. Examples thereof include those exemplified as for T, and these optional substituents may be substituted on the substitutable position and the number of substituents is preferably from 1 to 8, and more preferably from 1 to 5. When ring $J^2$, ring $J^3$, ring $J^4$ and ring $J^{2b}$ are substituted with a group having a basic group, these optional substituents may be substituted on the substitutable position and the number of substituents is preferably from 1 to 8, and more preferably from 1 to 4.

In the present specification, examples of the "substituent" represented by R include substituents exemplified as for T, a carboxyl group which may be protected with a protective group, a hydroxyl group which may be protected with a protective group, a C1-4 alkyl group which may be substituted with a hydroxyl group which may be protected with a protective group, and an amino group which may be protected with a protective group.

Herein, the "protective group" includes, for example, an aliphatic hydrocarbon group which may have a substituent(s), and examples of the "substituent" here include an oxo group, a thioxo group, a carbamoyl group, for example, an aminocarbonyl group substituted with an aliphatic hydrocarbon group, such as an N-butylaminocarbonyl group, an N-cyclohexylmethylaminocarbonyl group, an N-cyclohexylaminocarbonyl group, and a phenylcarbonyl group. The "aliphatic hydrocarbon group" in the "an aliphatic hydrocarbon group which may have a substituent(s)" in the "protective group" has the same meaning as in the "aliphatic hydrocarbon group", and the "substituents" may be substituted on the substitutable position and the number of substituents is from 1 to 5, and preferably from 1 to 2, and plural substituents may be the same or different. These optional substituents may be substituted on the substitutable position and the number of substituents is 1.

In R, examples of the "carboxyl group which may be protected with a protective group" include a C1-4 alkoxycarbonyl group (for example, methoxycarbonyl, ethoxycarbonyl, etc.), examples of the "C1-4 alkyl group which may be substituted with a hydroxyl group which may be protected with a protective group" includes a C1-4 alkyl group, a C1-4 hydroxyalkyl group (hydroxymethyl, hydroxyethyl, hydroxypropyl, hydroxybutyl group, and isomer groups thereof, etc.), and an a C1-4 acyl group (for example, formyl, acetyl, propionyl, butyryl group, etc.). Examples of the "hydroxyl group which may be protected with a protective group" includes a C1-4 alkoxy group (for example, a linear or branched C1-4 alkoxy group such as methoxy, ethoxy, n-propoxy, isopropoxy, n-butoxy, isobutoxy, sec-butoxy, tert-butoxy group, etc.), and a C1-8 acyloxy group (for example, formyloxy, acetyloxy, propanoyloxy, butanoyloxy, pentanoyloxy, hexanoyloxy, octanoyloxy group, isomer groups thereof, etc.) Examples of the "amino group which may be protected with a protective group" include an amino group, a mono- or di-C1-6 alkylamino group (for example, methylamino, ethylamino, n-propylamino, isopropylamino, n-butylamino, isobutylamino, tert-butylamino, n-pentylamino, isopentylamino, neopentylamino, n-hexylamino, dimethylamino, diethylamino, dipropylamino, N-ethyl-N-methylamino, etc.) and a C2-8 acylamino group (for example, acetylamino, propionylamino, butyryl amino, valerylamino, hexanoylamino, heptanoylamino, octanoylamino, isomers thereof, etc.).

In the present specification, the "carboxyl group which may be protected with a protective group", the "hydroxyl group which may be protected with a protective group", the "C1-4 alkyl group which may be substituted with a hydroxyl group which may be protected with a protective group" and the "amino group which may be protected with a protective group" represented by $R^c$ have the same meanings as in the "carboxyl group which may be protected with a protective group", the "hydroxyl group which may be protected with a protective group", the "C1-4 alkyl group which may be substituted with a hydroxyl group which may be protected with a protective group" and the "amino group which may be protected with a protective group" in the above described R.

In the present specification, examples of the "C1-4 alkyl group substituted with a hydroxyl group" represented by $R^{1C}$ include hydroxymethyl, hydroxyethyl, hydroxypropyl, hydroxybutyl and the like. Examples of the "C1-4 alkoxy group" in the "C1-4 alkyl group substituted with a C1-4 alkoxy group" represented by $R^{1C}$ include linear or branched C1-4 alkoxy groups such as methoxy, ethoxy, n-propoxy, isopropoxy, n-butoxy, isobutoxy, sec-butoxy, tert-butoxy group and the like. Examples of the "C1-4 alkyl group substituted with a C1-4 alkoxy group" include methoxymethyl, methoxyethyl, ethoxyethyl and the like.

In the present specification, the "carbon atom which may have a substituent(s)" represented by $G^A$ represents, in addition to —$CH_2$—, those wherein two hydrogen atoms in the "—$CH_2$-" group are, each independently, optionally substituted with an aliphatic hydrocarbon group, a C1-8 alkylidene group, an aliphatic hydrocarbon group substituted with a cyclic group, a hydroxyl group, an —O-aliphatic hydrocarbon group, a mercapto group, a —S— aliphatic hydrocarbon group, a —S(O)-aliphatic hydrocarbon-cyclic group, a —$SO_2$-aliphatic hydrocarbon group, a —CO-aliphatic hydrocarbon group, a carboxyl group, a —COO-aliphatic hydrocarbon group, a cyano group, a nitro group, a halogen atom, a methyl group which is substituted with 1 to 3 halogen atom(s), or a methoxy group which is substituted with 1 to 3 halogen atom(s) among those exemplified as for T, and those wherein two hydrogen atoms are substituted with an oxo group.

In the present specification, the "nitrogen atom which may have a substituent(s)" represented by $G^A$ represents, in addition to —NH—, those wherein a hydrogen atom in the "—NH—" group are optionally substituted with an aliphatic hydrocarbon group, an aliphatic hydrocarbon group substituted with a cyclic group, an —O-aliphatic hydrocarbon group, a —$SO_2$-aliphatic hydrocarbon group, a —CO-aliphatic hydrocarbon group, a —COO-aliphatic hydrocarbon group, a nitro group, or a methyl group which is substituted with 1 to 3 halogen atom(s) among those exemplified as for T.

In the present specification, the "carbon atom which may have a substituent(s)" represented by $G^{1A}$, $G^{2A}$ and $G^{3A}$ represents the same meaning as in the "carbon atom which may have a substituent(s)" defined in $G^A$.

In the present specification, the "nitrogen atom which may have a substituent(s)" represented by $G^{2A}$ represents, in addition to —NH—, those wherein a hydrogen atom in the "—NH—" group is optionally substituted with a C1-4 alkyl group which may have a substituent. Herein, examples of the substituent of the "C1-4 alkyl group which may have a substituent" include a 3- to 8-membered monocyclic heterocyclic ring, and (a) a hydroxyl group, (b) an amino group and (c) a carboxyl group, which may be protected with a protective group, respectively. Herein, examples of the "3- to 8-membered monocyclic heterocyclic ring" include rings exemplified as for the "3- to 8-membered monocyclic heterocyclic ring" of the "divalent 3- to 8-membered monocyclic group which may have a substituent(s)". Optional substituents exemplified as for the "substituent" of the "C1-4 alkyl group which may have a substituent(s)" may be substituted on the substitutable position and the number of substituents is from 1 to 4, and preferably from 1 to 2. Herein, the "protective group" includes, for example, an aliphatic hydrocarbon group which may have a substituent(s). Examples of the "substituent" here include an oxo group, a thioxo group, a carbamoyl group, an aminocarbonyl group substituted with an aliphatic hydrocarbon group, such as an N-butylaminocarbonyl group, an N-cyclohexylmethylaminocarbonyl group, an N-cyclohexylaminocarbonyl group, or a phenylcarbonyl group. The "aliphatic hydrocarbon group" in the "aliphatic hydrocarbon group which may have a substituent(s)" as the "protective group" has the same meaning as in the "aliphatic hydrocarbon group" and the "substituent" may be substituted on the substitutable position and the number of substituents is from 1 to 5, and preferably from 1 to 2 and plural substituents may be the same or different. These optional substituents may be substituted on the substitutable position and the number of substituents is 1.

In the present specification, the "optionally oxidized sulfur atom" represented by $G^{2A}$ means —S—, —SO— and —$SO_2$—.

In the present specification, the "substituent" represented by $R^1$ includes, for example, substituents exemplified as for the above described T.

In the present specification, the "C1-4 alkyl group" represented by $R^3$ has the same meaning as described above.

In the present specification, the "C5-7 saturated monocyclic carbocyclic ring" represented by $R^3$ includes, for example, cyclopentane, cyclohexane and cycloheptane rings.

In the present specification, examples of the substituents represented by $R^4$ and $R^5$ include substituents exemplified as for the substituent T.

In the present specification, examples of the "substituent" represented by $R^6$ include an aliphatic hydrocarbon group, an aliphatic hydrocarbon group substituted with a cyclic group, an —O-aliphatic hydrocarbon group, a —$SO_2$-aliphatic hydrocarbon group, a —CO-aliphatic hydrocarbon group, a —COO-aliphatic hydrocarbon group, a nitro group, a methyl group which is substituted with 1 to 3 halogen atoms and the like. Examples of the substituent include substituents which are defined and exemplified in the above described T.

In the present specification, the "carbon atom which may have a substituent(s)" represented by $L^{2B}$ has the same meaning as in the "divalent carbon atom which may have a substituent(s)".

In the present invention, all isomers are included unless otherwise specified. For example, an alkyl group, an alkenyl group, an alkynyl group, an alkylene group, an alkenylene group, an alkynylene group, an alkylidene group and the like include those which are linear and branched. Furthermore, all of isomers (E-, Z-, cis-, and trans-isomers) on the double bond, ring and condensed ring, isomers (R-isomer, S-isomer, α,β configuration, enantiomer, and diastereomer) due to the presence of asymmetric carbon, optically active substances with optical rotation (D-, L-, d-, and I-compounds), polar compounds (high polar compound and low polar compound) generated by chromatographic separation, equilibrium compounds, rotational isomers, mixtures in an optional mixing ratio and racemic mixtures are included in the present invention.

[Salts]

Salts of the compound represented by formula (I) include all of nontoxic salts and pharmaceutically acceptable salts. The pharmaceutically acceptable salt is preferably a water soluble salt which shows less toxicity. Examples of the suitable salt of the compound represented by formula (I) include salts of alkali metal (potassium, sodium, lithium, etc.), salts of alkali earth metal (calcium, magnesium, etc.), ammonium salts (tetramethylammonium salt, tetrabutylammonium salt, etc.), salts of organic amine (triethylamine, methylamine, dimethylamine, cyclopentylamine, benzylamine, phenethylamine, piperidine, monoethanolamine, diethanolamine, tris (hydroxymethyl)methylamine, lysine, arginine, N-methyl-D-glucamine, etc.), acid addition salts [inorganic acid salts (hydrochloride, hydrobromide, hydroiodide, sulfate, phosphate, nitrate, etc.), and organic acid salts (acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, etc.)] and the like.

Furthermore, salts include quaternary ammonium salts. The quaternary ammonium salt is obtained by quaternizing a nitrogen atom of the compound represented by formula (I) with a $R^0$ group ($R^0$ group represents a C1-8 alkyl group, or a C1-8 alkyl group substituted with a phenyl group).

Also, salts include N-oxide. The compound of the present invention can be converted into N-oxide by an optional method. N-oxide is obtained by oxidizing a nitrogen atom of the compound represented by formula (I).

Examples of suitable solvate of the compound represented by formula (I) include solvates such as water, alcoholic solvent (for example, methanol, ethanol, etc.) and the like. The solvate is preferably nontoxic and water soluble. The solvate of the compound of the present invention also includes solvates of alkali (earth) metal salts, ammonium salts, salts of organic amine, and acid addition salts of the compound of the present invention.

The compound of the present invention can be converted into the above salts and solvates by a known method.

[Prodrugs]

A prodrug of the compound represented by formula (I) means a compound which is converted into the compound represented by formula (I) in the living body by the reaction with an enzyme, gastric acid or the like. Examples of the prodrug of the compound represented by formula (I) include compound wherein an amino group is acylated, alkylated, or phosphorylated (for example, compound wherein an amino group of the compound represented by formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.) when the compound represented by formula (I) has an amino group; compound wherein a hydroxyl group is acylated, alkylated, phosphorylated, boricated or the like (for example, compound wherein a hydroxyl group of the compound represented by formula (I) is acetylated, palmitoylated, propanoylated, pivaloylated, succinylated, fumarylated, alanylated, dimethylaminomethylcarbonylated, etc.) when the compound represented by formula (I) has a hydroxyl group; and compound wherein a carboxy group is esterificated, amidated or the like (for example, compound wherein a carboxy group of the compound represented by formula (I) is ethylesterificated, phenylesterificated, carboxymethylesterificated, dimethylaminomethylesterificated, pivaloyloxymethylesterificated, 1-{[(ethoxy)carbonyl]oxy}ethylesterificated, phthalidylesterificated, (5-methyl-2-oxo-1,3-dioxolen-4-yl) methylesterificated, 1-{[(cyclohexyloxy)carbony] oxy}lethylesterificated, methylamidated, etc.) when the compound represented by formula (I) has a carboxy group. These compounds can be prepared by a per se known method. The prodrug of the compound represented by formula (I) may be either of a hydrate and a non-hydrate. Also, the prodrug of the compound represented by formula (I) may be converted into the compound represented by formula (I) under physiological conditions described in "Development of Drug" published in 1990 by Hirokawa Shoten, Vol. 7, "Molecular Design", pp. 163-198. Furthermore, the compound represented by formula (I) may be labelled with isotope (for example, $^{3}H$, $^{14}C$, $^{35}S$, $^{125}I$, etc.) and the like.

The compound represented by formula (I) of the present invention, a salt thereof, a solvate thereof, or a prodrug thereof (hereinafter abbreviated to a compound of the present invention, sometimes) is a compound which is excellent in solubility and oral absorption and maintain its pharmacological activity for a long period of time, and is also less likely to be inhibited by a drug metabolizing enzyme and has low toxicity. These properties are most important physical, chemical and pharmacological properties required when preparations are developed, and the inventive compound satisfies these conditions and is expected to be useful for developing extremely excellent (see The Merck Manual of Diagnosis and Therapy (17th Ed.), Merck & Co.).

The fact that the compound of the present invention is useful as a drug can be evaluated by methods described in various tests and biological examples described hereinafter, and methods which can be carried out by appropriately improving the above methods. The fact that the compound of the present invention is kinetically excellent in length of half-life in blood, stability in gastrointestinal tract, oral absorption and bioavailability can be easily evaluated by a known method, for example, a method described in "Drug Bioavailability (Science of Evaluation and Improvement)", Gendai Iryo-sha, published on Jul. 6, 1998.

(I) Evaluation Experiment of an Inhibitory Activity of the Compound of the Present Invention Against a Drug-Metabolizing Enzyme (i) Inhibitory Activity Against Human CYP2A9

An inhibitory activity against CYP2C9 of the compound of the present invention can be evaluated by improving accuracy and/or sensitivity of the measurement in accordance with the method of Sato et al. (Pharmacokinetic, Xenobio. Metabol. and Dispos., 16(2), pp. 115-126 (2001)).

(ii) Inhibitory Activity Against Human CYP3A4

Inhibitory activity against human CYP3A4 of the compound of the present invention can be evaluated by an improved method described in *Drug Metabolism and Disposition,* Vol. 28(12), 1440-1448 (2000).

(II) Evaluation Experiment of a Toxicity of the Compound of the Present Invention (i) Single Acute Toxicity Test in Rat The test compound is administered to six-week Crj:CD (SD) rat by single intravenous dose or single oral administration. Toxicity can be evaluated by contrast with value at no addition of the test compound. Basic evaluation of toxicity can be done by, for example, observation of performance status or locomotor activity, etc.

(ii) Evaluation of the Activity of the Compound of the Present Invention Against hERG $I_{Kr}$ Current According to the report by Zou et al. (*Biophys. J.*, Vol. 74, 230-241 (1998)), using HEK293 cell overexpressed of human ether-a-go-go-related gene (hERG), max tale current of hERG $I_{Kr}$ current induced by depolarization pulse followed by repolarization pulse is measured by patch-clamp recording. Rate of change (inhibition rate) is calculated by comparison max tale current between before addition of the test compound and 10 minutes after. The influence of the test compound against hERG $I_{Kr}$ current can be evaluated by the inhibition rate (iii) Evaluation of Action of Compound of the Present Invention Against phospholipidosis It is possible to easily evaluate in accordance with the report of Kasahara et al. (*Toxicol. Sci.*, Vol. 90, pp. 1330-141 (2006)) and the report of Narita at al. (document "in vitro Phospholipidosis Detection System using Fluorescent-Labeled Phospholipids Analogue" distributed in presentation of results of research of Human Science Synthetic Research Promotion Business focusing on Drug Innovation in fiscal year 2003).

(iv) Evaluation of the Influence of a Compound of the Present Invention on Blood Pressure and Heart Rate A rat is anesthetized with urethane (1.2 g/kg subcutaneous administration). After neck midline dissection, a catheter for measuring blood pressure is inserted into a right common carotid artery. Then, after dissecting inguinal region, a catheter for chemical injection is inserted into a femoral vein and fixed. A catheter for measurement of blood pressure is connected to a pressure transducer and then the pressure waveform is recorded on a thermal writing pen recorder through an amplifier for strain compression (AP-641G (manufactured by NIHON KOHDEN CORPORATION)). In this case, regarding a heart rate, a value through an cardiotachometer (AT-601G (manufactured by NIHON KOHDEN CORPORATION)) using the pressure waveform obtained from the amplifier for strain compression as a trigger is recorded on a thermal writing pen recorder. The test compound is dissolved in a 10% solubilizing agent/physiological saline solution (volume ratio of polyoxyethylene hydroxystearate:propylene glycol:physiological saline=7:3:190) so as to adjust the concentration to 0.1, 0.3, 1, 3 or 10 mg/mL to prepare solutions. Each solution is intravenous administered at 1 mL/Kg through the caudal vein over about 10 seconds. Accumulative administration of stepwise increasing in dosage is carried out to an individual.

The measuring methods (1) to (2) described above are not limited to the methods described above and a conventional method can be practically used based on a basic method. Also, the measuring method may be modified to improve accuracy and/or sensitivity of the measurement for evaluating the compound of the present invention.

In the formula (I) of the present invention, any of each definition by $A^1$, $A^2$, $B^1$, $B^2$, R, G, E, L and J is preferred. In the following, preferable groups will be listed. The symbols used herein have the same meaning as described above.

R is preferably a hydrogen atom, an aliphatic hydrocarbon group, an aliphatic hydrocarbon group substituted with a cyclic group, a carboxyl group which may be protected with a protective group, a hydroxyl group which may be protected with a protective group, a C1-4 alkyl group which may be substituted with a hydroxyl group which may be protected with a protective group, and an amino group which may be protected with a protective group.

$A^1$ and $A^2$ each is preferably a basic group, and more preferably a nitrogen-containing heterocyclic ring which may have a substituent(s). The "nitrogen-containing heterocyclic ring group" herein is preferably pyrrole, imidazole, triazole, pyrazole, pyridine, pyrazine, pyrimidine, benzimidazole, azabenzimidazole, or tetrahydroquinoline ring, more preferably imidazole or benzimidazole ring, and particularly preferably imidazol-2-yl or benzoimidazol-2-yl. The "substituent" herein is preferably absence or an aliphatic hydrocarbon group, more preferably absence, a C1-8 alkyl group or the like, and particularly preferably absence or a methyl group, and most preferably absence. $A^1$ and $A^2$ may be the same or different.

$B^1$ and $B^2$ each is preferably a spacer having a main chain of 1 atom, more preferably a carbon atom which may have a substituent(s), and particularly preferably —$CH_2$—. The "substituent" herein is preferably absence or a methyl group and more preferably absence. $B^1$ and $B^2$ may be the same or different.

G is preferably, for example, a bond, a carbon atom which may have a substituent(s), or a nitrogen atom which may have a substituent. The "substituent" here is preferably absence, a hydroxyl group or a methyl group, and more preferably a hydroxyl group or absence. G is more preferably —CO—, —$CH_2$—, —CH(OH)—, or —NH—.

E is preferably, for example, a divalent aliphatic hydrocarbon group having 1 to 4 carbon atom(s) which may have a substituent(s), a divalent 3- to 8-membered monocyclic group which may have a substituent(s), or -(a spacer having a main chain of 1 to 2 atom(s))-(a 3- to 8-membered monocyclic group which may have a substituent(s))-. The -(a 3- to 8-membered monocyclic group which may have a substituent(s))- has the same meaning as in the divalent 3- to 8-membered monocyclic group wherein a bond of the right side of the group is bonded to L. More preferably, it is a divalent 3- to 8-membered monocyclic group which may have a substituent(s) or -(a spacer having a main chain of 1 to 2 atom(s))-(a 3- to 8-membered monocyclic group which may have a substituent(s))-. Herein, the "spacer having a main chain of 1 to 2 atom(s)" means the space wherein 1 to 2 atom(s) of the main chain are arranged in a line. Herein, "number of atoms of main chain" is counted so that the number of atoms of the main chain is minimized. The "spacer having a main chain of 1 to 2 atom(s)" includes, for example, a divalent group composed of 1 to 2 groups selected optionally from —O—, —S—, —CO—, —SO—, —$SO_2$—, divalent nitrogen atom which may have a substituent, divalent aliphatic hydrocarbon group having one carbon atom which may have a substituent(s), wherein 1 to 2 atom(s) of the main chain are arranged in a line. The "divalent nitrogen atom which may have a substituent(s)" here has the same meaning as described above. Examples of the "divalent aliphatic hydrocarbon group having 1 to 2 carbon atom(s)" in the "divalent aliphatic hydrocarbon group having 1 to 2 carbon atom(s) which may have a substituent(s)" include methylene, ethylene and ethynylene groups. The "substituent" in the "divalent aliphatic hydrocarbon group having 1 to 2 carbon atom(s) which may have a substituent(s) includes, for example, substituents exemplified as for the above described T, and optional substituents may be substituted on the substitutable position and the number of substituents is from 1 to 2. The "divalent 3- to 8-membered monocyclic group which may have a substituent(s)" has the same meaning as in those defined in $B^1$. The "3- to 8-membered monocyclic group" here is preferably, for example, a C5-7 monocyclic carbocyclic ring (those having 5 to 7 carbon atoms are selected from the above C3-8 monocyclic carbocyclic ring) and a 5- to 7-membered monocyclic heterocyclic ring (those having 5 to 7 membered rings are selected from the above C3-8 monocyclic carbocyclic ring), more preferably, for example, a cyclopentane, cyclohexane, cyclohexene, cyclohexadiene, benzene, pyridine, pyrazine, pyrimidine, pyridazine, piperidine or piperazine ring, and particularly preferably, for example, a cyclohexane or benzene ring.

The "substituent" in the "divalent 3- to 8-membered monocyclic group which may have a substituent(s)" is preferably, for example, absence, a halogen atom or a methyl group, and more preferably absence.

The "3- to 8-membered monocyclic group" represented by ring $E^1$ is preferably, for example, a C5-7 monocyclic carbocyclic ring (those having 5 to 7 carbon atoms are selected from the above C3-8 monocyclic carbocyclic ring) or a 5- to 7-membered monocyclic heterocyclic ring (those having 5 to 7 membered rings are selected from the above C3-8 monocyclic carbocyclic ring), more preferably, for example, a cyclopentane, cyclohexane, cyclohexene, cyclohexadiene, benzene, pyridine, pyrazine, pyrimidine, pyridazine, piperidine, or a piperazine ring, and particularly preferably, for example, a cyclohexane or benzene ring. The "substituent" of the "divalent 3- to 8-membered monocyclic group which may have a substituent(s)" is preferably, for example, absence, a halogen atom or a methyl group, and particularly preferably absence.

L is preferably a spacer having a main chain of 1 to 2 atom(s). The "spacer having a main chain of 1 to 2 atom(s)" is preferably a divalent group composed of 1 to 2 groups selected optionally from —O—, —S—, —CO—, —SO—, —$SO_2$—, divalent nitrogen atom which may have a substituent, divalent aliphatic hydrocarbon group having one carbon atom which may have a substituent(s), wherein 1 to 2 atom(s) of the main chain are arranged in a line, or the like. The "divalent aliphatic hydrocarbon group having one carbon atom which may have a substituent(s)" is the same meaning as the "divalent aliphatic hydrocarbon group having one carbon atom which may have a substituent(s)" of the above described $G^A$. The "divalent nitrogen atom which may have a substituent" is the same meaning as the "divalent nitrogen atom which may have a substituent" of the above described G. The L is more preferably —$CH_2$—, —O—$CH_2$—, —S—$CH_2$—, —NH—$CH_2$—, —$CH_2$—$CH_2$—, —CH═CH—, —C≡C—, —$CH_2$—O—, —$CH_2$—S—, —$CH_2$—NH—, —CONH—, —$SO_2$—NH—, —NHCO— or —$NHSO_2$—, and particularly preferably —$CH_2$—, —CONH—, —$CH_2$—NH—, —O—$CH_2$—, —S—$CH_2$—, —$CH_2$—$CH_2$-(J is bonded to the right side). A bond is also preferable.

J is preferably an aliphatic hydrocarbon group which is substituted with a basic group, and also may have a substituent(s); a cyclic group which is substituted with an aliphatic hydrocarbon group substituted with a basic group, and also may have a substituent(s); or an aliphatic hydrocarbon group which is substituted with a cyclic group substituted with a basic group, and also may have a substituent(s). The "basic group" herein is preferably a mono- or di-substituted amino group, or a nitrogen-containing heterocyclic ring which may have a substituent(s). The "mono- or di-substituted amino group" herein is preferably a di-substituted amino group, more preferably dimethylamino, diethylamino, dipropylamino, dibutylamino, or N-cyclohexyl-N-propylamino, and particularly preferably dipropylamino or N-cyclohexyl-N-propylamino. The "nitrogen-containing heterocyclic ring which may have a substituent(s)" herein is preferably non-substituted nitrogen-containing heterocyclic ring, or a nitrogen-containing heterocyclic ring substituted with a C1-8 alkyl group or an oxo group, and the "nitrogen-containing heterocyclic ring" is preferably a pyrrolidine, piperidine, morpholine, thiomorpholine, perhydrodiazepine, tetrahydroisoquinoline, 2,8-diazaspiro[4.5]decane, 1,4,9-triazaspiro[5.5]undecane, 3,9-diazaspiro[5.5]undecane, or 2,9-diazaspiro[5.5]undecane ring.

The "aliphatic hydrocarbon group" in the "aliphatic hydrocarbon group which is substituted with a basic group, and also may have a substituent(s)" or "aliphatic hydrocarbon group which is substituted with a cyclic group substituted with a basic group, and also may have a substituent(s)" herein is preferably a C1-8 alkyl group or a C2-8 alkenyl group, and more preferably methyl, ethyl, propyl, butyl, pentyl, or hexyl. The "cyclic group" in the "cyclic group which is substituted with an aliphatic hydrocarbon group substituted with a basic group, and also may have a substituent(s)" is preferably a C5-7 monocyclic carbocyclic ring (ring having 5 to 7 carbon atoms is selected from among the above described C3-15 monocyclic or polycyclic carbocyclic ring) or a 5- to 7-membered monocyclic heterocyclic ring (5- to 7-membered heterocyclic ring is selected from among the above described 3- to 15-membered monocyclic or polycyclic heterocyclic ring), and more preferably a cyclopentane, cyclohexane, cyclohexene, adamantyl, cyclohexadiene, benzene, pyridine, pyrazine, tetrahydropyran, pyrimidine, pyridazine, piperidine, or piperazine ring. The "substituent" herein is preferably absence, a halogen atom, a methyl group, a hydroxyl group, an amino group or an oxo group, and more preferably absence.

Furthermore, J is preferably a "cyclic group which is substituted with a group having a basic group, and also may have a substituent(s)", a "spiro-bound cyclic group which may be substituted with a group having a basic group, and also may have a substituent(s)", or a "bridged cyclic group which may be substituted with a group having a basic group, and also may have a substituent(s)". The "cyclic group" or "spiro-bound cyclic group", or "bridged cyclic group" is preferably (1) a spiro-bound cyclic group, (2) a bridged polycyclic carbocyclic ring, (3) a bridged polycyclic heterocyclic ring composed of a carbon atom(s), an oxygen atom(s) and/or an optionally oxidized sulfur atom(s), (4) a bridged polycyclic heterocyclic ring which has at least one nitrogen atom, and also may have an oxygen atom(s) and/or an optionally oxidized sulfur atom(s), (5) a C3-15 monocyclic or condensed carbocyclic ring, (6) a 3- to 15-membered monocyclic or condensed heterocyclic ring composed of a carbon atom(s), an oxygen atom(s) and/or an optionally oxidized sulfur atom(s), or (7) a 3- to 15-membered monocyclic or condensed heterocyclic ring which has at least one nitrogen atom, and also has a carbon atom(s), oxygen atom(s) and/or an optionally oxidized sulfur atom(s).

The "spiro-bound cyclic group" is preferably 2,7-diazaspiro[3.5]nonane, 2,8-diazaspiro[4.5]decane, 2,7-diazaspiro[4.5]decane, 2,9-diazaspiro[5.5]undecane, 2,8-diazaspiro[5.5]undecane, 3,9-diazaspiro[5.5]undecane, 2,7-diazaspiro[4.4]nonane, 1,2-dihydrospiro[indole-3,4'-piperidine], 2,3-dihydro-1H-spiro[isoquinoline-4,4'-piperidine], 1',4'-dihydro-2'H-spiro[piperidine-4,3'-quinoline], 2',3'-dihydro-1'H-spiro[piperidine-4,4'-quinoline], 8-azaspiro[4.5]decane, 8-azaspiro[4.5]decane, 7-azaspiro[4.5]decane, 3-azaspiro[5.5]undecane, 2-azaspiro[5.5]undecane, 1-oxa-4,8-diazaspiro[5.5]undecane, 1-oxa-4,9-diazaspiro[5.5]undecane, 3,4-dihydrospiro[chromene-2,4'-piperidine], 2-azaspiro[4.4]nonane, 7-azaspiro[3.5]nonane, 2,3-dihydrospiro[indene-1,4'-piperidine], 3,4-dihydro-2H-spiro[naphthalene-1,4'-piperidine], 3,4-dihydro-1H-spiro[naphthalene-2,4'-piperidine], 2-azaspiro[4.5]decane, 2-azaspiro[3.5]nonane, 1',2'-dihydrospiro[cyclohexane-1,3'-indole], 2',3'-dihydro-1'H-spiro[cyclohexane-1,4'-isoquinoline], 1',4'-dihydro-2'H-spiro[cyclohexane-1,3'-quinoline], 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, 1-thia-4,8-diazaspiro[5.5]undecane, spiro[4.4]nonane, spiro[4.5]decane, spiro[5.5]undecane, spiro[3.4]octane, or spiro[3.5]nonane. The "spiro-bound cyclic group" is more preferably 2,7-diazaspiro[3.5]nonane, 2,8-diazaspiro[4.5]decane, 2,7-diazaspiro[4.5]decane, 2,9-diazaspiro[5.5]undecane, 2,8-diazaspiro[5.5]undecane, 3,9-diazaspiro[5.5]undecane, 2,7-diazaspiro[4.4]nonane, 1,2-dihydrospiro[indole-3,4'-piperidine], 2,3-dihydro-1H-spiro[isoquinoline-4,4'-piperidine], 1',4'-dihydro-2'H-spiro[piperidine-4,3'-quinoline], 2',3'-dihydro-1'H-spiro[piperidine-4,4'-quinoline], 8-azaspiro[4.5]decane, 1-oxa-4,8-diazaspiro[5.5]undecane, 1-oxa-4,9-diazaspiro[5.5]undecane, 3,4-dihydrospiro[chromene-2,4'-piperidine], 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, or 1-thia-4,8-diazaspiro[5.5]undecane. The "spiro-bound cyclic group" is particularly preferably 2,7-diazaspiro[4.5]decane, 2,8-diazaspiro[4.5]decane, 2,8-diazaspiro[5.5]undecane, 2,9-diazaspiro[5.5]undecane, 2,7-diazaspiro[3.5]nonane, or 1-oxa-4,9-diazaspiro[5.5]undecane. The most preferable "spiro-bound cyclic group" is a 2,8-diazaspiro[4.5]decane ring.

The "bridged polycyclic carbocyclic ring" is preferably bicyclo[2.1.1]hexane, bicyclo[2.2.1]heptane, bicyclo[2.2.2]octane, bicyclo[3.2.1]octane, adamantane, bicyclo[3.3.1]nonane, bicyclo[3.2.1]octane, or bicyclo[3.3.2]decane.

The "bridged polycyclic heterocyclic ring which has at least one nitrogen atom, and also may have an oxygen atom(s) and/or an optionally oxidized sulfur atom(s)" is preferably 1-azatricyclo[3.3.1.1$^{3,7}$]decane, 3-azabicyclo[3.3.1]nonane, or 3,7-diazabicyclo[3.3.1]nonane.

The "7- to 15-membered bicyclic spiro-bound heterocyclic ring wherein a ring comprising the spiro-bound heterocyclic ring is a monocyclic ring composed of at least one nitrogen atom and carbon atoms, and/or a monocyclic ring composed of at least one nitrogen atom, one oxygen atom and carbon atoms" is preferably a 9- to 11-membered bicyclic spiro-bound heterocyclic ring wherein a ring comprising the spiro-bound heterocyclic ring is a monocyclic ring composed of at least one nitrogen atom and carbon atoms, and/or a monocyclic ring composed of at least one nitrogen atom, one oxygen atom and carbon atoms.

The "9 to 11-membered bicyclic spiro-bound heterocyclic ring wherein a ring comprising the spiro-bound heterocyclic ring is a monocyclic ring composed of at least one nitrogen atom and carbon atom, and/or a monocyclic ring composed of at least one nitrogen atom, one oxygen atom and carbon atoms" is preferably 2,7-diazaspiro[4.5]decane, 2,8-diazaspiro[4.5]decane, 2,8-diazaspiro[5.5]undecane, 2,9-diazaspiro[5.5]undecane, 2,7-diazaspiro[3.5]nonane, or 1-oxa-4,9-diazaspiro[5.5]undecane. More preferably, it is cyclopentane, cyclohexane, or cyclooctane. Most preferably, it is 2,8-diazaspiro[4.5]decane.

The "C3-15 monocyclic or condensed carbocyclic ring" is preferably cyclopropane, cyclobutane, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, or 1,2,3,5,6,7-hexahydro-s-indacene. More preferably, it is cyclopentane, cyclohexane, or cyclooctane. Most preferably, it is cyclohexane.

The "3- to 15-membered monocyclic or condensed heterocyclic ring composed of a carbon atom(s), an oxygen atom(s) and/or an optionally oxidized sulfur atom(s)" is preferably a partially or completely saturated 3- to 15-membered monocyclic or condensed heterocyclic ring composed of a carbon atom(s), an oxygen atom(s) and/or an optionally oxidized sulfur atom(s).

The "3- to 15-membered monocyclic or condensed heterocyclic ring which has at least one nitrogen atom, and is composed of a carbon atom(s), an oxygen atom(s) and/or an optionally oxidized sulfur atom(s)" is preferably a partially or completely saturated 3- to 15-membered monocyclic or condensed heterocyclic ring which has at least one nitrogen atom, and is composed of a carbon atom(s), an oxygen atom and/or an optionally oxidized sulfur atom(s).

The "substituent" of the "which may be substituted with a substituent(s)" of ring $J^1$, ring $J^2$, ring $J^3$ and ring $J^4$ is preferably an aliphatic hydrocarbon group, a cyclic group, or an aliphatic hydrocarbon group substituted with a cyclic group, and more preferably an aliphatic hydrocarbon group having 1 to 8 carbon atom(s) or a C3-10 monocyclic or bicyclic carbocyclic ring.

The "group having a basic group" of the "which is substituted with a group having a basic group" or the "which may be substituted with a basic group" of ring $J^2$, ring $J^3$ and ring $J^4$ is preferably, for example, a mono- or di-substituted amino group, or a nitrogen-containing heterocyclic ring group which may have a substituent(s). The "mono- or di-substituted amino group" here is preferably a di-substituted amino group, more preferably, for example, dimethylamino, diethylamino, dipropylamino, dibutylamino, or N-cyclohexyl-N-propylamino, and particularly preferably dipropylamino or N-cyclohexyl-N-propylamino.

$R^A$ is preferably, for example, a mono- or di-substituted amino group, or a nitrogen-containing heterocyclic ring group which may have a substituent(s). The "mono- or di-substituted amino group" here is preferably a di-substituted amino group, and more preferably, for example, dimethylamino, diethylamino, dipropylamino, dibutylamino, or N-cyclohexyl-N-propylamino.

In the present specification, $G^A$ is preferably, for example, a carbon atom which may have a substituent(s), and the substituent of the carbon atom is preferably, for example, absence, a hydroxyl group, an oxo group, an aliphatic hydrocarbon group, or an aliphatic hydrocarbon group substituted with a cyclic group, and more preferably absence, a hydroxyl group, or an oxo group.

In the present specification, the "substituent" of the "carbon atom which may have a substituent(s)" represented by $G^{1A}$ is preferably, for example, absence, a hydroxyl group, an oxo group, or a C1-4 alkyl group, an aliphatic hydrocarbon group substituted with a cyclic group, and more preferably, for example, absence or an oxo group.

In the present specification, $G^{2A}$ is preferably a nitrogen atom which may have a substituent. Herein, the "substituent" of the "nitrogen atom which may have a substituent(s)" is preferably, for example, (1) absence, (2) a C1-4 alkyl group, (3) a C1-4 alkyl group substituted with a hydroxyl group which may be protected with a protective group, (4) a C1-4 alkyl group substituted with an amino group which may be protected with a protective group, (5) a C1-4 alkyl group substituted with a carboxyl group which may be protected with a protective group, or (6) a C1-4 alkyl group substituted with a pyrrolidine ring, piperidine ring or a morpholine ring. The protective group here is preferably a C1-4 alkyl group which may be substituted with an oxo group (for example, acetyl, propionyl, butyryl, isobutyryl, etc.). The "substituent" of "the nitrogen atom which may have a substituent(s)" is more preferably (1) a C1-4 alkyl group substituted with a hydroxyl group (for example, hydroxymethyl, hydroxyethyl, hydroxypropyl, etc.), (2) a C1-4 alkyl group which is substituted with a hydroxyl group substituted with an acetyl group (for example, acetyloxymethyl, acetyloxyethyl, acetyloxypropyl, etc.), (3) a C1-4 acyl group which may be substituted with a C1-4 alkyl group substituted with a hydroxyl group (for example, methanoyl, ethanoyl, propanoyl, butanoyl, hydroxymethylcarbonyl, etc.), (4) a C1-6 alkyl group (for example, aminoethyl, aminopropyl, aminobutyl, aminopentyl, aminohexyl, dimethylaminoethyl, acetylaminoethyl, etc.) substituted with an amino group which may be substituted with a C1-4 alkyl group or a C1-4 acyl group (for example, formyl, acetyl, propionyl, butyryl, isobutyryl group, etc.), (5) a C1-4 alkyl group (for example, pyrrolidinylethyl, morpholinylethyl, pyridinylethyl, etc.) substituted with pyrrolidine, morpholine or pyridine, (6) a C1-4 alkyl group (for example, methoxycarbonyl, ethoxycarbonyl, etc.) substituted with a C1-4 alkoxycarbonyl group, and (7) a C1-4 alkyl group (for example, carboxymethyl, carboxyethyl, carboxypropyl) substituted with a carboxyl group. The "substituent" of the "nitrogen atom which may have a substituent(s)" is particularly preferably a hydroxyethyl, acetyl, methoxyethyl, pyrrolidinylethyl, morpholinylethyl, hydroxymethylcarbonyl, dimethylaminoethyl, or acetylaminoethyl group. As the "nitrogen atom which may have a substituent(s)", a non-substituted nitrogen atom is also preferable.

In the present specification, $G^{3A}$ is preferably a carbon atom which may have a substituent(s). The "substituent" here is preferably, for example, absence, a hydroxyl group, oxo group, a C1-4 alkyl group, or an aliphatic hydrocarbon group substituted with a cyclic group, and more preferably, for example, absence or an oxo group.

In the present specification, G is preferably $G^{1A}$-$G^{2A}$-$G^{3A}$. $G^{1A}$-$G^{2A}$-$G^{3A}$ is preferably, for example, (carbon atom which may be substituted with an oxo group)-(a nitrogen atom which may have a substituent)-(carbon atom which may be substituted with an oxo group) and the "substituent" of the "nitrogen atom which may have a substituent(s)" is preferably, for example, absence, hydroxyethyl, acetyl, methoxyethyl, pyrrolidinylethyl, morpholinyl ethyl, hydroxymethylcarbonyl, dimethylaminoethyl, or acetylaminoethyl group.

In the present specification, $L^A$ is preferably, for example, aliphatic hydrocarbon group having 1 to 4 carbon atoms which may have a substituent(s), more preferably, for example, a carbon atom which may have a substituent(s), and particularly preferably, for example, $-CH_2-$ or —CO—.

In the present specification, $L^{2B}$ is preferably, for example, $-CH_2-$ or —CO—, and particularly preferably, for example, $-CH_2-$.

In the present specification, the "mono- or di-substituted amino group" in "the C4-7 monocyclic carbocyclic ring substituted with a mono- or di-substituted amino group" represented by $J^{1B}$ is preferably, for example, a mono- or di-C1-4 alkylamino group (for example, methylamino, ethylamino, propylamino, dimethylamino, diethylamino, etc.), and more preferably a dipropylamino group. Also, the "C4-7 monocyclic carbocyclic ring" is preferably, for example, a cyclohexane ring.

In the present specification, $R^C$ is preferably, for example, a hydrogen atom, a cyano group, a C1-4 alkyl group substituted with a hydroxyl group, or a C1-4 alkyl group substituted with a hydroxyl group protected with a protective group. The "protective group" here is preferably a C1-4 alkyl group which may be substituted with an oxo group. $R^C$ is more preferably, for example, a hydrogen atom, a cyano, hydroxymethyl, hydroxyethyl or acetoxymethyl group.

In the present specification, $R^1$ is preferably an aliphatic hydrocarbon group, a cyclic group, or an aliphatic hydrocarbon group substituted with a cyclic group which may have a substituent(s), and more preferably a C1-4 alkyl group, a monocyclic group, or a C1-4 alkyl group substituted with a monocyclic group which may have a substituent(s). The monocyclic group is preferably cyclopentane, cyclohexane, or thiophene. The substituent is preferably, for example, a C1-4 alkyl group.

In the present specification, $R^{1C}$ is preferably, for example, a hydrogen atom, a cyano, hydroxymethyl, hydroxyethyl or acetoxymethyl group.

In the present specification, $R^2$ is preferably, for example, a hydrogen atom, a hydroxyethyl, acetyl, methoxyethyl, pyrrolidinylethyl, morpholinylethyl or hydroxymethylcarbonyl group.

In the present specification, $R^3$ is preferably, for example, a C1-4 alkyl group or a C5-7 saturated monocyclic carbocyclic ring group, and more preferably, for example, sec-butyl or cyclohexyl.

In the present specification, $R^4$ and $R^5$ are preferably, for example, a hydrogen atom, a hydroxyl group or an oxo group.

In the present specification, $R^6$ is preferably, for example, a hydrogen atom or an aliphatic hydrocarbon group, and more preferably, for example, a hydrogen atom or a C1-4 alkyl group.

In the present invention, a compound of formula (I), which contains a combination of preferable groups listed previously, is preferable.

Among compounds represented by formula (I), a preferable compound is a compound represented by formula (I-1):

(I-1)

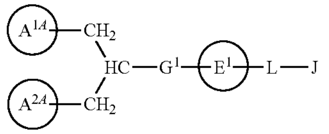

wherein all symbols are as defined above, formula (I-2):

(I-2)

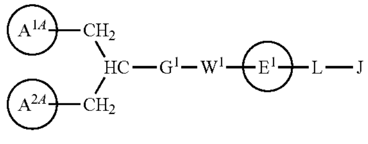

wherein $W^1$ represents a spacer having 1 to 2 atoms, and other symbols are as defined above, a salt thereof, an N-oxide thereof or a solvate thereof, or a prodrug thereof.

Among compounds represented by formula (I), a more preferable compound is a compound represented by formula (I-1-a):

(I-1-a)

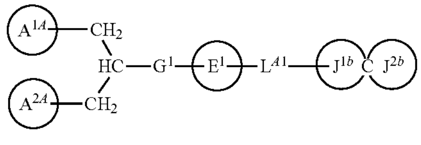

wherein all symbols are as defined above,
formula (I-2-a):

(I-2-a)

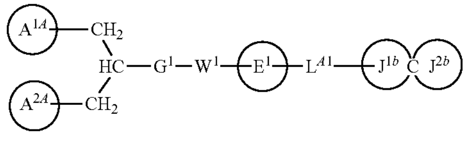

wherein all symbols are as defined above, or
formula (I-3):

(I-3)

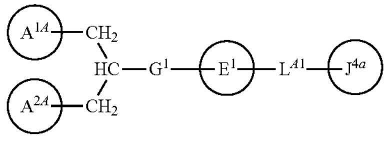

wherein ring $J^{4a}$ may be substituted with a group having a basic group or a 3- to 8-membered monocyclic heterocyclic ring which has at least one nitrogen atom, and also may have an oxygen atom and/or an optionally oxidized sulfur atom, ring $J^{4a}$ may have a substituent(s) in substitutable number on the substitutable position and, when two or more substituents are present, plural substituents may be the same or different, other symbols are as defined above; Other symbols are as defined above, formula (I-4):

(I-4)

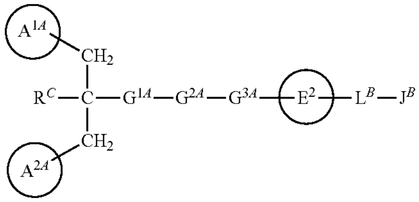

wherein all symbols are as defined above, formula (I-5):

(I-5)

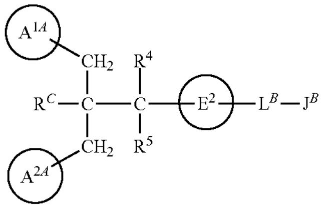

wherein all symbols are as defined above, or formula (I-6):

(I-6)

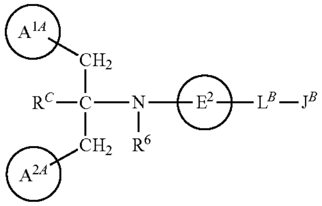

wherein all symbols are as defined above, a salt thereof, a solvate thereof, or a prodrug thereof.

In the specification, examples of the "3- to 8-membered monocyclic heterocyclic ring which has at least one nitrogen atom and also may have an oxygen atom(s) and/or an optionally oxidized sulfur atom(s)" of the "3- to 8-membered monocyclic heterocyclic ring which has at least one nitrogen atom and also may have an oxygen atom(s) and/or an optionally oxidized sulfur atom(s), and which may be substituted with a group having a basic group" represented by ring $J^{4a}$ include, for example, pyrrole, pyridine, azepine, oxazole, isoxazole, thiazole, isothiazole, oxazine, oxazepine, thiazine, thiazepine, aziridine, azetidine, pyrroline, pyrrolidine, dihydropyridine, tetrahydropyridine, piperidine, dihydroazepine, tetrahydroazepine, perhydroazepine, dihydrooxazole, tetrahydrooxazole (oxazolidine) dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrooxazine, tetrahydrooxazine, dihydrooxazepine, tetrahydrooxazepine, perhydrooxazepine, dihydrothiazine, tetrahydrothiazine, dihydrothiazepine, tetrahydrothiazepine, perhydrothiazepine, morpholine, thiomorpholine rings and the like. The "group having a basic group" here has the same meaning as the "group having a basic group" in the above described $A^1$ and $A^2$.

In the present specification, the "substituent" of the "a substituent(s) in substitutable number on the substitutable position" represented by ring $J^{4a}$ is not specifically limited, and includes, for example, substituents exemplified as for the above described T. Optional substituents may be substituted on the substitutable position, and the number of substituents may be from 1 to 8, and preferably from 1 to 5. When ring $J^{4a}$ is substituted with a group having a basic group, optional substituents may be substituted on the substitutable position, and the number of substituents may be from 1 to 8, and preferably from 1 to 4.

Among compounds represented by formula (I), a more preferable compound is a compound represented by formula (I-1-a1):

(I-1-a1)

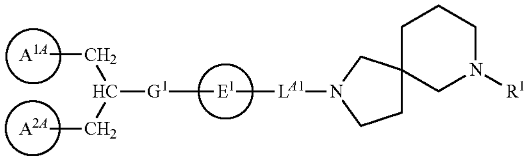

wherein all symbols are as defined above, formula (I-1-a2):

(I-1-a2)

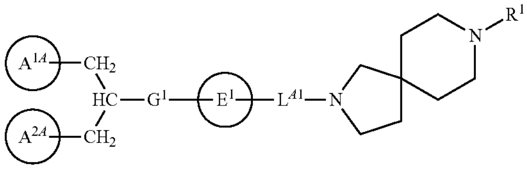

wherein all symbols are as defined above, formula (I-1-a3):

(I-1-a3)

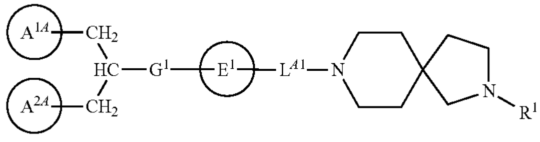

wherein all symbols are as defined above, formula (I-1-a4):

(I-1-a4)

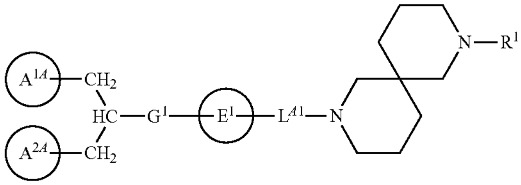

wherein all symbols are as defined above, formula (I-1-a5):

(I-1-a5)

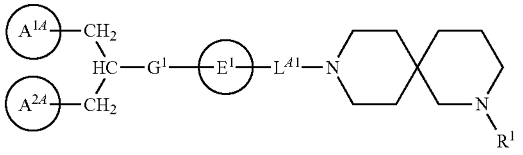

wherein all symbols are as defined above, formula (I-1-a6):

(I-1-a6)

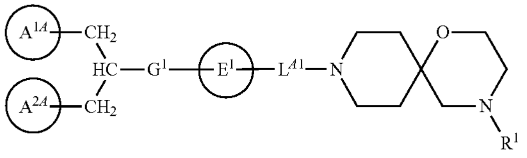

wherein all symbols are as defined above, formula (I-1-a7):

(I-1-a7)

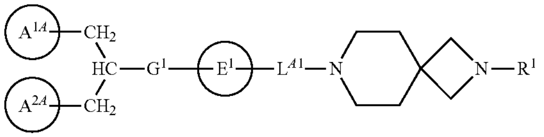

wherein all symbols are as defined above, formula (I-2-a1):

(I-2-a1)

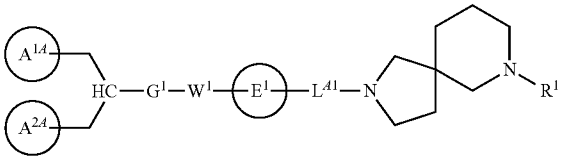

wherein all symbols are as defined above, formula (I-2-a2):

(I-2-a2)

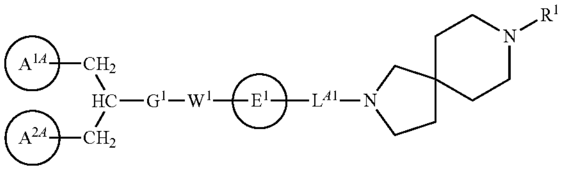

wherein all symbols are as defined above, formula (I-2-a3):

(I-2-a3)

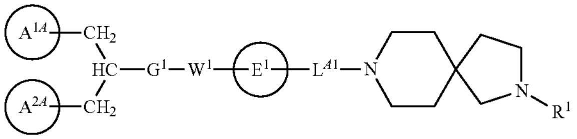

wherein all symbols are as defined above, formula (I-2-a4):

(I-2-a4)

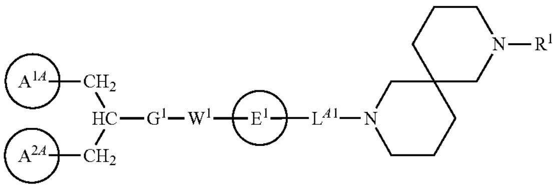

wherein all symbols are as defined above, formula (I-2-a5):

(I-2-a5)

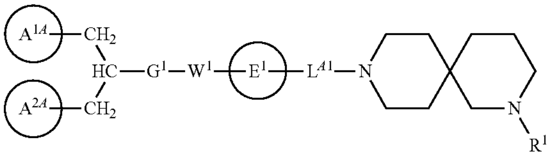

wherein all symbols are as defined above, formula (I-2-a6):

(I-2-a6)

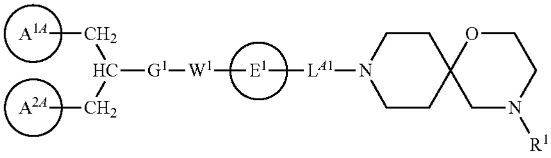

wherein all symbols are as defined above, formula (I-2-a7):

(I-2-a7)

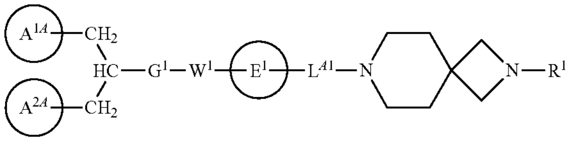

wherein all symbols are as defined above, or, formula (I-4-b):

(I-4-b)

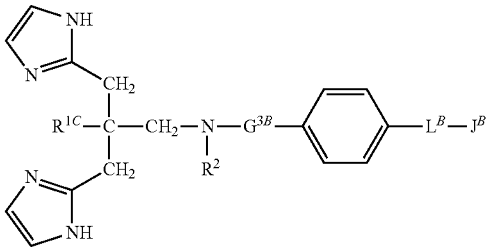

wherein all symbols are as defined above, a salt thereof, a solvate thereof, or a prodrug thereof.

Among compounds represented by formula (I), a particularly preferable compound is a compound represented by formula (I-4-b) wherein $-L^B-B^B$ is:

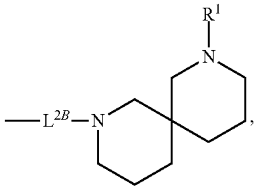
,
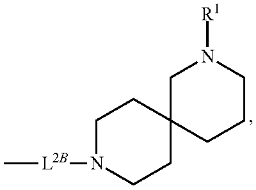
,
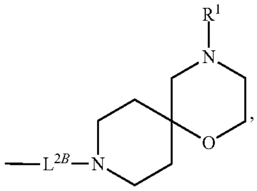
,
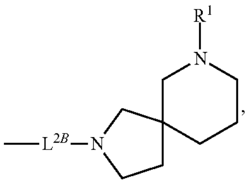
,
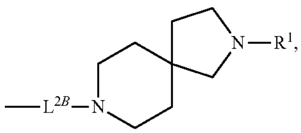

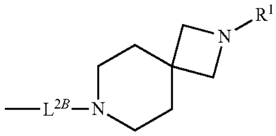
or

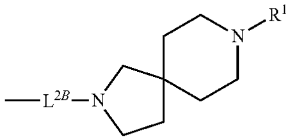

wherein all symbols are as defined above.

Among compounds represented by formula (I), a most preferable compound is a compound represented by formula (I-4-a):

(I-4-a)

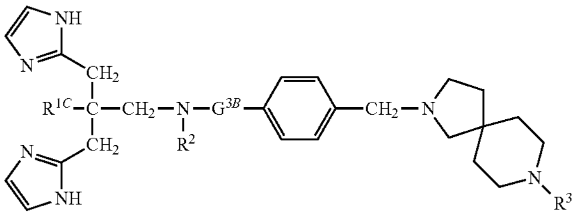

wherein all symbols are as defined above, a salt thereof, a solvate thereof, or a prodrug thereof.

Specific examples of the compound of the present invention include compound shown in the following (1) to (50), compounds described in Examples, salts thereof, N-oxides thereof or solvates thereof or prodrugs thereof:

(1) 1-[4-({[4-(dipropylamino)butyl]amino}methyl)phenyl]-3-(1H-imidazol-2-yl)-2-(1H-imidazol-2-ylmethyl)propan-1-one; (2) 1-[4-({[4-(dipropylamino)butyl]amino}methyl)phenyl]-3-(1H-imidazol-2-yl)-2-(1H-imidazol-2-ylmethyl)propan-1-ol; (3) N'-{4-[3-(1H-imidazol-2-yl)-2-(1H-imidazol-2-ylmethyl)propyl]benzyl}-N,N-dipropylbutane-1,4-diamine; (4) N-[4-(dipropylamino)butyl]-4-[3-(1H-imidazol-2-yl)-2-(1H-imidazol-2-ylmethyl)propanoyl]benzamide; (5) N-[4-(dipropylamino)butyl]-4-[1-hydroxy-3-(1H-imidazol-2-yl)-2-(1H-imidazol-2-ylmethyl)propyl]benzamide; (6) N-[4-(dipropylamino)butyl]-4-[3-(1H-imidazol-2-yl)-2-(1H-imidazol-2-ylmethyl)propyl]benzamide; (7) 1-[4-({[4-(dipropylamino)cyclohexyl]amino}methyl)phenyl]-3-(1H-imidazol-2-yl)-2-(1H-imidazol-2-ylmethyl)propan-1-one; (8) 1-{4-[(8-cyclohexyl-2,8-diazaspiro[4.5]dec-2-yl)methyl]phenyl}-3-(1H-imidazol-2-yl)-2-(1H-imidazol-2-ylmethyl)propan-1-one; (9) 1-{4-[(8-cyclohexyl-2,8-diazaspiro[4.5]dec-2-yl)methyl]cyclohexyl}-3-(1H-imidazol-2-yl)-2-(1H-imidazol-2-ylmethyl)propan-1-one; (10) N-{4-[(8-cyclohexyl-2,8-diazaspiro[4.5]dec-2-yl)methyl]benzyl}-1,3-di-1H-imidazol-2-ylpropan-2-amine; (11) 4-[(8-cyclohexyl-2,8-diazaspiro[4.5]dec-2-yl)methyl]-N-[2-(1H-imidazol-2-yl)-1-(1H-imidazol-2-ylmethyl)ethyl]benzamide; (12) N-{4-[(8-cyclohexyl-2,8-diazaspiro[4.5]dec-2-yl)carbonyl]benzyl}-1,3-di-1H-imidazol-2-ylpropan-2-amine; (13) 4-[(8-cyclohexyl-2,8-diazaspiro[4.5]dec-2-yl)methyl]-N-[2-(1H-imidazol-2-yl)-1-(1H-imidazol-2-ylmethyl)ethyl]cyclohexanamine; (14) N-({4-[(8-cyclohexyl-2,8-diazaspiro[4.5]dec-2-yl)methyl]cyclohexyl}methyl)-1,3-di-1H-imidazol-2-ylpropan-2-amine; (15) 4-[(8-cyclohexyl-2,8-diazaspiro[4.5]dec-2-yl)carbonyl]-N-[2-(1H-imidazol-2-yl)-1-(1H-imidazol-2-ylmethyl)ethyl]cyclohexanamine; (16) 4-[(8-cyclohexyl-2,8-diazaspiro[4.5]dec-2-yl)methyl]-N-[2-(1H-imidazol-2-yl)-1-(1H-imidazol-2-ylmethyl)ethyl]cyclohexanecarboxamide; (17) N-({4-[(8-cyclohexyl-2,8-diazaspiro[4.5]dec-2-yl)carbonyl]cyclohexyl}methyl)-1,3-di-1H-imidazol-2-ylpropan-2-amine; (18) 4-[(8-cyclohexyl-2,8-diazaspiro[4.5]dec-2-yl)carbonyl]-N-[2-(1H-imidazol-2-yl)-1-(1H-imidazol-2-ylmethyl)ethyl]cyclohexanecarboxamide; (19) 4-[(8-cyclohexyl-2,8-diazaspiro[4.5]dec-2-yl)methyl]-N-[2-(1H-imidazol-2-yl)-1-(1H-imidazol-2-ylmethyl)ethyl]benzenesulfonamide; (20) N'-({1-[3-(1H-imidazol-2-yl)-2-(1H-imidazol-2-ylmethyl)propanoyl]piperidin-4-yl}methyl)-N,N-dipropylcyclohexane-1,4-diamine; (21) 8-cyclohexyl-2-({1-[3-(1H-imidazol-2-yl)-

2-(1H-imidazol-2-ylmethyl)propanoyl]piperidin-4-yl}methyl)-2,8-diazaspiro[4.5]decane; (22) 4-{2-[3-(1H-imidazol-2-yl)-2-(1H-imidazol-2-ylmethyl)propanoyl]-2,8-diazaspiro[4.5]dec-8-yl}-N,N-dipropylbutan-1-amine; (23) N-({1-[(1-cyclohexylpiperidin-4-yl)methyl]piperidin-4-yl}methyl)-3-(1H-imidazol-2-yl)-2-(1H-imidazol-2-ylmethyl)propanamide; (24) 1-{5-[(8-cyclohexyl-2,8-diazaspiro[4.5]dec-2-yl)methyl]pyridin-2-yl}-3-(1H-imidazol-2-yl)-2-(1H-imidazol-2-ylmethyl)propan-1-one; (25) 1-{6-[(8-cyclohexyl-2,8-diazaspiro[4.5]dec-2-yl)methyl]pyridin-3-yl}-3-(1H-imidazol-2-yl)-2-(1H-imidazol-2-ylmethyl)propan-1-one; (26) 1-{5-[(8-cyclohexyl-2,8-diazaspiro[4.5]dec-2-yl)methyl]pyrazin-2-yl}-3-(1H-imidazol-2-yl)-2-(1H-imidazol-2-ylmethyl)propan-1-one; (27) 1-{2-[(8-cyclohexyl-2,8-diazaspiro[4.5]dec-2-yl)methyl]pyrimidin-5-yl}-3-(1H-imidazol-2-yl)-2-(1H-imidazol-2-ylmethyl)propan-1-one; (28) 1-{5-[(8-cyclohexyl-2,8-diazaspiro[4.5]dec-2-yl)methyl]pyrimidin-2-yl}-3-(1H-imidazol-2-yl)-2-(1H-imidazol-2-ylmethyl)propan-1-one; (29) 1-{5-[(8-cyclohexyl-2,8-diazaspiro[4.5]dec-2-yl)methyl]pyridin-2-yl}-3-(1H-imidazol-2-yl)-2-(1H-imidazol-2-ylmethyl)propan-1-one; (30) 3-(1H-imidazol-2-yl)-2-(1H-imidazol-2-ylmethyl)-1-(4-{[8-(2-thienylmethyl)-2,8-diazaspiro[4.5]dec-2-yl]methyl}phenyl)propan-1-one; (31) 3-(1H-imidazol-2-yl)-2-(1H-imidazol-2-ylmethyl)-1-(4-{[2-(2-thienylmethyl)-2,8-diazaspiro[4.5]dec-8-yl]methyl}phenyl)propan-1-one; (32) 1-{4-[(2-cyclohexyl-2,8-diazaspiro[4.5]dec-8-yl)methyl]phenyl}-3-(1H-imidazol-2-yl)-2-(1H-imidazol-2-ylmethyl)propan-1-one; (33) 1-{4-[(9-cyclohexyl-3,9-diazaspiro[5.5]undec-3-yl)methyl]phenyl}-3-(1H-imidazol-2-yl)-2-(1H-imidazol-2-ylmethyl)propan-1-one; (34) 1-{4-[(9-cyclohexyl-2,9-diazaspiro[5.5]undec-2-yl)methyl]phenyl}-3-(1H-imidazol-2-yl)-2-(1H-imidazol-2-ylmethyl)propan-1-one; (35) 1-{4-[(8-cyclohexyl-2,8-diazaspiro[5.5]undec-2-yl)methyl]phenyl}-3-(1H-imidazol-2-yl)-2-(1H-imidazol-2-ylmethyl)propan-1-one; (36) 1-{4-[(7-cyclohexyl-2,7-diazaspiro[4.4]non-2-yl)methyl]phenyl}-3-(1H-imidazol-2-yl)-2-(1H-imidazol-2-ylmethyl)propan-1-one; (37) 1-{5-[(8-cyclohexyl-2,8-diazaspiro[4.5]dec-2-yl)methyl]-1,3-oxazol-2-yl}-3-(1H-imidazol-2-yl)-2-(1H-imidazol-2-ylmethyl)propan-1-one; (38) 8-cyclohexyl-2-{4-[2-(1H-imidazol-2-yl)-1-(1H-imidazol-2-ylmethyl)ethyl]benzyl}-2,8-diazaspiro[4.5]decane; (39) 8-cyclohexyl-2-({4-[2-(1H-imidazol-2-yl)-1-(1H-imidazol-2-ylmethyl)ethyl]cyclohexyl}methyl)-2,8-diazaspiro[4.5]decane; (40) 8-cyclohexyl-2-({1-[2-(1H-imidazol-2-yl)-1-(1H-imidazol-2-ylmethyl)ethyl]piperidin-4-yl}methyl)-2,8-diazaspiro[4.5]decane; (41) 8-cyclohexyl-2-[7-(1H-imidazol-2-yl)-6-(1H-imidazol-2-ylmethyl)heptyl]-2,8-diazaspiro[4.5]decane; (42) 4-(8-cyclohexyl-2,8-diazaspiro[4.5]dec-2-yl)-N-[2-(1H-imidazol-2-yl)-1-(1H-imidazol-2-ylmethyl)ethyl]butan-1-amine; (43) 7-(8-cyclohexyl-2,8-diazaspiro[4.5]dec-2-yl)-1-(1H-imidazol-2-yl)-2-(1H-imidazol-2-ylmethyl)heptan-3-ol; (44) 7-(8-cyclohexyl-2,8-diazaspiro[4.5]dec-2-yl)-1-(1H-imidazol-2-yl)-2-(1H-imidazol-2-ylmethyl)heptan-3-one; (45) 1-[4-({[4-(dipropylamino)butyl]amino}methyl)phenyl]-3-pyridin-2-yl-2-(pyridin-2-ylmethyl)propan-1-one; (46) 1-[4-({[4-(dipropylamino)butyl]amino}methyl)phenyl]-3-(1H-imidazol-2-yl)-2-(1H-imidazol-2-ylmethyl)-2-methylpropan-1-one; (47) N-[3-(8-cyclohexyl-2,8-diazaspiro[4.5]dec-2-yl)propyl]-3-(1H-imidazol-2-yl)-2-(1H-imidazol-2-ylmethyl)propanamide; (48) 8-cyclohexyl-2-{3-[3-(1H-imidazol-2-yl)-2-(1H-imidazol-2-ylmethyl)propoxy]propyl}-2,8-diazaspiro[4.5]decane; (49) N-[3-(8-cyclohexyl-2,8-diazaspiro[4.5]dec-2-yl)propyl]-3-(1H-imidazol-2-yl)-2-(1H-imidazol-2-ylmethyl)propan-1-amine; (50) 1-{4-[(8-cyclohexyl-2,8-diazaspiro[4.5]dec-2-yl)methyl]phenyl}-3-(1H-imidazol-2-yl)-2-(1H-imidazol-2-ylmethyl)-2-methylpropan-1-one, salts thereof, N-oxides thereof or solvates thereof or prodrugs thereof.

Examples of more preferable compound include compounds described in Examples, salts thereof, N-oxides thereof or solvates thereof or prodrugs thereof.

Examples of particularly preferable compound include 2-{4-[3-(1H-imidazol-2-yl)-2-(1H-imidazol-2-ylmethyl)propoxy]benzyl}-8-[(3-methyl-2-thienyl)methyl]-2,8-diazaspiro[4.5]decane, N-[3-(1H-imidazol-2-yl)-2-(1H-imidazol-2-ylmethyl)propyl]-N-[4-({8-[(3-methyl-2-thienyl)methyl]-2,8-diazaspiro[4.5]dec-2-yl}methyl)benzyl]acetamide, 8-cyclohexyl-2-{4-[3-(1H-imidazol-2-yl)-2-(1H-imidazol-2-ylmethyl)propyl]benzyl}-2,8-diazaspiro[4.5]decane, 3-({4-[(8-cyclohexyl-2,8-diazaspiro[4.5]dec-2-yl)methyl]benzyl}amino)-2,2-bis(1H-imidazol-2-ylmethyl)-1-propanol, 2-{{4-[(8-cyclohexyl-2,8-diazaspiro[4.5]dec-2-yl)methyl]benzyl}[3-(1H-imidazol-2-yl)-2-(1H-imidazol-2-ylmethyl)propyl]amino}ethanol, N-[2-cyano-3-(1H-imidazol-2-yl)-2-(1H-imidazol-2-ylmethyl)propyl]-N-{4-[(8-cyclohexyl-2,8-diazaspiro[4.5]dec-2-yl)methyl]benzyl}acetamide, N-[3-(1H-imidazol-2-yl)-2-(1H-imidazol-2-ylmethyl)propyl]-4-[(8-isobutyl-2,8-diazaspiro[4.5]dec-2-yl)methyl]benzamide, N-[3-(1H-imidazol-2-yl)-2-(1H-imidazol-2-ylmethyl)propyl]-4-[(8-isobutyl-2,8-diazaspiro[4.5]dec-2-yl)methyl]-N-(2-methoxyethyl)benzamide, N-[3-(1H-imidazol-2-yl)-2-(1H-imidazol-2-ylmethyl)propyl]-4-[(8-isobutyl-2,8-diazaspiro[4.5]dec-2-yl)methyl]-N-[2-(-pyrrolidinyl)ethyl]benzamide, 2-hydroxy-N-[3-(1H-imidazol-2-yl)-2-(1H-imidazol-2-ylmethyl)propyl]-N-{4-[(8-isobutyl-2,8-diazaspiro[4.5]dec-2-yl)methyl]benzyl}acetamide, N-[3-hydroxy-2,2-bis(1H-imidazol-2-ylmethyl)propyl]-N-{4-[(8-isobutyl-2,8-diazaspiro[4.5]dec-2-yl)methyl]benzyl}acetamide, N-[2-(dimethylamino)ethyl]-N-[3-(1H-imidazol-2-yl)-2-(1H-imidazol-2-ylmethyl)propyl]-4-[(8-isobutyl-2,8-diazaspiro[4.5]dec-2-yl)methyl]benzamide, N-(2-acetamidoethyl)-N-[3-(1H-imidazol-2-yl)-2-(1H-imidazol-2-ylmethyl)propyl]-4-[(8-isobutyl-2,8-diazaspiro[4.5]dec-2-yl)methyl]benzamide, N-[3-(1H-imidazol-2-yl)-2-(1H-imidazol-2-ylmethyl)propyl]-4-[(8-isobutyl-2,8-diazaspiro[4.5]dec-2-yl)methyl]-N-[2-(4-morpholinyl)ethyl]benzamide, 3-({4-[(8-cyclohexyl-2,8-diazaspiro[4.5]dec-2-yl)methyl]benzoyl}amino)-2,2-bis(1H-imidazol-2-ylmethyl)propyl acetate, salts thereof, N-oxides thereof or solvates thereof or prodrugs thereof.

[Method for Producing Compound of the Present Invention]

The compound of the present invention represented by formula (I) can be prepared by appropriately improving a known method, for example, methods shown below, methods described in Examples, and a method described in Comprehensive Organic Transformations: A Guide to Functional Group Preparations, Second edition (written by Richard C. Larock, John Wiley & Sons Inc, 1999) and using improved methods in combination. In the following production methods, starting compounds may be used in the form of a salt. As the salt, those described as a salt of the above described formula (I) are used.

Among compounds represented by formula (I) of the present invention, a compound in which G represents $G^A$ and $G^A$ represents a carbon atom substituted with an oxo group, namely, a compound represented by formula (I-A):

(I-A)

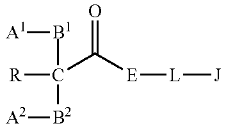

wherein all symbols are as defined above can be produced by subjecting a compound represented by formula (2):

(2)

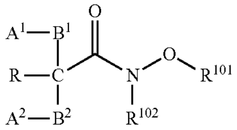

wherein $R^{101}$ and $R^{102}$ represent a C1-8 alkyl group, and other symbols are as defined above or formula (3):

(3)

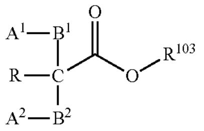

wherein $R^{103}$ represents C1-8 alkyl group, and other symbols are as defined above and a compound represented by formula (4):

M-E-L-J (4)

wherein M represents a metal atom (lithium, magnesium, zinc, etc.), and other symbols are as defined above to a coupling reaction and optionally subjecting to a deprotection reaction of a protective group and/or a cleavage reaction from a resin.

This coupling reaction is known and includes, for example:

(a) a method using an organolithium reagent, (b) a method using a Grignard reagent, and (c) a method using an organozinc reagent.

These methods are specifically described below.

(a) The method using an organolithium reagent is performed, for example, by reacting an aryl halide or an alkyl halide with lithium in an organic solvent (tetrahydrofuran, diethylether, etc.) at −78° C. to a reflux temperature and reacting the obtained lithium reagent, i.e. formula (4) with a compound represented by formula (2) or formula (3) in a solvent (tetrahydrofuran, diethylether, etc.) at −78° C. to a reflux temperature.

(b) The method using a Grignard reagent is performed, for example, by reacting an aryl halide or an alkyl halide with magnesium in an organic solvent (tetrahydrofuran, diethylether, etc.) at −78° C. to a reflux temperature and reacting the resulting Grignard reagent, i.e. formula (4) with a compound represented by formula (2) or formula (3) in a solvent (tetrahydrofuran, diethylether, etc.) at −78° C. to a reflux temperature.

(c) The method using an organozinc reagent is performed, for example, by reacting an aryl halide or an alkyl halide with a zinc reagent (zinc, dimethylzinc, diethylzinc, etc.) in an organic solvent (tetrahydrofuran, diethylether, acetonitrile, dimethylformamide, etc.) at −78° C. to a reflux temperature and reacting the resulting organozinc reagent, i.e. formula (4) with a compound represented by formula (3) in a solvent (tetrahydrofuran, diethylether, acetonitrile, dimethylformamide, etc.) at −78° C. to a reflux temperature.

Any of these reactions (a), (b) and (c) is preferably performed in an inert gas (argon, nitrogen, etc.) atmosphere under anhydrous conditions.

The "C1-8 alkyl group" represented by $R^{101}$, $R^{102}$ and $R^{103}$ here has the same meaning as in the "C1-8 alkyl group" exemplified as for the "aliphatic hydrocarbon group having 1 to 8 carbon atom(s)" in the "aliphatic hydrocarbon group".

The deprotection reaction of a protective group can be carried out by a known method, for example, a method described in Protective Groups in Organic Synthesis (written by T. W. Greene, John Wiley & Sons Inc, 1999). The protective group is not specifically limited as long as it is a group which is described in the above documents or other group that can be deprotected easily and selectively.

If the compound has a moiety to bind to a resin in the molecule and the resin is a polystyrene resin, the compound of the present invention can be cleaved from the resin by the following method. The reaction for cleavage from the resin is known and can be carried out, for example, by reacting in an organic solvent (dichloromethane, 1,2-dichloroethane, toluene, etc.) at 0 to 100° C. using an acid (acetic acid, trifluoroacetic acid, hydrochloric acid, etc.).

If necessary, the procedure of converting into the objective salt may be carried out by a known method after this reaction.

Among the compounds represented by formula (I) of the present invention, a compound wherein G represents $G^A$ and $G^A$ represents $-CH_2-$, namely, a compound represented by formula (I-B):

(I-B)

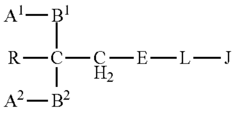

wherein all symbols are as defined above can be produced by subjecting a compound represented by formula (I-A):

(I-A)

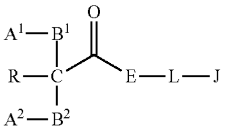

wherein all symbols are as defined above to a reductive reaction and optionally subjecting to a deprotection reaction of a protective group and/or a cleavage reaction from a resin.

This reductive reaction is known and includes, for example:

(a) a reduction with metal and a metal salt, (b) a reduction with a metal halide, (c) a reduction with a metal hydride complex, and (d) a reduction with hydrazine.

The methods are specifically described below.

(a) The method using metal and a metal salt is performed by reacting with metal and a metal salt (lithium, zinc, copper, mercury and a mixture thereof) in an organic solvent (tetrahydrofuran, diethylether, methanol, ammonia, water and a mixture thereof) at −78° C. to a reflux temperature.

(b) The method using a metal halide is performed by reacting with a metal halide (triethylsilane, trichlorosilane, diphenylsilane, etc.) with or without using an organic solvent (dichloromethane, 1,2-dichloroethane, trifluoroacetic acid and a mixture thereof) in the presence or absence of a base (triethylamine, tri-n-propylamine, etc.) at −78° C. to a reflux temperature.

(c) The reaction using a metal hydride complex is performed by reacting with a metal hydride complex (lithium aluminum hydride, lithium aluminum hydride-aluminum trichloride, lithium tri-tert-butoxyaluminum hydride, etc.) in an organic solvent (tetrahydrofuran, diethylether, 1,4-dioxane, etc.) at −78° C. to a reflux temperature.

(d) The method using hydrazine is performed by reacting with hydrazine in a solvent (methanol, ethanol, ethylene glycol, etc.) in the presence of a strong base (sodium methoxide, sodium ethoxide, sodium hydroxide, potassium hydroxide, etc.) at room temperature to a reflux temperature. Any of these reactions (a), (b), (c) and (d) is preferably performed in an inert gas (argon, nitrogen, etc.) atmosphere under anhydrous conditions. Also, the deprotection reaction of a protective group or the cleavage reaction from a resin can be performed by the same method described above.

Among the compounds represented by formula (I) of the present invention, a compound wherein G represents $G^A$, $G^A$ represents —$NR^{104}$— and R represents a hydrogen atom, namely, a compound represented by formula (I-C):

(I-C)

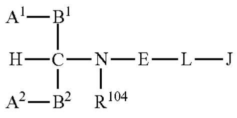

wherein $R^{104}$ represents a C1-8 alkyl group, other symbols are as defined above, provided that the "C1-8 alkyl group" here has the same meaning as in the "C1-8 alkyl group" among the "aliphatic hydrocarbon group having 1 to 8 carbon atom(s)" in the "aliphatic hydrocarbon group", and other symbols are as defined above can be produced by reacting a compound represented by formula (5):

(5)

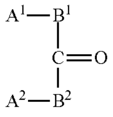

wherein all symbols are as defined above and a compound represented by formula (6):

(6)

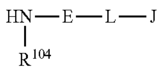

wherein all symbols are as defined above to a reductive amination reaction and optionally subjecting to a deprotection reaction of a protective group and/or a cleavage reaction from a resin. The "C1-8 alkyl group" represented by $R^{104}$ here has the same meaning as in the "C1-8 alkyl group" exemplified as for the "aliphatic hydrocarbon group having 1 to 8 carbon atom(s)" in the above described "aliphatic hydrocarbon group".

This reductive amination reaction is known and is preferably performed in an organic solvent (dichloromethane, 1,2-dichloroethane, dimethylformamide, methanol, ethanol, acetic acid and a mixture thereof) in the presence of a reducing agent (sodium triacetoxyborohydride, sodium cyanoborohydride, sodium borohydride, etc.) at a temperature of 0 to 40° C. The reductive amination reaction is preferably performed in an inert gas (argon, nitrogen, etc.) atmosphere under anhydrous conditions. Also, a deprotection reaction of a protective group and/or a cleavage reaction from a resin can be performed by the same method as described above.

Among compounds represented by formula (I) of the present invention, a compound wherein $A^1$ and $A^2$ represents an imidazol-2-yl group, namely, a compound represented by formula (I-D):

(I-D)

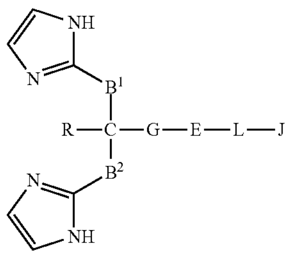

wherein all symbols are as defined above can be produced by subjecting to a cyclization reaction using a compound represented by formula (7):

(7)

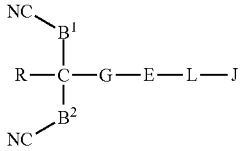

wherein all symbols are as defined above and [2,2-bis(methyloxy)ethyl]amine or [2,2-bis(ethyloxy)ethyl]amine and optionally subjecting to a deprotection reaction of a protective group and/or a cleavage reaction from a resin.

This cyclization reaction is known and can be performed, for example, by improving the method described in Synthesis, 2001, (10), 1546-1550. For example, it is performed by reacting a nitrile compound in an organic solvent (methanol, ethanol, etc.) in the presence of a base (sodium methoxide, sodium ethoxide, etc.) at 0 to 40° C. and then reacting the solution in the presence of acetal and a dehydrating agent (glacial acetic acid) at 40 to 150° C. Also, a deprotection reaction of a protective group or a cleavage reaction from a resin can be performed by the same method as described above.

Among compounds represented by formula (I) of the present invention, a compound wherein G represents $G^{1A}$-$G^{2A}$-$G^{3A}$, $G^{1A}$ is a carbonyl group and $G^{2A}$ is a nitrogen atom which may have a substituent, namely, a compound represented by formula (I-E):

(I-E)

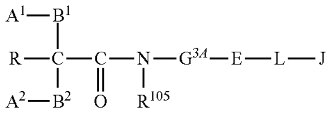

wherein $R^{105}$ has the same meaning as in the "substituent" represented by $G^{2A}$ in the "nitrogen atom which may have a substituent(s)" and other symbols are as defined above can be produced by subjecting a compound represented by formula (8):

(8)

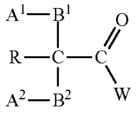

wherein W represents a hydroxyl group or a chlorine atom, and other symbols are as defined above and a compound represented by formula (9):

(9)

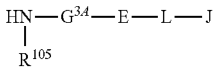

wherein all symbols are as defined above to an amidation reaction and optionally subjecting to a deprotection reaction of a protective group and/or a cleavage reaction from a resin.

This amidation reaction is known and examples thereof include:

(1) a method using an acyl halide, (2) a method using a mixed acid anhydride, and (3) a method using a condensing agent.

These methods are described in detail below.

(1) The method using an acyl halide is carried out, for example, by reacting carboxylic acid with an acid halogenating agent (oxalyl chloride, thionyl chloride, etc.) in an organic solvent (chloroform, dichloromethane, diethylether, tetrahydrofuran, etc.) or in the absence of the solvent at −20° C. to reflux temperature. Then the obtained acyl halide derivative may be with amine in the presence of a base (pyridine, triethylamine, N,N-dimethylaniline, 4-dimethylaminopyridine, diisopropylethylamine, etc.) in an organic solvent (chloroform, dichloromethane, diethylether, tetrahydrofuran, etc.) at 0 to 40° C. Alternatively, the obtained acyl halide can be reacted with amine in an organic solvent (dioxane, tetrahydrofuran, etc.) at 0 to 40° C. using an aqueous alkali solution (sodium bicarbonate water or sodium hydroxide solution, etc.).

(2) The method using a mixed acid anhydride is carried out, for example, by reacting carboxylic acid with an acyl halide (pivaloyl chloride, tosyl chloride, mesyl chloride, etc.) or an acid derivative (ethyl chloroformate, butyl chloroformate, etc.) in the presence of a base (pyridine, triethylamine, N,N-dimethylaniline, 4-dimethylaminopyridine, diisopropylethylamine, etc.) in an organic solvent (chloroform, dichloromethane, diethylether, tetrahydrofuran, etc.) or in the absence of the solvent at 0 to 40° C., and reacting the resulting mixed acid anhydride with amine in an organic solvent (chloroform, dichloromethane, diethylether, tetrahydrofuran, etc.) at 0 to 40° C.

(3) The method using a condensing agent is carried out, for example, by reacting carboxylic acid with amine in an organic solvent (chloroform, dichloromethane, dimethyl formamide, diethylether, tetrahydrofuran, etc.) or in the absence of the solvent at 0 to 40° C. in the presence or absence of a base (pyridine, triethylamine, diisopropylethylamine, N,N-dimethylaniline, N-methylmorpholine, 4-dimethylaminopyridine, etc.), using a condensing agent (1,3-dicyclohexylcarbodiimide (DCC), 1-ethyl-3-[3-(dimethylamino)propyl] carbodiimide (EDC), 1,1'-carbonyldiimidazole (CDI), O-(7-azabenzotriazol-1-yl)N,N,N',N'-tetramethyluronium hexafluorophosphate (HATU), 2-chloro-1-methylpyridiniumiodine, 1-propylphosphonic acid cyclic anhydride (1-propanephosphonic acid cyclic anhydride, PPA), etc.) and using, or not using, 1-hydroxybenztriazole (HOBt) or 1-hydroxy-7-azabenzotriazole (HOAt).

The reactions described in (1), (2) and (3) are preferably carried out under an inert gas (argon, nitrogen, etc.) atmosphere on anhydrous condition.

The deprotection reaction of a protective group can be carried out by the same method as described above.

Among the compounds represented by formula (I) of the present invention, a compound wherein G represents $G^{1A}$-$G^{2A}$-$G^{3A}$, $G^{2A}$ is a nitrogen atom which may have a substituent and $G^{3A}$ is a carbonyl group, namely, a compound represented by formula (I-F):

(I-F)

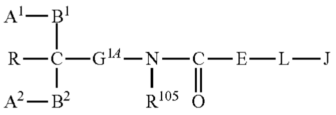

wherein all symbols are as defined above can be produced by subjecting a compound represented by formula (10):

(10)

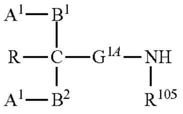

wherein all symbols are as defined above and a compound represented by formula (11):

(11)

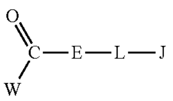

wherein all symbols are as defined above to an amidation reaction and optionally subjecting to a deprotection reaction of a protective group and/or a cleavage reaction from a resin.

The amidation reaction and the deprotection reaction of a protective group can be carried out by the same method as described above.

Among the compounds represented by formula (I) of the present invention, a compound wherein L is a methylene group and J is 2,8-diazaspiro[4.5]decane substituted with $R^1$, namely, a compound represented by formula (I-G):

(I-G)

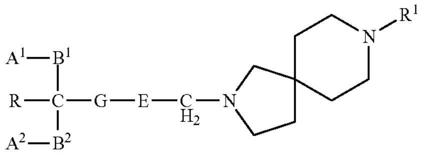

wherein all symbols are as defined above can be produced by subjecting a compound represented by formula (12):

(12)

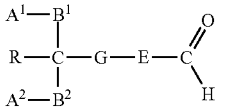

wherein all symbols are as defined above and a compound represented by formula (13):

(13)

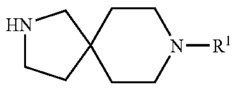

wherein all symbols are as defined above to a reductive amination reaction and optionally subjecting to a deprotection reaction of a protective group and/or a cleavage reaction from a resin.

The amidation reaction and the deprotection reaction of a protective group can be carried out by the same method as described above.

Among the compound of the present invention represented by formula (I), a compound wherein G is $G^{1A}$-$G^{2A}$-$G^{3A}$, both $G^{1A}$ and $G^{2A}$ are a methylene group, and $G^{2A}$ is a nitrogen atom which may have a substituent, namely, a compound represented by formula (I-H):

(I-H)

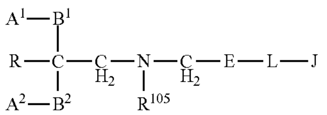

can be prepared by subjecting a compound represented by formula (14):

(14)

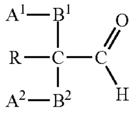

wherein all symbols are as defined above, and a compound represented by formula (15):

(15)

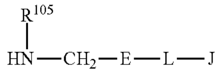

wherein all symbols are as defined above, to the reductive amination reaction, and if necessary to the deprotection reaction of a protective group and/or the cleavage reaction from the resin, or by subjecting a compound represented by formula (16):

(16)

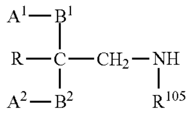

wherein all symbols are as defined above, and a compound represented by formula (17):

(17)

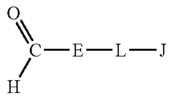

wherein all symbols are as defined above, to the reductive amination reaction, and if necessary to the deprotection reaction of a protective group and/or the cleavage reaction from the resin.

The reductive amination reaction, the deprotection reaction of a protective group, or the cleavage reaction from the resin can be carried out by the same method as described above.

The compounds represented by formulae (2) to (17) used as other starting materials or reagents can be easily prepared by using per se known methods or known methods, for example, methods described in Comprehensive Organic Transformations: A Guide to Functional Group Preparations, Second edition (written by Richard C. Larock, John Wiley & Sons Inc, 1999) in combination.

In the respective reactions in the present specification, as is apparent to those skilled in the art, the reaction with heating can be carried out using a water bath, an oil bath, a sand bath, or microwave.

In the respective reactions in the present specification, a solid phase supported reagent obtained by supporting on a polymer (for example, polystyrene, polyacrylamide, polypropylene, polyethylene glycol, etc.) may be used.

In the respective reactions in the present specification, the reaction product can be purified by conventional purification means, for example, distillation under normal pressure or reduced pressure, high performance liquid chromatography using a silica gel or magnesium silicate, thin layer chromatography, ion-exchange resin, scavenger resin or chromatography or washing, or recrystallization. The purification may be carried out for every reaction, or may be carried out after the completion of some reactions.

In the reaction using a polystyrene resin in the present specification, the reaction product can be purified by conventional purification methods, for example, washing plural times with a solvent (N,N-dimethyl formamide, dichloromethane, methanol, tetrahydrofuran, toluene, acetic acid/toluene, etc.).

[Toxicity]

The compound of the present invention has very low toxicity and is considered to be safe enough for pharmaceutical use.

[Application to Pharmaceuticals]

The compound of the present invention has CXCR4 antagonistic activity in an animal including human, particularly human, and is therefore effective, for example, for a preventive and/or therapeutic agent for inflammatory and immune diseases, allergic diseases, infections, particularly HIV infection, and diseases associated with the infection, psychoneurotic diseases, cerebral diseases, cardiovascular diseases, metabolic diseases, and cancerous diseases. Also, the compound is useful as an agent for regeneration therapy for the purpose of in vitro or in vivo amplification of stem cells for gene therapy as well as peripheral blood stem cells mobilization and tissue repair. The compound is particularly useful as an agent for transplantation medical treatment used in organ transplantation including bone marrow transplantation, peripheral blood stem cell transplantation and tissue repair among in the regeneration therapy. Furthermore, the compound is useful as an antiangiogenic agent that is effective for prevention and/or treatment of diseases associated with neoangiogenesis, such as retinopathy (diabetic retinopathy, aged macular degeneration, glaucoma, etc.) and cancer proliferation.

Examples of the inflammatory and immune disease include rheumatoid arthritis, arthritis, retinopathy, gout, replacement organ rejection, graft-versus-host disease (GVHD), nephritis, psoriasis, rhinitis, conjunctivitis, multiple sclerosis, ulcerative colitis, Crohn's disease, shock associated with bacterial infection, pulmonary fibrosis, systemic inflammatory response syndrome (SIRS), acute lung injury, diabetes and the like.

Examples of the allergic disease include asthma, atopic dermatitis, rhinitis, conjunctivitis and the like.

Examples of the disease associated with infection, particularly HIV infection, include acquired immunodeficiency syndrome (AIDS), candidiasis, *Pneumocystis carinii* pneumonia, Cytomegalovirus retinitis, Kaposi's sarcoma, malignant lymphoma, AIDS encephalopathy, bacterial sepsis and the like.

Examples of the psychoneurotic disease and cerebral disease include dementia including Alzheimer's disease, Parkinson's disease, stroke, cerebral infarction, cerebral hemorrhage, epilepsia, schizophrenia, peripheral nerve disorder and the like.

Examples of the cardiovascular disease include arteriosclerosis, ischemia reperfusion, hypertension, myocardial infarction, stenocardia, heart failure and the like.

Examples of the metabolic diseases include diabetes, osteoporosis, enlarged prostate, frequent micturition and the like.

Examples of the cancerous disease include malignant tumor such as breast cancer or malignant lymphoma, cancer metastasis, myelosuppression or thrombocytopenia after radiation therapy/chemotherapy and the like.

The compound of the present invention may be administered as a concomitant drug by using in combination with other drugs for the purpose of:

1) complementation and/or enhancement of the preventive and/or therapeutic effects of the compound,
2) improvement of pharmacokinetics and absorption of the compound and reduction of the dosage, and/or
3) reduction of side effects of the compound.

Also, other drugs may be administered as a concomitant drug by using in combination with the compound of the present invention the purpose of (1) complementation and/or enhancement of preventive and/or therapeutic effects, (2) improvement of pharmacokinetics and absorption of the compound and reduction of the dosage, and/or (3) reduction of side effects.

The concomitant drug of the compound of the present invention and other drugs may be administered in the form of a compounding agent(s) comprising both these components, or may be in the form of separately. In case of separately administering a preparation, simultaneous administration and administration with time-lag are included. In case of administration with time-lag, other drugs may be administered after the compound of the present invention is administered, or the compound of the present invention may be administered after other drugs may be administered. The administration method may be the same or different.

The disease, on which the preventive and/or therapeutic effects are exerted by the concomitant drug, is not specifically limited, and may be any disease which complements and/or enhances the preventive and/or therapeutic effects of the compound of the present invention.

A mass ratio of the compound of the present invention drug to other drugs is not specifically limited.

A combination of any two or more kinds other drugs may be administered.

The other drugs, which complements and/or enhances the preventive and/or therapeutic effects of the compound of the present invention, includes not only those which have ever been found based on the above described mechanism, but also those which may be found in future.

Examples of the preventive and/or therapeutic agents for HIV infection and acquired immunodeficiency syndrome, which is used in combination of the compound of the present invention, include reverse transcriptase inhibitors, protease inhibitors, chemokine (for example, CCR2, CCR3, CCR4, CCR5, CXCR4, etc.) antagonists, CD4 antagonists, antibody against surface antigen of HIV (for example, HIV-1, HIV-2, etc.), vaccine of HIV (for example, HIV-1, HIV-2, etc.), short-interfering RNAs targeting a HIV-related factor and the like.

Examples of the reverse transcriptase inhibitors include (1) nucleoside reverse transcriptase inhibitors such as zidovudine (trade name: Retrovir), didanosine (trade name: Videx), zalcitabine (trade name: Hivid), stavudine (trade name: Zerit), lamivudine (trade name: Epivir), abacavir (trade name: Ziagen), didanosine (trade name: videx), adefovir, dipivoxil, emtricitabine (trade name: coviracil), tenofovir (trade name: viread), Combivir, Trizivir, truvada, epzicom, and the like, (2) non-nucleoside reverse transcriptase inhibitors such as nevirapine (trade name: viramune), delavirdine (trade name: Rescriptor), efavirenz (trade name: Sustiva, Stocrin), capravirine (AG1549), and the like.

Examples of the protease inhibitors include indinavir (trade name: Kurikisiban), ritonavir (trade name: norvir), nelfinavir (trade name: Viracept), saquinavir (trade name: Invirase, Fortovase), amprenavir (trade name: agenerase), lopinavir (trade name: Kaletra), atazanavir (trade name: Reyataz), fosamprenavir (trade name: lexiva), tipranavir and the like.

Examples of the chemokine antagonists include endogenous ligands of a chemokine receptor, or derivatives and nonpeptidic low molecular compounds thereof, an antibody against a chemokine receptor and the like.

Examples of the endogenous ligands of the chemokine receptor include MIP-1$\alpha$, MIP-1$\beta$, RANTES, SDF-1$\alpha$, SDF-1$\beta$, MCP-1, MCP-2, MCP-4, eotaxin, MDC and the like.

Examples of the derivative of the endogenous ligands include AOP-RANTES, Met-SDF-1α, Met-SDF-1β and the like.

Examples of the antibody of the chemokine receptor include Pro-140 and the like.

Examples of the CCR2 antagonists include compounds described in WO99/07351, WO99/40913, WO00/46195, WO00/46196, WO00/46197, WO00/46198, WO00/46199, WO00/69432, WO00/69815, and Bioorg. Med. Chem. Lett., 10, 1803 (2000), and the like.

Examples of the CCR3 antagonists include compounds described in DE19837386, WO99/55324, WO99/55330, WO00/04003, WO00/27800, WO00/27835, WO00/27843, WO00/29377, WO00/31032, WO00/31033, WO00/34278, WO00/35449, WO00/35451, WO00/35452, WO00/35453, WO00/35454, WO00/35876, WO00/35877, WO00/41685, WO00/51607, WO00/51608, WO00/51609, WO00/51610, WO00/53172, WO00/53600, WO00/58305, WO00/59497, WO00/59498, WO00/59502, WO00/59503, WO00/62814, WO00/73327, and WO01/09088, and the like.

Examples of the CCR4 antagonists include compounds described in WO02/030357 and WO02/030358, and the like.

Examples of the CCR5 antagonists include compounds described in WO99/17773, WO99/32100, WO00/06085, WO00/06146, WO00/10965, WO00/06153, WO00/21916, WO00/37455, EP1013276, WO00/38680, WO00/39125, WO00/40239, WO00/42045, WO00/53175, WO00/42852, WO00/66551, WO00/66558, WO00/66559, WO00/66141, WO00/68203, JP2000-309598, WO00/51607, WO00/51608, WO00/51609, WO00/51610, WO00/56729, WO00/59497, WO00/59498, WO00/59502, WO00/59503, WO00/76933, WO98/25605, WO99/04794, WO99/38514 and Bioorg. Med. Chem. Lett., 10, 1803 (2000), TAK-779, SCH-351125 (SCH-C), SCH-417690 (SCH-D), UK-427857, GW 873140A (ONO-4128), TAK-220, TAK-652, and the like.

Examples of the CXCR4 antagonists include AMD-3100, AMD-070, T-22, KRH-1120, KRH-1636, KRH-2731, CS-3955, and compounds described in WO00/66112, WO2004/024697, WO2004/052862, EP01493438, JP2002-371042, JP2004-196769, US2004/0132642, US2005/0192272, US2005/0215543, US2005/0215544, US2005/0215545, WO99/36091, WO02/094261, WO02/096397, WO03/029218, WO03079020, WO2004/020462, WO2004/024178, WO2004/024697, WO2004/054603, WO2004/059285, WO2004/087068, WO2004/093817, WO2004/096838, WO2004/096839, WO2004/096840, WO2005/002522, WO2005/002551, WO2005/025565, WO2005/085209, WO2005/085219, WO2006/020415, WO2006/022454, WO2006/023400, WO2006/039252, and the like.

Examples of the fusion inhibitors include T-20 (pentafuside) T-1249, and the like.

Examples of the HIV integrase inhibitors include Equisetin, Temacrazine, PL-2500, V-165, NSC-618929, L-870810, L-708906 analog, S-1360, 1838 and the like.

The Short Interfering short-interfering RNAs targeting a HIV-related factor include those which target a gene of a HIV-related factor. Examples of the HIV-related factors include reverse transcriptase, protease, chemokine (CCR2, CCR3, CCR4, CCR5, CXCR4, etc.), CD4, HIV (HIV1, HIV2, etc.) and the like.

The conventional clinical dosage of typical reverse transcriptase inhibitors and protease inhibitors is, for example, as described below, but is not limited thereto in the present invention.

Zidovudine: 100 mg capsule, three times per day in a dosage of 200 mg;
300 mg tablet, twice per day in a dosage of 300 mg;
Didanosine: 25 to 200 mg tablet, twice per day in a dosage of 125 to 200 mg;
Zalcitabine: 0.375 mg to 0.75 mg tablet, three times per day in a dosage of 0.75 mg;
Stavudine: 15 to 40 mg capsule, twice per day in a dosage of 30 to 40 mg;
Lamivudine: 150 mg tablet, twice per day in a dosage of 150 mg;
Abacavir: 300 mg tablet, twice per day in a dosage of 300 mg;
Nevirapine: 200 mg tablet, once per day for 14 days in a dosage of 200 mg, followed by twice per day;
Delavirdine: 100 mg tablet, three times per day in a dosage of 400 mg;
Efavirenz: 50 to 200 mg capsule, once per day in a dosage of 600 mg;
Indinavir: 200 to 400 mg capsule, three times per day in a dosage of 800 mg;
Ritonavir: 100 mg capsule, twice per day in a dosage of 600 mg;
Nelfinavir: 250 mg tablet, three times per day in a dosage of 750 mg;
Saquinavir: 200 mg capsule, three times per day in a dosage of 1,200 mg;
Amprenavir: 50 to 150 mg tablet, twice per day in a dosage of 1,200 mg.

Examples of the other drugs for complementation and/or enhancement of the preventive and/or therapeutic effects of the compound of the present invention against asthma include antihistaminic agents, antiallergic agents (chemical mediator release inhibitors, histamine antagonists, thromboxane synthetase inhibitors, thromboxane antagonists, Th2 cytokine inhibitors), steroids, bronchodilator agents (xanthine derivatives, sympathomimetic agents, parasympathomimetic agents), vaccinotherapeutic agents, gold preparations, Chinese medicines, basic nonsteroidal anti-inflammatory drugs, 5-lipoxygenase inhibitors, 5-lipoxygenase activation protein antagonists, leukotriene synthesis inhibitors, prostaglandins, cannabinoid-2 receptor stimulants, antitussive drugs, expectorants, and the like.

Examples of the antihistaminic agents include diphenhydramine, diphenylpyraline hydrochloride, diphenylpyraline chlorotheophyllinate, clemastine fumarate, dimenhydrinate, dl-chlorpheniramine maleate, d-chlorpheniramine maleate, triprolidine hydrochloride, promethazine hydrochloride, alimemazine tartrate, isothipendyl hydrochloride, homochlorcyclizine hydrochloride, hydroxyzine, cyproheptadine hydrochloride, levocabastine hydrochloride, astemizole, bepotastine, desloratadine, TAK-427, ZCR-2060, NIP-530, mometasone furoate, mizolastine, BP-294, andolast, auranofin, acrivastine and the like.

Examples of the chemical mediator release inhibitors include disodium cromoglycate, tranilast, amlexanox, repirinast, ibudilast, pemirolast potassium, tazanolast, nedocromil, cromoglicate, israpafant and the like.

Examples of the histamine antagonists include ketotifen fumarate, azelastine hydrochloride, oxatomide, mequitazine, terfenadine, emedastine fumarate, epinastine hydrochloride, ebastine, cetirizine hydrochloride, olopatadine hydrochloride, loratadine, fexofenadine and the like.

Examples of the thromboxane synthetase inhibitors include ozagrel hydrochloride imitrodast sodium and the like.

Examples of the thromboxane antagonists include seratrodast, ramatroban, domitroban calcium hydrate, KT-2-962 and the like.

Examples of the Th2 cytokine inhibitors include suplatast tosilate and the like.

Examples of the steroids include, for example, external medicine such as clobetasol propionate, diflorasone diacetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclometasone dipropionate, triamcinolone acetonide, flumetasone pivalate, alclometasone propionate, clobetasone butyrate, prednisolone, beclomethasone propionate, fludroxycortide, and the like; internal use and injections such as cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methyl prednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone and the like; and inhalations such as beclometasone dipropionate, fluticasone propionate, budesonide, flunisolide, triamcinolone, ST-126P, ciclesonide, dexamethasone palmitate, mometasone furoate, prasterone sulfonate, deflazacort, methylprednisolone suleptanate, methylprednisolone sodium succinate and the like.

Examples of the xanthine derivative include aminophylline, theophylline, doxophylline, cipamfylline, diprophylline, proxyphylline, and choline theophylline.

Examples of the sympathomimetic agents include epinephrine, ephedrine hydrochloride, dl-methylephedrine hydrochloride, methoxyphenamine hydrochloride, isoproterenol sulfate, isoproterenol hydrochloride, orciprenaline sulfate, chloroprenaline hydrochloride, trimetoquinol hydrochloride, salbutamol sulfate, terbutaline sulfate, hexoprenaline sulfate, tulobuterol hydrochloride, procaterol hydrochloride, fenoterol hydrobromate, formoterol fumarate, clenbuterol hydrochloride, mabuterol hydrochloride, salmeterol xinafoate, R,R-formoterol, tulobuterol, pirbuterol hydrochloride, ritodrine hydrochloride, bambuterol, dopexamine hydrochloride, meluadrine tartrate, AR-C68397, levosalbutamol, KU R-1246, KUL-7211, AR-C89855, S-1319 and the like.

Examples of the parasympathomimetic agents include ipratropium bromide, flutropium bromide, oxitropium bromide, cimetropium bromide, temiverine, tiotropium bromide, revatropate (UK-112166) and the like.

Examples of the vaccinotherapeutic agents include paspat, asthremedin, Broncasma Berna, CS-560 and the like.

Examples of the gold preparations include gold sodium thiomalate and the like.

Examples of the basic nonsteroidal anti-inflammatory drugs include tiaramide hydrochloride, tinoridine hydrochloride, epirizole, emorfazone and the like.

Examples of the 5-lipoxygenase inhibitors include zyleuton, docebenone, piriprost, SCH-40120, WY-50295, E-6700, ML-3000, TMK-688, ZD-2138, dalbufelone mesilate, R-68151, E-6080, DuP-654, SC-45662, CV-6504, NE-11740, CMI-977, NC-2000, E-3040, PD-136095, CMI-392, TZI-41078, Orf-20485, IDB-18024, BF-389, A-78773, TA-270, FLM-5011, CGS-23885, A-79175, ETH-615 and the like.

Examples of the 5-lipoxygenase activation protein antagonists include MK-591, MK-886 and the like.

Examples of the leukotriene synthesis inhibitors include auranofin, proglumetacin maleate, L-674636, A-81834, UPA-780, A-93178, MK-886, REV-5901A, SCH-40120, MK-591, Bay-x-1005, Bay-y-1015, DTI-0026, Amlexanox, E-6700 and the like.

Examples of the prostaglandins (hereinafter abbreviated to as PG) include PG receptor agonists, PG receptor antagonists and the like.

Examples of the PG receptor include PGE receptor (EP1, EP2, EP3, and EP4), PGD receptor (DP, CRTH2), PGF receptor (FP), PGI receptor (IP), TX receptor (TP) and the like.

Examples of the antitussive drugs include codeine phosphate, dihydrocodeine phosphate, oxymetebanol, dextromethorphan hydrobromate, pentoxyverine citrate, dimemorfan phosphate, oxeladin citrate, cloperastine, benproperine phosphate, clofedanol hydrochloride, fominoben hydrochloride, noscapine, tipepidine hibenzate, eprazinone hydrochloride, *plantago* herb extract and the like.

Examples of the expectorants include foeniculated ammonia spirit, sodium hydrogencarbonate, potassium iodide, bromhexine hydrochloride, cherry bark extract, carbocysteine, fudosteine, ambroxol hydrochloride, ambroxol hydrochloride sustained-release tablet, methylcysteine hydrochloride, acetylcysteine, L-ethylcysteine hydrochloride, tyloxapol and the like.

Examples of the other drugs for complementation and/or enhancement of the preventive and/or therapeutic effects against atopic dermatitis (urticaria, etc.) of the compound of the present invention include steroids, non-steroid anti-inflammatory drug (NSAID), immune inhibitor, prostaglandins, antiallergic agent, mediator release inhibitor, antihistaminic agent, forskolin preparation, phosphodiesterase inhibitor, and cannabinoid-2 receptor stimulant.

Examples of the other drugs for complementation and/or enhancement of the preventive and/or therapeutic effects against allergic diseases (allergic bronchopulmonary aspergillosis, allergic eoisinophilic gastroenteritis, etc.) of the compound of the present invention include antiasthmatic drug, inhaled steriod drug, inhaled β2 stimulant, methylxanthine-based stimulant, antiallergic agent, anti-inflammatory agent, anticholinergic agent, thromboxane antagonist, leukotriene antagonist, LTD4 antagonist, PAF antagonist, phosphodiesterase inhibitor, β2 agonist, steroid drug, mediator release inhibitor, eosinophile leukocytechemotaxis inhibitor, macrolide-based antibiotic, immune inhibitor, hyposensitization (allergen) injection and the like.

Examples of the antiasthmatic drug include theophylline, procaterol, ketotifen, azelastine and the like.

Examples of the inhaled steriod drug include beclomethasone, fluticasone, budesonide and the like.

Examples of the inhaled β2 stimulant include fenoterol, s albutamol, formoterol, salmeterol and the like.

Examples of the methylxanthine-based stimulant include theophylline and the like.

Examples of the antiallergic agent include ketotifen, terfenadine, azelastine, epinastine, suplatast, disodium cromoglycate and the like.

Examples of the anti-inflammatory agent include dichlofenac sodium, ibuprofen, indomethacin and the like.

Examples of the anticholinergic agent include ipratropium bromide, flutropium bromide, oxitropium bromide, tiotropium bromide and the like.

Examples of the thromboxane antagonists include ozagrel hydrochloride imitrodast sodium and the like.

Examples of the leukotriene antagonist include pranlukast, montelukast, zafirlukast, zyleuton and the like.

Examples of the macrolide-based antibiotic include erythromycin, roxithromycin and the like.

Examples of the immune inhibitor include cyclosporine, tacrolimus, FTY720, and the like.

Examples of the other drug for complementation and/or enhancement of the preventive and/or therapeutic effects against hepatitis of the compound of the present invention include liver hydrolysate preparation, polyenephosphatidylcholine, glycyrrhizin preparation, protoporphyrin sodium, ursodeoxycholic acid, steroids, anticholinergic agent, gastric antiacid, propagermanium, lipid peroxidase inhibitor, and mitochondrial benzodiazepine receptor antagonist.

Examples of the other drug for complementation and/or enhancement of the preventive and/or therapeutic effects against arthritis and rheumatoid arthritis of the compound of the present invention include metalloproteinase inhibitor, immune inhibitor, non-steroid anti-inflammatory drug (NSAID), steroid drug, prostaglandins, phosphodiesterase inhibitor, cannabinoid-2 receptor stimulant, disease modifying anti-rheumatic drug (slow-acting anti-rheumatic drug), anti-inflammatory enzyme preparation, cartilage protective agent, T cell inhibitor, TNFα inhibitor, prostaglandin synthetase inhibitor, IL-6 inhibitor, interferon γ agonist, IL-1 inhibitor and the like.

Examples of the other drug for complementation and/or enhancement of the preventive and/or therapeutic effects against psoriasis of the compound of the present invention include steroid drug, vitamin D derivative and the like.

Examples of the other drug for complementation and/or enhancement of the preventive and/or therapeutic effects against conjunctivitis of the compound of the present invention include leukotriene receptor antagonist, antihistaminic agent, mediator release inhibitor, non-steroid anti-inflammatory drug, prostaglandins, steroid drug, nitrogen monoxide synthetase inhibitor, cannabinoid-2 receptor stimulant and the like.

Examples of the other drug for complementation and/or enhancement of the preventive and/or therapeutic effects against multiple sclerosis of the compound of the present invention include immune inhibitor, cannabinoid-2 receptor stimulant and the like.

Examples of the other drug for complementation and/or enhancement of the preventive and/or therapeutic effects against multiple sclerosis of the compound of the present invention include immune inhibitor, cannabinoid-2 receptor stimulant and the like.

Examples of the other drug for complementation and/or enhancement of the preventive and/or therapeutic effects against ulcerative colitis of the compound of the present invention include mesalazine, salazosulfapyridine, digestive tract ulcer therapeutic substance, anticholinergic agent, steroid drug, 5-lipoxygenase inhibitor, antioxidant, LTB4 antagonist, local anesthetic, immune inhibitor, protection factor enhancer, MMP inhibitor, and mitochondrial benzodiazepine receptor antagonist.

Examples of the other drug for complementation and/or enhancement of the preventive and/or therapeutic effects against diabetic complication of the compound of the present invention include sulfonyl urea-based hypoglycemic agent, biguanide-based drug, α-glucosidase inhibitor, ultrashort-acting insulinotropic agent, insulin drug, PPAR agonist, insulin sensitive enhancer having no PPAR antagonism, β3 adrenalin receptor agonist, aldose reductase inhibitor, dipeptidyl peptidase IV inhibitor and the like.

Examples of the sulfonyl urea-based hypoglycemic agent include acetohexamide, glibenclamide, gliclazide, glyclopyramide, chlorpropamide, tolazamide, tolbutamide, Glimepiride and the like.

Examples of the biguanide-based drug include buformin hydrochloride, metformin hydrochloride and the like.

Examples of the α-glucosidase inhibitor include acarbose, voglibose and the like.

Examples of the ultrashort-acting insulinotropic agent include nateglinide, repaglinide and the like.

Examples of the PPAR agonist include pioglitazone, troglitazone, rosiglitazone, JTT-501, and the like.

Examples of the insulin sensitive enhancer having no PPAR antagonism include ONO-5816, YM-440 and the like.

Examples of the β3 adrenalin receptor agonist include AJ9677, L750355, CP331648 and the like.

Examples of the aldose reductase inhibitor include epalrestat, fidarestat, zenarestat and the like.

Examples of the other drug for complementation and/or enhancement of the preventive and/or therapeutic effects against cancer (malignant tumor) and cancer metastasis of the compound of the present invention include anticancer agent (for example, MMP inhibitor, alkylation agent (for example, cyclophosphamide, melphalan, thiotepa, mytomycin C, busulfan, procarbazine hydrochloride, etc.), antimetabolite (for example, methotrexate, mercaptpurine, azathiopurine, fluorouracil, tegafur, cytarabine, azaserine, etc.), antibiotic (for example, mytomycin C, bleomycin, Peplomycin, doxorubicin hydrochloride, aclarubicin, daunorubicin, actinomycin D, etc.), mitosis inhibitor, platinum complex (for example, Cisplatin), plant-derived antineoplastic agent (for example, vincristine sulfate, vinblastine sulfate, etc.), anticancerous hormone (for example, methyltestosterone, testosterone propionate, testosterone enanthate, mepitiostane, fosfestrol, chlormadinone acetate, etc.), immunopotentiator (for example, picibanil, krestin, etc.), and interferon (for example, IFNα, IFNα-2a, IFNα-2b, IFNβ, IFNγ-1a, etc.). Examples thereof include biologics capable of conducting T cell activation (for example, anti-CTLA-4 antibody, anti-PD-1 antibody, etc.), antiangiogenic agent (for example, bevacizumab, pegaptanib, SU-6668, vatalanib, ranibizumab, sorafenib, SU-11248, neovastat), etc.), and the like.

Examples of the other drug for complementation and/or enhancement of the preventive and/or therapeutic effects against immune disease (for example, autoimmune disease, rejection of transplanted organ, etc.) of the compound of the present invention include immune inhibitor (for example, cyclosporine, tacrolimus, FTY720, etc.) and the like.

Examples of the other drug for complementation and/or enhancement of the preventive and/or therapeutic effects against dementia such as Senile dementia with Alzheimer's type of the compound of the present invention include acetylcholine esterase inhibitor, nicotinic receptor modifier, cerebral ameliorator, monoamineoxidase inhibitor, vitamin E, aldose reductase inhibitor and the like.

Examples of the other drug for complementation and/or enhancement of the preventive and/or therapeutic effects against epilepsia of the compound of the present invention include phenyloin, trimethadione, ethosuximide, carbamazepine, phenobarbitone, primidone, acetazolamide, sultiame, sodium valproate, clonazepam, diazepam, nitrazepam and the like.

Examples of the other drug for complementation and/or enhancement of the preventive and/or therapeutic effects against arteriosclerosis of the compound of the present invention include HMG-COA reductase inhibitor, fibrates, probucol preparation, anion-exchange resin, EPA preparation, nicotinic acid preparation, MTP inhibitor, other anti-high cholesterol agent, EDG-2 antagonist and the like.

Examples of the other drug for complementation and/or enhancement of the effects when the compound of the present invention is used in a regeneration therapy include cytokines and various growth factors, for example, various CSFs (for example, G-CSF, GM-CSF, etc.), various interleukins (for example, IL-3, 6, 7, 11, 12, etc.), EPO, TPO, SCF, FLT3 ligand, MIP-1α and the like.

Examples of the other drug for complementation and/or enhancement of the preventive and/or therapeutic effects against retinopathy of the compound of the present invention include antiangiogenic agent (for example, bevacizumab, pegaptanib, SU-6668, vatalanib, ranibizumab, sorafenib, SU-11248, neovastat, etc.) and the like.

The compound of the present invention is safe and has low toxicity and therefore can be administered to human and mammal other than human (for example, rat, mouse, rabbit, sheep, pig, cow, cat, dog, monkey, etc.).

In order to use a pharmaceutical composition comprising the compound of the present invention or a concomitant drug of the compound of the present invention and other drugs, it is commonly administered, systematically or locally, in an oral or parenteral dosage form.

The dosage of the pharmaceutical preparation varies depending on the age, body weight, symptom, the desired therapeutic effect, the route of administration and duration of treatment. For the human adult, the dosage per person is between 1 ng and 1000 mg, by oral administration, up to several times per day, between 0.1 ng and 100 mg, by parenteral administration, or continuous administration 1 hour to 24 hours per day from vein.

As mentioned above, the doses to be used depend upon various conditions. Therefore, there are cases in which doses lower than or greater than the ranges specified above may be used.

In case of administering a pharmaceutical composition comprising the compound of the present invention, or a concomitant drug of the compound of the present invention and other drugs, it is used as solid preparations for internal use and solutions for internal use for oral administration, and injections, external preparations, suppositories, ophthalmic solutions, nasal drops, inhalants for parenteral administration and the like.

Examples of the solid preparation for internal use for oral administration include tablets, pills, capsules, powders, and granules. Capsules include hard capsules and soft capsules.

In such a solid preparation for internal use, one or more active substances are used as they are, or used after mixing with excipients (lactose, mannitol, glucose, microcrystalline cellulose, starch, etc.), binders (hydroxypropyl cellulose, polyvinyl pyrrolidone, magnesium aluminometasilicate, etc.), disintegrants (calcium carboxymethyl cellulose, etc.), lubricants (magnesium stearate, etc.), stabilizers and solubilizing agents (glutamic acid, aspartic acid, etc.) and forming into a preparation according to a conventional method. If necessary, the preparation may be coated with a coating agent (saccharose, gelatin, hydroxypropyl cellulose, hydroxypropylmethyl cellulosephthalate, etc.) or may be coated with two or more layers. Furthermore, capsules made of an absorbable substance such as gelatin is included.

The solutions for internal use for oral administration include pharmaceutically acceptable water, suspensions, emulsions, syrups, and elixirs. In such a solution, one or more active substances are dissolved, suspended or emulsified in a diluent used commonly (purified water, ethanol, mixed solution thereof, etc.). Furthermore, this solution may contain humectants, suspending agents, emulsifiers, sweeteners, flavors, aromatics, preservatives, buffers, and the like.

The dosage form of the external preparation for parenteral administration includes, for example, ointment, gel, cream, fomentation, patch, liniment, propellant, inhalant, spray, aerosol, ophthalmic solution, and nasal drop. These products contain one or more active substances and are prepared according to the formulation which is known or commonly used.

An ointment is prepared in accordance with a well known formulation or a commonly employed formulation. For example, it is prepared by triturating or dissolving one or more active substances in a base. An ointment base is selected from well known ones or those commonly employed. For example, those selected from higher fatty acids or higher fatty acid esters (adipic acid, myristic acid, palmitic acid, stearic acid, oleic acid, adipate ester, myristate ester, palmitate ester, stearate ester, oleate ester, etc.), waxes (beeswax, whale wax, ceresin, etc.), surfactants (polyoxyethylene alkyl ether phosphate ester, etc.), higher alcohols (cetanol, stearyl alcohol, cetostearyl alcohol, etc.), silicone oils (dimethylpolysiloxane, etc.), hydrocarbons (hydrophilic petrolatum, white petrolatum, purified lanolin, liquid paraffin, etc.), glycols (ethylene glycol, diethylene glycol, propylene glycol, polyethylene glycol, macrogol, etc.), vegetable oils (castor oil, olive oil, sesame oil, turpentine oil, etc.), animal oils (mink oil, egg yolk oil, squalane, squalene, etc.), water, absorption accelerators, agents for preventing contact dermatitis are used alone or in combination. Furthermore, it may contain humectants, preservatives, stabilizers, antioxidizing agents, flavors, and the like.

A gel is prepared according to the formulation which is known or commonly used. For example, it is prepared by dissolving one or more active substances in a base. A gel base is selected from a base which is known or commonly used. For example, those selected from lower alcohols (ethanol, isopropyl alcohol, etc.), gelling agents (carboxymethyl cellulose, hydroxyethyl cellulose, hydroxypropyl cellulose, ethyl cellulose, etc.), neutralizers (triethanolamine, diisopropanolamine, etc.), surfactants (monostearic acid polyethylene glycol, etc.), gums, water, absorption accelerator, and agent for preventing contact dermatitis are used alone or in combination. Furthermore, it may contain preservatives, antioxidizing agents, flavoring agent and the like.

A cream is prepared according to the formulation which is known or commonly used. For example, it is prepared by dissolving or emulsifying one or more active substances in a base. A cream base is selected from a base which is known or commonly used. For example, those selected from higher fatty acid esters, lower alcohols, hydrocarbons, polyhydric alcohols (propylene glycol, 1,3-butylene glycol, etc.), higher alcohols (2-hexyl decanol, cetanol, etc.), emulsifiers (polyoxyethylene alkyl ethers, fatty acid esters, etc.), water, absorption accelerators, and agents for preventing contact dermatitis are used alone or in combination. Furthermore, it may contain preservatives, antioxidizing agents, flavoring agent and the like.

A fomentation is prepared according to the formulation which is known or commonly used. For example, it is prepared by dissolving one or more active substances in a base to obtain a kneaded mixture and spreading the kneaded mixture over a substrate. A fomentation base is selected from a base which is known or commonly used. For example, those selected from thickeners (polyacrylic acid, polyvinyl pyrrolidone, gum arabic, starch, gelatin, methyl cellulose, etc.), humectants (urea, glycerin, propylene glycol, etc.), fillers (kaolin, zinc oxide, talc, calcium, magnesium, etc.), water, solubilizing agents, tackifiers, and agents for preventing contact dermatitis are used alone or in combination. Furthermore, it may contain preservatives, antioxidizing agents, flavoring agent and the like.

A patch is prepared according to the formulation which is known or commonly used. For example, it is prepared by dissolving one or more active substances in a base, and spreading the solution over a substrate. A patch base is selected from a base which is known or commonly used. For example, those selected from polymer bases, fats and oils, higher fatty acids, tackifiers, and agents for preventing contact dermatitis are used alone or in combination. Furthermore, it may contain preservatives, antioxidizing agents, flavoring agent and the like.

A liniment is prepared according to the formulation which is known or commonly used. For example, it is prepared by dissolving, suspending or emulsifying one or more active substances in one or more kinds selected from water, alcohol (ethanol, polyethylene glycol, etc.), higher fatty acid, glycerin, soap, emulsifier, and suspending agent. Furthermore, it may contain preservatives, antioxidizing agents, flavoring agent and the like.

A propellant, an inhalant, and a spray may contain, in addition to a diluent used commonly, a stabilizer such as sodium hydrogensulfite and a buffer capable of imparting isotonicity, for example, an isotonicity such as sodium chloride, sodium citrate or citric acid. The method for producing a spray is described in detail in U.S. Pat. Nos. 2,868,691 and 3,095,355.

An injection for parenteral administration includes all injections and also includes a drop. For example, it includes intramuscular injection, subcutaneous injection, endodermic injection, intraarterial injection, intravenous injection, intraperitoneal injection, intraspinal injection, and intravenous drop.

The injection for parenteral administration includes solutions, suspensions, emulsions, and solid injections used by dissolving or suspending in a solvent before use. The injection is used after dissolving, suspending, or emulsifying one or more active substances in a solvent. As the solvent, for example, distilled water for injection, physiological saline, vegetable oil, and alcohols such as propylene glycol, polyethylene glycol or ethanol are used alone or in combination. Furthermore, the injection may contain stabilizers, solubilizing agents (glutamic acid, aspartic acid, polysolvate 80®, etc.), suspending agents, emulsifiers, soothing agents, buffers, and preservatives. These injections are prepared by sterilizing in the final process, or prepared by an aseptic treatment. Also, a sterile solid, for example, a freeze-dried product is prepared and can be used after dissolving in sterilized distilled water or distilled water for sterile injection, or the other solvent before use.

An ophthalmic solution for parenteral administration includes ophthalmic solution, suspension type ophthalmic solution, emulsion type ophthalmic solution, ophthalmic solution soluble when used, and eye ointment.

These ophthalmic solutions are prepared according to a known method. For example, one or more active substances are dissolved, suspended or emulsified in a solvent before use. As the solvent for ophthalmic solution, for example, sterilized purified water, physiological saline, and other aqueous solvent or non-aqueous agent for injection (for example, vegetable oil, etc.) are used alone or in combination. If necessary, the ophthalmic solution may contain appropriately selected isotonizing agents (sodium chloride, concentrated glycerin, etc.), buffering agents (sodium phosphate, sodium acetate, etc.), surfactants (polysolvate 80 (trade name), polyoxyl 40 stearate, polyoxyethylene hardened castor oil, etc.), stabilizers (sodium citrate, sodium edetate, etc.), and antiseptics (benzalkonium chloride, paraben, etc.) These ophthalmic solutions are prepared by sterilizing in the final process, or prepared by an aseptic treatment. Also, a sterile solid, for example, a freeze-dried product is prepared and can be used after dissolving in sterilized distilled water or distilled water for sterile injection, or the other solvent before use.

An inhalant for parenteral administration includes aerozol, inhalation powder, and inhalation solution, and the inhalation solution may be such a configuration that it is used after dissolving in water or other suitable medium at the point of use.

These inhalants are prepared according to a known method.

For example, an inhalation solution is prepared by appropriately selecting antiseptics (benzalkonium chloride, paraben, etc.), colorants, buffering agents (sodium phosphate, sodium acetate, etc.), isotonizing agents (sodium chloride, concentrated glycerin, etc.), thickeners (carboxyvinyl polymer, etc.), and absorption accelerator, if necessary.

An inhalation powder is prepared by appropriately selecting lubricants (stearic acid and a salt thereof, etc.), binders (starch, dextrin, etc.), excipients (lactose, cellulose, etc.), colorants, antiseptics (benzalkonium chloride, paraben, etc.), and absorption accelerator if necessary.

In case of administering the inhalation solution, a spraying apparatus (atomizer, nebulizer) is commonly used. In case of administering the inhalation powder, an inhalation administration apparatus for powder is commonly used.

The other composition for parenteral administration includes suppositories for intrarectal injection and pessaries for vaginal administration, which contain one or more active substances and are formulate by a conventional method.

Designation of the compound of the present invention is described below.

The compounds used in the present invention were commonly designated using a computer program ACD/Name Batch® (manufactured by Advanced Chemistry Development Inc.) which designates according to the regulation of IUPAC, or commonly designated according to IUPAC Nomenclature. For example, a compound wherein $A^1$ and $A^2$ represent an imidazol-2-yl group, $B^1$ and $B^2$ represent a methylene group, G represents a carbon atom substituted by a oxo group, E represents a 1,4-phenylene group, L represents —$CH_2$—, and J represents:

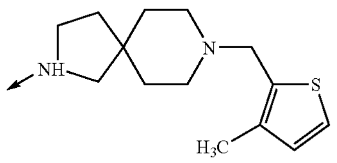

wherein the arrow represent the point to bind to L; namely, a compound represented by the following formula:

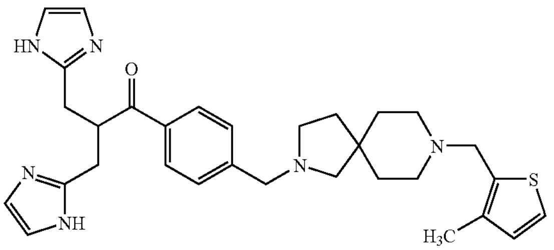

is designated as 3-(1H-imidazol-2-yl)-2-(1H-imidazol-2-ylmethyl)-1-[4-({8-[(3-methyl-2-thienyl)methyl]-2,8-diazaspiro[4.5]dec-2-yl}methyl)phenyl]propan-1-one.

Also, in the compound in which two hydrogen atoms bonded to two different carbon atoms of cycloalkane are substituted, a substituent is sometimes substituted on both faces formed by ring or a substituent is sometimes substituted on the same side, and the former was named "trans-isomer" while the latter was named "cis-isomer".

BEST MODE FOR CARRYING OUT THE INVENTION

The present invention is described in detail based on Examples, but the present invention is not limited thereto.

The point of separation by chromatography and the solvent in the parentheses shown in TLC indicate a dissolution medium or an eluent used, and the proportion indicates a volume ratio.

NMR is a measured value of $^1$HNMR at 300 MHz and the solvent shown in the parentheses of NMR indicates a solvent used in the measurement.

EXAMPLE 1

1-{[2-(trimethylsilyl)ethoxy]methyl}-1H-imidazole

Under an argon atmosphere, a dimethylformamide (500 mL) suspension of sodium hydride (60%, 18.9 g) was ice-cooled and then imidazole (30.9 g) was added so as to prevent an inner temperature from rising to 5° C. or higher. The reaction solution was stirred at 0° C. for 45 minutes. To the reaction solution, 2-(trimethylsilyl)ethoxymethyl chloride (72.4 g) was added dropwise. The reaction solution was stirred at room temperature for 14 hours. To the reaction solution, ice water (200 mL) was added. The aqueous layer was extracted twice with a solution (n-hexane:ethyl acetate=1:1 (200 mL)). The combined organic layer was washed with saturated sodium chloride solution and then dried over anhydrous magnesium sulfate. After removing anhydrous magnesium sulfate by filtration, the filtrate was concentrated to obtain the title compound (116 g) having the following physical properties.

TLC: Rf 0.50 (ethyl acetate:methanol=9:1);

NMR ($CDCl_3$): δ −0.05-0.05 (m, 9H), 0.90 (dd, J=9.3, 8.4 Hz, 2H), 3.48 (m, 2H), 5.29 (s, 2H), 7.06 (m, 1H), 7.12 (m, 1H), 7.71. (m, 1H).

EXAMPLE 2

(1-{[2-(trimethylsilyl)ethoxy]methyl}-1H-imidazol-2-yl)methanol

To an anhydrous tetrahydrofuran (1,000 mL) solution of compound (115 g) produced in Example 1, a tetrahydrofuran solution (260 mL) of 2N lithium diisopropylamide was added at −78° C. under an argon atmosphere. The reaction solution was stirred at −78° C. for 2 hours. To this solution, dimethylformamide (100 mL) was added. The reaction solution was stirred at 0° C. for 30 minutes. To the reaction solution, water (200 mL) was added. The reaction solution was concentrated under reduced pressure. The aqueous layer was extracted three times with ethyl acetate (200 mL). The combined organic layer was washed in turn with water (100 mL) and saturated sodium chloride solution (100 mL), and then dried over anhydrous magnesium sulfate. After removing the anhydrous magnesium sulfate by filtration, the filtrate was concentrated. The residue was purified by silica gel chromatography (n-hexane:ethyl acetate=4:1→2:1) to obtain the title compound (24.5 g) having the following physical properties.

TLC: Rf 0.63 (ethyl acetate:methanol:28% aqueous ammonia=90:10:1);

NMR ($CDCl_3$): δ −0.10-0.05 (m, 9H), 0.92 (m, 2H), 3.53 (m, 2H), 4.72 (s, 2H), 5.36 (s, 2H), 6.94 (m, 1H), 6.98 (m, 1H).

EXAMPLE 3

2-(chloromethyl)-1-{[2-(trimethylsilyl)ethoxy]methyl}-1H-imidazole Hydrochloride To a dichloromethane (30 mL) solution of the compound (2.44 g) produced in Example 2, thionyl chloride (1.85 mL) was added at 0° C. under an argon atmosphere. The reaction solution was stirred at room temperature for 30 minutes. To the reaction solution, a solution (n-hexane:ethyl acetate=1:1 (100 mL)) was added. The precipitated solid was collected by filtration. The solid was dried under reduced pressure to obtain the title compound (2.42 g) having the following physical properties.

TLC: Rf 0.71 (ethyl acetate:methanol:28% aqueous ammonia=90:10:1);

NMR ($CDCl_3$): δ 0.00-0.08 (m, 9H), 0.98 (dd, J=8.4, 7.8 Hz, 2H), 3.62 (t, J=8.4 Hz, 2H), 5.20 (s, 2H), 5.57 (s, 2H), 7.29 (d, J=1.8 Hz, 1H), 7.38 (d, J=1.8 Hz, 1H).

EXAMPLE 4

Diethyl bis[(1-{[2-(trimethylsilyl)ethoxy]methyl}-1H-imidazol-2-yl)methyl]malonate To an anhydrous tetrahydrofuran (10 mL) solution of diethyl malonate (566 mg), an ethanol solution (6 mL) of 20% sodium methoxide and the compound (2.20 g) produced in Example 3 were added in this order. The reaction solution was stirred at room temperature for 15 hours. To the reaction solution, a saturated aqueous ammonium chloride solution (10 mL) was added and the aqueous layer was extracted twice with dichloromethane (50 mL). The combined organic layer was washed with saturated sodium chloride solution (20 mL) and then dried over anhydrous magnesium sulfate. After removing the anhydrous magnesium sulfate by filtration, the filtrate was concentrated. The residue was purified by silica gel chromatography (n-hexane:ethyl acetate=3:1→1:1) to obtain the title compound (1.60 g) having the following physical properties.

TLC: Rf 0.21 (n-hexane:ethyl acetate=1:2);

NMR ($CDCl_3$): δ −0.08-0.00 (m, 18H), 0.85 (t, J=8.1 Hz, 4H), 1.17 (t, J=7.2 Hz, 6H), 3.41 (t, J=8.1 Hz, 4H), 3.65 (s, 4H), 4.21 (q, J=7.2 Hz, 4H), 5.12 (s, 4H), 6.86 (d, J=1.5 Hz, 2H), 6.93 (d, J=1.5 Hz, 2H).

EXAMPLE 5

3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propanoic Acid To an ethanol (7 mL) solution of the compound (1.60 g) produced in Example 4, an aqueous 5N sodium hydroxide solution (7 mL) was added. The reaction solution was heated at reflux for 3 hours. The reaction solution was concentrated under reduced pressure. 5N hydrochloric acid was added to the residue so as to adjust the pH to 5. The aqueous layer was saturated by adding sodium chloride and the solution was extracted three times with dichloromethane (50 mL). The combined organic layer was dried over anhydrous magnesium sulfate. After removing the anhydrous magnesium sulfate by filtration, the filtrate was concentrated. The residue was purified by silica gel chromatography (ethyl acetate→dichloromethane:methanol: 28% aqueous ammonia=80:20:3) to obtain the title compound (828 mg) having the following physical properties.

TLC: Rf 0.36(dichloromethane:methanol:28% aqueous ammonia=80:20:3);

NMR ($CDCl_3$): δ −0.05-1.12 (m, 18H), 0.93 (t, J=8.4 Hz, 4H), 3.22-3.65 (m, 9H), 5.48 (s, 4H), 6.98-7.08 (m, 4H).

EXAMPLE 6

N-methoxy-N-methyl-3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propanamide To a dichloromethane (5 mL) solution of the compound (488 mg) produced in Example 5, methoxymethylamine hydrochloride (156 mg), N-methylmorpholine (0.34 mL), 1-ethyl-3-[3-(dimethylamino)propyl]carbodiimide (376 mg) and 1-hydroxybenzimidazole (216 mg) were added in this order. The reaction solution was stirred at room temperature for 15 hours. To the reaction solution, water (10 mL) was added. The aqueous layer was extracted twice with dichloromethane (50 mL). The combined organic layer was dried over anhydrous magnesium sulfate. After removing the anhydrous magnesium sulfate by filtration, the filtrate was concentrated. The residue was purified by silica gel chromatography (ethyl acetate:methanol: 28% aqueous ammonia=1:0:0→100:10:1) to obtain the title compound (510 mg) having the following physical properties.

TLC: Rf 0.60 (ethyl acetate:methanol:28% aqueous ammonia=90:5:1);

NMR ($CDCl_3$): δ −0.05-0.20 (m, 18H), 0.89 (m, 4H), 2.95 (dd, J=15.0, 7.2 Hz, 2H), 3.13 (s, 3H), 3.15 (dd, J=15.0, 7.8 Hz, 2H), 3.46 (t, J=8.1 Hz, 4H), 3.67 (s, 3H), 4.00 (m, 1H), 5.18 (m, 2H), 5.33 (m, 2H), 6.88 (d, J=1.5 Hz, 2H), 6.90 (d, J=1.5 Hz, 2H).

EXAMPLE 7

[(4-bromobenzyl)oxy](tert-butyl)dimethylsilane

To a dimethylformamide (30 mL) solution of (4-bromophenyl)methanol (3.00 g), imidazole (2.18 g) and tert-butyldimethylsilyl chloride (2.89 g) were added in this order. The reaction solution was stirred at room temperature for one hour. To the reaction solution, water (10 mL) was added and the aqueous layer was extracted twice with ethyl acetate (50 mL). The combined organic layer was washed in turn with 1N hydrochloric acid (10 mL) and saturated sodium chloride solution (10 mL) and then dried over anhydrous magnesium sulfate. After removing the anhydrous magnesium sulfate by filtration, the filtrate was concentrated. The residue was purified by silica gel chromatography (n-hexane:ethyl acetate=1:0→9:1) to obtain the title compound (3.77 g) having the following physical properties.

TLC: Rf 0.90 (ethyl acetate:methanol=4:1);

NMR ($CDCl_3$): δ 0.09 (s, 6H), 0.93 (s, 9H), 4.68 (s, 2H), 7.19 (d, J=8.1 Hz, 2H), 7.45 (d, J=8.1 Hz, 2H).

EXAMPLE 8

1-[4-({[tert-butyl(dimethyl)silyl]oxy}methyl)phenyl]-3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propan-1-one To an anhydrous tetrahydrofuran (20 mL) solution of the compound (3.01 g) produced in Example 7, n-butyl lithium (1.6N n-hexanesolution, 8.1 mL) was added at −78° C. The reaction solution was stirred at −78° C. for 30 minutes.

To an anhydrous tetrahydrofuran (5 mL) solution of the compound (255 mg) produced in Example 6, a preliminarily prepared lithium reagent (4 mL) was slowly added at −78° C. The reaction solution was stirred at room temperature for one hour. To the reaction solution, an aqueous ammonium chloride solution (10 mL) and 1N hydrochloric acid (10 mL) were added. The aqueous layer was extracted twice with ethyl acetate (50 mL). The combined organic layer was washed with saturated sodium chloride solution and then dried over anhydrous magnesium sulfate. After removing the anhydrous magnesium sulfate by filtration, the filtrate was concentrated. The residue was purified by silica gel chromatography (ethyl acetate:methanol: 28% aqueous ammonia=1:0:0→100:5:1) to obtain the title compound (275 mg) having the following physical properties.

TLC: Rf 0.67 (ethyl acetate:methanol:28% aqueous ammonia=19:1:0.05);

NMR ($CDCl_3$): δ −0.05-0.00 (m, 18H), 0.09 (s, 6H), 0.86 (m, 4H), 0.96 (s, 9H), 3.03 (dd, J=15.3, 6.9 Hz, 2H), 3.19 (dd, J=15.3, 7.2 Hz, 2H), 3.42 (m, 4H), 4.75 (s, 2H), 4.78 (m, 1H), 5.13 (d, J=11.1 Hz, 2H), 5.23 (d, J=11.1 Hz, 2H), 6.80 (d, J=1.2 Hz, 2H), 6.86 (d, J=1.2 Hz, 2H), 7.35 (d, J=8.4 Hz, 2H), 7.96 (d, J=8.4 Hz, 2H).

EXAMPLE 9

1-[4-(hydroxymethyl)phenyl]-3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propan-1-one To a tetrahydrofuran (2 mL) solution of the compound (56 mg) produced in Example 8, tetrahydroammonium fluoride (1N tetrahydrofuran solution, 1.5 mL) was added. The reaction solution was stirred at room temperature for 30 minutes. To the reaction solution, water (5 mL) was added. The aqueous layer was washed twice with dichloromethane (20 mL). The combined organic layer was washed with saturated sodium chloride solution and the dried over anhydrous magnesium sulfate. After removing the anhydrous magnesium sulfate by filtration, the filtrate was concentrated. The residue was purified by silica gel chromatography (ethyl acetate: methanol: 28% aqueous ammonia=1:0:0→100:10:1) to obtain the title compound (48 mg) having the following physical properties.

TLC: Rf 0.30 (ethyl acetate:methanol:28% aqueous ammonia=19:1:0.05);

NMR ($CDCl_3$): δ −0.05-0.00 (m, 18H), 0.87 (m, 4H), 3.03 (dd, J=15.6, 6.9 Hz, 2H), 3.20 (dd, J=15.6, 7.2 Hz, 2H), 3.46 (m, 4H), 4.73 (s, 2H), 4.78 (m, 1H), 5.13 (d, J=11.1 Hz, 2H), 5.23 (d, J=11.1 Hz, 2H), 6.79 (m, 2H), 6.83 (m, 2H), 7.37 (d, J=8.1 Hz, 2H), 7.93 (d, J=8.1 Hz, 2H).

EXAMPLE 10

4-{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propanoyl}benzaldehyde To a solution (ethyl acetate:dimethyl sulfoxide=3:2 (1.25 mL)) of the compound (48 mg) produced in Example 9, triethylamine (0.12 mL) and a sulfur trioxide-pyridine complex (39 mg) were added. The reaction solution was stirred at room temperature for one hour. To the reaction solution, water (5 mL) was added. The aqueous layer was extracted twice with ethyl acetate (20 mL). The combined organic layer was washed with saturated sodium chloride solution and then dried over anhydrous magnesium sulfate. After removing the anhydrous magnesium sulfate by filtration, the filtrate was concentrated. The residue was purified by silica gel chromatography (ethyl acetate:methanol: 28% aqueous ammonia=1:0:0→100:10:1) to obtain the title compound (30 mg) having the following physical properties.

TLC: Rf 0.59 (ethyl acetate:methanol:28% aqueous ammonia=19:1:0.05);

NMR ($CDCl_3$): δ −0.05-0.00 (m, 18H), 0.87 (m, 4H), 3.06 (dd, J=15.6, 6.6 Hz, 2H), 3.22 (dd, J=15.2, 7.8 Hz, 2H), 3.44 (m, 4H), 4.85 (m, 1H), 5.14 (d, J=10.8 Hz, 2H), 5.23 (d, J=10.8 Hz, 2H), 6.81 (d, J=1.5 Hz, 1H), 6.83 (d, J=1.5 Hz, 2H), 7.90 (d, J=8.4 Hz, 2H), 8.13 (d, J=8.4 Hz, 2H), 10.1 (s, 1H).

EXAMPLE 11

4-[3-(1H-imidazol-2-yl)-2-(1H-imidazol-2-ylmethyl)propanoyl]benzaldehyde

To an aqueous 95% trifluoroacetic acid solution (1 mL) solution of the compound (100 mg) produced in Example 10 was stirred at 50° C. for one hour. The reaction solution was concentrated under reduced pressure. To the residue, methanol (20 mL) was added and then MP-carbonate (trade name, manufactured by Argonaut Technologies Inc., product number: 800267,100 mg) was added to the solution, followed by shaking for 30 minutes. The resin was removed by filtration and the filtrate was concentrated under reduced pressure. Without purifying the residue, the title compound having the following physical properties was obtained.

TLC: Rf 0.63 (ethyl acetate:methanol:28% aqueous ammonia=80:20:2);

NMR ($CDCl_3$): δ 2.82 (d, J=14.4, 7.2 Hz, 2H), 3.15 (dd, J=14.4, 4.5 Hz, 2H), 4.03 (m, 1H), 7.05 (m, 4H), 8.01 (d, J=8.4 Hz, 2H), 8.20 (d, J=8.4 Hz, 2H), 10.1 (s, 1H).

EXAMPLE 12

Tert-butyl 8-[(3-methyl-2-thienyl)methyl]-2,8-diazaspiro[4.5]decane-2-carboxylate To a 1% acetic acid-dimethylformamide (10 mL) solution of tert-butyl 2,8-diazaspiro[4.5]decane-2-carboxylate (1.28 g) and 3-methylthiophene-2-carboaldehyde (700 mg), sodium triacetoxyborohydride (1.96 g) was added. The reaction solution was stirred at room temperature for 15 hours. To the reaction solution, an aqueous 5N sodium hydroxide solution (10 mL) was added. The aqueous layer was washed twice with dichloromethane (100 mL) The combined organic layer was washed with saturated sodium chloride solution (50 mL) and then dried over anhydrous magnesium sulfate. After removing the anhydrous magnesium sulfate by filtration, the filtrate was concentrated. The residue was purified by silica gel chromatography (n-hexane:ethyl acetate=1:1→1:3) to obtain the title compound (1.14 g) having the following physical properties.

TLC: Rf 0.23 (ethyl acetate:methanol=1:2);

NMR ($CDCl_3$): δ 1.45 (s, 9H), 1.50-1.75 (m, 6H), 2.18 (s, 3H), 2.25-2.45 (m, 2H), 2.45-2.63 (m, 2H), 3.06-3.22 (m, 2H), 3.28-3.42 (m, 2H), 3.60 (s, 2H), 6.76 (d, J=5.1 Hz, 1H) 7.10 (d, J=5.1 Hz, 1H).

EXAMPLE 13

8-[(3-methyl-2-thienyl)methyl]-2,8-diazaspiro[4.5]decane

To a methanol (5 mL) solution of the compound (1.14 g) produced in Example 12, a 1,4-dioxane solution (3 mL) of 4N hydrogen chloride was added. The reaction solution was stirred at room temperature for 3 hours. The reaction solution was concentrated under reduced pressure. To the residue, methanol (30 mL) was added and then MP-carbonate (trade name, manufactured by Argonaut Technologies Inc., product number: 800267, 100 mg) was added, followed by stirring for 30 minutes. After removing the resin by filtration, the filtrate was concentrated under reduced pressure. Without purifying the residue, the title compound (768 mg) having the following physical properties was obtained.

TLC: Rf 0.06 (dichloromethane:methanol:28% aqueous ammonia=80:20:2);

NMR ($CDCl_3$): δ 1.50-1.72 (m, 6H), 2.18 (s, 3H), 2.38-2.58 (m, 4H), 2.83 (s, 2H), 3.09 (t, J=7.5 Hz, 2H), 3.60 (s, 2H), 6.78 (d, J=5.1 Hz, 1H), 7.12 (d, J=5.1 Hz, 1H).

EXAMPLE 14

3-(1H-imidazol-2-yl)-2-(1H-imidazol-2-ylmethyl)-1-[4-({8-[(3-methyl-2-thienyl)methyl]-2,8-diazaspiro[4.5]dec-2-yl}methyl)phenyl]propan-1-one

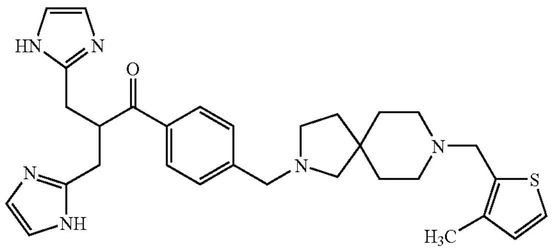

Using the compound (64 mg) produced in Example 13 and the compound (54 mg) produced in Example 11, the same operation as in Example 12 was performed. The resulting residue was purified by silica gel chromatography (ethyl acetate:methanol:28% aqueous ammonia=100:10:2) to obtain the title compound (14 mg) having the following physical properties.

TLC: Rf 0.48 (ethyl acetate:methanol:28% aqueous ammonia=90:10:1);

NMR ($CDCl_3$): δ 1.55-1.72 (m, 6H), 2.17 (s, 3H), 2.30-2.55 (m, 6H), 2.60 (t, J=7.5 Hz, 2H), 2.79 (dd, J=14.7, 5.7 Hz, 2H), 3.16 (dd, J=14.7, 4.2 Hz, 2H), 3.57 (s, 2H), 3.64 (s, 2H), 4.04 (m, 1H), 6.77 (d, J=5.1 Hz, 1H), 7.05 (s, 4H), 7.11 (d, J=5.1 Hz, 1H), 7.48 (d, J=8.1 Hz, 2H), 8.03 (d, J=8.1 Hz, 2H).

EXAMPLE 14(1)-EXAMPLE 14(2)

Except for using the corresponding amine in place of the compound produced in Example 13, the same operation as in Example 14 was performed to obtain the following compounds.

EXAMPLE 14(1)

1-[4-({[4-(dipropylamino)butyl]amino}methyl)phenyl]-3-(1H-imidazol-2-yl)-2-(1H-imidazol-2-ylmethyl)-1-propanone TLC: Rf 0.35 (dichloromethane:methanol:28% aqueous ammonia=8:2:0.4);

NMR ($CDCl_3$): δ 0.86 (t, J=7.2 Hz, 6H), 1.38-1.60 (m, 8H), 2.30-2.48 (m, 6H), 2.60-2.68 (m, 2H), 2.77 (dd, J=14.4, 7.2 Hz, 2H), 3.16 (dd, J=14.4, 4.5 Hz, 2H), 3.87 (s, 2H), 4.00 (m, 1H), 7.06 (s, 4H), 7.48 (d, J=8.1 Hz, 2H), 8.04 (d, J=8.1 Hz, 2H).

EXAMPLE 14(2)

1-{4-[({trans-4-[cyclohexyl(propyl)amino]cyclohexyl}amino)methyl]phenyl}-3-(1H-imidazol-2-yl)-2-(1H-imidazol-2-ylmethyl)-1-propanone TLC: Rf 0.45 (dichloromethane:methanol:28% aqueous ammonia=8:2:0.2);

NMR ($CDCl_3$): δ 0.84 (t, J=7.2 Hz, 3H), 1.00-2.10 (m, 20H), 2.30-2.82 (m, 5H), 2.77 (dd, J=14.1, 7.2 Hz, 2H), 3.15 (dd, J=14.1 Hz, 4.5 Hz, 2H), 3.88 (s, 2H), 4.01 (m, 1H), 7.06 (s, 4H), 7.47 (d, J=8.1 Hz, 2H), 8.03 (d, J=8.1 Hz, 2H).

EXAMPLE 15

3-(1H-imidazol-2-yl)-2-(1H-imidazol-2-ylmethyl)-1-[4-({8-[(3-methyl-2-thienyl)methyl]-2,8-diazaspiro[4.5]dec-2-yl}methyl)phenyl]-1-propanol To a methanol (2 mL) solution of the compound (26 mg) produced in Example 14, sodium borohydride (26 mg) was added. The reaction solution was stirred at room temperature for 30 minutes. To the reaction solution, water (10 mL) was added. The aqueous layer was extracted twice with dichloromethane (20 mL). The combined organic layer was washed with saturated sodium chloride solution (20 mL) and then dried over anhydrous magnesium sulfate. After removing the anhydrous magnesium sulfate by filtration, the filtrate was concentrated. The residue was purified by silica gel chromatography (ethyl acetate:methanol: 28% aqueous ammonia=8:2:0.4) to obtain the title compound (25 mg) having the following physical properties.

TLC: Rf 0.22 (ethyl acetate:methanol:28% aqueous ammonia=9:1:0.2);

NMR ($CDCl_3$): δ 1.50-1.70 (m, 6H), 2.17 (s, 3H), 2.25-2.90 (m, 11H), 3.05 (dd, J=14.7, 5.7 Hz, 2H), 3.57 (s, 2H), 3.59 (s, 2H), 4.46 (d, J=6.6 Hz, 1H), 6.77 (d, J=5.1 Hz, 1H), 6.97 (d, J=2.7 Hz, 4H), 7.10 (d, J=5.1 Hz, 1H), 7.20-7.32 (m, 4H).

EXAMPLE 15(1)-EXAMPLE 15(2)

Except for using the corresponding carbonyl compound in place of the compound produced in Example 14, the same operation as in Example 15 was performed to obtain the following compounds.

EXAMPLE 15(1)

1-[4-({[4-(dipropylamino)butyl]amino}methyl)phenyl]-3-(1H-imidazol-2-yl)-2-(1H-imidazol-2-ylmethyl)-1-propanol TLC: Rf 0.24 (dichloromethane:methanol:28% aqueous ammonia=8:2:0.4);

NMR ($CDCl_3$): δ 0.87 (t, J=7.2 Hz, 6H), 1.38-1.80 (m, 8H), 2.20-2.88 (m, 12H), 2.98 (m, 1H), 3.83 (s, 2H), 4.50 (m, 1H), 6.85-7.00 (m, 4H), 7.10-7.35 (m, 4H).

EXAMPLE 15(2)

1-{4-[({trans-4-[cyclohexyl(propyl)amino]cyclohexyl}amino)methyl]phenyl}-3-(1H-imidazol-2-yl)-2-(1H-imidazol-2-ylmethyl)-1-propanol TLC: Rf 0.44 (dichloromethane:methanol:28% aqueous ammonia=8:2:0.2);

NMR ($CDCl_3$): δ 0.83 (t, J=7.5 Hz, 3H), 1.00-2.72 (m, 28H), 2.92 (m, 2H), 3.77 (s, 2H), 4.38 (d, J=5.7 Hz, 1H), 6.82-6.98 (m, 4H), 7.10-7.28 (m, 4H).

EXAMPLE 16

Tert-butyl[4-({8-[(3-methyl-2-thienyl)methyl]-2,8-diazaspiro[4.5]dec-2-yl}methyl)benzyl]carbamate Except for using the compound (150 mg) produced in Example 13 in place of tert-butyl 2,8-diazaspiro[4.5]decane-2-carboxylate and using 4-(N-tert-butoxyaminomethyl)benzaldehyde (169 mg) in place of 3-methylthiophene-2-carboaldehyde, the same operation as in Example 12 was performed to obtain the title compound (211 mg) having the following physical properties.

TLC: Rf 0.76 (ethyl acetate:methanol:28% aqueous ammonia=9:1:0.2);

NMR ($CDCl_3$): δ 1.46 (s, 9H), 1.50-1.75 (m, 6H), 2.17 (s, 3H), 2.28-2.50 (m, 6H), 2.55 (t, J=6.9 Hz, 2H), 3.55 (s, 2H), 3.56 (s, 2H), 4.20-4.40 (m, 2H), 4.81 (m, 1H), 6.77 (d, J=5.1 Hz, 1H), 7.11 (d, J=5.1 Hz, 1H), 7.22 (d, J=7.8 Hz, 2H), 7.31 (d, J=7.8 Hz, 2H).

EXAMPLE 17

1-[4-({8-[(3-methyl-2-thienyl)methyl]-2,8-diazaspiro[4.5]dec-2-yl}methyl)phenyl]methanamine To a methanol (5 mL) solution of the compound (211 mg) produced in Example 16, 4N hydrogen chloride-1,4-dioxane (5 mL) was added. The reaction solution was stirred at room temperature for one hour. The reaction solution was concentrated under reduced pressure. To the residue, an aqueous 5N sodium hydroxide solution (10 mL) was added. The aqueous layer was extracted twice with dichloromethane (20 mL). The combined organic layer was washed with saturated sodium chloride solution (20 mL) and then dried over anhydrous magnesium sulfate. After removing the anhydrous magnesium sulfate by filtration, the filtrate was concentrated. Without purifying the residue, the title compound (140 mg) having the following physical properties was obtained.

TLC: Rf 0.13 (ethyl acetate:methanol:28% aqueous ammonia=9:1:0.2);

NMR ($CDCl_3$): δ 1.40-1.75 (m, 6H), 2.17 (s, 3H), 2.28-2.52 (m, 6H), 2.56 (t, J=6.9 Hz, 2H), 3.56 (s, 4H), 3.86 (s, 2H), 6.77 (d, J=5.4 Hz, 1H), 7.11 (d, J=5.4 Hz, 1H), 7.22-7.38 (m, 4H).

EXAMPLE 18

3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]-1-propanol To a tetrahydrofuran (2 mL) suspension of lithium aluminum hydride (16 mg), a tetrahydrofuran (1 mL) solution of the compound (100 mg) produced in Example 5 was added. The reaction solution was stirred at room temperature for 15 minutes. To the reaction solution, an aqueous saturated sodium sulfate solution (1 mL) was added. The reaction solution was diluted with ethyl acetate (5 mL) and then dried over anhydrous magnesium sulfate. After removing the anhydrous magnesium sulfate by filtration through Celite (trade name), the filtrate was concentrated. Without purifying the residue, the title compound (80 mg) having the following physical properties was obtained.

TLC: Rf 0.36 (ethyl acetate:methanol:28% aqueous ammonia=9:1:0.1);

NMR ($CDCl_3$): δ −0.03 (s, 18H), 0.87 (t, J=8.1 Hz, 4H), 2.58 (m, 1H), 2.82-2.98 (m, 4H), 3.45 (t, J=8.1 Hz, 4H), 3.63 (d, J=3.9 Hz, 2H), 5.16 (d, J=11.1 Hz, 2H), 5.21 (d, J=11.1 Hz, 2H), 6.89 (d, J=1.2 Hz, 2H), 6.93 (d, J=1.2 Hz, 2H).

EXAMPLE 19

3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propanal Except for using the compound (350 mg) produced in Example 18 in place of the compound produced in Example 9, the same operation as in Example 10 was performed to obtain the title compound (370 mg) having the following physical properties.

TLC: Rf 0.63 (ethyl acetate:methanol:28% aqueous ammonia=9:1:0.1);

NMR ($CDCl_3$): δ −0.03 (s, 18H), 0.87 (t, J=8.4 Hz, 4H), 3.07 (dd, J=15.9, 6.9 Hz, 2H), 3.25 (dd, J=15.9, 6.6 Hz, 2H), 3.45 (t, J=8.4 Hz, 4H), 3.58 (m, 1H), 5.19 (s, 4H), 6.89 (d, J=1.5 Hz, 2H), 6.92 (d, J=1.5 Hz, 2H), 9.96 (s, 1H).

EXAMPLE 20

N-[4-({8-[(3-methyl-2-thienyl)methyl]-2,8-diazaspiro[4.5]dec-2-yl}methyl)benzyl]-3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]-1-propanamine Except for using the compound (140 mg) produced in Example 17 in place of tert-butyl 2,8-diazaspiro[4.5]decane-2-carboxylate and using the compound (211 mg) produced in Example 19 in place of 3-methylthiophene-2-carboaldehyde, the same operation as in Example 12 was performed to obtain the title compound (300 mg) having the following physical properties.

TLC: Rf 0.51 (ethyl acetate:methanol:28% aqueous ammonia=8:2:0.2);

NMR ($CDCl_3$): δ −0.03 (s, 18H), 0.87 (t, J=8.4 Hz, 4H), 1.50-1.70 (m, 6H), 2.17 (s, 3H), 2.30-2.45 (m, 6H), 2.54 (t, J=6.9 Hz, 2H), 2.58-2.68 (m, 3H), 2.80-2.98 (m, 4H), 3.45 (t, J=8.4 Hz, 4H), 3.54 (s, 2H), 3.58 (s, 2H), 3.71 (s, 2H), 5.18 (d, J=10.8 Hz, 2H), 5.26 (d, J=10.8 Hz, 2H), 6.76 (d, J=5.1 Hz, 1H), 6.88 (d, J=1.5 Hz, 2H), 6.91 (d, J=1.5 Hz, 2H), 7.10 (d, J=5.1 Hz, 1H), 7.22 (s, 4H).

EXAMPLE 21

3-(1H-imidazol-2-yl)-2-(1H-imidazol-2-ylmethyl)-N-[4-({8-[(3-methyl-2-thienyl)methyl]-2,8-diazaspiro[4.5]dec-2-yl}methyl)benzyl]-1-propanamine

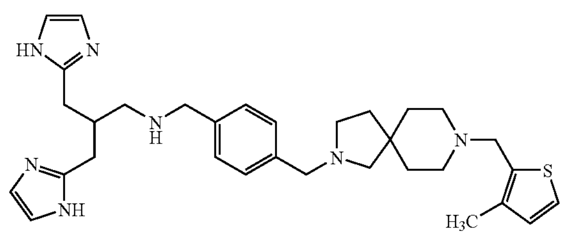

An aqueous 95% trifluoroacetic acid solution (4.2 mL) of the compound (38 mg) produced in Example 20 was stirred at 60° C. for 4 hours. The reaction solution was concentrated under reduced pressure. To the residue, an aqueous 5N sodium hydroxide solution (10 mL) was added. The aqueous layer was extracted twice with dichloromethane (20 mL). The combined organic layer was washed with saturated sodium chloride solution (20 mL) and then dried over anhydrous magnesium sulfate. After removing the anhydrous magnesium sulfate by filtration, the filtrate was concentrated. The residue was purified by silica gel chromatography (ethyl acetate:methanol:28% aqueous ammonia=8:2:0.4) to obtain the title compound (13 mg) having the following physical properties.

TLC: Rf 0.35 (ethyl acetate:methanol:28% aqueous ammonia=8:2:0.2);

NMR ($CDCl_3$): δ 1.52-1.70 (m, 6H), 2.17 (s, 3H), 2.32-2.50 (m, 6H), 2.50 (m, 1H), 2.61 (t, J=6.9 Hz, 2H), 2.71-2.95 (m, 6H), 3.58 (s, 2H), 3.62 (s, 2H), 3.92 (s, 2H), 6.77 (d, J=5.1 Hz, 1H), 6.87 (s, 4H), 7.12 (d, J=5.1 Hz, 1H), 7.28-7.40 (m, 4H).

EXAMPLE 21 (1)

N-[3-(1H-imidazol-2-yl)-2-(1H-imidazol-2-ylmethyl)propyl]-4-({8-[(3-methyl-2-thienyl)methyl]-2,8-diazaspiro[4.5]dec-2-yl}methyl)aniline Except for using the corresponding amine in place of the compound produced in Example 17 in Example 20, the same operation as in Example 20→Example 21 was performed to obtain the title compound having the following physical properties.

TLC: Rf 0.39 (ethyl acetate:methanol:28% aqueous ammonia=8:2:0.2);

NMR ($CDCl_3$): δ 1.50-1.70 (m, 6H), 2.17 (s, 3H), 2.28-2.78 (m, 13H), 3.00 (d, J=6.6 Hz, 2H), 3.54 (s, 2H), 3.56 (s, 2H), 6.53 (d, J=8.4 Hz, 2H), 6.77 (d, J=5.1 Hz, 1H), 7.02 (s, 4H), 7.06-7.15 (m, 3H).

EXAMPLE 22

N-methyl-N-[4-({8-[(3-methyl-2-thienyl)methyl]-2,8-diazaspiro[4.5]dec-2-yl}methyl)benzyl]-3-(1-{[2-(trimethylsilyl)ethoxy]methyl}-1H-imidazol-2-yl)-2-[(1-{[(trimethylsilyl)methoxy]methyl}-1H-imidazol-2-yl)methyl]-1-propanamine To a 10% acetic acid-dimethylformamide (2 mL) solution of the compound (100 mg) produced in Example 20, an aqueous 37% formaldehyde solution (28 μL) and sodium triacetoxyborohydride (80 mg) were added. The reaction solution was stirred at room temperature for 30 minutes. To the reaction solution, an aqueous 5N sodium hydroxide solution (10 mL) was added. The aqueous layer was extracted twice with dichloromethane (20 mL). The combined organic layer was washed with saturated sodium chloride solution (20 mL) and then dried over anhydrous magnesium sulfate. After removing the anhydrous magnesium sulfate by filtration, the filtrate was concentrated. Without purifying the residue, the title compound (100 mg) having the following physical properties was obtained.

TLC: Rf 0.68 (ethyl acetate:methanol:28% aqueous ammonia=8:2:0.2);

EXAMPLE 23

3-(1H-imidazol-2-yl)-2-(1H-imidazol-2-ylmethyl)-N-methyl-N-[4-({8-[(3-methyl-2-thienyl)methyl]-2,8-diazaspiro[4.5]dec-2-yl}methyl)benzyl]-1-propanamine Except for using the compound (100 mg) produced in Example 22 in place of N-[4-({8-[(3-methyl-2-thienyl)methyl]-2,8-diazaspiro[4.5]dec-2-yl}methyl)benzyl]-3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]-1-propaneamine, the same operation as in Example 21 was performed to obtain the title compound (100 mg) having the following physical properties.

TLC: Rf 0.49 (ethyl acetate:methanol:28% aqueous ammonia=8:2:0.4);

NMR ($CDCl_3$): δ 1.50-1.72 (m, 6H), 2.00-2.75 (m, 21H), 3.48 (s, 2H), 3.57 (s, 2H), 3.62 (s, 2H), 6.77 (d, J=5.1 Hz, 1H), 6.84 (s, 4H), 7.11 (d, J=5.1 Hz, 1H), 7.25-7.42 (m, 4H).

EXAMPLE 24

N-[4-({8-[(3-methyl-2-thienyl)methyl]-2,8-diazaspiro[4.5]dec-2-yl}methyl)benzyl]-N-{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propyl}acetamide To a dichloromethane (3 mL) solution of the compound (100 mg) produced in Example 23, pyridine (31 μL) and anhydrous acetic acid (24 μL) were added. The reaction solution was stirred at room temperature for 30 minutes. To the reaction solution, water (10 mL) was added. The aqueous layer was extracted twice with ethyl acetate (20 mL). The combined organic layer was washed with saturated sodium chloride solution (20 mL) and then dried over anhydrous magnesium sulfate. After removing the anhydrous magnesium sulfate by filtration, the filtrate was concentrated. Without purifying the residue, the title compound (100 mg) having the following physical properties was obtained.

TLC: Rf 0.61 (ethyl acetate:methanol:28% aqueous ammonia=8:2:0.2);

NMR ($CDCl_3$): δ −0.03 (s, 18H), 0.70-0.98 (m, 4H), 1.60-1.90 (m, 6H), 1.90-2.30 (m, 6H), 2.35-3.10 (m, 9H), 3.25-3.98 (m, 14H), 4.42-4.65 (m, 2H), 5.02-5.28 (m, 4H), 6.68-7.50 (m, 10H).

EXAMPLE 25

N-[3-(1H-imidazol-2-yl)-2-(1H-imidazol-2-ylmethyl)propyl]-N-[4-({8-[(3-methyl-2-thienyl)methyl]-2,8-diazaspiro[4.5]dec-2-yl}methyl)benzyl]acetamide

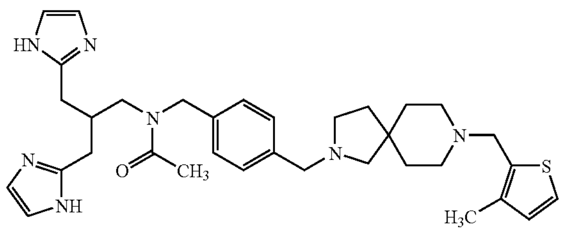

Except for using the compound (100 mg) produced in Example 24 in place of the compound produced in Example 20, the same operation as in Example 21 was performed to obtain the title compound (17 mg) having the following physical properties.

TLC: Rf 0.54 (ethyl acetate:methanol:28% aqueous ammonia=8:2:0.4);

NMR ($CDCl_3$): δ 1.50-1.70 (m, 6H), 2.17 (s, 3H), 2.26 (s, 3H), 2.28-2.84 (m, 13H), 3.34 (m, 2H), 3.59 (s, 2H), 3.62 (s, 2H), 4.63 (s, 2H), 6.77 (d, J=5.1 Hz, 1H), 7.06 (s, 4H), 7.08-7.18 (m, 3H), 7.34 (d, J=8.1 Hz, 2H).

EXAMPLE 25(1)

N-{4-[(8-cyclohexyl-2,8-diazaspiro[4.5]dec-2-yl)methyl]phenyl}-N-[3-(1H-imidazol-2-yl)-2-(1H-imidazol-2-ylmethyl)propyl]acetamide Except for using the corresponding amine (66 mg) in place of the compound produced in Example 17 in Example 20, the same operation as in Example 20→Example 24→Example 21 was performed to obtain the title compound (23 mg) having the following physical properties.

TLC: Rf 0.26 (ethyl acetate:methanol:28% aqueous ammonia=8:2:0.4);

NMR ($CDCl_3$): δ 1.00-1.98 (m, 16H), 1.92 (s, 3H), 2.06-2.65 (m, 12H), 2.70 (dd, J=14.4, 4.2 Hz, 2H), 3.60 (s, 2H), 3.62-3.78 (m, 2H), 6.92-7.14 (m, 4H), 7.06 (d, J=8.4 Hz, 2H), 7.38 (d, J=8.4 Hz, 2H), 12.61 (brs, 2H).

EXAMPLE 26

2-[4-(diethoxymethyl)benzyl]-8-isobutyl-2,8-diazaspiro[4.5]decane

To a 10% acetic acid-dimethylformamide (10 mL) solution of 8-isobutyl-2,8-diazaspiro[4.5]decane (600 mg) and 4-(diethoxymethyl)benzaldehyde (661 mg), sodium triacetoxyborohydride (1.30 g) was added. The reaction solution was stirred at room temperature for 14 hours. To the reaction solution, an aqueous 5N sodium hydroxide solution (10 mL) was added. The aqueous layer was extracted twice with dichloromethane (20 mL). The combined organic layer was washed with saturated sodium chloride solution (20 mL) and then dried over anhydrous magnesium sulfate. After removing the anhydrous magnesium sulfate by filtration, the filtrate was concentrated. The residue was purified by silica gel chromatography (ethyl acetate:methanol: 28% aqueous ammonia=1:0:0→100:5:1→100:10:2) to obtain the title compound (730 mg) having the following physical properties.

TLC: Rf 0.77 (ethyl acetate:methanol:28% aqueous ammonia=9:1:0.1);

NMR ($CDCl_3$): δ 0.87 (d, J=6.6 Hz, 6H), 1.24 (t, J=7.2 Hz, 6H), 1.50-1.64 (m, 6H), 1.78 (m, 1H), 2.01 (d, J=7.2 Hz, 2H), 2.20-2.32 (m, 4H), 2.34 (s, 2H), 2.56 (t, J=7.2 Hz, 2H), 3.45-3.68 (m, 6H), 5.49 (s, 1H), 7.25-7.38 (m, 2H), 7.38-7.45 (m, 2H).

EXAMPLE 27

4-[(8-isobutyl-2,8-diazaspiro[4.5]dec-2-yl)methyl]benzaldehyde

To a dichloromethane (10 mL) solution of the compound (730 mg) produced in Example 26, trifluoroacetic acid (5 mL) was added, followed by stirring at room temperature for one hour. To the reaction solution, an aqueous 5N sodium hydroxide solution (10 mL) was added. The aqueous layer was extracted twice with dichloromethane (20 mL). The combined organic layer was washed in turn with water (20 mL) and saturated sodium chloride solution (20 mL), and then dried over anhydrous magnesium sulfate. After removing the anhydrous magnesium sulfate by filtration, the filtrate was concentrated. Without purifying the residue, the title compound (611 mg) having the following physical properties was obtained.

TLC: Rf 0.80 (ethyl acetate:methanol:28% aqueous ammonia=8:2:0.4);

NMR ($CDCl_3$): δ 0.88 (d, J=6.3 Hz, 6H), 1.48-1.68 (m, 6H), 1.78 (m, 1H), 2.00-2.14 (m, 2H), 2.20-2.40 (m, 4H), 2.37 (s, 2H), 2.58 (t, J=7.2 Hz, 2H), 3.65 (s, 2H), 7.49 (d, J=8.4 Hz, 2H), 7.81 (d, J=8.4 Hz, 2H), 9.99 (s, 1H).

EXAMPLE 28

N-benzyl-3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]-1-propanamine Except for using the compound (4.50 g) produced in Example 19 in place of 4-(diethoxymethyl)benzaldehyde and using 1-phenylmethaneamine (3.40 g) in place of 8-isobutyl-2,8-diazaspiro[4.5]decane, the same operation as in Example 26 was performed to obtain the title compound (3.41 g) having the following physical properties.

TLC: Rf 0.46 (ethyl acetate:methanol:28% aqueous ammonia=8:2:0.4);

NMR ($CDCl_3$): δ −0.03 (s, 18H), 0.87 (t, J=8.4 Hz, 4H), 2.50-2.65 (m, 3H), 2.80-2.98 (m, 4H), 3.44 (t, J=8.4 Hz, 4H), 3.72 (s, 2H), 5.18 (d, J=10.8 Hz, 2H), 5.26 (d, J=10.8 Hz, 2H), 6.88 (d, J=1.5 Hz, 2H), 6.91 (d, J=1.5 Hz, 2H), 7.18-7.40 (m, 5H).

EXAMPLE 29

3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]-1-propanamine To an ethanol (80 mL) suspension of palladium hydroxide 20% supported on carbon (2.40 g), an ethanol (20 mL) solution of the compound (2.41 g) produced in Example 28 was added. The atmosphere in the reaction system was replaced by hydrogen, followed by stirring at 50° C. for 2 hours. After removing the palladium hydroxide by filtering the reaction solution through Celite (trade name), the filtrate was concentrated. Without purifying the residue, the title compound (1.42 g) having the following physical properties was obtained.

TLC: Rf 0.46 (ethyl acetate:methanol:28% aqueous ammonia=8:2:0.4);

NMR ($CDCl_3$): δ −0.03 (s, 18H), 0.87 (t, J=8.4 Hz, 4H), 2.48 (m, 1H), 2.75 (d, J=5.4 Hz, 2H), 2.80-2.94 (m, 4H), 3.46 (t, J=8.4 Hz, 4H), 5.20 (d, J=10.8 Hz, 2H), 5.27 (d, J=10.8 Hz, 2H), 6.89 (d, J=1.5 Hz, 2H), 6.93 (d, J=1.5 Hz, 2H).

EXAMPLE 30

N-{4-[(8-isobutyl-2,8-diazaspiro[4.5]dec-2-yl)methyl]benzyl}-3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]-1-propanamine Except for using the compound (200 mg) produced in Example 29 in place of 8-isobutyl-2,8-diazaspiro[4.5]decane and using the compound (135 mg) produced in Example 27 in place of 4-(diethoxymethyl)benzaldehyde, the same operation as in Example 26 was performed to obtain the title compound (142 mg) having the following physical properties.

TLC: Rf 0.55 (ethyl acetate:methanol:28% aqueous ammonia=9:1:0.2);

NMR ($CD_3OD$): δ −0.03 (s, 18H), 0.86 (t, J=8.4 Hz, 4H), 0.90 (d, J=6.6 Hz, 6H), 1.55-1.70 (m, 6H), 1.80 (m, 1H), 2.09 (d, J=6.9 Hz, 2H), 2.25-2.98 (m, 15H), 3.40-3.60 (m, 6H), 3.67 (s, 2H), 5.20-5.32 (m, 4H), 6.85 (m, 2H), 7.10 (m, 2H), 7.20-7.30 (m, 4H).

EXAMPLE 31

2-({4-[(8-isobutyl-2,8-diazaspiro[4.5]dec-2-yl)methyl]benzyl}{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propyl}amino)-2-oxoethyl Acetate To a dichloromethane (2 mL) solution of the compound (77 mg) produced in Example 30, triethylamine (140 μL) and acetoxyacetyl chloride (65 μL) were added. The reaction solution was stirred at room temperature for 3 hours. To the reaction solution, water (10 mL) was added. The aqueous layer was extracted twice with ethyl acetate (20 mL). The combined organic layer was washed with saturated sodium chloride solution (20 mL) and then dried over anhydrous magnesium sulfate. After removing the anhydrous magnesium sulfate by filtration, the filtrate was concentrated. The residue was purified by silica gel chromatography (n-hexane: ethyl acetate=1:1→ethyl acetate:methanol: 28% aqueous ammonia=100:10:0→100:10:1) to obtain the title compound (50 mg) having the following physical properties.

TLC: Rf 0.73 (ethyl acetate:methanol:28% aqueous ammonia=9:1:0.2);

NMR ($CDCl_3$): δ −0.03 (s, 18H), 0.80-0.95 (m, 10H), 1.50-1.63 (m, 6H), 1.78 (m, 1H), 1.78-2.20 (m, 11H), 2.57 (t,

J=6.9 Hz, 2H), 2.60-3.62 (m, 11H), 4.38-4.72 (m, 4H), 5.05-5.28 (m, 6H), 6.85-6.95 (m, 4H), 7.02-7.30 (m, 4H).

EXAMPLE 32

2-hydroxy-N-[3-(1H-imidazol-2-yl)-2-(1H-imidazol-2-ylmethyl)propyl]-N-{4-[(8-isobutyl-2,8-diazaspiro[4.5]dec-2-yl)methyl]benzyl}acetamide

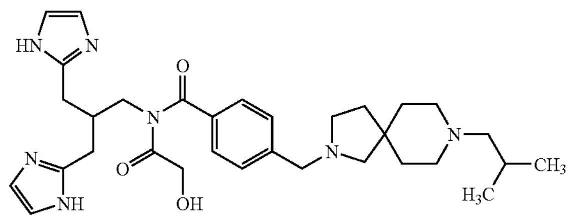

An aqueous 95% trifluoroacetic acid solution (2.2 mL) solution of the compound (94 mg) produced in Example 31 was stirred at 50° C. for 3 hours. The reaction solution was concentrated under reduced pressure. To the residue, a 2N potassium carbonate/methanol solution (2 mL) was added, followed by stirring at room temperature for 30 minutes. To the reaction solution, water (10 mL) was added. The aqueous layer was extracted twice with dichloromethane (20 mL). The combined organic layer was washed with saturated sodium chloride solution (20 mL) and then dried over anhydrous magnesium sulfate. After removing the anhydrous magnesium sulfate by filtration, the filtrate was concentrated. The residue was purified by silica gel chromatography (dichloromethane:methanol: 28% aqueous ammonia=9:1:0.2) to obtain the title compound (22 mg) having the following physical properties.

TLC: Rf 0.28 (ethyl acetate:methanol:28% aqueous ammonia=8:2:0.4);

NMR ($CDCl_3$): δ 0.87 (d, J=6.6 Hz, 6H), 1.50-2.46 (m, 18H), 2.55 (t, J=6.9 Hz, 2H), 2.65-2.80 (m, 2H), 3.35-3.46 (m, 2H), 3.57 (s, 2H), 4.34 (s, 2H), 4.44 (s, 2H), 7.04 (s, 4H), 7.06 (d, J=8.1 Hz, 2H), 7.34 (d, J=8.1 Hz, 2H).

EXAMPLE 33

Ethyl 2-cyano-3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propanoate Except for using cyanoethyl acetate (1.00 g) in place of diethyl malonate, the same operation as in Example 4 was performed to obtain the title compound (2.50 g) having the following physical properties.

TLC: Rf 0.36 (ethyl acetate:methanol:28% aqueous ammonia=9:1:0.1);

NMR ($CDCl_3$): δ −0.03 (s, 18H), 0.89 (t, J=8.4 Hz, 4H), 1.29 (t, J=7.2 Hz, 3H), 3.46 (t, J=8.4 Hz, 4H), 3.61 (s, 4H), 4.22-4.38 (m, 2H), 5.26 (d, J=10.8 Hz, 2H), 5.36 (d, J=10.8 Hz, 2H), 6.95 (d, J=1.5 Hz, 2H), 6.99 (J=1.5 Hz, 2H).

EXAMPLE 34

3-amino-2,2-bis[(1-{[2-(trimethylsilyl)ethoxy]methyl}-1H-imidazol-2-yl)methyl]-1-propanol Except for using the compound (800 mg) produced in Example 33 in place of the compound produced in Example 5, the same operation as in Example 18 was performed to obtain the title compound (620 mg) having the following physical properties.

TLC: Rf 0.29 (ethyl acetate:methanol:28% aqueous ammonia=8:2:0.2);

NMR ($CDCl_3$): δ −0.03 (s, 18H), 0.89 (d, J=8.4 Hz, 4H), 2.46 (s, 2H), 2.86 (d, J=15.0 Hz, 2H), 2.98 (d, J=15.0 Hz, 2H), 3.25 (s, 2H), 3.48 (d, J=8.4 Hz, 4H), 5.26 (d, J=10.8 Hz, 2H), 5.42 (d, J=10.8 Hz, 2H), 6.89-7.00 (m, 4H).

EXAMPLE 35

3-({4-[(8-cyclohexyl-2,8-diazaspiro[4.5]dec-2-yl)methyl]benzyl}amino)-2,2-bis[(1-{[2-(trimethylsilyl)ethoxy]methyl}-1H-imidazol-2-yl)methyl]-1-propanol Except for using the compound (111 mg) produced in Example 34 in place of 8-isobutyl-2,8-diazaspiro[4.5]decane and using the corresponding aldehyde (92 mg) in place of 4-(diethoxymethyl)benzaldehyde, the same operation as in Example 26 was performed to obtain the title compound (100 mg) having the following physical properties.

TLC: Rf 0.39 (ethyl acetate:methanol:28% aqueous ammonia=8:2:0.4);

NMR ($CDCl_3$): δ −0.03 (s, 18H), 0.87 (t, J=8.4 Hz, 4H), 1.00-1.95 (m, 16H), 2.15-2.60 (m, 11H), 2.88 (d, J=15.0 Hz, 2H), 3.01 (d, J=15.0 Hz, 2H), 3.29 (s, 2H), 3.45 (t, J=8.4 Hz, 4H), 3.55 (s, 2H), 3.68 (s, 2H), 5.25 (d, J=10.8 Hz, 2H), 5.38 (d, J=10.8 Hz, 2H), 6.90 (d, J=1.2 Hz, 2H), 6.94 (d, J=1.2 Hz, 2H), 7.20-7.35 (m, 4H).

EXAMPLE 36

3-(acetyl{4-[(8-cyclohexyl-2,8-diazaspiro[4.5]dec-2-yl)methyl]benzyl}amino)-2,2-bis[(1-{[2-(trimethylsilyl)ethoxy]methyl}-1H-imidazol-2-yl)methyl]propyl Acetate To a dichloromethane (2 mL) solution of the compound (33 mg) produced in Example 35, pyridine (31 μL), anhydrous acetic acid (24 μL) and 4-dimethylaminopyridine (2 mg) were added. The reaction solution was stirred at room temperature overnight. To the reaction solution, water (10 mL) was added. The aqueous layer was extracted twice with dichloromethane (20 mL). The combined organic layer was washed with saturated sodium chloride solution (20 mL) and then dried over anhydrous magnesium sulfate. After removing the anhydrous magnesium sulfate by filtration, the filtrate was concentrated. Without purifying the residue, the title compound (33 mg) having the following physical properties was obtained.

TLC: Rf 0.58 (ethyl acetate:methanol:28% aqueous ammonia=8:2:0.4);

NMR ($CDCl_3$): δ −0.03 (s, 18H), 0.87 (t, J=8.4 Hz, 4H), 1.00-3.75 (m, 41H), 3.95-4.38 (m, 4H), 4.60-4.78 (m, 2H), 5.05-5.22 (m, 4H), 6.82-6.95 (m, 4H), 7.06 (d, J=8.1 Hz, 2H), 7.20-7.35 (m, 2H).

EXAMPLE 37

3-(acetyl{4-[(8-cyclohexyl-2,8-diazaspiro[4.5]dec-2-yl)methyl]benzyl}amino)-2,2-bis(1H-imidazol-2-ylmethyl)propyl Acetate Except for using the compound (33 mg) produced in Example 36 in place of the compound produced in Example 20, the same operation as in Example 21 was performed to obtain the title compound (13 mg) having the following physical properties.

TLC: Rf 0.22 (ethyl acetate:methanol:28% aqueous ammonia=8:2:0.4);

NMR ($CDCl_3$): δ 1.00-1.95 (m, 16H), 2.14 (s, 3H), 2.21 (s, 3H), 2.30-2.68 (m, 15H), 3.57 (s, 2H), 3.73 (s, 2H), 4.62 (s, 2H), 6.92-7.08 (m, 6H), 7.34 (d, J=8.1 Hz, 2H).

EXAMPLE 38

3-({4-[(8-cyclohexyl-2,8-diazaspiro[4.5]dec-2-yl) methyl]benzyl}amino)-2,2-bis(1H-imidazol-2-ylmethyl)-1-propanol

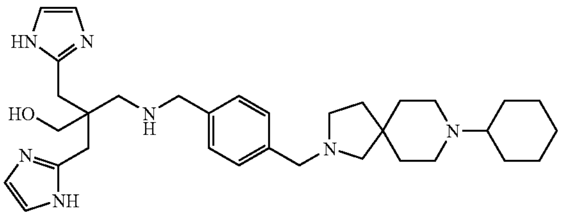

A 2N potassium hydroxide/methanol solution (2 mL) of the compound (11 mg) produced in Example 37 was stirred at room temperature for 2 hours. After concentrating the reaction solution under reduced pressure, water (10 mL) was added to the residue. The aqueous layer was extracted twice with dichloromethane (20 mL). The combined organic layer was washed with saturated sodium chloride solution (20 mL) and then dried over anhydrous magnesium sulfate. After removing the anhydrous magnesium sulfate by filtration, the filtrate was concentrated. Without purifying the residue, the title compound (8 mg) having the following physical properties was obtained.

TLC: Rf 0.21 (ethyl acetate:methanol:28% aqueous ammonia=8:2:0.4);

NMR ($CDCl_3$): δ 0.80-1.95 (m, 16H), 2.10-2.62 (m, 15H), 3.34 (m, 2H), 3.59 (m, 2H), 3.77 (m, 2H), 6.93 (m, 4H), 7.22-7.38 (m, 4H).

EXAMPLE 39

3-hydroxy-2,2-bis[(1-{[2-(trimethylsilyl)ethoxy] methyl}-1H-imidazol-2-yl)methyl]propanenitrile A methanol (300 mL) solution of the compound (10.0 g) produced in Example 33 was cooled to 0° C. and sodium borohydride (2.13 g) was added. The reaction solution was stirred for 3 hours with heating to room temperature. To the reaction solution, water (200 mL) was added. The aqueous layer was extracted twice with ethyl acetate (200 mL). The combined organic layer was washed with saturated sodium chloride solution (100 mL) and then dried over anhydrous magnesium sulfate. After removing the anhydrous magnesium sulfate by filtration, the filtrate was concentrated. The residue was purified by a medium pressure liquid chromatograph W-prep 2XY (trade name, manufactured by YAMAZEN CORPORATION, column: main column 3L, inject column 3L, (n-hexane:ethyl acetate=1:1→1:3→ethyl acetate: methanol: 28% aqueous ammonia=95:5:0.5→90:10:1, isolation mode GR) to obtain the title compound (5.70 g) having the following physical properties.

TLC: Rf 0.45 (ethyl acetate:methanol:28% aqueous ammonia=9:1:0.1);

NMR ($CDCl_3$): δ −0.03 (s, 18H), 0.89 (dd, J=9.0, 7.2 Hz, 4H), 3.32 (s, 4H), 3.48 (dd, J=10.8, 9.0 Hz, 4H), 3.85 (s, 2H), 5.31 (d, J=10.8 Hz, 2H), 5.42 (d, J=10.8 Hz, 2H), 6.97 (d, J=1.2 Hz, 2H), 7.01 (J=1.2 Hz, 2H).

EXAMPLE 40

2-formyl-3-(1-{[2-(trimethylsilyl)ethoxy]methyl}-1H-imidazol-2-yl)-2-[(1-{[2-(trimethylsilyl)ethoxy] methyl}-1H-imidazol-2-yl)methyl]propanenitrile Except for using the compound (475 mg) produced in Example 39 in place of the compound produced in Example 9, the same operation as in Example 10 was performed to obtain the title compound (460 mg) having the following physical properties.

TLC: Rf 0.82 (ethyl acetate:methanol:28% aqueous ammonia=9:1:0.2);

NMR ($CDCl_3$): δ −0.03 (s, 18H), 0.80-1.00 (m, 4H), 3.40-3.70 (m, 8H), 5.20-5.40 (m, 4H), 6.90-7.10 (m, 4H), 9.52 (brs, 1H).

EXAMPLE 41

3-({4-[(8-cyclohexyl-2,8-diazaspiro[4.5]dec-2-yl) methyl]benzyl}amino)-2,2-bis[(1-{[2-(trimethylsilyl)ethoxy]methyl}-1H-imidazol-2-yl)methyl]propanenitrile Except for using the compound (200 mg) produced in Example 40 in place of 4-(diethoxymethyl)benzaldehyde and using 1-{4-[(8-cyclohexyl-2,8-diazaspiro[4.5]dec-2-yl)methyl]phenyl}methaneamine (100 mg) in place of 8-isobutyl-2,8-diazaspiro[4.5]decane, the same operation as in Example 26 was performed to obtain the title compound (200 mg) having the following physical properties.

TLC: Rf 0.55 (ethyl acetate:methanol:28% aqueous ammonia=8:2:0.4);

NMR ($CDCl_3$): δ −0.03 (s, 18H), 0.80-0.98 (m, 4H), 1.00-1.92 (m, 16H), 1.95-2.60 (m, 11H), 3.20-3.60 (m, 10H), 3.84 (s, 2H), 5.27 (d, J=10.8 Hz, 2H), 5.40 (d, J=10.8 Hz, 2H), 6.96-7.02 (m, 4H), 7.18-7.35 (m, 4H).

EXAMPLE 42

3-({4-[(8-cyclohexyl-2,8-diazaspiro[4.5]dec-2-yl) methyl]benzyl}amino)-2,2-bis(1H-imidazol-2-ylmethyl)propanenitrile

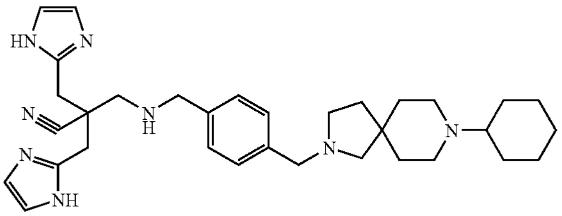

An aqueous 95% trifluoroacetic acid solution (2.2 mL) of the compound (100 mg) produced in Example 41 was stirred at 50° C. for 4 hours. Subsequently, methanol (2 mL) and 5N hydrochloric acid (2 mL) were added, followed by stirring at 50° C. for 2 days. The reaction solution was concentrated under reduced pressure. The residue was purified by silica gel chromatography (ethyl acetate:methanol: 28% aqueous ammonia=8:2:0→0.4) to obtain the title compound (20 mg) having the following physical properties.

TLC: Rf 0.76 (ethyl acetate:methanol:28% aqueous ammonia=8:2:0.5);

NMR ($CDCl_3$): δ 1.00-1.35 (m, 6H), 1.52-1.95 (m, 10H), 2.30 (m, 1H), 2.36 (s, 2H), 2.42-2.60 (m, 4H), 2.58 (t, J=6.9 Hz, 2H), 2.69 (s, 2H), 2.97 (s, 4H), 3.58 (s, 2H), 3.87 (s, 2H), 7.02 (s, 4H), 7.30 (s, 4H).

EXAMPLE 43

3-(methoxymethoxy)-2,2-bis[(1-{[2-(trimethylsilyl)ethoxy]methyl}-1H-imidazol-2-yl)methyl]propanenitrile To a dimethylformamide (5 mL) suspension of sodium hydride (22 mg), a dimethylformamide (5 mL) solution of the compound (500 mg) produced in Example 39 was added. The reaction solution was stirred at 50° C. for 30 minutes. The reaction solution was cooled to room temperature and chloromethylmethylether (150 μL) was added. The reaction solution was stirred at room temperature for 2 hours. To the reaction solution, water (10 mL) was added, followed by extraction twice with dichloromethane (20 mL). The combined organic layer was washed with saturated sodium chloride solution (20 mL) and then dried over anhydrous magnesium sulfate. After removing the anhydrous magnesium sulfate by filtration, the filtrate was concentrated. The residue was purified by silica gel chromatography (n-hexane:ethyl acetate=1:1→1:3→ethyl acetate:methanol: 28% aqueous ammonia=95:5:0.5→90:10:1) to obtain the title compound (310 mg) having the following physical properties.

TLC: Rf 0.65 (ethyl acetate:methanol:28% aqueous ammonia=19:1:0.1);

NMR ($CDCl_3$): δ −0.03 (s, 18H), 0.87 (m, 4H), 3.30-3.60 (m, 11H), 3.98 (s, 2H), 4.73 (s, 2H), 5.29 (d, J=10.8 Hz, 2H), 5.35 (d, J=10.8 Hz, 2H), 6.97 (d, J=1.5 Hz, 2H), 7.01 (d, J=1.5 Hz, 2H).

EXAMPLE 44

3-(methoxymethoxy)-2,2-bis[(1-{[2-(trimethylsilyl)ethoxy]methyl}-1H-imidazol-2-yl)methyl]-1-propanamine Except for using the compound (880 mg) produced in Example 43, the same operation as in Example 18 was performed to obtain the title compound (870 mg) having the following physical properties.

TLC: Rf 0.69 (ethyl acetate:methanol:28% aqueous ammonia=8:2:0.2);

NMR ($CDCl_3$): δ −0.03 (s, 18H), 0.88 (t, J=8.4 Hz, 4H), 2.80 (s, 2H), 2.85 (d, J=15.3 Hz, 2H), 2.96 (d, J=15.3 Hz, 2H), 3.28 (s, 3H), 3.35-3.62 (m, 6H), 4.57 (s, 2H), 5.24 (d, J=10.8 Hz, 2H), 5.36 (d, J=10.8 Hz, 2H), 6.89 (d, J=1.5 Hz, 2H), 6.97 (d, J=1.5 Hz, 2H).

EXAMPLE 45

N-{4-[(8-isobutyl-2,8-diazaspiro[4.5]dec-2-yl)methyl]benzyl}-3-(methoxymethoxy)-2,2-bis[(1-{[2-(trimethylsilyl)ethoxy]methyl}-1H-imidazol-2-yl)methyl]-1-propanamine Except for using the compound (350 mg) produced in Example 44 in place of 8-isobutyl-2,8-diazaspiro[4.5]decane and using the compound (247 mg) produced in Example 27 in place of 4-(diethoxymethyl)benzaldehyde, the same operation as in Example 26 was performed to obtain the title compound (320 mg) having the following physical properties.

TLC: Rf 0.73 (ethyl acetate:methanol:28% aqueous ammonia=19:1:0.1);

NMR ($CDCl_3$): δ −0.03 (s, 18H), 0.80-0.98 (m, 4H), 0.87 (d, J=6.6 Hz, 6H), 1.48-1.85 (m, 7H), 2.02 (d, J=7.2 Hz, 2H), 2.20-2.65 (m, 10H), 2.91 (d, J=15.0 Hz, 2H), 2.99 (d, J=15.0 Hz, 2H), 3.24 (s, 3H), 3.42 (t, J=8.4 Hz, 4H), 3.51 (s, 2H), 3.55 (s, 2H), 3.70 (s, 2H), 4.55 (s, 2H), 5.27 (d, J=10.8 Hz, 2H), 5.37 (d, J=10.8 Hz, 2H), 6.88 (d, J=1.2 Hz, 2H), 6.95 (d, J=1.2 Hz, 2H), 7.20-7.35 (m, 4H).

EXAMPLE 46

3-(1H-imidazol-2-yl)-2-(1H-imidazol-2-ylmethyl)-2-[({4-[(8-isobutyl-2,8-diazaspiro[4.5]dec-2-yl)methyl]benzyl}amino)methyl]-1-propanol An aqueous 95% trifluoroacetic acid solution (2.2 mL) solution of the compound (84 mg) produced in Example 45 was stirred at 50° C. for 4 hours. The reaction solution was concentrated under reduced pressure. To the residue, 6N hydrochloric acid (10 mL) was added, followed by stirring at 90° C. for 22 hours. The reaction solution was concentrated under reduced pressure. The residue was purified by silica gel chromatography (n-hexane:ethyl acetate=1:3→ethyl acetate:methanol: 28% aqueous ammonia=100:0:0→100:10:1) to obtain the title compound (48 mg) having the following physical properties.

TLC: Rf 0.51 (ethyl acetate:methanol:28% aqueous ammonia=8:2:0.4);

NMR ($CDCl_3$): δ 0.87 (d, J=6.6 Hz, 6H), 1.50-1.70 (m, 6H), 1.78 (m, 1H), 2.02 (d, J=7.2 Hz, 2H), 2.20-2.62 (m, 14H), 3.33 (s, 2H), 3.58 (s, 2H), 3.77 (s, 2H), 6.92 (s, 4H), 7.20-7.40 (m, 4H).

EXAMPLE 47

N-{4-[(8-isobutyl-2,8-diazaspiro[4.5]dec-2-yl)methyl]benzyl}-3-(methoxymethoxy)-N-methyl-2,2-bis[(1-{[2-(trimethylsilyl)ethoxy]methyl}-1H-imidazol-2-yl)methyl]-1-propanamine Except for using the compound (75 mg) produced in Example 45 in place of the compound produced in Example 20, the same operation as in Example 22 was performed to obtain the title compound (56 mg) having the following physical properties.

TLC: Rf 0.77 (ethyl acetate:methanol:28% aqueous ammonia=9:1:0.1);

NMR ($CDCl_3$): δ −0.03 (s, 18H), 0.80-0.98 (m, 4H), 0.87 (d, J=6.6 Hz, 6H), 1.48-1.85 (m, 7H), 1.98-2.08 (m, 2H), 2.15-2.62 (m, 13H), 2.90-3.80 (m, 17H), 4.57 (s, 2H), 5.13 (d, J=10.8 Hz, 2H), 5.19 (d, J=10.8 Hz, 2H), 6.85 (s, 2H), 6.95 (s, 2H), 7.18-7.40 (m, 4H).

EXAMPLE 48

3-(1H-imidazol-2-yl)-2-(1H-imidazol-2-ylmethyl)-2-{[{4-[(8-isobutyl-2,8-diazaspiro[4.5]dec-2-yl)methyl]benzyl}(methyl)amino]methyl}-1-propanol An aqueous 95% trifluoroacetic acid solution (2.2 mL) of the compound (56 mg) produced in Example 47 was stirred at 50° C. for one hour. Subsequently, methanol (3 mL) and concentrated hydrochloric acid (3 mL) were added, followed by stirring at 50° C. for 3 hours. The reaction solution was concentrated under reduced pressure. The residue was purified by silica gel chromatography (ethyl acetate:methanol: 28% aqueous ammonia=8:2:0→0.2) to obtain the title compound (17 mg) having the following physical properties.

TLC: Rf 0.38 (ethyl acetate:methanol:28% aqueous ammonia=8:2:0.4);

NMR ($CDCl_3$): δ 0.87 (d, J=6.6 Hz, 6H), 1.45-1.90 (m, 7H), 2.01 (d, J=7.5 Hz, 2H), 2.16-2.80 (m, 17H), 3.30 (s, 2H), 3.56 (s, 4H), 7.00 (s, 4H), 7.22-7.38 (m, 4H).

EXAMPLE 48(1)

3-[{4-[(8-cyclohexyl-2,8-diazaspiro[4.5]dec-2-yl) methyl]benzyl}(methyl)amino]-2,2-bis(1H-imidazol-2-ylmethyl)propanenitrile Except for using the compound (50 mg) produced in Example 41 in place of the compound produced in Example 20, the same operation as in Example 22→Example 21 was performed to obtain the title compound (9 mg) having the following physical properties.

TLC: Rf 0.57 (ethyl acetate:methanol:28% aqueous ammonia=8:2:0.5);

NMR ($CDCl_3$): δ 1.00-1.35 (m, 6H), 1.52-1.92 (m, 10H), 2.22 (m, 1H), 2.35 (s, 2H), 2.40-2.58 (m, 4H), 2.45 (s, 3H), 2.54 (t, J=7.2 Hz, 2H), 2.74 (s, 2H), 2.80 (d, J=14.4 Hz, 2H), 3.07 (d, J=14.4 Hz, 2H), 3.55 (s, 2H), 3.68 (s, 2H), 7.04 (s, 4H), 7.24 (s, 4H), 11.3 (brs, 2H).

EXAMPLE 49

N-{4-[(8-isobutyl-2,8-diazaspiro[4.5]dec-2-yl)methyl]benzyl}-N-{3-(methoxymethoxy)-2,2-bis[(1-{[2-(trimethylsilyl)ethoxy]methyl}-1H-imidazol-2-yl)methyl]propyl}acetamide Except for using the compound (100 mg) produced in Example 45 in place of the compound produced in Example 35, the same operation as in Example 36 was performed to obtain the title compound (75 mg) having the following physical properties.

TLC: Rf 0.65 (ethyl acetate:methanol:28% aqueous ammonia=9:1:0.1);

NMR ($CDCl_3$): δ −0.03 (s, 18H), 0.80-0.98 (m, 10H), 1.50-2.75 (m, 20H), 2.95-3.78 (m, 15H), 3.90-4.10 (m, 2H), 4.52-4.63 (m, 2H), 4.68-4.72 (m, 2H), 5.00-5.28 (m, 4H), 6.80-6.98 (m, 4H), 7.00-7.38 (m, 4H).

EXAMPLE 50

N-[3-hydroxy-2,2-bis(1H-imidazol-2-ylmethyl)propyl]-N-{4-[(8-isobutyl-2,8-diazaspiro[4.5]dec-2-yl) methyl]benzyl}acetamide

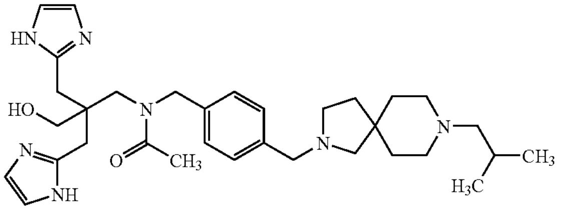

An aqueous 95% trifluoroacetic acid solution (2.2 mL) of the compound (75 mg) produced in Example 49 was stirred at 50° C. for one hour. The reaction solution was concentrated under reduced pressure. The residue was purified by silica gel chromatography (ethyl acetate:methanol: =10:0→10:1) to obtain the title compound (40 mg) having the following physical properties.

TLC: Rf 0.72 (ethyl acetate:methanol:28% aqueous ammonia=8:2:0.4);

NMR (DMSO-$d_6$): δ 0.85 (d, J=6.6 Hz, 6H), 1.45-1.58 (m, 6H), 1.73 (m, 1H), 1.98-2.05 (m, 5H), 2.22-2.68 (m, 12H), 3.22 (s, 2H), 3.40 (s, 2H), 3.54 (s, 2H), 4.80 (s, 2H), 6.94 (s, 4H), 7.08 (d, J=8.1 Hz, 2H), 7.25 (d, J=8.1 Hz, 2H).

EXAMPLE 50(1)

N-[2-cyano-3-(1H-imidazol-2-yl)-2-(1H-imidazol-2-ylmethyl)propyl]-N-{4-[(8-cyclohexyl-2,8-diazaspiro[4.5]dec-2-yl)methyl]benzyl}acetamide

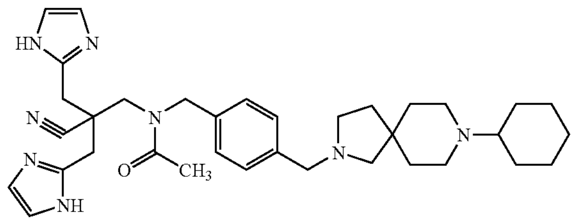

Except for using the compound (50 mg) produced in Example 41 in place of the compound produced in Example 35, the same operation as in Example 36→Example 21 was performed to obtain the title compound (10 mg) having the following physical properties.

TLC: Rf 0.51 (ethyl acetate:methanol:28% aqueous ammonia=8:2:0.5);

NMR ($CDCl_3$): δ 1.00-1.38 (m, 6H), 1.52-1.95 (m, 10H), 2.27 (m, 1H), 2.30 (s, 3H), 2.35 (s, 2H), 2.40-2.58 (m, 4H), 2.55 (t, J=6.6 Hz, 2H), 2.85 (d, J=14.4 Hz, 2H), 3.03 (d, J=14.4 Hz, 2H), 3.53 (brs, 2H), 3.57 (s, 2H), 5.00 (s, 2H), 7.07 (d, J=7.8 Hz, 2H), 7.09 (s, 4H), 7.34 (d, J=7.8 Hz, 2H), 12.7 (brs, 2H).

EXAMPLE 51 ethyl({4-[(8-cyclohexyl-2,8-diazaspiro[4.5]dec-2-yl) methyl]benzyl}amino)acetate To an ethanol solution (2 mL) of 1-{4-[(8-cyclohexyl-2,8-diazaspiro[4.5]dec-2-yl)methyl]phenyl}methaneamine (132 mg) and a toluene solution (93 μL) of 50% ethyl oxoacetate, 10% palladium carbon (30 mg) was added and the atmosphere in the reaction system was replaced by hydrogen. The reaction solution was stirred at room temperature for 6 hours. After palladium carbon was removed by filtering the reaction solution through Celite (trade name), the filtrate was concentrated. Without purifying the residue, the title compound (200 mg) having the following physical properties was obtained.

TLC: Rf 0.53 (ethyl acetate:methanol:28% aqueous ammonia=8:2:0.4);

NMR ($CDCl_3$): δ 1.00-2.00 (m, 19H), 2.10-2.68 (m, 9H), 3.41 (s, 2H), 3.56 (s, 2H), 3.78 (s, 2H), 4.08-4.22 (m, 2H), 7.08-7.35 (m, 4H).

EXAMPLE 52

2-({4-[(8-cyclohexyl-2,8-diazaspiro[4.5]dec-2-yl)methyl]benzyl}amino)ethanol

Except for using the compound (100 mg) produced in Example 51 in place of the compound produced in Example 5, the same operation as in Example 18 was performed to obtain the title compound the title compound (64 mg) having the following physical properties.

TLC: Rf 0.18 (ethyl acetate:methanol:28% aqueous ammonia=8:2:0.4);

NMR ($CDCl_3$): δ 1.00-1.98 (m, 16H), 2.12-2.60 (m, 9H), 2.82 (dd, J=5.7, 4.8 Hz, 2H), 3.56 (s, 2H), 3.58-3.70 (m, 2H), 3.79 (s, 2H), 7.08-7.35 (m, 4H).

EXAMPLE 53

2-({4-[(8-cyclohexyl-2,8-diazaspiro[4.5]dec-2-yl)methyl]benzyl}{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propyl}amino)ethanol Except for using the compound (64 mg) produced in Example 52 in place of 8-isobutyl-2,8-diazaspiro[4.5]decane and using the compound (90 mg) produced in Example 19 in place of 4-(diethoxymethyl)benzaldehyde, the same operation as in Example 26 was performed to obtain the title compound (75 mg) having the following physical properties.

TLC: Rf 0.65 (ethyl acetate:methanol:28% aqueous ammonia=8:2:0.4);

NMR ($CDCl_3$): δ −0.03 (s, 18H), 0.88-0.95 (m, 4H), 1.00-1.92 (m, 16H), 2.10-3.00 (m, 18H), 3.32-3.70 (m, 10H), 5.08 (s, 4H), 6.80-7.00 (m, 4H), 7.04-7.30 (m, 4H).

EXAMPLE 54

2-{{4-[(8-cyclohexyl-2,8-diazaspiro[4.5]dec-2-yl)methyl]benzyl}[3-(1H-imidazol-2-yl)-2-(1H-imidazol-2-ylmethyl)propyl]amino}ethanol

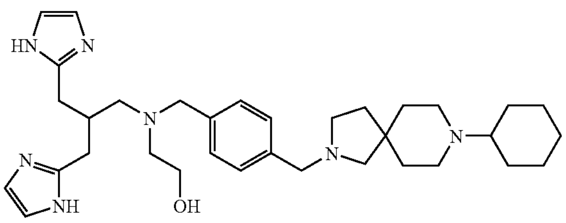

Except for using the compound (38 mg) produced in Example 53 in place of the compound produced in Example 20, the same operation as in Example 21 was performed to obtain the title compound (15 mg) having the following physical properties.

TLC: Rf 0.30 (ethyl acetate:methanol:28% aqueous ammonia=8:2:0.4);

NMR ($CDCl_3$): δ 1.00-1.35 (m, 6H), 1.50-1.92 (m, 10H), 2.18-2.70 (m, 16H), 2.74 (dd, J=14.1, 7.5 Hz, 2H), 3.57 (s, 2H), 3.59 (s, 2H), 3.64 (t, J=5.4 Hz, 2H), 6.97 (s, 4H), 7.29 (s, 4H).

EXAMPLE 55

2-({4-[(8-cyclohexyl-2,8-diazaspiro[4.5]dec-2-yl)methyl]benzyl}{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propyl}amino)ethyl Acetate Except for using the compound (38 mg) produced in Example 53 in place of the compound produced in Example 35, the same operation as in Example 36 was performed to obtain the title compound (38 mg) having the following physical properties.

TLC: Rf 0.62 (ethyl acetate:methanol:28% aqueous ammonia=8:2:0.4);

NMR ($CDCl_3$): δ −0.03 (s, 18H), 0.88-1.00 (m, 4H), 1.00-3.10 (m, 37H), 3.38-3.90 (m, 8H), 4.00-4.18 (m, 2H), 5.10-5.32 (m, 4H), 6.78-6.95 (m, 4H), 7.00-7.38 (m, 4H).

EXAMPLE 56

2-({4-[(8-cyclohexyl-2,8-diazaspiro[4.5]dec-2-yl)methyl]benzyl}[3-(1H-imidazol-2-yl)-2-(1H-imidazol-2-ylmethyl)propyl]amino)ethyl Acetate Except for using the compound (38 mg) produced in Example 55 in place of the compound produced in Example 20, the same operation as in Example 21 was performed to obtain the title compound (6 mg) having the following physical properties.

TLC: Rf 0.62 (ethyl acetate:methanol:28% aqueous ammonia=8:2:0.4);

NMR ($CDCl_3$): δ 1.05-2.90 (m, 32H), 2.05 (s, 3H), 2.77 (t, J=6.0 Hz, 2H), 3.59 (s, 2H), 3.61 (s, 2H), 4.23 (t, J=6.0 Hz, 2H), 6.87 (s, 4H), 7.25-7.38 (m, 4H).

EXAMPLE 57

N-{4-[(8-cyclohexyl-2,8-diazaspiro[4.5]dec-2-yl)methyl]benzyl}-3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]-1-propanamine Except for using the compound (164 mg) produced in Example 19 in place of 4-(diethoxymethyl)benzaldehyde and using 1-{4-[(8-cyclohexyl-2,8-diazaspiro[4.5]dec-2-yl)methyl]phenyl}methaneamine (100 mg) in place of 8-isobutyl-2,8-diazaspiro[4.5]decane, the same operation as in Example 26 was performed to obtain the title compound (220 mg) having the following physical properties.

TLC: Rf 0.42 (ethyl acetate:methanol:28% aqueous ammonia=8:2:0.2);

NMR ($CDCl_3$): δ −0.03 (s, 18H), 0.87 (t, J=8.4 Hz, 4H), 1.00-1.95 (m, 16H), 2.12-2.95 (m, 16H), 3.40-3.50 (m, 4H), 3.54 (s, 2H), 3.70 (s, 2H), 5.19 (d, J=10.8 Hz, 2H), 5.27 (d, J=10.8 Hz, 2H), 6.88 (d, J=1.5 Hz, 2H), 6.92 (d, J=1.5 Hz, 2H), 7.18-7.28 (m, 4H).

EXAMPLE 58 ethyl({4-[(8-cyclohexyl-2,8-diazaspiro[4.5]dec-2-yl)methyl]benzyl}{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propyl}amino)acetate To a 10% acetic acid-dimethylformamide (2.2 mL) solution of the compound (125 mg) produced in Example 57 and a 50% ethyl glyoxylate/toluene solution (148 μL), sodium triacetoxyborohydride (337 mg) was added. The reaction solution was stirred at room temperature for 17 hours. 1N hydrochloric acid was added to the reaction solution so as to adjust the pH to about 5. The aqueous layer was extracted twice with dichloromethane (20 mL). The combined organic layer was washed with saturated sodium chloride solution (20 mL) and then dried over anhydrous magnesium sulfate. After removing the anhydrous magnesium sulfate by filtration, the filtrate was concentrated. The residue was purified by silica gel chromatography (n-hexane:ethyl acetate=1:1→0:1→ethyl acetate:methanol=100:0→30:1) to obtain the title compound (53 mg) having the following physical properties.

TLC: Rf 0.78 (ethyl acetate:methanol:28% aqueous ammonia=8:2:0.2);

NMR ($CDCl_3$): δ d-0.03 (s, 18H), 0.87 (t, J=8.1 Hz, 4H), 1.00-1.90 (m, 16H), 1.23 (t, J=7.2 Hz, 3H), 2.12-2.68 (m, 12H), 2.72-2.82 (m, 2H), 2.88-3.00 (m, 2H), 3.26 (s, 2H), 3.44 (t, J=8.1 Hz, 4H), 3.53 (s, 2H), 3.70 (s, 2H), 4.09 (q, J=7.2 Hz, 2H), 5.15 (d, J=10.8 Hz, 2H), 5.24 (d, J=10.8 Hz, 2H), 6.87 (d, J=1.5 Hz, 2H), 6.89 (d, J=1.5 Hz, 2H), 7.21 (s, 4H).

EXAMPLE 59 ethyl({4-[(8-cyclohexyl-2,8-diazaspiro[4.5]dec-2-yl)methyl]benzyl}[3-(1H-imidazol-2-yl)-2-(1H-imidazol-2-ylmethyl)propyl]amino)acetate

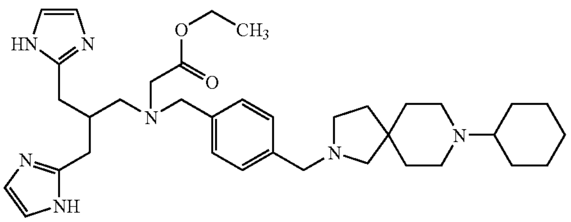

Except for using the compound (52 mg) produced in Example 58 in place of the compound produced in Example 20, the same operation as in Example 21 was performed to obtain the title compound (38 mg) having the following physical properties.

TLC: Rf 0.34 (ethyl acetate:methanol:28% aqueous ammonia=8:2:0.4);

NMR ($CDCl_3$): δ 1.00-1.36 (m, 6H), 1.24 (t, J=7.2 Hz, 3H), 1.48-1.92 (m, 10H), 2.18-2.55 (m, 10H), 2.58 (t, J=6.9 Hz, 2H), 2.60-2.80 (m, 4H), 3.26 (s, 2H), 3.57 (s, 2H), 3.62 (s, 2H), 4.15 (q, J=7.2 Hz, 2H), 6.99 (m, 4H), 7.31 (m, 4H), 11.8 (brs, 2H).

EXAMPLE 60

({4-[(8-cyclohexyl-2,8-diazaspiro[4.5]dec-2-yl)methyl]benzyl}[3-(1H-imidazol-2-yl)-2-(1H-imidazol-2-ylmethyl)propyl]amino)acetic Acid To the compound (28 mg) produced in Example 59, concentrated hydrochloric acid (2 mL) was added, followed by stirring at 90° C. for 6 hours. The reaction solution was azeotroped with toluene. The residue was purified by silica gel chromatography (manufactured by FUJI SILYSIA CHEMICAL LTD., CHROMATOREX NH (trade name) (dichloromethane:methanol=10:0→7:3) to obtain the title compound (13 mg) having the following physical properties.

TLC: Rf 0.35 (dichloromethane:methanol:28% aqueous ammonia=8:2:0.5);

NMR ($CD_3OD$): δ 1.04-2.05 (m, 16H), 2.30-2.95 (m, 16H), 3.00 (s, 2H), 3.58 (s, 2H), 3.59 (s, 2H), 6.94 (s, 4H), 7.22 (d, J=8.4 Hz, 2H), 7.26 (d, J=8.4 Hz, 2H).

EXAMPLE 61

N-(2-methoxyethyl)-3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]-1-propanamine Except for using the compound (120 mg) produced in Example 19 and using 2-methoxyethylamine (39 mg) in place of 8-isobutyl-2,8-diazaspiro[4.5]decane, the same operation as in Example 26 was performed to obtain the title compound (107 mg) having the following physical properties.

TLC: Rf 0.49 (ethyl acetate:methanol:28% aqueous ammonia=8:2:0.2);

NMR ($CDCl_3$): δ −0.03 (s, 18H), 0.87 (t, J=8.1 Hz, 4H), 2.58 (m, 1H), 2.64 (d, J=5.7 Hz, 2H), 2.72 (t, J=5.4 Hz, 2H), 2.80-2.98 (m, 4H), 3.32 (s, 3H), 3.40-3.48 (m, 6H), 5.19 (d, J=10.8 Hz, 2H), 5.29 (d, J=10.8 Hz, 2H), 6.88 (s, 2H), 6.91 (s, 2H).

EXAMPLE 62

N-{4-[(8-cyclohexyl-2,8-diazaspiro[4.5]dec-2-yl)methyl]benzyl}-N-(2-methoxyethyl)-3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]-1-propanamine Except for using the compound (55 mg) produced in Example 61 in place of 8-isobutyl-2,8-diazaspiro[4.5]decane and using (43 mg) in place of 4-(diethoxymethyl)benzaldehyde, the same operation as in Example 26 was performed to obtain the title compound (50 mg) having the following physical properties.

TLC: Rf 0.56 (ethyl acetate:methanol:28% aqueous ammonia=8:2:0.2);

NMR ($CDCl_3$): δ −0.03 (s, 18H), 0.80-0.95 (m, 4H), 1.00-1.95 (m, 16H), 2.18-2.95 (m, 18H), 3.22-3.65 (m, 13H), 5.10-5.32 (m, 4H), 6.82-6.95 (m, 4H), 7.19 (s, 4H).

EXAMPLE 63

N-{4-[(8-cyclohexyl-2,8-diazaspiro[4.5]dec-2-yl)methyl]benzyl}-3-(1H-imidazol-2-yl)-2-(1H-imidazol-2-ylmethyl)-N-(2-methoxyethyl)-1-propanamine Except for using the compound (50 mg) produced in Example 62 in place of the compound produced in Example 20, the same operation as in Example 21 was performed to obtain the title compound (12 mg) having the following physical properties.

TLC: Rf 0.52 (ethyl acetate:methanol:28% aqueous ammonia=8:2:0.4);

NMR ($CDCl_3$): δ 0.80-1.94 (m, 16H), 2.20-2.75 (m, 18H), 3.32 (s, 3H), 3.42 (t, J=5.1 Hz, 2H), 3.57 (s, 2H), 3.59 (s, 2H), 6.96 (s, 4H), 7.28 (s, 4H).

EXAMPLE 63(1)-EXAMPLE 63(2)

Except for using the corresponding amine in place of 2-methoxyethylamine and using the corresponding aldehyde in place of the compound produced in Example 19 in Example 61, the same operation as in Example 61→Example 62→Example 63 was performed to obtain the following compounds.

EXAMPLE 63(1)

N-{4-[(8-cyclohexyl-2,8-diazaspiro[4.5]dec-2-yl)methyl]benzyl}-3-(1H-imidazol-2-yl)-2-(1H-imidazol-2-ylmethyl)-N-[2-(1-pyrrolidinyl)ethyl]-1-propanamine TLC: Rf 0.35 (ethyl acetate:methanol:28% aqueous ammonia=8:2:0.4);

NMR ($CDCl_3$): δ 0.80-2.03 (m, 20H), 2.20-2.82 (m, 24H), 3.48 (s, 2H), 3.57 (s, 2H), 6.98 (s, 4H), 7.24 (s, 4H).

EXAMPLE 63(2)

N-[3-(1H-imidazol-2-yl)-2-(1H-imidazol-2-ylmethyl)propyl]-N-{4-[(8-isobutyl-2,8-diazaspiro[4.5]dec-2-yl)methyl]benzyl}-1,2-ethanediamine TLC: Rf 0.38 (ethyl acetate:methanol:28% aqueous ammonia=8:2:0.4);

NMR ($CDCl_3$): δ 0.87 (d, J=6.3 Hz, 6H), 1.45-1.70 (m, 6H), 1.77 (m, 1H), 2.04 (d, J=7.2 Hz, 2H), 2.20-2.85 (m, 19H), 3.54 (s, 2H), 3.57 (s, 2H), 6.98 (s, 4H), 7.18-7.38 (m, 4H).

EXAMPLE 64

2-formyl-N,N-dimethyl-1H-imidazole-1-sulfonamide

To an acetonitrile (500 mL) solution of 2-formylimidazole (64 g) and triethylamine (140 mL), dimethylsulfamoyl chloride (100 g) was added at room temperature. The reaction solution was stirred at 50° C. for 16 hours. The reaction solution was cooled to room temperature and the precipitated crystal was removed by filtration, and then the filtrate was concentrated under reduced pressure. The residue was washed with ethyl acetate to obtain a crude compound. The wash solution was washed with saturated sodium chloride solution and then dried over anhydrous sodium sulfate. After removing the anhydrous sodium sulfate by filtration, the filtrate was concentrated. The residue was purified by silica gel chromatography (ethyl acetate) to obtain a crude product. The crude product was combined with the crude product obtained previously, followed by washing with ether to obtain the title compound (88.3 g) having the following physical properties.

TLC: Rf 0.69 (Chloroform:methanol=9:1);

NMR ($CDCl_3$): δ 3.02 (s, 6H), 7.32 (d, J=1.3 Hz, 1H), 7.59 (dd, J=1.3, 0.8 Hz, 1H), 9.95 (d, J=0.8 Hz, 1H).

EXAMPLE 65

2-(hydroxymethyl)-N,N-dimethyl-1H-imidazole-1-sulfonamide

A methanol (5 mL) solution of the compound (470 mg) produced in Example 64 was cooled to 0° C. and sodium borohydride (87.8 mg) was added. After stirring the reaction solution at 0° C. for 30 minutes, water was added. The reaction solution was concentrated under reduced pressure, extracted with ethyl acetate. Then the organic layer was dried over anhydrous sodium sulfate and concentrated under reduced pressure. The precipitated powder was washed with ether to obtain the title compound (367 mg) having the following physical properties.

TLC: Rf 0.63 (dichloromethane: methanol=9:1);

NMR ($CDCl_3$): δ 2.94 (s, 6H), 4.87 (s, 2H), 7.02 (d, J=1.5 Hz, 1H), 7.26 (d, J=1.5 Hz, 1H).

EXAMPLE 66

2-(chloromethyl)-N,N-dimethyl-1H-imidazole-1-sulfonamide

To a tetrahydrofuran (100 mL) solution of the compound (15.0 g) produced in Example 65, triethylamine (20 mL) was added, followed by cooling to 0° C. Methanesulfonyl chloride (7.03 mL) and lithium chloride (9.30 g) were added. The reaction solution was stirred for 3 hours with heating to room temperature. To the reaction solution, water (100 mL) was added. The aqueous layer was extracted twice with ethyl acetate (100 mL). The combined organic layer was washed with saturated sodium chloride solution (50 mL) and then dried over anhydrous magnesium sulfate. After removing the anhydrous magnesium sulfate by filtration, the filtrate was concentrated. Without purifying the residue, the title compound (15.7 g) having the following physical properties was obtained.

TLC: Rf 0.85 (ethyl acetate:methanol=19:1);

NMR ($CDCl_3$): δ 3.00 (s, 6H), 4.91 (s, 2H), 7.09 (d, J=1.5 Hz, 1H), 7.28 (d, J=1.5 Hz, 1H).

EXAMPLE 67 diethyl bis({1-[(dimethylamino)sulfonyl]-1H-imidazol-2-yl}methyl)malonate

Except for using the compound (13.0 mg) produced in Example 66 in place of the compound produced in Example 3, the same operation as in Example 4 was performed to obtain the title compound (12.8 g) having the following physical properties.

TLC: Rf 0.17 (n-hexane:ethyl acetate:methanol=1:2);

NMR ($CDCl_3$): δ 1.17 (t, J=7.2 Hz, 6H), 2.86 (s, 12H), 4.00 (s, 4H), 4.20 (q, J=7.2 Hz, 4H), 6.86 (d, J=1.5 Hz, 2H), 7.19 (d, J=1.5 Hz, 2H).

EXAMPLE 68

3-{1-[(dimethylamino)sulfonyl]-1H-imidazol-2-yl}-2-({1-[(dimethylamino)sulfonyl]-1H-imidazol-2-yl}methyl)propanoic Acid Except for using the compound (5.98 mg) produced in Example 67 in place of the compound produced in Example 4, the same operation as in Example 5 was performed to obtain the title compound (1.50 g) having the following physical properties.

TLC: Rf 0.35 (dichloromethane:methanol:28% aqueous ammonia=8:2:0.5);

NMR ($CDCl_3$): δ 2.94 (s, 12H), 3.26-3.45 (m, 4H), 3.82 (m, 1H), 6.94 (d, J=1.5 Hz, 2H), 7.02 (d, J=1.5 Hz, 2H).

EXAMPLE 69 benzyl[2-{1-[(dimethylamino)sulfonyl]-1H-imidazol-2-yl}-1-({1-[(dimethylamino)sulfonyl]-1H-imidazol-2-yl}methyl)ethyl]carbamate A benzyl alcohol (4 mL) solution of the compound (567 mg) produced in Example 68, triethylamine (643 μL) and diphenyl phosphorylazide (527 μL) were added. The reaction solution was stirred at 85° C. for 8 hours. To the reaction solution, water (20 mL) was added. The aqueous layer was extracted twice with ethyl acetate (20 mL). The combined organic layer was washed with saturated sodium chloride solution (20 mL) and then dried over anhydrous magnesium sulfate. After removing the anhydrous magnesium sulfate by filtration, the filtrate was concentrated. The residue was purified by silica gel chromatography (n-hexane:ethyl acetate=1:1→0:1→ethyl acetate:methanol: 28% aqueous ammonia=20:1:0.2→10:1:0.1) to obtain the title compound (472 mg) having the following physical properties.

TLC: Rf 0.40 (ethyl acetate:methanol:28% aqueous ammonia=9:1:0.2);

NMR ($CDCl_3$): δ 2.82 (s, 12H), 3.20-3.40 (m, 4H), 4.71 (m, 1H), 5.03 (s, 2H), 6.55 (m, 1H), 6.84-7.00 (m, 4H), 7.02-7.38 (m, 5H).

EXAMPLE 70

2,2'-(2-amino-1,3-propanediyl)bis(N,N-dimethyl-1H-imidazole-1-sulfonamide)

To an ethanol solution (5 mL) of the compound (470 mg) produced in Example 69, 10% palladium carbon (100 mg) was added and the atmosphere in the reaction system was replaced by hydrogen. The reaction solution was stirred at room temperature for 8 hours. After removing palladium carbon by filtering the reaction solution through Celite (trade name), the filtrate was concentrated. The residue was purified by silica gel chromatography (n-hexane:ethyl acetate=1:1→ethyl acetate:methanol:28% aqueous ammonia=100:0:0→80:20:2) to obtain the title compound (160 mg) having the following physical properties.

TLC: Rf 0.50 (ethyl acetate:methanol:28% aqueous ammonia=8:1:0.5);

NMR ($CDCl_3$): δ 2.86 (s, 12H), 3.22-3.40 (m, 4H), 4.03 (m, 1H), 6.95 (d, J=1.5 Hz, 2H), 7.22 (d, J=1.5 Hz, 2H).

EXAMPLE 71

4-(hydroxymethyl)cyclohexanol

Except for using ethyl 4-oxocyclohexanecarboxylate (1.00 g) in place of the compound produced in Example 5, the same operation as in Example 18 was performed to obtain the title compound (1.00 g) having the following physical properties.

TLC: Rf 0.16 (n-hexane:ethyl acetate=1:3);

NMR ($CDCl_3$): δ 0.92-2.10 (m, 9H), 3.40-3.62 (m, 2H), 4.01 (m, 1H).

EXAMPLE 72

4-oxocyclohexanecarbaldehyde

Except for using the compound (1.00 mg) produced in Example 71 in place of the compound produced in Example 9, the same operation as in Example 10 was performed to obtain the title compound (1.00 g) having the following physical properties.

TLC: Rf 0.31 (n-hexane:ethyl acetate=1:1);

NMR ($CDCl_3$): δ 1.65-2.50 (m, 8H), 2.66 (m, 1H), 9.76 (s, 1H).

EXAMPLE 73

4-[(8-cyclohexyl-2,8-diazaspiro[4.5]dec-2-yl)methyl]cyclohexanone

Except for using the compound (550 mg) produced in Example 72 in place of 4-(diethoxymethyl)benzaldehyde and using 8-cyclohexyl-2,8-diazaspiro[4.5]decane (295 mg) in place of 8-isobutyl-2,8-diazaspiro[4.5]decane, the same operation as in Example 26 was performed to obtain the title compound (100 mg) having the following physical properties.

TLC: Rf 0.55 (ethyl acetate:methanol:28% aqueous ammonia=8:2:0.4);

NMR ($CDCl_3$): δ 0.82-2.00 (m, 21H), 2.00-2.60 (m, 15H).

EXAMPLE 74

2,2'-[2-({4-[(8-cyclohexyl-2,8-diazaspiro[4.5]dec-2-yl)methyl]cyclohexyl}amino)-1,3-propanediyl]bis(N,N-dimethyl-1H-imidazole-1-sulfonamide)

Except for using the compound (90 mg) produced in Example 73 in place of 4-(diethoxymethyl)benzaldehyde and using the compound (143 mg) produced in Example 70 in place of 8-isobutyl-2,8-diazaspiro[4.5]decane, the same operation as in Example 26 was performed to obtain the title compound (100 mg) having the following physical properties.

TLC: Rf 0.43 (ethyl acetate:methanol:28% aqueous ammonia=8:2:0.5);

NMR ($CD_3OD$): δ 0.80-2.05 (m, 25H), 2.25-2.95 (m, 12H), 2.86 (s, 12H), 3.02-3.22 (m, 4H), 3.58 (m, 1H), 6.94-6.98 (m, 2H), 7.40-7.42 (m, 2H).

EXAMPLE 75

4-[(8-cyclohexyl-2,8-diazaspiro[4.5]dec-2-yl)methyl]-N-[2-(1H-imidazol-2-yl)-1-(1H-imidazol-2-ylmethyl)ethyl]cyclohexanamine

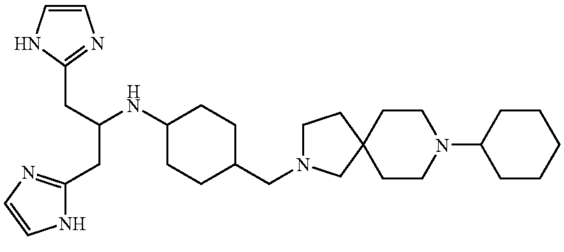

A 4N dioxane solution (2 mL) of the compound (50 mg) produced in Example 74 was stirred at 50° C. for 2 hours. The reaction solution was concentrated under reduced pressure. The residue was purified by silica gel chromatography (ethyl acetate:methanol: 28% aqueous ammonia=90:10:0→80:20:2→dichloromethane:methanol:28% aqueous ammonia=80:20:2→80:20:4) to obtain the title compound (23 mg) having the following physical properties.

TLC: Rf 0.21 (dichloromethane:methanol:28% aqueous ammonia=8:2:0.2);

NMR ($CDCl_3$): δ 0.82-3.00 (m, 41H), 3.32 (m, 1H), 6.92-7.08 (m, 4H).

EXAMPLE 76

2,2'-{2-[{4-[(8-cyclohexyl-2,8-diazaspiro[4.5]dec-2-yl)methyl]cyclohexyl}(methyl)amino]-1,3-propanediyl}bis(N,N-dimethyl-1H-imidazole-1-sulfonamide)

Except for using the compound (47 mg) produced in Example 74 in place of the compound produced in Example 20, the same operation as in Example 22 was performed to obtain the title compound (42 mg) having the following physical properties.

TLC: Rf 0.54 (ethyl acetate:methanol:28% aqueous ammonia=8:2:0.4);

NMR ($CDCl_3$): δ 0.76-2.70 (m, 40H), 2.80-2.95 (m, 12H), 2.95-3.10 (m, 2H), 3.20-3.25 (m, 2H), 4.14 (m, 1H), 6.90-6.95 (m, 2H), 7.14-7.20 (m, 2H).

EXAMPLE 77

4-[(8-cyclohexyl-2,8-diazaspiro[4.5]dec-2-yl)methyl]-N-[2-(1H-imidazol-2-yl)-1-(1H-imidazol-2-ylmethyl)ethyl]-N-methylcyclohexanamine To a methanol (3 mL) solution of the compound (42 mg) produced in Example 76, a 4N dioxane solution (3 mL) was added, followed by stirring at 50° C. for 2 hour. The reaction solution was concentrated under reduced pressure. The residue was purified by silica gel chromatography (dichloromethane:methanol: 28% aqueous ammonia=100:10:0→80:20:3) to obtain the title compound (16 mg) having the following physical properties.

TLC: Rf 0.32 (dichloromethane:methanol:28% aqueous ammonia=8:2:0.4);

NMR ($CDCl_3$): δ 0.80-2.60 (m, 40H), 2.60-2.78 (m, 2H), 2.80-2.92 (m, 2H), 3.45 (m, 1H), 6.95 (m, 4H).

EXAMPLE 78

4-formyl-N-{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propyl}benzamide To a dimethylformamide (2 mL) solution of the compound (300 mg) produced in Example 29 and 4-formylbenzoic acid (116 mg), 1-ethyl-3-[3-(dimethylamino)propyl]carbodiimide (hereafter abbreviated to EDC) (274 mg) and 1-hydroxybenzimidazole (104 mg) were added in this order. The reaction solution was stirred at room temperature for 17 hour. To the reaction solution, water (10 mL) was added. The aqueous layer was extracted twice with dichloromethane (20 mL). The combined organic layer was washed with saturated sodium chloride solution (20 mL) and then dried over anhydrous magnesium sulfate. After removing the anhydrous magnesium sulfate by filtration, the filtrate was concentrated. The residue was purified by silica gel chromatography (ethyl acetate:methanol: 28% aqueous ammonia=1:0:0→100:10:1) to obtain the title compound (510 mg).

TLC: Rf 0.76 (ethyl acetate:methanol:28% aqueous ammonia=8:2:0.2);

NMR ($CDCl_3$): δ −0.03 (s, 18H), 0.86 (t, J=8.4 Hz, 4H), 2.78-3.02 (m, 5H), 3.44 (t, J=8.4 Hz, 4H), 3.60 (t, J=5.1 Hz, 2H), 5.18 (s, 4H), 6.92 (d, J=1.2 Hz, 2H), 6.95 (d, J=1.2 Hz, 2H), 7.94 (d, J=8.4 Hz, 2H), 8.10 (d, J=8.4 Hz, 2H), 9.47 (m, 1H), 10.08 (s, 1H).

EXAMPLE 79

4-[(8-isobutyl-2,8-diazaspiro[4.5]dec-2-yl)methyl]-N-{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propyl}benzamide Except for using the compound (60 mg) produced in Example 78 in place of 4-(diethoxymethyl)benzaldehyde, the same operation as in Example 26 was performed to obtain the title compound (82 mg) having the following physical properties.

TLC: Rf 0.62 (ethyl acetate:methanol:28% aqueous ammonia=9:1:0.2);

NMR ($CDCl_3$): δ −0.03 (s, 18H), 0.80-1.02 (m, 10H), 1.40-3.80 (m, 30H), 5.20 (s, 4H), 6.93 (d, J=2.1 Hz, 2H), 6.96 (d, J=2.1 Hz, 2H), 7.37 (d, J=8.1 Hz, 2H), 8.84 (d, J=8.1 Hz, 2H), 8.71 (m, 1H).

EXAMPLE 80

N-[3-(1H-imidazol-2-yl)-2-(1H-imidazol-2-ylmethyl)propyl]-4-[(8-isobutyl-2,8-diazaspiro[4.5]dec-2-yl)methyl]benzamide

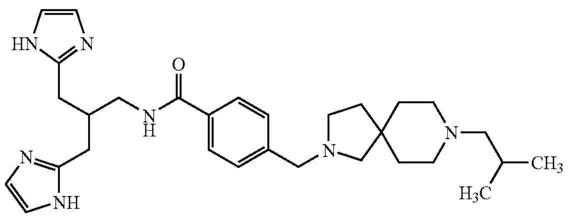

Except for using the compound (82 mg) produced in Example 79 in place of the compound produced in Example 20, the same operation as in Example 21 was performed to obtain the title compound (65 mg) having the following physical properties.

TLC: Rf 0.29 (ethyl acetate:methanol:28% aqueous ammonia=8:2:0.4);

NMR ($CD_3OD$): δ 1.03 (d, J=6.6 Hz, 6H), 1.88-2.24 (m, 7H), 2.77 (m, 1H), 2.92-3.66 (m, 16H), 4.46 (s, 2H), 7.42 (s, 4H), 7.64 (d, J=8.1 Hz, 2H), 7.94 (d, J=8.1 Hz, 2H).

EXAMPLE 80(1)-EXAMPLE 80(4)

Except for using the corresponding amine in place of 8-isobutyl-2,8-diazaspiro[4.5]decane in Example 79, the same operation as in Example 79→Example 80 was performed to obtain the following compounds.

EXAMPLE 80(1)

4-[(8-cyclohexyl-2,8-diazaspiro[4.5]dec-2-yl)methyl]-N-[3-(1H-imidazol-2-yl)-2-(1H-imidazol-2-ylmethyl)propyl]benzamide TLC: Rf 0.59 (ethyl acetate:methanol:28% aqueous ammonia=8:2:0.4);

NMR ($CDCl_3$): δ 1.00-1.92 (m, 16H), 2.18-2.65 (m, 8H), 2.34 (s, 2H), 2.56 (t, J=6.9 Hz, 2H), 2.78 (dd, J=14.4, 5.4 Hz, 2H), 3.45 (t, J=6.9 Hz, 2H), 3.62 (s, 2H), 6.90-7.10 (m, 4H), 7.41 (d, J=8.1 Hz, 2H), 7.84 (d, J=8.1 Hz, 2H), 8.26 (m, 1H).

EXAMPLE 80(2)

4-({[4-(dipropylamino)butyl]amino}methyl)-N-[3-(1H-imidazol-2-yl)-2-(1H-imidazol-2-ylmethyl)propyl]benzamide TLC: Rf 0.29 (ethyl acetate:methanol:28% aqueous ammonia=8:2:0.4);

NMR ($CD_3OD$): δ 1.01 (t, J=7.2 Hz, 6H), 1.64-1.90 (m, 8H), 2.65 (m, 1H), 2.82-3.20 (m, 12H), 3.40 (d, J=6.0 Hz, 2H), 4.27 (s, 2H), 7.25 (s, 4H), 7.61 (d, J=8.4 Hz, 2H), 7.94 (d, J=8.4 Hz, 2H).

EXAMPLE 80(3)

Ethyl 2-(4-{[3-(1H-imidazol-2-yl)-2-(1H-imidazol-2-ylmethyl)propyl]carbamoyl}benzyl)-8-isobutyl-2,8-diazaspiro[4.5]decane-3-carboxylate TLC: Rf 0.69 (ethyl acetate:methanol:28% aqueous ammonia=8:2:0.4);

NMR ($CDCl_3$): δ 0.85 (d, J=6.3 Hz, 6H), 1.25 (t, J=7.2 Hz, 3H), 1.40-2.40 (m, 15H), 2.59 (dd, J=14.4, 6.9 Hz, 2H), 2.78 (dd, J=14.4, 5.1 Hz, 2H), 2.86 (d, J=9.3 Hz, 1H), 3.36 (t, J=8.1 Hz, 1H), 3.45 (t, J=5.4 Hz, 2H), 3.51 (d, J=13.8 Hz, 1H), 4.02 (d, J=13.8 Hz, 1H), 4.10-4.22 (m, 2H), 7.00 (s, 4H), 7.43 (d, J=8.4 Hz, 2H), 7.85 (d, J=8.4 Hz, 2H), 8.47 (m, 1H).

EXAMPLE 80(4)

4-({[4-(1-azepanyl)cyclohexyl]amino}methyl)-N-[3-(1H-imidazol-2-yl)-2-(1H-imidazol-2-ylmethyl)propyl]benzamide TLC: Rf 0.25, 0.15 (ethyl acetate:methanol:28% aqueous ammonia=8:2:0.4);

NMR ($CD_3OD$): δ 1.22-2.26 (m, 16H), 2.42-3.40 (m, 13H), 3.89 (s, 2H), 6.96 (s, 4H), 7.42-7.58 (m, 2H), 7.80-7.94 (m, 2H).

EXAMPLE 81

2-(4-{[3-(1H-imidazol-2-yl)-2-(1H-imidazol-2-ylmethyl)propyl]carbamoyl}benzyl)-8-isobutyl-2,8-diazaspiro[4.5]decane-3-carboxylic Acid To a tetrahydrofuran (2 mL)-methanol (2 mL) solution of the compound (51 mg) produced in Example 80(3), an aqueous 2N sodium hydroxide solution (0.5 mL) was added. The reaction solution was stirred at 50° C. for 3 hours. To the reaction solution, 1N hydrochloric acid was added so as to adjust the pH to about 5. The reaction solution was concentrated under reduced pressure. The residue was washed with ethanol. An insoluble salt was removed by filtration, and then the filtrate was concentrated. The residue was purified by silica gel chromatography (dichloromethane:methanol: 28% aqueous ammonia=8:2:0.5) to obtain the title compound (35 mg) having the following physical properties.

TLC: Rf 0.35 (dichloromethane:methanol:28% aqueous ammonia=8:2:0.5);

NMR ($CD_3OD$): δ 0.95 (d, J=6.6 Hz, 6H), 1.65-2.20 (m, 7H), 2.40-2.95 (m, 12H), 3.08 (d, J=12.0 Hz, 1H), 3.20-3.38 (m, 2H), 3.49 (m, 1H), 3.78 (d, J=12.6 Hz, 1H), 4.29 (d, J=12.6 Hz, 1H), 6.97 (s, 4H), 7.56 (d, J=8.4 Hz, 2H), 7.83 (d, J=8.4 Hz, 2H).

EXAMPLE 82

N-[2-(4-morpholinyl)ethyl]-3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]-1-propanamine Except for using the compound (200 mg) produced in Example 19 in place of 4-(diethoxymethyl)benzaldehyde and using 2-morpholin-4-ylethaneamine (112 mg) in place of 8-isobutyl-2,8-diazaspiro[4.5]decane, the same operation as in Example 26 was performed to obtain the title compound (184 mg) having the following physical properties.

TLC: Rf 0.42 (ethyl acetate:methanol:28% aqueous ammonia=8:2:0.2);

NMR ($CDCl_3$): δ −0.03 (s, 18H), 0.88 (t, J=8.4 Hz, 4H), 2.30-2.95 (m, 15H), 3.45 (t, J=8.4 Hz, 4H), 3.62-3.78 (m, 4H), 5.20 (d, J=10.8 Hz, 2H), 5.28 (d, J=10.8 Hz, 2H), 6.88 (d, J=1.2 Hz, 2H), 6.91 (d, J=1.2 Hz, 2H).

EXAMPLE 83

4-formyl-N-[2-(4-morpholinyl)ethyl]-N-{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propyl}benzamide Except for using the compound (184 mg) produced in Example 82 and 4-formylbenzoic acid (63 mg), the same operation as in Example 78 was performed to obtain the title compound (88 mg) having the following physical properties.

TLC: Rf 0.47 (ethyl acetate:methanol:28% aqueous ammonia=8:2:0.2);

NMR ($CDCl_3$): δ −0.03 (s, 18H), 0.88 (t, J=7.5 Hz, 4H), 2.10-3.86 (m, 23H), 5.00-5.35 (m, 4H), 6.75-7.00 (m, 4H), 7.48 (d, J=8.1 Hz, 2H), 7.88 (d, J=8.1 Hz, 2H), 10.03 (s, 1H).

EXAMPLE 84

4-[(8-isobutyl-2,8-diazaspiro[4.5]dec-2-yl)methyl]-N-[2-(4-morpholinyl)ethyl]-N-{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propyl}benzamide Except for using the compound (88 mg) produced in Example 83 in place of 4-(diethoxymethyl)benzaldehyde and using 8-isobutyl-2,8-diazaspiro[4.5]decane (38 mg) in place of 8-isobutyl-2,8-diazaspiro[4.5]decane, the same operation as in Example 26 was performed to obtain the title compound (122 mg) having the following physical properties.

TLC: Rf 0.33 (ethyl acetate:methanol:28% aqueous ammonia=9:1:0.1);

NMR ($CDCl_3$): δ −0.03 (s, 18H), 0.80-0.98 (m, 10H), 1.20-3.86 (m, 42H), 5.00-5.38 (m, 4H), 6.78-7.00 (m, 4H), 7.08-7.41 (m, 4H).

EXAMPLE 85

N-[3-(1H-imidazol-2-yl)-2-(1H-imidazol-2-ylmethyl)propyl]-4-[(8-isobutyl-2,8-diazaspiro[4.5]dec-2-yl)methyl]-N-[2-(4-morpholinyl)ethyl]benzamide

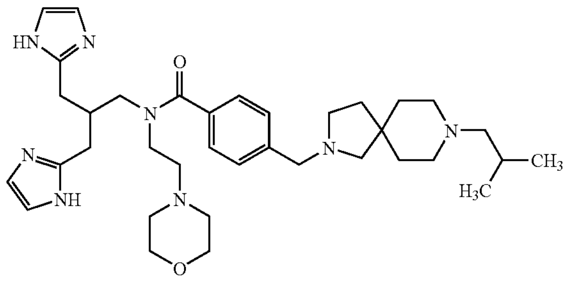

Except for using the compound (122 mg) produced in Example 84 in place of the compound produced in Example 20, the same operation as in Example 21 was performed to obtain the title compound (49 mg) having the following physical properties.

TLC: Rf 0.63 (ethyl acetate:methanol:28% aqueous ammonia=8:2:0.4);

NMR ($CDCl_3$): δ 0.87 (d, J=6.6 Hz, 6H), 1.45-1.86 (m, 7H), 2.02 (d, J=7.2 Hz, 2H), 2.15-2.52 (m, 15H), 2.54 (t, J=7.2 Hz, 2H), 2.80 (dd, J=13.5, 3.3 Hz, 2H), 3.40-3.72 (m, 10H), 7.03 (s, 4H), 7.35 (d, J=8.1 Hz, 2H), 7.41 (d, J=8.1 Hz, 2H).

EXAMPLE 85(1)-EXAMPLE 85(9)

Except for using the corresponding amine in place of 2-morpholin-4-ylethaneamine in Example 82, the same operation as in Example 82→Example 83→Example 84→Example 85 was sequentially performed to obtain the following compounds.

EXAMPLE 85(1)

N-(2-acetamidoethyl)-N-[3-(1H-imidazol-2-yl)-2-(1H-imidazol-2-ylmethyl)propyl]-4-[(8-isobutyl-2,8-diazaspiro[4.5]dec-2-yl)methyl]benzamide

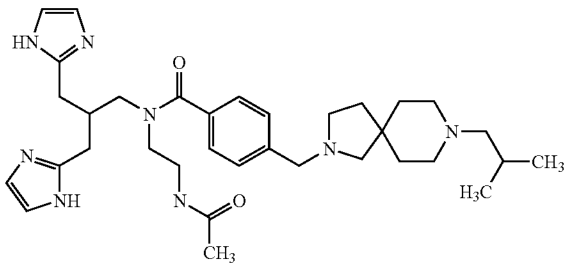

TLC: Rf 0.60 (ethyl acetate:methanol:28% aqueous ammonia=8:2:0.4);

NMR ($CDCl_3$): δ 0.87 (d, J=6.6 Hz, 6H), 1.48-1.68 (m, 6H), 1.76 (m, 1H), 1.85-2.62 (m, 16H), 2.75-2.88 (m, 2H), 3.30-3.90 (m, 8H), 5.85 (m, 1H), 6.80-7.20 (m, 4H), 7.33 (d, J=7.5 Hz, 2H), 7.41 (d, J=7.5 Hz, 2H).

EXAMPLE 85(2)

N-(2-aminoethyl)-N-[3-(1H-imidazol-2-yl)-2-(1H-imidazol-2-ylmethyl)propyl]-4-[(8-isobutyl-2,8-diazaspiro[4.5]dec-2-yl)methyl]benzamide TLC: Rf 0.29 (ethyl acetate:methanol:28% aqueous ammonia=8:2:0.4);

NMR ($CDCl_3$): δ 0.87 (d, J=6.6 Hz, 6H), 1.45-1.90 (m, 7H), 2.02 (d, J=7.2 Hz, 2H), 2.20-2.90 (m, 15H), 3.43 (t, J=7.2 Hz, 2H), 3.50-3.72 (m, 4H), 7.03 (s, 4H), 7.34 (d, J=8.1 Hz, 2H), 7.40 (d, J=8.1 Hz, 2H).

EXAMPLE 85(3)

N-(3-aminopropyl)-N-[3-(1H-imidazol-2-yl)-2-(1H-imidazol-2-ylmethyl)propyl]-4-[(8-isobutyl-2,8-diazaspiro[4.5]dec-2-yl)methyl]benzamide TLC: Rf 0.19 (ethyl acetate:methanol:28% aqueous ammonia=8:2:0.4);

NMR ($CDCl_3$): δ 0.87 (d, J=6.6 Hz, 6H), 1.45-1.88 (m, 9H), 1.98-2.62 (m, 15H), 2.72-2.90 (m, 2H), 3.43 (t, J=7.8 Hz, 2H), 3.50-3.66 (m, 2H), 3.61 (s, 2H), 7.03 (s, 4H), 7.33 (d, J=8.1 Hz, 2H), 7.41 (d, J=8.1 Hz, 2H).

EXAMPLE 85(4)

N-(4-aminobutyl)-N-[3-(1H-imidazol-2-yl)-2-(1H-imidazol-2-ylmethyl)propyl]-4-[(8-isobutyl-2,8-diazaspiro[4.5]dec-2-yl)methyl]benzamide TLC: Rf 0.48 (dichloromethane:methanol:28% aqueous ammonia=8:2:0.4);

NMR ($CDCl_3$): δ 0.87 (d, J=6.6 Hz, 6H), 1.20-1.94 (m, 11H), 2.03 (d, J=7.5 Hz, 2H), 2.20-2.62 (m, 13H), 2.75-2.90 (m, 2H), 3.34 (t, J=7.2 Hz, 2H), 3.48-3.66 (m, 2H), 3.61 (s, 2H), 7.03 (s, 4H), 7.32 (d, J=8.1 Hz, 2H), 7.41 (d, J=8.1 Hz, 2H).

EXAMPLE 85(5)

N-(5-aminopentyl)-N-[3-(1H-imidazol-2-yl)-2-(1H-imidazol-2-ylmethyl)propyl]-4-[(8-isobutyl-2,8-diazaspiro[4.5]dec-2-yl)methyl]benzamide TLC: Rf 0.47 (dichloromethane:methanol:28% aqueous ammonia=8:2:0.4);

NMR ($CDCl_3$): δ 0.87 (d, J=6.6 Hz, 6H), 1.06-1.72 (m, 12H), 1.77 (m, 1H), 1.98-2.68 (m, 15H), 2.75-2.90 (m, 2H), 3.32 (t, J=7.8 Hz, 2H), 3.46-3.66 (m, 2H), 3.61 (s, 2H), 7.03 (s, 4H), 7.31 (d, J=8.1 Hz, 2H), 7.41 (d, J=8.1 Hz, 2H).

EXAMPLE 85(6)

N-(6-aminohexyl)-N-[3-(1H-imidazol-2-yl)-2-(1H-imidazol-2-ylmethyl)propyl]-4-[(8-isobutyl-2,8-diazaspiro[4.5]dec-2-yl)methyl]benzamide TLC: Rf 0.15 (ethyl acetate:methanol:28% aqueous ammonia=8:2:0.4);

NMR ($CDCl_3$): δ 0.87 (d, J=6.6 Hz, 6H), 1.05-1.84 (m, 15H), 2.02 (d, J=7.5 Hz, 2H), 2.15-2.66 (m, 13H), 2.80 (dd, J=13.5, 3.6 Hz, 2H), 3.30 (t, J=7.8 Hz, 2H), 3.46-3.62 (m, 2H), 3.61 (s, 2H), 7.04 (s, 4H), 7.31 (d, J=8.1 Hz, 2H), 7.41 (d, J=8.1 Hz, 2H).

EXAMPLE 85(7)

N-[2-(dimethylamino)ethyl]-N-[3-(1H-imidazol-2-yl)-2-(1H-imidazol-2-ylmethyl)propyl]-4-[(8-isobutyl-2,8-diazaspiro[4.5]dec-2-yl)methyl]benzamide

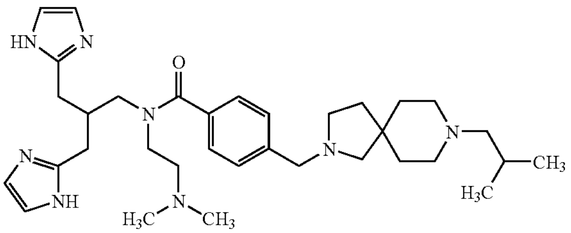

TLC: Rf 0.66 (ethyl acetate:methanol:28% aqueous ammonia=8:2:0.4);

NMR ($CDCl_3$): δ 0.87 (d, J=6.6 Hz, 6H), 1.42-1.82 (m, 7H), 1.98-2.05 (m, 2H), 2.03 (s, 6H), 2.16-2.52 (m, 11H), 2.55 (t, J=6.6 Hz, 2H), 2.81 (dd, J=13.5, 3.3 Hz, 2H), 3.43 (t, J=6.9 Hz, 2H), 3.50-3.62 (m, 2H), 3.60 (s, 2H), 7.03 (s, 4H), 7.33 (d, J=8.1 Hz, 2H), 7.40 (d, J=8.1 Hz, 2H).

EXAMPLE 85(8)

N-[3-(1H-imidazol-2-yl)-2-(1H-imidazol-2-ylmethyl)propyl]-4-[(8-isobutyl-2,8-diazaspiro[4.5]dec-2-yl)methyl]-N-(2-methoxyethyl)benzamide

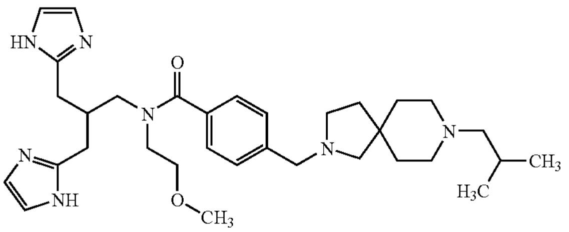

TLC: Rf 0.56 (ethyl acetate:methanol:28% aqueous ammonia=8:2:0.4);

NMR (DMSO-$d_6$): δ 0.93 (d, J=6.6 Hz, 6H), 1.68-2.12 (m, 7H), 2.30-4.20 (m, 26H), 7.18-7.60 (m, 8H).

EXAMPLE 85(9)

N-[3-(1H-imidazol-2-yl)-2-(1H-imidazol-2-ylmethyl)propyl]-4-[(8-isobutyl-2,8-diazaspiro[4.5]dec-2-yl)methyl]-N-[2-(1-pyrrolidinyl)ethyl]benzamide

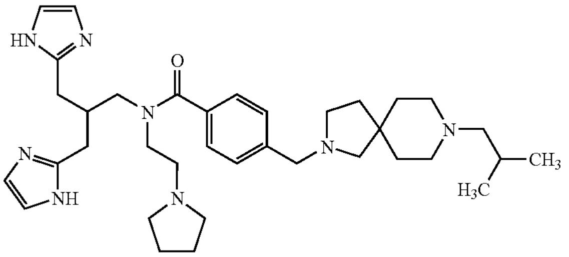

TLC: Rf 0.34 (ethyl acetate:methanol:28% aqueous ammonia=8:2:0.4);

NMR (DMSO-$d_6$): δ 0.83 (d, J=6.6 Hz, 6H), 1.42-1.88 (m, 11H), 1.98-2.80 (m, 21H), 3.10-3.60 (m, 4H), 3.58 (s, 2H), 6.78-7.00 (m, 4H), 7.18-7.38 (m, 4H).

EXAMPLE 86

4-[(8-cyclohexyl-2,8-diazaspiro[4.5]dec-2-yl)methyl]benzoic Acid

Except for using 4-formylbenzoic acid (112 mg) in place of 4-(diethoxymethyl)benzaldehyde and using 8-cyclohexyl-2,8-diazaspiro[4.5]decane (170 mg) in place of 8-isobutyl-2,8-diazaspiro[4.5]decane, the same operation as in Example 26 was performed to obtain the title compound (450 mg) having the following physical properties.

TLC: Rf 0.28 (dichloromethane:methanol:28% aqueous ammonia=8:2:0.2);

NMR ($CD_3OD$): δ 1.05-2.18 (m, 16H), 2.57 (s, 2H), 2.75 (t, J=6.9 Hz, 2H), 3.00-3.25 (m, 5H), 3.74 (s, 2H), 7.37 (d, J=8.1 Hz, 2H), 7.95 (d, J=8.1 Hz, 2H).

EXAMPLE 87

4-[(8-cyclohexyl-2,8-diazaspiro[4.5]dec-2-yl)methyl]-N-{3-hydroxy-2,2-bis[(1-{[2-(trimethylsilyl)ethoxy]methyl}-1H-imidazol-2-yl)methyl]propyl}benzamide Except for using the compound (137 mg) produced in Example 86 in place of 4-formylbenzoic acid and using the compound (73 mg) produced in Example 34 in place of the compound produced in Example 29, the same operation as in Example 78 was performed to obtain the title compound (100 mg) having the following physical properties.

TLC: Rf 0.74 (ethyl acetate:methanol:28% aqueous ammonia=8:2:0.4);

NMR ($CDCl_3$): δ −0.03 (s, 18H), 0.80-1.98 (m, 20H), 2.00-3.60 (m, 21H), 3.62 (s, 2H), 5.15-5.38 (m, 4H), 6.82-7.02 (m, 4H), 7.41 (d, J=8.4 Hz, 2H), 7.92 (d, J=8.4 Hz, 2H), 9.40 (m, 1H).

EXAMPLE 88

3-({4-[(8-cyclohexyl-2,8-diazaspiro[4.5]dec-2-yl)methyl]benzoyl}amino)-2,2-bis[(1-{[2-(trimethylsilyl)ethoxy]methyl}-1H-imidazol-2-yl)methyl]propyl Acetate Except for using the compound (100 mg) produced in Example 87 in place of the compound produced in Example 35, the same operation as in Example 36 was performed to obtain the title compound (10 mg) having the following physical properties.

TLC: Rf 0.52 (ethyl acetate:methanol:28% aqueous ammonia=9:1:0.2);

NMR ($CDCl_3$): δ −0.03 (s, 18H), 0.87 (t, J=8.4 Hz, 4H), 1.00-1.98 (m, 16H), 2.05 (s, 3H), 2.10-2.62 (m, 9H), 2.95 (d, J=15.9 Hz, 2H), 3.16 (d, J=15.9 Hz, 2H), 3.45 (t, J=8.4 Hz, 4H), 3.50 (s, 2H), 3.63 (s, 2H), 4.09 (s, 2H), 5.14 (d, J=11.1

Hz, 2H), 5.36 (d, J=11.1 Hz, 2H), 6.90 (d, J=1.5 Hz, 2H), 6.97 (d, J=1.5 Hz, 2H), 7.39 (d, J=8.1 Hz, 2H), 7.92 (d, J=8.1 Hz, 2H), 9.78 (m, 1H).

EXAMPLE 89

3-({4-[(8-cyclohexyl-2,8-diazaspiro[4.5]dec-2-yl)methyl]benzoyl}amino)-2,2-bis(1H-imidazol-2-ylmethyl)propyl Acetate

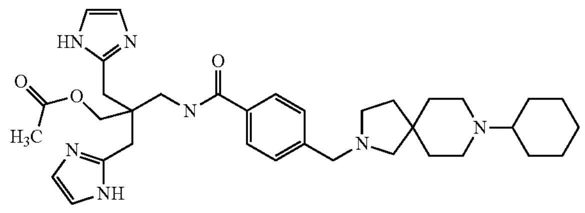

Except for using the compound (10 mg) produced in Example 88 in place of the compound produced in Example 20, the same operation as in Example 21 was performed to obtain the title compound (8 mg) having the following physical properties.

TLC: Rf 0.35 (ethyl acetate:methanol:28% aqueous ammonia=8:2:0.4);

NMR ($CD_3OD$): δ 1.10-2.25 (m, 16H), 1.95 (s, 3H), 2.98-3.64 (m, 15H), 3.97 (s, 2H), 4.45-4.52 (m, 2H), 7.45 (s, 4H), 7.64-7.72 (m, 2H), 8.03 (d, J=8.4 Hz, 2H).

EXAMPLE 90

Tert-butyl 4-[(benzoyloxy)methyl]-1-piperidinecarboxylate

To a dichloromethane (30 mL) solution of N-boc-4-piperidine methanol (2.29 g), triethylamine (4.45 mL) was added. After cooling to 0° C., benzoylchloride (2.49 mL) was added. The reaction solution was stirred for 2 hours with heating to room temperature. To the reaction solution, water (50 mL) was added. The aqueous layer was extracted twice with ethyl acetate (50 mL). The combined organic layer was washed with saturated sodium chloride solution (50 mL) and then dried over anhydrous magnesium sulfate. After removing the anhydrous magnesium sulfate by filtration, the filtrate was concentrated. The residue was purified by silica gel chromatography (n-hexane:ethyl acetate=100:0→10:1→ethyl acetate:methanol=90:10) to obtain (2.30 g) having the following physical properties.

TLC: Rf 0.41 (n-hexane:ethyl acetate=1:1);

NMR ($CDCl_3$): δ 1.20-1.88 (m, 13H), 1.97 (m, 1H), 2.60-2.85 (m, 2H), 4.00-4.30 (m, 4H), 7.40-7.65 (m, 3H), 8.00-8.15 (m, 2H).

EXAMPLE 91

4-piperidinylmethyl benzoate

To a methanol (30 mL) solution of the compound (1.91 g) produced in Example 90, a 4N dioxane solution (10 mL) was added, followed by stirring at room temperature for 3 hours. The reaction solution was concentrated under reduced pressure. Without purifying the residue, the title compound (1.44 g) having the following physical properties was obtained.

TLC: Rf 0.56 (dichloromethane:methanol:28% aqueous ammonia=8:2:0.5);

NMR (DMSO-$d_6$): δ 1.42-1.62 (m, 2H), 1.82-1.95 (m, 2H), 2.05 (m, 1H), 2.80-2.98 (m, 2H), 3.20-3.40 (m, 2H), 4.18 (d, J=6.0 Hz, 2H), 7.50-7.60 (m, 2H), 7.64-7.72 (m, 1H), 7.98-8.04 (m, 2H), 8.40-8.95 (m, 2H).

EXAMPLE 92

{1-[3-{1-[(dimethylamino)sulfonyl]-1H-imidazol-2-yl}-2-({1-[(dimethylamino)sulfonyl]-1H-imidazol-2-yl}methyl)propanoyl]-4-piperidinyl}methyl Benzoate To a dichloromethane (5 mL) solution of the compound (327 mg) produced in Example 91 and the compound (370 mg) produced in Example 68, N-methylmorpholine (280 μL), EDC (452 mg) and 1-hydroxybenzimidazole (138 mg) were added in this order. The reaction solution was stirred at room temperature overnight. To the reaction solution, water (10 mL) was added. The aqueous layer was extracted twice with dichloromethane (20 mL). The combined organic layer was washed with saturated sodium chloride solution (20 mL) and then dried over anhydrous magnesium sulfate. After removing the anhydrous magnesium sulfate by filtration, the filtrate was concentrated. The residue was purified by silica gel chromatography (n-hexane:ethyl acetate=1:1→0:1→ethyl acetate:methanol:28% aqueous ammonia=90:10:0→90:10:1) to obtain the title compound (400 mg) having the following physical properties.

TLC: Rf 0.54 (ethyl acetate:methanol:28% aqueous ammonia=9:1:0.2);

NMR ($CDCl_3$): δ 1.12-1.50 (m, 2H), 1.72-1.92 (m, 2H), 2.02 (m, 1H), 2.66 (m, 1H), 2.88 (s, 12H), 2.95-3.44 (m, 5H), 4.15-4.32 (m, 4H), 4.62 (m, 1H), 6.85 (d, J=1.8 Hz, 1H), 6.90 (d, J=1.8 Hz, 1H), 7.17 (d, J=1.8 Hz, 1H), 7.20 (d, J=1.8 Hz, 1H), 7.42-7.48 (m, 2H), 7.58-7.60 (m, 1H), 8.00-8.08 (m, 2H).

EXAMPLE 93

2,2'-(2-{[4-(hydroxymethyl)-1-piperidinyl]carbonyl}-1,3-propanediyl)bis(N,N-dimethyl-1H-imidazole-1-sulfonamide)

To a tetrahydrofuran (2 mL)-methanol (2 mL) solution of the compound (400 mg) produced in Example 92, an aqueous 2N sodium hydroxide solution (3 mL) was added. The reaction solution was stirred at 50° C. for one hour. The reaction solution was concentrated under reduced pressure. To the residue, water (20 mL) was added. The aqueous layer was extracted twice with dichloromethane (50 mL). The combined organic layer was washed in turn with an aqueous 5N sodium hydroxide solution (50 mL) and saturated sodium chloride solution (50 mL), and then dried over anhydrous magnesium sulfate. After removing the anhydrous magnesium sulfate by filtration, the filtrate was concentrated. Without purifying the residue, the title compound (260 mg) was obtained.

TLC: Rf 0.49 (ethyl acetate:methanol:28% aqueous ammonia=8:2:0.2);

NMR ($CDCl_3$): δ 1.00-1.85 (m, 5H), 2.53 (m, 1H), 2.90 (s, 12H), 2.92-3.42 (m, 5H), 3.48 (d, J=6.0 Hz, 2H), 4.15-4.30 (m, 2H), 4.58 (m, 1H), 6.86 (d, J=1.5 Hz, 1H), 6.88 (d, J=1.5 Hz, 1H), 7.15-7.20 (m, 2H).

EXAMPLE 94

2,2'-{2-[(4-formyl-1-piperidinyl)carbonyl]-1,3-propanediyl}bis(N,N-dimethyl-1H-imidazole-1-sulfonamide)

Except for using the compound (130 mg) produced in Example 93 in place of the compound produced in Example 9, the same operation as in Example 10 was performed to obtain the title compound (128 mg) having the following physical properties.

TLC: Rf 0.39 (ethyl acetate:methanol:28% aqueous ammonia=9:1:0.2);

NMR ($CDCl_3$): δ 0.92-2.02 (m, 4H), 2.40-3.45 (m, 6H), 2.92 (s, 12H), 4.04-4.72 (m, 4H), 6.82-6.92 (m, 2H), 7.22 (s, 2H), 9.66 (s, 1H).

EXAMPLE 95

2,2'-(2-{[4-({8-[(3-methyl-2- dienyl)methyl]-2,8-diazaspiro[4.5]dec-2-yl}methyl)-1-piperidinyl]carbonyl}-1,3-propanediyl)bis(N,N-dimethyl-1H-imidazole-1-sulfonamide)

Except for using the compound (128 mg) produced in Example 94 in place of 4-(diethoxymethyl)benzaldehyde and using the compound (61 mg) produced in Example 13 in place of 8-isobutyl-2,8-diazaspiro[4.5]decane, the same operation as in Example 26 was performed to obtain the title compound (42 mg) having the following physical properties.

TLC: Rf 0.56 (ethyl acetate:methanol:28% aqueous ammonia=8:2:0.2);

NMR ($CDCl_3$): δ 0.90-3.42 (m, 27H), 2.19 (s, 3H), 2.90 (s, 12H), 3.60 (s, 2H), 4.10-4.28 (m, 2H), 4.52 (m, 1H), 6.77 (d, J=5.1 Hz, 1H), 6.86 (d, J=1.8 Hz, 1H), 6.87 (d, J=1.8 Hz, 1H), 7.11 (d, J=5.1 Hz, 1H), 7.17 (d, J=1.8 Hz, 2H).

EXAMPLE 96

2-({1-[3-(1H-imidazol-2-yl)-2-(1H-imidazol-2-ylmethyl)propanoyl]-4-piperidinyl}methyl)-8-[(3-methyl-2-thienyl)methyl]-2,8-diazaspiro[4.5]decane

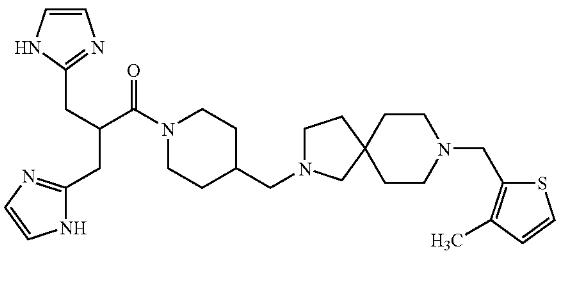

To the compound (78 mg) produced in Example 95, 2N hydrochloric acid (3 mL) was added, followed by stirring at 70° C. for 6 hours. The reaction solution was concentrated under reduced pressure. The residue was purified by silica gel chromatography (ethyl acetate:methanol: 28% aqueous ammonia=8:2:0.2) to obtain the title compound (32 mg) having the following physical properties.

TLC: Rf 0.22 (ethyl acetate:methanol:28% aqueous ammonia=8:2:0.2);

NMR ($CDCl_3$): δ 1.02-1.22 (m, 2H), 1.58-2.00 (m, 9H), 2.19 (s, 3H), 2.35-3.20 (m, 16H), 3.65 (s, 2H), 3.73 (m, 1H), 4.21 (m, 1H), 4.51 (m, 1H), 6.78 (d, J=5.4 Hz, 1H), 7.03 (s, 4H), 7.13 (d, J=5.4 Hz, 1H).

EXAMPLE 96(1)

N'-({1-[3-(1H-imidazol-2-yl)-2-(1H-imidazol-2-ylmethyl)propanoyl]-4-piperidinyl}methyl)-N,N-dipropyl-1,4-butanediamine Except for using the corresponding amine in place of the compound produced in Example 13 in Example 95, the same operation as in Example 95→Example 96 was sequentially performed to obtain the title compound having the following physical properties.

TLC: Rf 0.34 (dichloromethane:methanol:28% aqueous ammonia=8:2:0.2);

NMR ($CDCl_3$): δ 0.89 (t, J=7.2 Hz, 6H), 1.08-1.96 (m, 13H), 2.40-2.85 (m, 13H), 2.90-3.05 (m, 2H), 3.14 (m, 1H), 3.27 (m, 1H), 4.14 (m, 1H), 4.63 (m, 1H), 7.01 (s, 4H).

EXAMPLE 97

2-({1-[3-(1H-imidazol-2-yl)-2-(1H-imidazol-2-ylmethyl)propyl]-4-piperidinyl}methyl)-8-[(3-methyl-2-thienyl)methyl]-2,8-diazaspiro[4.5]decane Except for using the compound (170 mg) produced in Example 92 in place of the compound produced in Example 5 in Example 18, the same operation as in Example 18→Example 94→Example 95→Example 96 was sequentially performed to obtain the title compound having the following physical properties.

TLC: Rf 0.54 (dichloromethane:methanol:28% aqueous ammonia=9:1:0.2);

NMR ($CDCl_3$): δ 1.18-2.72 (m, 33H), 2.80-2.98 (m, 2H), 3.59 (s, 2H), 6.78 (d, J=5.4 Hz, 1H), 6.90-7.02 (m, 4H), 7.12 (d, J=5.4 Hz, 1H).

EXAMPLE 98

N-{4-[(8-cyclohexyl-2,8-diazaspiro[4.5]dec-2-yl)methyl]benzyl}-3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propanamide Except for using the compound (50 mg) produced in Example 5 and 1-{4-[(8-cyclohexyl-2,8-diazaspiro[4.5]dec-2-yl)methyl]phenyl}methaneamine (37 mg), the same operation as in Example 78 was performed to obtain the title compound (65 mg) having the following physical properties.

TLC: Rf 0.47 (ethyl acetate:methanol:28% aqueous ammonia=8:2:0.2);

NMR ($CDCl_3$): δ −0.03 (s, 18H), 0.80-0.92 (m, 4H), 1.00-1.90 (m, 16H), 1.95-2.60 (m, 9H), 2.98-3.68 (m, 11H), 4.28 (d, J=5.7 Hz, 2H), 5.10 (d, J=10.8 Hz, 2H), 5.26 (d=10.8 Hz, 2H), 6.82-6.90 (m, 4H), 6.97 (d, J=8.1 Hz, 2H), 7.17 (d, J=8.1 Hz, 2H), 7.60 (m, 1H).

EXAMPLE 99

N-{4-[(8-cyclohexyl-2,8-diazaspiro[4.5]dec-2-yl)methyl]benzyl}-3-(1H-imidazol-2-yl)-2-(1H-imidazol-2-ylmethyl)propanamide

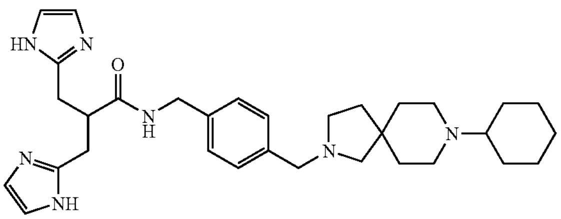

Except for using the compound (65 mg) produced in Example 98 in place of the compound produced in Example 20, the same operation as in Example 21 was performed to obtain the title compound (8 mg) having the following physical properties.

TLC: Rf 0.18 (ethyl acetate:methanol:28% aqueous ammonia=8:2:0.4);

NMR ($CDCl_3$): δ 1.00-1.92 (m, 16H), 2.12-2.60 (m, 9H), 2.75-3.02 (m, 5H), 3.55 (brs, 2H), 4.41 (brs, 2H), 6.98 (s, 4H), 7.15 (d, J=8.4 Hz, 2H), 7.24-7.28 (m, 2H).

EXAMPLE 99(1)-EXAMPLE 99(4)

Except for using the corresponding amine in place of 1-{4-[(8-cyclohexyl-2,8-diazaspiro[4.5]dec-2-yl)methyl]phenyl}methaneamine in Example 98, the same operation as in Example 98→Example 99 was sequentially performed to obtain the following compounds.

EXAMPLE 99(1)

N-({1-[(1-cycloheptyl-4-piperidinyl)methyl]-4-piperidinyl}methyl)-3-(1H-imidazol-2-yl)-2-(1H-imidazol-2-ylmethyl)propanamide TLC: Rf 0.63 (ethyl acetate:methanol:28% aqueous ammonia=8:2:0.4);

NMR ($CDCl_3$): δ 1.10-2.06 (m, 23H), 2.15 (d, J=6.0 Hz, 2H), 2.18-3.12 (m, 13H), 3.11 (t, J=6.0 Hz, 2H), 7.00 (s, 4H), 7.68 (m, 1H).

EXAMPLE 99(2)

Ethyl({4-[(8-cyclohexyl-2,8-diazaspiro[4.5]dec-2-yl)methyl]benzyl}[3-(1H-imidazol-2-yl)-2-(1H-imidazol-2-ylmethyl)propanoyl]amino)acetate TLC: Rf 0.24 (ethyl acetate:methanol:28% aqueous ammonia=8:2:0.4);

NMR ($CDCl_3$): δ 1.00-2.04 (m, 16H), 1.30 (t, J=7.2 Hz, 3H), 2.25 (m, 1H), 2.34 (s, 2H), 2.40-2.60 (m, 4H), 2.54 (t, J=6.9 Hz, 2H), 2.93 (dd, J=14.7, 6.9 Hz, 2H), 3.06 (dd, J=14.7 Hz, 2H), 3.44 (m, 1H), 3.55 (s, 2H), 4.00 (s, 2H), 4.25 (q, J=7.2 Hz, 2H), 4.58 (s, 2H), 7.01 (s, 4H), 7.03 (d, J=8.1 Hz, 2H), 7.28 (d, J=8.1 Hz, 2H).

EXAMPLE 99(3)

N-{4-[(8-cyclohexyl-2,8-diazaspiro[4.5]dec-2-yl)methyl]phenyl}-3-(1H-imidazol-2-yl)-2-(1H-imidazol-2-ylmethyl)propanamide TLC: Rf 0.23 (ethyl acetate:methanol:28% aqueous ammonia=8:2:0.4);

NMR ($CDCl_3$): δ 1.00-1.98 (m, 16H), 2.22-2.66 (m, 9H), 2.97 (dd, J=15.0, 6.3 Hz, 2H), 3.08 (dd, J=15.0, 5.7 Hz, 2H), 3.23 (m, 1H), 3.54 (s, 2H), 7.02 (s, 4H), 7.22-7.32 (m, 2H), 7.51 (d, J=8.7 Hz, 2H), 10.16 (s, 1H).

EXAMPLE 99(4)

N-{4-[(8-cyclohexyl-2,8-diazaspiro[4.5]dec-2-yl)methyl]benzyl}-N-ethyl-3-(1H-imidazol-2-yl)-2-(1H-imidazol-2-ylmethyl)propanamide TLC: Rf 0.29 (ethyl acetate:methanol:28% aqueous ammonia=8:2:0.4);

NMR (DMSO-$d_6$): δ 0.82-1.80 (m, 19H), 2.18-3.36 (m, 15H), 3.51 (s, 2H), 3.73 (m, 1H), 4.42 (s, 2H), 6.83 (s, 4H), 6.90-7.04 (m, 2H), 7.15 (d, J=7.5 Hz, 2H).

EXAMPLE 100

4-{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propoxy}benzaldehyde To a tetrahydrofuran (2 mL) solution of the compound (120 mg) produced in Example 18 and a 4-hydroxybenzaldehyde (31 mg), triphenylphosphine (81 mg) and diethylazodicarboxylate (175 μL) were added in this order. The reaction solution was stirred at room temperature for 15 hours. To the reaction solution, water (20 mL) was added. The aqueous layer was extracted twice with ethyl acetate (50 mL). The combined organic layer was washed with saturated sodium chloride solution (50 mL) and then dried over anhydrous magnesium sulfate. After removing the anhydrous magnesium sulfate by filtration, the filtrate was concentrated. The residue was purified by silica gel chromatography (n-hexane: ethyl acetate=80:20→0:100→ethyl acetate:methanol: 28% aqueous ammonia=100:0:0→80:20:2) to obtain the title compound (85 mg) having the following physical properties.

TLC: Rf 0.31 (ethyl acetate:methanol:28% aqueous ammonia=19:1:0.1);

NMR ($CDCl_3$): δ −0.03 (s, 18H), 0.80-0.94 (m, 4H), 2.80-3.05 (m, 5H), 3.45 (t, J=8.4 Hz, 4H), 3.90-4.35 (m, 2H), 5.10-5.30 (m, 4H), 6.80-6.98 (m, 4H), 6.97 (d, J=9.0 Hz, 2H), 7.80 (d, J=9.0 Hz, 2H), 9.86 (s, 1H).

EXAMPLE 101

8-[(3-methyl-2-thienyl)methyl]-2-(4-{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propoxy}benzyl)-2,8-diazaspiro[4.5]decane Except for using the compound (85 mg) produced in Example 100 in place of 4-(diethoxymethyl)benzaldehyde and using the compound (37 mg) produced in Example 13 in place of 8-isobutyl-2,8-diazaspiro[4.5]decane, the same operation as in Example 26 was performed to obtain the title compound (40 mg) having the following physical properties.

TLC: Rf 0.14 (ethyl acetate:methanol:28% aqueous ammonia=19:1:0.2);

NMR ($CDCl_3$): δ −0.03 (s, 18H), 0.78-0.98 (m, 4H), 1.20-3.82 (m, 30H), 3.90-4.10 (m, 2H), 5.18-5.35 (m, 4H), 6.70-7.00 (m, 6H), 7.08-7.20 (m, 2H), 7.44 (d, J=7.8 Hz, 2H).

EXAMPLE 102

2-{4-[3-(1H-imidazol-2-yl)-2-(1H-imidazol-2-ylmethyl)propoxy]benzyl}-8-[(3-methyl-2-thienyl)methyl]-2,8-diazaspiro[4.5]decane

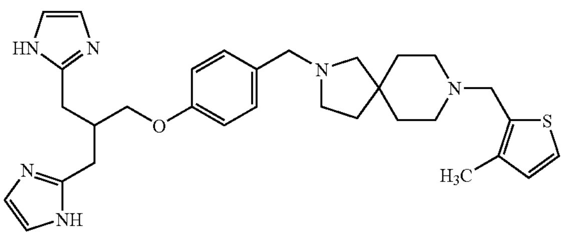

Except for using the compound (40 mg) produced in Example 101, the same operation as in Example 21 was performed to obtain the title compound (7 mg) having the following physical properties.

TLC: Rf 0.36 (ethyl acetate:methanol:28% aqueous ammonia=8:2:0.2);

NMR ($CDCl_3$): δ 1.52-1.68 (m, 6H), 2.17 (s, 3H), 2.25-2.48 (m, 6H), 2.57 (t, J=6.9 Hz, 2H), 2.60 (m, 1H), 2.75 (dd, J=14.4, 7.5 Hz, 2H), 2.89 (dd, J=14.4, 4.5 Hz, 2H), 3.53 (s, 2H), 3.57 (s, 2H), 3.85 (d, J=7.2 Hz, 2H), 6.77 (d, J=5.1 Hz, 1H), 6.85 (d, J=8.7 Hz, 2H), 7.02 (s, 4H), 7.11 (d, J=5.1 Hz, 1H), 7.23 (d, J=8.7 Hz, 2H).

EXAMPLE 103

4-{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propoxy}benzoic Acid To a tert-butanol (2 mL) solution of the compound (50 mg) produced in Example 100, water (0.5 mL), sodium dihydrogen phosphate (11 mg), 2-methyl-2-butene (46 μL) and sodium chlorite (32 mg) were added in this order. The reaction solution was stirred for 3 hours at room temperature. To the reaction solution, 1N hydrochloric acid was added so as to adjust the pH to 5. The aqueous layer was extracted twice with ethyl acetate (50 mL). The combined organic layer was washed with saturated sodium chloride solution (50 mL) and then dried over anhydrous magnesium sulfate. After removing the anhydrous magnesium sulfate by filtration, the filtrate was concentrated. Without purifying the residue, the title compound (50 mg) having the following physical properties was obtained.

TLC: Rf 0.24 (dichloromethane:methanol:28% aqueous ammonia=8:2:0.4);

NMR ($CDCl_3$): δ −0.03 (s, 18H), 0.88 (t, J=8.4 Hz, 4H), 2.82 (m, 1H), 3.00-3.12 (m, 2H), 3.18 (dd, J=15.6, 5.4 Hz, 2H), 3.47 (t, J=8.4 Hz, 4H), 4.07 (d, J=4.5 Hz, 2H), 5.23 (d, J=11.1 Hz, 2H), 5.34 (d, J=11.1 Hz, 2H), 6.94 (d, J=1.5 Hz, 2H), 7.00 (d, J=9.0 Hz, 2H), 7.07 (d, J=1.5 Hz, 2H), 8.05 (d, J=9.0 Hz, 2H).

EXAMPLE 104

8-cyclohexyl-2-(4-{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propoxy}benzoyl)-2,8-diazaspiro[4.5]decane Except for using the compound (50 mg) produced in Example 103 in place of the compound produced in Example 68 and using 8-cyclohexyl-2,8-diazaspiro[4.5]decane (38 mg) in place of the compound produced in Example 91, the same operation as in Example 92 was performed to obtain the title compound (54 mg) having the following physical properties.

TLC: Rf 0.25 (ethyl acetate:methanol:28% aqueous ammonia=9:1:0.2);

NMR ($CDCl_3$): δ −0.03 (s, 18H), 0.87 (t, J=8.4 Hz, 4H), 1.00-1.92 (m, 16H), 2.10-3.58 (m, 19H), 3.66 (m, 1H), 4.00-4.10 (m, 2H), 5.19 (d, J=10.8 Hz, 2H), 5.24 (d, J=10.8 Hz, 2H), 6.86 (d, J=9.0 Hz, 2H), 6.91 (s, 1H), 6.94 (s, 1H), 7.45 (d, J=9.0 Hz, 2H).

EXAMPLE 105

8-cyclohexyl-2-{4-[3-(1H-imidazol-2-yl)-2-(1H-imidazol-2-ylmethyl)propoxy]benzoyl}-2,8-diazaspiro[4.5]decane Except for using the compound (54 mg) produced in Example 104 in place of the compound produced in Example 20, the same operation as in Example 21 was performed to obtain the title compound (20 mg) having the following physical properties.

TLC: Rf 0.40 (ethyl acetate:methanol:28% aqueous ammonia=8:2:0.4);

NMR ($CDCl_3$): δ 1.00-1.95 (m, 16H), 2.18-2.78 (m, 8H), 2.87 (dd, J=14.7, 4.8 Hz, 2H), 3.28-3.50 (m, 2H), 3.45-3.75 (m, 2H), 3.84 (d, J=6.9 Hz, 2H), 6.80-6.90 (m, 2H), 7.02 (s, 4H), 7.46 (d, J=8.7 Hz, 2H).

EXAMPLE 106

1-[4-({[tert-butyl(dimethyl)silyl]oxy}methyl)phenyl]-3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]-1-propanol Except for using the compound (250 mg) produced in Example 8 in place of the compound produced in Example 14, the same operation as in Example 15 was performed to obtain the title compound (190 mg) having the following physical properties.

TLC: Rf 0.54 (ethyl acetate:methanol:28% aqueous ammonia=19:1:0.2);

NMR ($CDCl_3$): δ −0.80-0.20 (m, 27H), 0.70-0.95 (m, 4H), 0.93 (s, 6H), 2.60-3.15 (m, 5H), 3.25-3.50 (m, 4H), 4.71 (s, 2H), 4.89 (s, 2H), 4.91 (d, J=3.0 Hz, 1H), 4.98 (d, J=10.8 Hz, 1H), 5.10 (d, J=10.8 Hz, 1H), 6.84 (m, 1H), 6.89 (m, 1H), 6.94 (m, 1H), 6.96 (m, 1H), 7.18-7.30 (m, 2H), 7.37 (d, J=7.8 Hz, 2H).

EXAMPLE 107

1-[4-({[tert-butyl(dimethyl)silyl]oxy}methyl)phenyl]-3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propyl Acetate Except for using the compound (90 mg) produced in Example 106 in place of the compound produced in Example 35, the same operation as in Example 36 was performed to obtain the title compound (90 mg) having the following physical properties.

TLC: Rf 0.44 (ethyl acetate:methanol:28% aqueous ammonia=19:1:0.2);

NMR ($CDCl_3$): δ −0.80-0.20 (m, 27H), 0.75-0.90 (m, 4H), 0.93 (s, 6H), 2.02-2.15 (m, 3H), 2.68-3.52 (m, 9H), 4.70 (s, 2H), 4.93 (d, J=11.1 Hz, 1H), 5.00-5.15 (m, 3H), 5.92 (d, J=5.4 Hz, 1H), 6.80 (d, J=1.2 Hz, 2H), 6.86 (d, J=1.8 Hz, 1H), 6.88 (d, J=1.8 Hz, 1H), 7.20-7.40 (m, 4H).

EXAMPLE 108

1-[4-(hydroxymethyl)phenyl]-3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propyl Acetate To the compound (90 mg) produced in Example 107, a 1M tetrabutylammonium fluoride tetrahydrofuran solution (1 mL) was added, followed by stirring at room temperature for 2 hours. To the reaction solution, water (20 mL) was added. The aqueous layer was extracted twice with ethyl acetate (50 mL). The combined organic layer was washed in turn with water (20 mL) and saturated sodium chloride solution (20 mL), and then dried over anhydrous magnesium sulfate. After removing the anhydrous magnesium sulfate by filtration, the filtrate was concentrated. The residue was purified by silica gel chromatography (n-hexane:ethyl acetate=50:50→0:100 ethyl acetate:methanol: 28% aqueous ammonia=100:0:0→100:10:1) to obtain the title compound (70 mg) having the following physical properties.

TLC: Rf 0.40 (ethyl acetate:methanol:28% aqueous ammonia=19:1:0.1);

NMR ($CDCl_3$): δ −0.04 (m, 18H), 0.82 (t, J=8.4 Hz, 4H), 2.08 (s, 3H), 2.68 (dd, J=15.3, 6.9 Hz, 1H), 2.78-2.88 (m, 2H), 2.98 (dd, J=15.3, 8.7 Hz, 1H), 3.10 (m, 1H), 3.28-3.42 (m, 4H), 4.66 (s, 2H), 4.93 (d, J=10.8 Hz, 1H), 5.03 (s, 2H), 5.08 (d, J=10.8 Hz, 1H), 5.99 (d, J=5.1 Hz, 1H), 6.81 (d, J=1.2 Hz, 2H), 6.87 (d, J=0.9 Hz, 1H), 6.88 (d, J=0.9 Hz, 1H), 7.28-7.40 (m, 4H).

EXAMPLE 109

(4-{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propyl}phenyl)methanol To an ethanol solution (3 mL) of the compound (35 mg) produced in Example 108, 10% palladium carbon (20 mg) was added and the atmosphere in the reaction system was replaced by hydrogen. The reaction solution was stirred at 50° C. for 6 hours. After removing palladium carbon by filtering the reaction solution through Celite (trade name), the filtrate was concentrated. Without purifying the residue, the title compound (20 mg) having the following physical properties was obtained.

TLC: Rf 0.22 (ethyl acetate:methanol:28% aqueous ammonia=19:1:0.1);

NMR ($CDCl_3$): δ 0.00 (m, 18H), 0.87 (t, J=8.4 Hz, 4H), 2.65-2.95 (m, 7H), 3.41 (t, J=8.4 Hz, 4H), 4.69 (s, 2H), 5.05 (d, J=10.8 Hz, 2H), 5.17 (d, J=10.8 Hz, 2H), 6.88-6.92 (m, 2H), 6.98-7.00 (m, 2H), 7.22 (d, J=8.1 Hz, 2H), 7.30 (d, J=8.1 Hz, 2H).

EXAMPLE 110

4-{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propyl}benzaldehyde Except for using the compound (140 mg) produced in Example 109 in place of the compound produced in Example 9, the same operation as in Example 10 was performed to obtain the title compound (132 mg) having the following physical properties.

TLC: Rf 0.42 (ethyl acetate:methanol:28% aqueous ammonia=9:1:0.1);

NMR ($CDCl_3$): δ −0.05 (m, 18H), 0.82 (t, J=8.1 Hz, 4H), 2.45-3.30 (m, 7H), 3.40 (t, J=8.4 Hz, 4H), 5.13 (d, J=10.5 Hz, 2H), 5.27 (d, J=10.5 Hz, 2H), 6.90 (d, J=1.5 Hz, 2H), 6.98 (d, J=1.5 Hz, 2H), 7.42 (d, J=8.1 Hz, 2H), 7.77 (d, J=8.1 Hz, 2H), 9.95 (s, 1H).

EXAMPLE 111

8-cyclohexyl-2-(4-{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propyl}benzyl)-2,8-diazaspiro[4.5]decane Except for using the compound (50 mg) produced in Example 110 in place of 4-(diethoxymethyl)benzaldehyde, the same operation as in Example 26 was performed to obtain (58 mg) having the following physical properties.

TLC: Rf 0.28 (ethyl acetate:methanol:28% aqueous ammonia=9:1:0.2);

NMR ($CDCl_3$): δ −0.05 (m, 18H), 0.82 (dd, J=8.7, 7.5 Hz, 4H), 1.00-2.90 (m, 32H), 3.36 (dd, J=8.7, 7.5 Hz, 4H), 3.52 (s, 2H), 4.98 (d, J=10.8 Hz, 2H), 5.10 (d, J=10.8 Hz, 2H), 6.86 (d, J=1.5 Hz, 2H), 6.92 (d, J=1.5 Hz, 2H), 7.11 (d, J=8.1 Hz, 2H), 7.20 (d, J=8.1 Hz, 2H).

EXAMPLE 112

8-cyclohexyl-2-{4-[3-(1H-imidazol-2-yl)-2-(1H-imidazol-2-ylmethyl)propyl]benzyl}-2,8-diazaspiro[4.5]decane

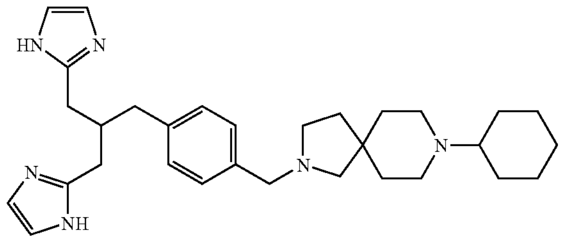

Except for using the compound (58 mg) produced in Example 111 in place of the compound produced in Example 20, the same operation as in Example 21 was performed to obtain the title compound (22 mg) having the following physical properties.

TLC: Rf 0.22 (ethyl acetate:methanol:28% aqueous ammonia=8:2:0.4);

NMR ($CDCl_3$): δ 1.00-1.92 (m, 16H), 2.18-2.65 (m, 14H), 2.71 (dd, J=14.7, 4.2 Hz, 2H), 3.55 (s, 2H), 7.02 (s, 4H), 7.14 (d, J=8.4 Hz, 2H), 7.22-7.30 (m, 2H).

EXAMPLE 113

4-{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propyl}benzoic Acid Except for using the compound (79 mg) produced in Example 110, the same operation as in Example 103 was performed to obtain the title compound (79 mg) having the following physical properties.

TLC: Rf 0.31 (dichloromethane:methanol:28% aqueous ammonia=8:2:0.4);

NMR ($CDCl_3$): δ −0.04 (m, 18H), 0.85 (t, J=8.4 Hz, 4H), 2.90 (d, J=6.3 Hz, 2H), 3.00-3.60 (m, 5H), 3.43 (t, J=8.4 Hz, 4H), 5.18-5.60 (m, 4H), 6.90 (d, J=1.5 Hz, 2H), 6.98 (d, J=1.5 Hz, 2H), 7.30 (d, J=8.1 Hz, 2H), 7.89 (d, J=8.1 Hz, 2H).

EXAMPLE 114

8-cyclohexyl-2-(4-{3-(1-{[2-(trimethylsilyl)ethoxy]methyl}-1H-imidazol-2-yl)-2-[(1-{[2-(trimethylsilyl)ethoxy]methyl}-1H-imidazol-2-yl)methyl]propyl}benzoyl)-2,8-diazaspiro[4.5]decane Except for using the compound (79 mg) produced in Example 113 in place of the compound produced in Example 100 and using 8-cyclohexyl-2,8-diazaspiro[4.5]decane (41 mg) in place of the compound produced in Example 91, the same operation as in Example 92 was performed to obtain the title compound (74 mg) having the following physical properties.

TLC: Rf 0.29 (ethyl acetate:methanol:28% aqueous ammonia=9:1:0.2);

NMR ($CDCl_3$): δ −0.04 (m, 18H), 0.75-0.95 (m, 4H), 1.00-1.92 (m, 16H), 2.00-3.85 (m, 20H), 4.98-5.20 (m, 4H), 6.88 (s, 2H), 6.93 (s, 2H), 7.18-7.28 (m, 2H), 7.41 (d, J=7.8 Hz, 2H).

EXAMPLE 115

8-cyclohexyl-2-{4-[3-(1H-imidazol-2-yl)-2-(1H-imidazol-2-ylmethyl)propyl]benzoyl}-2,8-diazaspiro[4.5]decane Except for using the compound (74 mg) produced in Example 114 in place of the compound produced in Example 20, the same operation as in Example 21 was performed to obtain the title compound (28 mg) having the following physical properties.

TLC: Rf 0.42 (ethyl acetate:methanol:28% aqueous ammonia=8:2:0.4);

NMR ($CDCl_3$): δ 1.00-1.95 (m, 16H), 2.18-2.65 (m, 12H), 3.25-3.55 (m, 2H), 3.45-3.75 (m, 2H), 7.02 (s, 4H), 7.18-7.25 (m, 2H), 7.42 (d, J=7.8 Hz, 2H).

BIOLOGICAL EXAMPLES

Efficacy of the compound of the present invention, for example the fact that the compound of the present invention has CXCR4 antagonistic activity, has been demonstrated by the following experiment.

A measuring method of the present invention was modified to improve accuracy and/or sensitivity of the measurement for evaluating the compound of the present invention. The detailed experimental methods are shown bellow.

As mentioned above, a more direct procedure is a screening a compound that prevents for HIV from binding to CXCR4, which is a receptor on CD4+ cell, on an assay system using HIV viruses. However, using HIV viruses for a large-scale screening is not practical due to its difficult handling. On the other hand, both of T cell-directed (X4) HIV-1 and SDF-1 bind to CXCR4 and therefore CXCR4 binding sites at both of HIV-side and SDF-1-side as well as SDF-1- and HIV-binding sites at the CXCR4 side may presumably have any common characteristics. Thus, to find a compound inhibiting absorption of HIV viruses to a cell that is a different mechanism from those of pre-existing anti-AIDS drugs (reverse transcriptase inhibitors and protease inhibitors), an assay system using an endogenous ligand for CXCR4, SDF-1 instead of HIV may be available.

Specifically, as a system of screening a compound that inhibits the binding between SDF-1 and CXCR4, for example a system of measuring the binding between iodine-labeled SDF-1 and a human T cell strain in which CXCR4 is known to be expressed is operable. The identical idea is possible since macrophage (R5) HIV and RANTES, MIP-1α, and MIP-1β all bind to CCR5.

TEST METHODS

Test Example 1

Study for Inhibition of Binding Human SDF-1 to CEM Cells

To human T cell strain CEM cells in a binding buffer (containing HEPES and BSA), the test compound and $^{125}$I-SDF-1 (NEN) were added and the mixture was incubated at 4° C. for 60 minutes. The reacted CEM cells were rapidly filtrated with a GF/B membrane filter plate (Packard) to adsorb. The plate was washed with PBS three times and then dried. Microscint+20 (Packard) was added thereto. An amount of the radioactivity bound to the CEM cells was measured using Top Count (Packard) and inhibition (%) of the test compound was calculated according to the following equation:

$$\text{Inhibition}=\{(Et-Ea)/(Et-Ec)\}\times 100$$

wherein

Et: amount of radioactivity when the test compound is not added,

Ec: amount of radioactivity when non-radioactive SDF-1 (Pepro Tech) is added in an amount of 1000 times as much as $^{125}$I-SDF-1 as a test compound, and Ea: amount of radioactivity when the test compound is added.

All compounds of the present invention shown in the Example exhibited inhibition of 50% or more in a concentration of 10 μM. For example, $IC_{50}$ value for compound 14 was 11 nM.

FORMULATION EXAMPLES

Formulation Example 1

3-(1H-imidazol-2-yl)-2-(1H-imidazol-2-ylmethyl)-1-[4-({8-[(3-methyl-2-thienyl)methyl]-2,8-diazaspiro[4.5]dec-2-yl}methyl)phenyl]propan-1-one (200 g), calcium carboxymethyl cellulose (disintegrant, 20.0 g), magnesium stearate (lubricants, 10.0 g) and microcrystalline cellulose (870 g)

were mixed by a conventional method and then compressed to obtain 10,000 tablets each containing 20 mg of an active ingredient.

Formulation Example 2

3-(1H-imidazol-2-yl)-2-(1H-imidazol-2-ylmethyl)-1-[4-({8-[(3-methyl-2-thienyl)methyl]-2,8-diazaspiro[4.5]dec-2-yl}methyl)phenyl]propan-1-one (100 g), mannitol (2 kg) and distilled water (50 L) were mixed by a conventional method and filtered with a dust filter, and then each ampoule was filled with 5 mL of the obtained mixture and subjected to heat sterilization in an autoclave to obtain 10,000 ampoules each containing 10 mg of an active ingredient.

INDUSTRIAL APPLICABILITY

The compound of the present invention has CXCR4 antagonistic activity and is therefore useful as a preventive and/or therapeutic agent for CXCR4-mediated diseases. Accordingly, the compound of the present invention can be available as a drug. For example, the compound of the present invention is useful as a preventive and/or therapeutic agent for inflammatory and immune diseases (for example, rheumatoid arthritis, arthritis, retinopathy, pulmonary fibrosis, rejection of transplanted organ, etc.), allergic diseases, infections (for example, human immunodeficiency virus infection, acquired immunodeficiency syndrome, etc.), psychoneurotic diseases, cerebral diseases, cardiovascular disease, metabolic diseases, and cancerous diseases (for example, cancer, cancer metastasis, etc.), or an agent for regeneration therapy.

The invention claimed is:

1. A compound represented by formula (I):

(I)

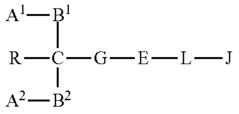

wherein $A^1$ and $A^2$ each independently represents an imidazole ring which may have a substituent(s);

$B^1$ and $B^2$ each independently represents a —$CH_2$;

E represents a benzene ring which may have a substituent(s);

L represents a divalent aliphatic hydrocarbon having 1 to 4 carbon atom(s) which may have a substituent(s);

J represents a 2,8-diazaspiro[4.5]decane which may have a substituent(s);

G represents $G^A$ or $G^{1A}$-$G^{2A}$-$G^{3A}$;

$G^A$ represents a bond, a carbon atom which may have a substituent(s), or a nitrogen atom which may have a substituent;

$G^{1A}$ represents a carbon atom which may have a substituent(s);

$G^{2A}$ represents a carbon atom which may have a substituent(s), a nitrogen atom which may have a substituent, an optionally oxidized sulfur atom or an oxygen atom;

$G^{3A}$ represents a bond, or a carbon atom which may have a substituent(s); and R represents a hydrogen atom, a salt thereof, or an N-oxide thereof.

2. The compound according to claim 1, wherein G is —CO—, —$CH_2$—, —CH(OH)—, or —NH—, a salt thereof, or an N-oxide thereof.

3. The compound according to claim 1, wherein formula (I) is formula (I-1):

(I-1)

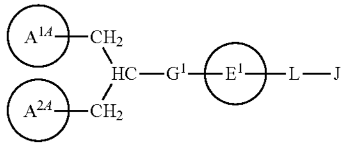

wherein ring $A^{1A}$ and ring $A^{2A}$ each independently represents an imidazole ring which may have a substituent(s), a benzoimidazole ring which may have a substituent(s), or a pyridine ring which may have a substituent(s), $G^1$ represents —CO—, —$CH_2$—, —CH(OH)—, or —NH—, ring $E^1$ represents a benzene ring which may have a substituent(s), and other symbols are as defined in claim 1, a salt thereof, or an N-oxide thereof.

4. The compound according to claim 1, wherein formula (I) is formula (I-4):

(I-4)

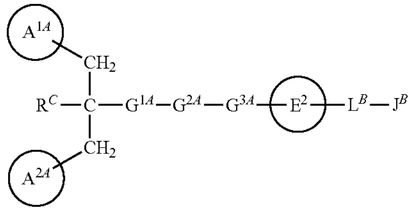

wherein ring $A^{1A}$ and ring $A^{2A}$ each independently represents an imidazole ring which may have a substituent(s), a benzoimidazole ring which may have a substituent(s), or a pyridine ring which may have a substituent(s);

ring $E^2$ represents a benzene ring which may have a substituent(s);

$R^C$ represents (1) a hydrogen atom; and

-$L^B$-$J^B$ represents

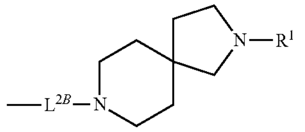

or

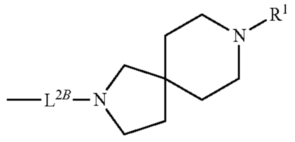

wherein $L^{2B}$ represents a carbon atom which may have a substituent(s) and $R^1$ represents a hydrogen atom or a substituent, and other symbols are as defined in claim 1, a salt thereof, or an N-oxide thereof.

5. The compound according to claim 4, wherein the substituent of the carbon atom which may have a substituent(s)

represented by $G^{1A}$ is absent, a hydroxyl group, an oxo group, or a C1-4 alkyl group, a salt thereof, or an N-oxide thereof.

6. The compound according to claim 4, wherein $G^{2A}$ is a nitrogen atom which may have a substituent and $G^{3A}$ is a carbon atom which may have a substituent(s), a salt thereof, or an N-oxide thereof.

7. The compound according to claim 6, wherein the substituent of the nitrogen atom which may have a substituent(s) represented by $G^{2A}$ is (1) a C1-4 alkyl group substituted with a hydroxyl group, (2) a C1-4 alkyl group which is substituted with a hydroxyl group substituted with an acetyl group, (3) a C1-4 acyl group which may be substituted with a C1-4 alkyl group substituted with a hydroxyl group, (4) a C1-6 alkyl group substituted with an amino group which may be substituted with a C1-4 alkyl group or a C1-4 acyl group, (5) a C1-4 alkyl group substituted with pyrrolidine, morpholine or pyridine, (6) a C1-4 alkyl group substituted with a C1-4 alkoxycarbonyl group, or (7) a C1-4 alkyl group substituted with a carboxyl group, a salt thereof, or an N-oxide thereof.

8. The compound according to claim 6, wherein the substituent of the carbon atom which may have a substituent(s) represented by $G^{3A}$ is absent, a C1-4 alkyl group, a hydroxyl group or an oxo group, a salt thereof, or an N-oxide thereof.

9. The compound according to claim 4, wherein formula (I-4) is formula (I-4-a):

(I-4-a)

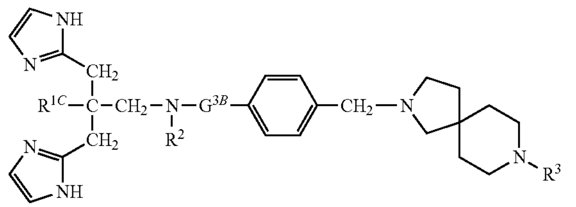

wherein $G^{3B}$ represents —$CH_2$— or —CO—, $R^{1C}$ represents a hydrogen atom, $R^2$ represents a hydrogen atom, or a hydroxyethyl, acetyl, methoxyethyl, pyrrolidinylethyl, morpholinylethyl, hydroxymethylcarbonyl, dimethylaminoethyl or acetylaminoethyl group, and $R^3$ represents a C1-4 alkyl group, a C5-7 saturated monocyclic carbocyclic ring or a (3-methyl-2-thienyl)methyl group, a salt thereof, or an N-oxide thereof.

10. The compound according to claim 1, wherein formula (I) is formula (I-5):

(I-5)

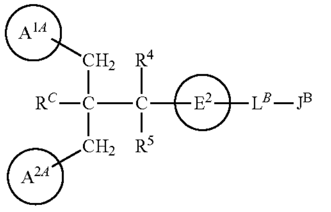

wherein ring $A^{1A}$ and ring $A^{2A}$ each independently represents an imidazole ring which may have a substituent(s), a benzoimidazole ring which may have a substituent(s), or a pyridine ring which may have a substituent(s);

ring $E^2$ represents a benzene ring which may have a substituent(s);

$R^C$ represents (1) a hydrogen atom;

—$L^B$—$J^B$ represents

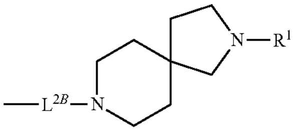

or

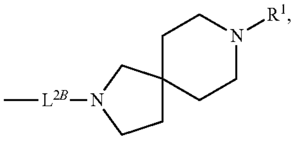

wherein $L^{2B}$ represents a carbon atom which may have a substituent(s) and $R^1$ represents a hydrogen atom or a substituent, and $R^4$ and $R^5$ represent a hydrogen atom or a substituent, a salt thereof, or an N-oxide thereof.

11. The compound according to claim 1, wherein formula (I) is formula (I-6):

(I-6)

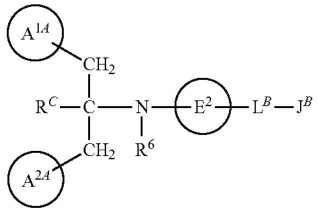

wherein ring $A^{1A}$ and ring $A^{2A}$ each independently represents an imidazole ring which may have a substituent(s), a benzoimidazole ring which may have a substituent(s), or a pyridine ring which may have a substituent(s);

ring $E^2$ represents a benzene ring which may have a substituent(s);

$R^C$ represents (1) a hydrogen atom;

—$L^B$—$J^B$ represents

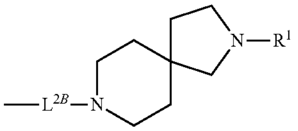

or

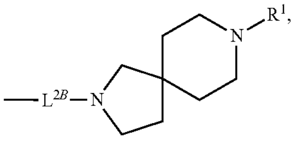

wherein $L^{2B}$ represents a carbon atom which may have a substituent(s) and $R^1$ represents a hydrogen atom or a substituent, and $R^6$ represents a hydrogen atom or a substituent, a salt thereof, or an N-oxide thereof.

12. The compound according to claim 1, which is (1) 2-{4-[3-(1H-imidazol-2-yl)-2-(1H-imidazol-2-ylmethyl)propoxy]benzyl}-8-[(3-methyl-2-thienyl)methyl]-2,8-diazaspiro[4.5]decane, (2) N-[3-(1H-imidazol-2-yl)-2-(1H-imidazol-2-ylmethy) propyl]-N-[4-({8-[(3-methyl-2-thienyl)methyl]-2,8-diazaspiro[4.5]dec-2-yl}methyl)benzyl]acetoamide, (3) 8-cyclohexyl-2-{4-[3-(1H-imidazol-2-yl)-2-(1H-imidazol-2-ylmethyl)propyl]benzyl}-2,8-diazaspiro[4.5] decane, (4) 2-{{4-[(8-cyclohexyl-2,8-diazaspiro[4.5]dec-2-yl)methy]benzyl}[3-(1 H-imidazol-2-yl)-2-(1H-imidazol-2-ylmethyl)propyl]amino}ethanol, (5) N-[3-(1H-imidazol-2-yl)-2-(1H-imidazol-2-ylmethyl) propyl]-4-[(8-isobutyl-2,8-diazaspiro[4.5]dec-2-yl)methyl]benzamide, (6) N-[3-(1H-imidazol-2-yl)-2-(1H-imidazol-2-ylmethyl) propyl]-4-[(8-isobutyl-2,8-diazaspiro[4.5]dec-2-yl)methyl]-N-(2-methoxyethyl)benzamide, (7) N-[3-(1H-imidazol-2-yl)-2-(1H-imidazol-2-ylmethyl) propyl]-4-[(8-isobutyl-2,8-diazaspiro[4.5]dec-2-yl)methyl]-N- [2-(1-pyrrolidinyl)ethyl]benzamide, (8) 2-hydroxy-N-[3-(1H-imidazol-2-yl)-2-(1H -imidazol-2-ylmethy)propyl]-N-{4-[(8-isobutyl-2,8-diazaspiro [4.5]dec-2-yl)methyl]benzyl}acetoamide, (9) N-[2-(dimethylamino)ethyl]-N-[3(1H-imidazol-2-yl)-2-(1H-imidazol-2-ylmethy)propyl]-4-[(8-isobutyl-2,8-diazaspiro[4.5]dec-2-yl)methyl]benzamide,

(10) N-(2-acetoamideethyl)-N-[3-(1H-imidazol-2-yl)-2-(1H-imidazol-2-ylmethy)propyl]-4-[(8-isobutyl-2,8-diazaspiro[4.5]dec-2-ylmethyl]benzamide,

(11) N-[3-(1 H-imidazol-2-yl)-2-(1H-imidazol-2-ylmethyl)propyl]-4-[(8-isobutyl-2,8-diazaspiro[4.5]dec-2-yl)methyl]-N-[2-(4-morpholinyl)ethyl]benzamide,

(12) 3-(1H-imidazol-2-yl)-2-(1H-imidazol-2-ylmethyl)-1-[4-({8-[(3-methyl-2-thienyl)methyl]-2,8-diazaspiro [4.5]dec-2-yl}methyl)phenyl]propan-1-one,

(13) 3-(1H-imidazol-2-yl)-2-(1H-imidazol-2-ylmethyl)-1-[4-({8-[(3-methyl-2-thienyl)methyl]-2,8-diazaspiro [4.5]dec-2-yl}methyl)phenyl]-1-propanol,

(14) 3-(1H-imidazol-2-yl)-2-(1H-imidazol-2-ylmethyl)-N-[4-({8-[(3-methyl-2-thienyl)methyl]-2,8-diazaspiro [4.5]dec-2-yl}methyl)benzyl]-1-propanamine,

(15) N-[3-(1H-imidazol-2-yl)-2-(1H-imidazol-2-ylmethy)propyl]-4-({8-[(3-methyl-2-thienyl)methyl]-2,8-diazaspiro[4.5]dec-2-yl}methyl)aniline,

(16) 3-(1H-imidazol-2-yl)-2-(1H-imidazol-2-ylmethyl)-N-methyl-N-[4-({8-[(3-methyl-2-thienyl)methyl]-2,8-diazaspiro[4.5]dec-2-yl}methyl)benzyl]-1-propanamine,

(17) N-{4[(8-cyclohexyl-2,8-diazaspiro[4.5]dec-2-yl)methyl]phenyl}-N-[3-(1H-imidazol-2-yl)-2-(1H-imidazol-2-ylmethyl)propyl]acetamide,

(18) 2-({4-[(8-cyclohexyl-2,8-diazaspiro[4.5]dec-2-yl) methyl]benzyl}[3-(1H-imidazol-2-yl)-2-(1H-imidazol-2-ylmethyl)propyl]amino)ethyl acetate,

(19) ethyl ({4[(8-cyclohexyl-2,8-diazaspiro[4.5]dec-2-yl) methyl]benzyl}[3-(1H-imidazol-2-yl)-2-(1H-imidazol-2-ylmethyl)propyl]amino)acetate,

(20) ({4[(8-cyclohexyl-2,8-diazaspiro[4.5]dec-2-yl)methyl]benzyl}[3-(1H-imidazol-2-yl)-2-(1H-imidazol-2-ylmethyl)propyl]amino)acetic acid,

(21) N-{4-[(8-cyclohexyl-2,8-diazaspiro[4.5]dec-2-yl) methyl]benzyl}-3-(1H-imidazol-2-yl)-2-(1H-imidazol-2-ylmethyl)-N-(2-methoxyethyl)-1-propanamine,

(22) N-{4-[(8-cyclohexyl-2,8-diazaspiro[4.5]dec-2-yl) methyl]benzyl}-3-(1H-imidazol-2-yl)-2-(1H-imidazol-2-ylmethyl)-N-[2-(1-pyrrolidiny)ethyl]-1-propanamine,

(23) N-[3-(1H-imidazol-2-yl)-2-(1H-imidazol-2-ylmethyl)propyl]-N-{4-[(8-isobutyl-2,8-diazaspiro[4.5] dec-2-yl)methyl]benzyl}-1,2-ethanediamine,

(24) 4-[(8-cyclohexyl-2,8-diazaspiro[4.5]dec-2-yl)methyl]-N-[3-(1H-imidazol-2-yl)-2-(1H-imidazol-2-ylmethyl)propyl]benzamide,

(25) Ethyl 2-(4-{[3-(1H-imidazol-2-yl)-2-(1H-imidazol-2-ylmethyl)propyl]carbamoyl}benzyl)-8-isobutyl-2,8-diazaspiro[4.5]decane-3-carboxylate,

(26) 2-(4-{[3-(1H-imidazol-2-yl)-2-(1H-imidazol-2-ylmethyl)propyl]carbamoyl} benzyl)-8-isobutyl-2,8-diazaspiro[4.5]decane-3-carboxylic acid

(27) N-(2-aminoethyl)-N-[3-(1H-imidazol-2-yl)-2-(1H-imidazol-2-ylmethyl)propyl]-4-[(8-isobutyl-2,8-diazaspiro[4.5]dec-2-yl)methyl]benzamide,

(28) N-(3-aminopropyl)-N-[3-(1H-imidazol-2-yl)-2-(1H-imidazol-2-ylmethyl)propyl]-4-[(8-isobutyl-2,8-diazaspiro[4.5]dec-2-yl)methyl]benzamide, 29) N-(4-aminobutyl)-N-[3-(1H-imidazol-2-yl)-2-(1H-imidazol-2-ylmethyl)propyl]-4-[(8-isobutyl-2,8-diazaspiro[4.5]dec-2-yl)methy]benzamide,

(30) N-(5-aminopentyl)-N-[3-(1H-imidazol-2-yl)-2-(1H-imidazol-2-ylmethyl)propyl]-4-[(8-isobutyl-2,8-diazaspiro[4.5]dec-2-yl)methyl]benzamide,

(31) N-(6-aminohexyl)-N-[3-(1H-imidazol-2-yl)-2-(1H-imidazol-2-ylmethyl)propyl]-4-[(8-isobutyl-2,8-diazaspiro[4.5]dec-2-ylmethyl]benzamide,

(32) N-{4-[(8-cyclohexyl-2,8-diazaspiro[4.5]dec-2-yl) methyl]benzyl}-3-(1H-imidazol-2-yl)-2-(1H-imidazol-2-ylmethyl)propanamide,

(33) Ethyl ({4-[(8-cyclohexyl-2,8-diazaspiro[4.5]dec-2-yl)methyl]benzyl}[3-(1H-imidazol-2-yl)-2-(1H-imidazol-2-ylmethyl)propanoyl]amino)acetate,

(34) N-{4-[(8-cyclohexyl-2,8-diazaspiro[4.5]dec-2-yl) methyl]phenyl}-3-(1H-imidazol-2-yl)-2-(1H-imidazol-2-ylmethyl)propanamide,

(35) N-{4-[(8-cyclohexyl-2,8-diazaspiro[4.5]dec-2-yl) methyl]benzyl}-N-ethyl-3-(1H-imidazol-2-yl)-2-(1H-imidazol-2-ylmethyl)propnanamide,

(36) 8-cyclohexyl-2-{4-[3-(1H-imidazol-2-yl)-2-(1H-imidazol-2-ylmethyl)propoxy]benzoyl}-2,8-diazaspiro [4.5]decane, or

(37) 8-cyclohexyl-2-{4-[3-(1H-imidazol-2-yl)-2-(1H-imidazol-2-ylmethyl)propyl]benzoyl}-2,8-diazaspiro [4.5]decane, a salt thereof, or an N-oxide thereof.

13. A pharmaceutical composition comprising a compound represented by formula (I) according to claim 1, a salt thereof, or an N-oxide thereof.

14. A medicament comprising a compound represented by formula (I) according to claim 1, a salt thereof, or an N-oxide thereof, and one or more kinds selected from reverse transcriptase inhibitor, protease inhibitor, CCR2 antagonist, CCR3 antagonist, CCR4 antagonist, CCR5 antagonist, CXCR4 antagonist, HIV integrase inhibitor, fusion inhibitor, CD4 antagonist, antibody against surface antigen of HIV, Short Interfering RNA targeting a HIV-related factor, and vaccine of HIV.

15. A compound represented by formula (I):

(I)

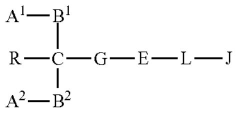

wherein $A^1$ and $A^2$ each independently represents an imidazole ring which may have a substituent(s);

$B^1$ and $B^2$ each independently represents a —$CH_2$—;

E represents a benzene ring which may have a substituent(s);

—L—J is

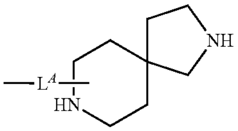

or

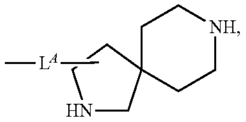

$L^A$ is a divalent aliphatic hydrocarbon having 1 to 4 carbon atom(s) which may have a substituent(s), provided that $L^A$ may be bonded to the nitrogen atom of —NH— and the nitrogen atom of —NH— may have a substituent(s);

G represents $G^A$ or $G^{1A}$-$G^{2A}$-$G^{3A}$;

$G^A$ represents a bond, a carbon atom which may have a substituent(s), or a nitrogen atom which may have a substituent(s);

$G^{1A}$ represents a carbon atom which may have a substituent(s);

$G^{2A}$ represents a carbon atom which may have a substituent(s), a nitrogen atom which may have a substituent, an optionally oxidized sulfur atom or an oxygen atom;

$G^{3A}$ represents a bond, or a carbon atom which may have a substituent(s); and R represents a hydrogen atom, a salt thereof, or an N-oxide thereof.

* * * * *